United States Patent
Weisser et al.

(10) Patent No.: US 12,076,400 B2
(45) Date of Patent: Sep. 3, 2024

(54) METHODS OF USING A BISPECIFIC ANTIGEN-BINDING CONSTRUCT TARGETING HER2 IN COMBINATION WITH CDK4/6 INHIBITORS FOR THE TREATMENT OF BREAST CANCER

(71) Applicant: c/o Zymeworks BC Inc., Vancouver (CA)

(72) Inventors: Nina E. Weisser, Vancouver (CA); Diana F. Hausman, Seattle, WA (US); Patrick Kaminker, Seattle, CA (US)

(73) Assignee: Zymeworks BC Inc., Vancouver (CA)

( * ) Notice: Subject to any disclaimer, the term of this patent is extended or adjusted under 35 U.S.C. 154(b) by 651 days.

(21) Appl. No.: 16/887,460

(22) Filed: May 29, 2020

(65) Prior Publication Data

US 2021/0170023 A1   Jun. 10, 2021

Related U.S. Application Data

(60) Provisional application No. 62/944,822, filed on Dec. 6, 2019.

(51) Int. Cl.
| | | |
|---|---|---|
| A61K 39/395 | (2006.01) | |
| A61K 31/519 | (2006.01) | |
| A61K 31/7068 | (2006.01) | |
| A61K 33/243 | (2019.01) | |
| A61K 47/68 | (2017.01) | |

(52) U.S. Cl.
CPC ........ *A61K 39/3955* (2013.01); *A61K 31/519* (2013.01); *A61K 31/7068* (2013.01); *A61K 33/243* (2019.01); *A61K 47/6817* (2017.08)

(58) Field of Classification Search
None
See application file for complete search history.

(56) References Cited

U.S. PATENT DOCUMENTS

| | | | |
|---|---|---|---|
| 4,683,195 | A | 7/1987 | Mullis et al. |
| 4,816,567 | A | 3/1989 | Cabilly et al. |
| 5,571,894 | A | 11/1996 | Wels et al. |
| 5,587,458 | A | 12/1996 | King et al. |
| 5,648,237 | A | 7/1997 | Carter |
| 5,789,199 | A | 8/1998 | Joly et al. |
| 5,840,523 | A | 11/1998 | Simmons et al. |
| 5,959,177 | A | 9/1999 | Hein et al. |
| 6,040,498 | A | 3/2000 | Stomp et al. |
| 6,214,345 | B1 | 4/2001 | Firestone et al. |
| 6,420,548 | B1 | 7/2002 | Vezina et al. |
| 7,125,978 | B1 | 10/2006 | Vezina et al. |
| 7,375,078 | B2 | 5/2008 | Feng |
| 7,553,816 | B2 | 6/2009 | Senter et al. |
| 8,507,654 | B2 | 8/2013 | Baker et al. |
| 9,315,581 | B2 | 4/2016 | Hudson et al. |
| 2006/0018899 | A1 | 1/2006 | Kao et al. |
| 2014/0286968 | A1 | 9/2014 | Leanna et al. |
| 2016/0136298 | A1 | 5/2016 | Grawunder et al. |
| 2016/0289335 | A1 | 10/2016 | Weisser et al. |
| 2019/0091227 | A1 | 3/2019 | Czibere et al. |

FOREIGN PATENT DOCUMENTS

| | | |
|---|---|---|
| WO | 199316185 A2 | 8/1993 |
| WO | 199845479 A1 | 10/1998 |
| WO | 2002088172 A2 | 11/2002 |
| WO | 2012058768 A1 | 5/2012 |
| WO | 2013063702 A1 | 5/2013 |
| WO | 2015077891 A1 | 6/2015 |
| WO | 2016041082 A1 | 3/2016 |

OTHER PUBLICATIONS

Schroeder et al. (J Allergy Clin Immunol 2010, 125:S41-S52).*
Lloyd et al. (Protein Engineering, Design & Selection 2009, 22:159-168).*
Rudikoff et al. (Proc Natl Acad Sci USA 1982 vol. 79 p. 1979).*
MacCallum et al. (J. Mol. Biol. 1996 262, 732-745).*
Pascalis et al. (The Journal of Immunology (2002) 169, 3076-3084).*
Casset et al. (BBRC 2003, 307:198-205).*
Vajdos et al. (J. Mol. Biol. (2002) 320, 415-428).*
Chen et al. (J. Mol. Bio. (1999) 293, 865-881).*
Wu et al. (J. Mol. Biol. (1999) 294, 151-162).*
Padlan et al. (PNAS 1989, 86:5938-5942).*
Lamminmaki et al. (JBC 2001, 276:36687-36694).*
Piche-Nicholas et al. MABS 2018, 10:81-94.*
Beeram et al. (Annals of Oncology, vol. 28, Supplement 5, Sep. 2017, 255P).*
Zanardi et al. (Seminars in Oncology, vol. 42, No. 6, Dec. 2015, pp. 887-895).*
FASLODEX prescribing information (Revised Aug. 2017).*
Breast Cancer Fact Sheet. Global Cancer Observatory (https://gco.iarc.fr/today/data/factsheets/cancers/20-Breast-fact-sheet.pdf), Dec. 2020, 2 pages.
Cancer Facts & Figures 2019, American Cancer Society (https://www.cancer.org/content/dam/cancer-org/research/cancer-facts-and-statistics/annual-cancer-facts-and-figures/2019/cancer-facts-and-figures-2019.pdf), 76 pages.
Cho, H.-S., et al., Structure of the extracellularregion of HER2 alone and incomplex with the Herceptin Fab. Nature. 2003;421: 756-760.
ECIS—European Cancer Information System from https://ecis.jrc.ec.europa.eu <https://protect-us.mimecast.com/s/iDCEC4x9WwunkmGBHx0cAQ?domain=ecis.jrc.ec.europa.eu>, accessed in 2018.
Franklin, M.C., et al., Insights into ErbB signaling from the structure of the ErbB2-pertuzumab complex. Cancer Cell. 2004;5(4):317-328.

(Continued)

*Primary Examiner* — Sharon X Wen
(74) *Attorney, Agent, or Firm* — DLA Piper LLP (US)

(57) ABSTRACT

Described herein is a method of treating breast cancer comprising administering a bispecific antigen-binding construct targeting HER2 or a bispecific antigen-binding construct targeting HER2 linked to an auristatin analogue (ADC) in combination with a CDK4/6 inhibitor to a subject.

18 Claims, 3 Drawing Sheets
Specification includes a Sequence Listing.

(56) References Cited

OTHER PUBLICATIONS

Garrett, T. P. J., et al., The Crystal Structure of a Truncate ErbB2 EctodomainReveals an Active Conformation, Poised to Interactwith Other ErbB Receptors. Mol. Cell. 2003;11:495-505.

Giordano, S. H., et al., Systemic therapy for patients with advanced human epidermal growth factor receptor 2-positive breast cancer: American Society of Clinical Oncology clinical practice guideline. J Clin Oncol. 2014;32(19):2078-2099.

Moasser, Mm, "The oncogene HER2: it's signaling and transforming functions and its role in human cancer pahtogenesis". Oncogene. 2007; 26(45):6469-87.

Plowman G.D., et al., Ligand-specific activation of HER4/p180erbB4, a fourth member of the epidermal growth factor receptor family. Proc Natl Acad Sci U S A. 1993;90(5):1746-1750.

Pohlmann, P.R. et al., "Resistance to Trastuzumab in Breast Cancer", Clin Cancer Res. 2009; 15(24):7479-91.

Sammons, S. L., et al., HR+, HER2-Advanced Breast Cancer and CDK4/6 Inhibitors: Mode of Action, Clinical Activity, and Safety Profiles. Curr Cancer Drug Targets. 2017; 17(7):637-649.

Schramm, A., et al., Targeted Therapies in HER2-Positive Breast Cancer—a Systematic Review. Breast Care (Basel). 2015; 10(3);173-8.

Semba, K. et al., A v-erbB-related protooncogene, c-erbB-2, is distinct from the c-erbB-1/epidermal growth factor-receptor gene and is amplified in a human salivary gland adenocarcinoma. Proc Natl Acad Sci U S A. 1985;82(19):6497-6501.

Tse, C. et al., HER2 shedding and serum HER2 extracellular domain: biology and clinical utility in breast cancer [published correction appears in Cancer Treat Rev. Nov. 2013;39(7):831]. Cancer Treat Rev. 2012;38(2):133-142.

Yamamoto, T., et al., Similarity of protein encoded by the human c-erb-B-2 gene to epidermal growth factor receptor. Nature. 1986;319(6050):230-234.

Gianni et al., "Neoadjuvant treatment with trastuzumab and pertuzumab plus Palbociclib and fulvestrant in HER2-positive, ER-positive breast cancer (NA-PHER2): an exploratory, open-label, phase 2 study", Lancet Oncol, Jan. 2018, 19:249-256.

Tolany et al., "Abemaciclib plus trastuzumab with or without fulvestrant versus trastuzumab plus standard-of-care chemotherapy in women with hormone receptor-positive, HERS2-positive advanced breast cancer (monarcHER): a randomised, open-label, phase 2 trial", Lancet Oncol, Apr. 2020, 13 pages.

\* cited by examiner

SEQUENCE LISTING

```
<160> NUMBER OF SEQ ID NOS: 72

<210> SEQ ID NO 1
<211> LENGTH: 607
<212> TYPE: PRT
<213> ORGANISM: Artificial Sequence
<220> FEATURE:
<223> OTHER INFORMATION: ECD boundaries are Domain I: 1-165; Domain II:
      166-322; Domain III: 323-488; Domain IV: 489-607

<400> SEQUENCE: 1
```

```
Thr Gln Val Cys Thr Gly Thr Asp Met Lys Leu Arg Leu Pro Ala Ser
1               5                   10                  15

Pro Glu Thr His Leu Asp Met Leu Arg His Leu Tyr Gln Gly Cys Gln
                20                  25                  30

Val Val Gln Gly Asn Leu Glu Leu Thr Tyr Leu Pro Thr Asn Ala Ser
            35                  40                  45

Leu Ser Phe Leu Gln Asp Ile Gln Glu Val Gln Gly Tyr Val Leu Ile
        50                  55                  60

Ala His Asn Gln Val Arg Gln Val Pro Leu Gln Arg Leu Arg Ile Val
65                  70                  75                  80

Arg Gly Thr Gln Leu Phe Glu Asp Asn Tyr Ala Leu Ala Val Leu Asp
                85                  90                  95

Asn Gly Asp Pro Leu Asn Asn Thr Thr Pro Val Thr Gly Ala Ser Pro
            100                 105                 110

Gly Gly Leu Arg Glu Leu Gln Leu Arg Ser Leu Thr Glu Ile Leu Lys
        115                 120                 125

Gly Gly Val Leu Ile Gln Arg Asn Pro Gln Leu Cys Tyr Gln Asp Thr
    130                 135                 140

Ile Leu Trp Lys Asp Ile Phe His Lys Asn Asn Gln Leu Ala Leu Thr
145                 150                 155                 160

Leu Ile Asp Thr Asn Arg Ser Arg Ala Cys His Pro Cys Ser Pro Met
                165                 170                 175

Cys Lys Gly Ser Arg Cys Trp Gly Glu Ser Ser Glu Asp Cys Gln Ser
            180                 185                 190

Leu Thr Arg Thr Val Cys Ala Gly Gly Cys Ala Arg Cys Lys Gly Pro
        195                 200                 205

Leu Pro Thr Asp Cys Cys His Glu Gln Cys Ala Ala Gly Cys Thr Gly
    210                 215                 220

Pro Lys His Ser Asp Cys Leu Ala Cys Leu His Phe Asn His Ser Gly
225                 230                 235                 240

Ile Cys Glu Leu His Cys Pro Ala Leu Val Thr Tyr Asn Thr Asp Thr
                245                 250                 255

Phe Glu Ser Met Pro Asn Pro Glu Gly Arg Tyr Thr Phe Gly Ala Ser
            260                 265                 270

Cys Val Thr Ala Cys Pro Tyr Asn Tyr Leu Ser Thr Asp Val Gly Ser
        275                 280                 285

Cys Thr Leu Val Cys Pro Leu His Asn Gln Glu Val Thr Ala Glu Asp
    290                 295                 300

Gly Thr Gln Arg Cys Glu Lys Cys Ser Lys Pro Cys Ala Arg Val Cys
305                 310                 315                 320

Tyr Gly Leu Gly Met Glu His Leu Arg Glu Val Arg Ala Val Thr Ser
                325                 330                 335

Ala Asn Ile Gln Glu Phe Ala Gly Cys Lys Lys Ile Phe Gly Ser Leu
            340                 345                 350

Ala Phe Leu Pro Glu Ser Phe Asp Gly Asp Pro Ala Ser Asn Thr Ala
        355                 360                 365

Pro Leu Gln Pro Glu Gln Leu Gln Val Phe Glu Thr Leu Glu Glu Ile
    370                 375                 380

Thr Gly Tyr Leu Tyr Ile Ser Ala Trp Pro Asp Ser Leu Pro Asp Leu
385                 390                 395                 400

Ser Val Phe Gln Asn Leu Gln Val Ile Arg Gly Arg Ile Leu His Asn
                405                 410                 415
```

Gly Ala Tyr Ser Leu Thr Leu Gln Gly Leu Gly Ile Ser Trp Leu Gly
            420                 425                 430

Leu Arg Ser Leu Arg Glu Leu Gly Ser Gly Leu Ala Leu Ile His His
            435                 440                 445

Asn Thr His Leu Cys Phe Val His Thr Val Pro Trp Asp Gln Leu Phe
450                 455                 460

Arg Asn Pro His Gln Ala Leu Leu His Thr Ala Asn Arg Pro Glu Asp
465                 470                 475                 480

Glu Cys Val Gly Glu Gly Leu Ala Cys His Gln Leu Cys Ala Arg Gly
            485                 490                 495

His Cys Trp Gly Pro Gly Pro Thr Gln Cys Val Asn Cys Ser Gln Phe
            500                 505                 510

Leu Arg Gly Gln Glu Cys Val Glu Glu Cys Arg Val Leu Gln Gly Leu
            515                 520                 525

Pro Arg Glu Tyr Val Asn Ala Arg His Cys Leu Pro Cys His Pro Glu
            530                 535                 540

Cys Gln Pro Gln Asn Gly Ser Val Thr Cys Phe Gly Pro Glu Ala Asp
545                 550                 555                 560

Gln Cys Val Ala Cys Ala His Tyr Lys Asp Pro Pro Phe Cys Val Ala
            565                 570                 575

Arg Cys Pro Ser Gly Val Lys Pro Asp Leu Ser Tyr Met Pro Ile Trp
            580                 585                 590

Lys Phe Pro Asp Glu Glu Gly Ala Cys Gln Pro Cys Pro Ile Asn
            595                 600                 605

<210> SEQ ID NO 2
<211> LENGTH: 217
<212> TYPE: PRT
<213> ORGANISM: Artificial Sequence
<220> FEATURE:
<223> OTHER INFORMATION: Human IgG1 Fc sequence 231-447 (EU-numbering)

<400> SEQUENCE: 2

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
            35                  40                  45

Val Asp Gly Val Glu Val His Asn Ala Lys Thr Lys Pro Arg Glu Glu
        50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
            85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
            115                 120                 125

Thr Lys Asn Gln Val Ser Leu Thr Cys Leu Val Lys Gly Phe Tyr Pro
        130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
            165                 170                 175

```
Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215

<210> SEQ ID NO 3
<211> LENGTH: 449
<212> TYPE: PRT
<213> ORGANISM: Artificial Sequence
<220> FEATURE:
<223> OTHER INFORMATION: CLONE# 3468 FULL

<400> SEQUENCE: 3

Gly Glu Val Gln Leu Val Glu Ser Gly Gly Leu Val Gln Pro Gly
1               5                   10                  15

Gly Ser Leu Arg Leu Ser Cys Ala Ala Ser Gly Phe Thr Phe Thr Asp
            20                  25                  30

Tyr Thr Met Asp Trp Val Arg Gln Ala Pro Gly Lys Gly Leu Glu Trp
        35                  40                  45

Val Ala Asp Val Asn Pro Asn Ser Gly Gly Ser Ile Tyr Asn Gln Arg
50                  55                  60

Phe Lys Gly Arg Phe Thr Leu Ser Val Asp Arg Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Arg Asn Leu Gly Pro Ser Phe Tyr Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Gly Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Lys Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320
```

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
        340                 345                 350

Val Leu Pro Pro Ser Arg Asp Glu Leu Thr Lys Asn Gln Val Ser Leu
    355                 360                 365

Leu Cys Leu Val Lys Gly Phe Tyr Pro Ser Asp Ile Ala Val Glu Trp
370                 375                 380

Glu Ser Asn Gly Gln Pro Glu Asn Asn Tyr Leu Thr Trp Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445
Gly

<210> SEQ ID NO 4
<211> LENGTH: 1347
<212> TYPE: DNA
<213> ORGANISM: Artificial Sequence
<220> FEATURE:
<223> OTHER INFORMATION: CLONE# 3468 FULL

<400> SEQUENCE: 4

| | | | | | |
|---|---|---|---|---|---|
| ggggaagtgc | agctggtcga | atctggagga | ggactggtgc | agccaggagg | gtccctgcgc | 60 |
| ctgtcttgcg | ccgctagtgg | cttcactttt | accgactaca | ccatggattg | ggtgcgacag | 120 |
| gcacctggaa | agggcctgga | gtgggtcgcc | gatgtgaacc | aaatagcgg | aggctccatc | 180 |
| tacaaccagc | ggttcaaggg | ccggttcacc | ctgtcagtgg | accggagcaa | aaacaccctg | 240 |
| tatctgcaga | tgaatagcct | gcgagccgaa | gatactgctg | tgtactattg | cgcccggaat | 300 |
| ctggggcccct | ccttctactt | tgactattgg | gggcagggaa | ctctggtcac | cgtgagctcc | 360 |
| gcctccacca | agggaccttc | tgtgttccca | ctggctccct | ctagtaaatc | cacatctggg | 420 |
| ggaactgcag | ccctgggctg | tctggtgaag | gctacttcc | agagcccgt | cacagtgtct | 480 |
| tggaacagtg | gcgctctgac | ttctggggtc | cacacctttc | ctgcagtgct | gaagtcaagc | 540 |
| gggctgtaca | gcctgtcctc | tgtggtcacc | gtgccaagtt | caagcctggg | aacacagact | 600 |
| tatatctgca | acgtgaatca | caagccatcc | aatacaaaag | tcgacaagaa | agtggaaccc | 660 |
| aagtcttgtg | ataaaaccca | tacatgcccc | ccttgtcctg | caccagagct | gctgggagga | 720 |
| ccaagcgtgt | tcctgtttcc | acccaagcct | aaagatacac | tgatgattag | taggacccca | 780 |
| gaagtcacat | gcgtggtcgt | ggacgtgagc | cacgaggacc | ccgaagtcaa | gtttaactgg | 840 |
| tacgtggacg | gcgtcgaggt | gcataatgcc | aagactaaac | caggagga | acagtacaac | 900 |
| agtacctatc | gcgtcgtgtc | agtcctgaca | gtgctgcatc | aggattggct | gaacgggaaa | 960 |
| gagtataagt | gcaaagtgag | caataaggct | ctgcccgcac | ctatcgagaa | aacaatttcc | 1020 |
| aaggcaaaag | gacagcctag | agaaccacag | gtgtacgtgc | tgcctccatc | aagggatgag | 1080 |
| ctgacaaaga | accaggtcag | cctgctgtgt | ctggtgaaag | gattctatcc | ctctgacatt | 1140 |
| gctgtggagt | gggaaagtaa | tggccagcct | gagaacaatt | acctgacctg | gcccctgtg | 1200 |
| ctggactcag | atggcagctt | ctttctgtat | agcaagctga | ccgtcgacaa | atcccggtgg | 1260 |
| cagcagggga | atgtgtttag | ttgttcagtc | atgcacgagg | cactgcacaa | ccattacacc | 1320 |

```
cagaagtcac tgtcactgtc accaggg                                     1347
```

<210> SEQ ID NO 5
<211> LENGTH: 119
<212> TYPE: PRT
<213> ORGANISM: Artificial Sequence
<220> FEATURE:
<223> OTHER INFORMATION: CLONE# 3468 VH
<400> SEQUENCE: 5

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Thr Met Asp Trp Val Arg Gln Ala Pro Gly Lys Gly Leu Glu Trp Val
        35                  40                  45

Ala Asp Val Asn Pro Asn Ser Gly Gly Ser Ile Tyr Asn Gln Arg Phe
    50                  55                  60

Lys Gly Arg Phe Thr Leu Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Leu Gly Pro Ser Phe Tyr Phe Asp Tyr Trp Gly Gln Gly
            100                 105                 110

Thr Leu Val Thr Val Ser Ser
        115
```

<210> SEQ ID NO 6
<211> LENGTH: 8
<212> TYPE: PRT
<213> ORGANISM: Artificial Sequence
<220> FEATURE:
<223> OTHER INFORMATION: CLONE# 3468, 3057, 3041,3317 H1

<400> SEQUENCE: 6

```
Gly Phe Thr Phe Thr Asp Tyr Thr
1               5
```

<210> SEQ ID NO 7
<211> LENGTH: 12
<212> TYPE: PRT
<213> ORGANISM: Artificial Sequence
<220> FEATURE:
<223> OTHER INFORMATION: CLONE# 3468, 3057, 3041, 3317 H3

<400> SEQUENCE: 7

```
Ala Arg Asn Leu Gly Pro Ser Phe Tyr Phe Asp Tyr
1               5                   10
```

<210> SEQ ID NO 8
<211> LENGTH: 8
<212> TYPE: PRT
<213> ORGANISM: Artificial Sequence
<220> FEATURE:
<223> OTHER INFORMATION: CLONE# 3468, 3057, 3041, 3317 H2

<400> SEQUENCE: 8

```
Val Asn Pro Asn Ser Gly Gly Ser
1               5
```

<210> SEQ ID NO 9
<211> LENGTH: 215

<212> TYPE: PRT
<213> ORGANISM: Artificial Sequence
<220> FEATURE:
<223> OTHER INFORMATION: CLONE# 1811 FULL

<400> SEQUENCE: 9

Gly Asp Ile Gln Met Thr Gln Ser Pro Ser Ser Leu Ser Ala Ser Val
1               5                   10                  15

Gly Asp Arg Val Thr Ile Thr Cys Lys Ala Ser Gln Asp Val Ser Ile
            20                  25                  30

Gly Val Ala Trp Tyr Gln Gln Lys Pro Gly Lys Ala Pro Lys Leu Leu
        35                  40                  45

Ile Tyr Ser Ala Ser Tyr Arg Tyr Thr Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gln Gln Tyr Tyr Ile Tyr Pro
                85                  90                  95

Tyr Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 10
<211> LENGTH: 645
<212> TYPE: DNA
<213> ORGANISM: Artificial Sequence
<220> FEATURE:
<223> OTHER INFORMATION: CLONE# 1811 FULL

<400> SEQUENCE: 10 gggatattc agatgaccca gtccccaagc tccctgagtg cctcagtggg cgaccgagtc      60
accatcacat gcaaggcttc ccaggatgtg tctattggag tcgcatggta ccagcagaag    120
ccaggcaaag cacccaagct gctgatctat agcgcctcct accggtatac cggcgtgccc    180
tctagattct ctggcagtgg gtcaggaaca gactttactc tgaccatctc tagtctgcag    240
cctgaggatt tcgctaccta ctattgccag cagtactata tctacccata cctttggc      300 caggggacaa agtggagat caagaggact gtggccgctc cctccgtctt cattttccc     360 ccttctgacg aacagctgaa aagtggcaca gccagcgtgg tctgtctgct gaacaatttc    420
taccctcgcg aagccaaagt gcagtggaag gtcgataacg ctctgcagag cggcaacagc    480
caggagtctg tgactgaaca ggacagtaaa gattcaacct atagcctgtc aagcacactg    540
actctgagca aggcagacta cgagaagcac aaagtgtatg cctgcgaagt cacacatcag    600

```
gggctgtcct ctcctgtgac taagagcttt aacagaggag agtgt         645
```

<210> SEQ ID NO 11
<211> LENGTH: 107
<212> TYPE: PRT
<213> ORGANISM: Artificial Sequence
<220> FEATURE:
<223> OTHER INFORMATION: CLONE# 1811 VL

<400> SEQUENCE: 11

```
Asp Ile Gln Met Thr Gln Ser Pro Ser Ser Leu Ser Ala Ser Val Gly
1               5                   10                  15
Asp Arg Val Thr Ile Thr Cys Lys Ala Ser Gln Asp Val Ser Ile Gly
            20                  25                  30
Val Ala Trp Tyr Gln Gln Lys Pro Gly Lys Ala Pro Lys Leu Leu Ile
        35                  40                  45
Tyr Ser Ala Ser Tyr Arg Tyr Thr Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Tyr Tyr Ile Tyr Pro Tyr
                85                  90                  95
Thr Phe Gly Gln Gly Thr Lys Val Glu Ile Lys
            100                 105
```

<210> SEQ ID NO 12
<211> LENGTH: 6
<212> TYPE: PRT
<213> ORGANISM: Artificial Sequence
<220> FEATURE:
<223> OTHER INFORMATION: CLONE# 1811, 3904, 3317 L1

<400> SEQUENCE: 12

```
Gln Asp Val Ser Ile Gly
1               5
```

<210> SEQ ID NO 13
<211> LENGTH: 9
<212> TYPE: PRT
<213> ORGANISM: Artificial Sequence
<220> FEATURE:
<223> OTHER INFORMATION: CLONE# 1811, 3904, 3317 L3

<400> SEQUENCE: 13

```
Gln Gln Tyr Tyr Ile Tyr Pro Tyr Thr
1               5
```

<210> SEQ ID NO 14
<211> LENGTH: 3
<212> TYPE: PRT
<213> ORGANISM: Artificial Sequence
<220> FEATURE:
<223> OTHER INFORMATION: CLONE# 1811, 3904, 3317 L2

<400> SEQUENCE: 14

```
Ser Ala Ser
1
```

<210> SEQ ID NO 15
<211> LENGTH: 223
<212> TYPE: PRT
<213> ORGANISM: Artificial Sequence
<220> FEATURE:
<223> OTHER INFORMATION: CLONE# 5034 FULL

<400> SEQUENCE: 15

Gly Asp Tyr Lys Asp Asp Asp Lys Asp Ile Gln Met Thr Gln Ser
1               5                   10                  15

Pro Ser Ser Leu Ser Ala Ser Val Gly Asp Arg Val Thr Ile Thr Cys
            20                  25                  30

Arg Ala Ser Gln Asp Val Asn Thr Ala Val Ala Trp Tyr Gln Gln Lys
        35                  40                  45

Pro Gly Lys Ala Pro Lys Leu Leu Ile Tyr Ser Ala Ser Phe Leu Tyr
50                  55                  60

Ser Gly Val Pro Ser Arg Phe Ser Gly Ser Arg Ser Gly Thr Asp Phe
65                  70                  75                  80

Thr Leu Thr Ile Ser Ser Leu Gln Pro Glu Asp Phe Ala Thr Tyr Tyr
                85                  90                  95

Cys Gln Gln His Tyr Thr Thr Pro Pro Thr Phe Gly Gln Gly Thr Lys
            100                 105                 110

Val Glu Ile Lys Arg Thr Val Ala Ala Pro Ser Val Phe Ile Phe Pro
        115                 120                 125

Pro Ser Asp Glu Arg Leu Lys Ser Gly Thr Ala Ser Val Val Cys Leu
130                 135                 140

Leu Asn Asn Phe Tyr Pro Arg Glu Ala Lys Val Gln Trp Lys Val Asp
145                 150                 155                 160

Asn Ala Leu Gln Ser Gly Asn Ser Gln Glu Ser Val Thr Glu Gln Asp
                165                 170                 175

Ser Lys Asp Ser Thr Tyr Ser Leu Ser Ser Thr Leu Thr Leu Ser Lys
            180                 185                 190

Ala Asp Tyr Glu Lys His Lys Val Tyr Ala Cys Glu Val Thr His Gln
        195                 200                 205

Gly Leu Ser Ser Pro Val Thr Lys Ser Phe Asn Arg Gly Glu Cys
210                 215                 220

<210> SEQ ID NO 16
<211> LENGTH: 669
<212> TYPE: DNA
<213> ORGANISM: Artificial Sequence
<220> FEATURE:
<223> OTHER INFORMATION: CLONE# 5034 FULL

<400> SEQUENCE: 16

```
gggactaca aagacgacga tgacaaagat atccagatga cccagtcccc tagctccctg      60
tccgcttctg tgggcgatag ggtcactatt acctgccgcg catctcagga cgtgaacacc    120
gcagtcgcct ggtaccagca gaagcctggg aaagctccaa agctgctgat ctacagtgca    180
tcattcctgt attcaggagt gcccagccgg tttagcggca gcagatctgg caccgatttc    240
acactgacta tttctagtct gcagcctgag gactttgcca catactattg ccagcagcac    300
tataccacac cccctacttt cggccagggg accaaagtgg agatcaagcg aactgtggcc    360
gctccaagtg tcttcatttt tccacccagc gatgaaagac tgaagtccgg cacagcttct    420
gtggtctgtc tgctgaacaa ttttttaccccc agagaggcca agtgcagtg gaaggtcgac    480
aacgctctgc agagtggcaa cagccaggag agcgtgacaa acaggattc caaagactct    540
acttatagtc tgtcaagcac cctgacactg agcaaggcag actacgaaaa gcataaagtg    600
tatgcctgtg aggtcacaca tcaggggctg tcatcaccag tcaccaaatc attcaatcgg    660
ggggagtgc                                                            669
```

```
<210> SEQ ID NO 17
<211> LENGTH: 107
<212> TYPE: PRT
<213> ORGANISM: Artificial Sequence
<220> FEATURE:
<223> OTHER INFORMATION: CLONE# 5034 VL

<400> SEQUENCE: 17

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
            100                 105

<210> SEQ ID NO 18
<211> LENGTH: 223
<212> TYPE: PRT
<213> ORGANISM: Artificial Sequence
<220> FEATURE:
<223> OTHER INFORMATION: CLONE# 5037 FULL

<400> SEQUENCE: 18

Gly Asp Tyr Lys Asp Asp Asp Lys Asp Ile Gln Met Thr Gln Ser
1               5                   10                  15

Pro Ser Ser Leu Ser Ala Ser Val Gly Asp Arg Val Thr Ile Thr Cys
            20                  25                  30

Arg Ala Ser Gln Asp Val Asn Thr Ala Val Ala Trp Tyr Gln Gln Lys
        35                  40                  45

Pro Gly Lys Ala Pro Lys Leu Leu Ile Tyr Ser Ala Ser Phe Leu Tyr
    50                  55                  60

Ser Gly Val Pro Ser Arg Phe Ser Gly Ser Arg Ser Gly Thr Asp Phe
65                  70                  75                  80

Thr Leu Thr Ile Ser Ser Leu Gln Pro Glu Asp Phe Ala Thr Tyr Tyr
                85                  90                  95

Cys Gln Gln His Tyr Thr Thr Pro Pro Thr Phe Gly Gln Gly Thr Lys
            100                 105                 110

Val Glu Ile Lys Arg Thr Val Ala Ala Pro Ser Val Phe Ile Phe Pro
        115                 120                 125

Pro Ser Asp Glu Arg Leu Lys Ser Gly Thr Ala Ser Val Val Cys Leu
    130                 135                 140

Leu Asn Asn Phe Tyr Pro Arg Glu Ala Lys Val Gln Trp Lys Val Asp
145                 150                 155                 160

Asn Ala Leu Gln Ser Gly Asn Ser Lys Glu Ser Val Thr Glu Gln Asp
                165                 170                 175

Ser Lys Asp Ser Thr Tyr Ser Leu Ser Ser Arg Leu Thr Leu Ser Lys
            180                 185                 190

Ala Asp Tyr Glu Lys His Lys Val Tyr Ala Cys Glu Val Thr His Gln
        195                 200                 205
```

<210> SEQ ID NO 19
<211> LENGTH: 669
<212> TYPE: DNA
<213> ORGANISM: Artificial Sequence
<220> FEATURE:
<223> OTHER INFORMATION: CLONE# 5037 FULL

<400> SEQUENCE: 19

```
ggggactaca aagacgacga tgacaaagat atccagatga cccagtcccc tagctccctg      60
tccgcttctg tgggcgatag ggtcactatt acctgccgcg catctcagga cgtgaacacc     120
gcagtcgcct ggtaccagca gaagcctggg aaagctccaa agctgctgat ctacagtgca     180
tcattcctgt attcaggagt gcccagccgg tttagcggca gcagatctgg caccgatttc     240
acactgacta tttctagtct gcagcctgag gactttgcca catactattg ccagcagcac     300
tataccacac cccctacttt cggccagggg accaaagtgg agatcaagcg aactgtggcc     360
gctccaagtg tcttcatttt tccacccagc gatgaaagac tgaagtccgg cacagcttct     420
gtggtctgtc tgctgaacaa ttttacccc agagaggcca agtgcagtg aaggtcgac       480
aacgctctgc agagtggcaa cagcaaggag agcgtgacag aacaggattc caaagactct     540
acttatagtc tgtcaagcag actgacactg agcaaggcag actacgaaaa gcataaagtg     600
tatgcctgtg aggtcacaca tcaggggctg tcatcaccag tcaccaaatc attcaatcgg     660
ggggagtgc                                                             669
```

<210> SEQ ID NO 20
<211> LENGTH: 107
<212> TYPE: PRT
<213> ORGANISM: Artificial Sequence
<220> FEATURE:
<223> OTHER INFORMATION: CLONE# 5037 VL

<400> SEQUENCE: 20

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
            100                 105

<210> SEQ ID NO 21
<211> LENGTH: 6
<212> TYPE: PRT
<213> ORGANISM: Artificial Sequence
<220> FEATURE:
<223> OTHER INFORMATION: CLONE# 5037 L1

<400> SEQUENCE: 21

Gln Asp Val Asn Thr Ala
1               5

<210> SEQ ID NO 22
<211> LENGTH: 9
<212> TYPE: PRT
<213> ORGANISM: Artificial Sequence
<220> FEATURE:
<223> OTHER INFORMATION: CLONE# 5037 L3

<400> SEQUENCE: 22

Gln Gln His Tyr Thr Thr Pro Pro Thr
1               5

<210> SEQ ID NO 23
<211> LENGTH: 3
<212> TYPE: PRT
<213> ORGANISM: Artificial Sequence
<220> FEATURE:
<223> OTHER INFORMATION: CLONE# 5037 L2

<400> SEQUENCE: 23

Ser Ala Ser
1

<210> SEQ ID NO 24
<211> LENGTH: 215
<212> TYPE: PRT
<213> ORGANISM: Artificial Sequence
<220> FEATURE:
<223> OTHER INFORMATION: CLONE# 3382 FULL

<400> SEQUENCE: 24

Gly Asp Ile Gln Met Thr Gln Ser Pro Ser Ser Leu Ser Ala Ser Val
1               5                   10                  15

Gly Asp Arg Val Thr Ile Thr Cys Lys Ala Ser Gln Asp Val Ser Ile
                20                  25                  30

Gly Val Ala Trp Tyr Gln Gln Lys Pro Gly Lys Ala Pro Lys Leu Leu
            35                  40                  45

Ile Tyr Ser Ala Ser Tyr Arg Tyr Thr Gly Val Pro Ser Arg Phe Ser
50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gln Gln Tyr Tyr Ile Tyr Pro
                85                  90                  95

Ala Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys

<210> SEQ ID NO 25
<211> LENGTH: 645
<212> TYPE: DNA
<213> ORGANISM: Artificial Sequence
<220> FEATURE:
<223> OTHER INFORMATION: CLONE# 3382 FULL

<400> SEQUENCE: 25

```
ggggatattc agatgaccca gtccccaagc tccctgagtg cctcagtggg cgaccgagtc      60
accatcacat gcaaggcttc ccaggatgtg tctattggag tcgcatggta ccagcagaag     120
ccaggcaaag cacccaagct gctgatctat agcgcctcct accggtatac cggcgtgccc     180
tctagattct ctggcagtgg gtcaggaaca gactttactc tgaccatctc tagtctgcag     240
cctgaggatt tcgctaccta ctattgccag cagtactata tctacccagc cacctttggc     300
caggggacaa agtggagat caagaggact gtggccgctc cctccgtctt catttttccc      360
ccttctgacg aacagctgaa aagtggcaca gccagcgtgg tctgtctgct gaacaatttc     420
taccctcgcg aagccaaagt gcagtggaag gtcgataacg ctctgcagag cggcaacagc     480
caggagtctg tgactgaaca ggacagtaaa gattcaacct atagcctgtc aagcacactg     540
actctgagca aggcagacta cgagaagcac aaagtgtatg cctgcgaagt cacacatcag     600
gggctgtcct ctcctgtgac taagagcttt aacagaggag agtgt                     645
```

<210> SEQ ID NO 26
<211> LENGTH: 107
<212> TYPE: PRT
<213> ORGANISM: Artificial Sequence
<220> FEATURE:
<223> OTHER INFORMATION: CLONE# 3382 VL

<400> SEQUENCE: 26

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ile Tyr Pro Ala
                85                  90                  95

Thr Phe Gly Gln Gly Thr Lys Val Glu Ile Lys
            100                 105
```

<210> SEQ ID NO 27
<211> LENGTH: 6
<212> TYPE: PRT
<213> ORGANISM: Artificial Sequence
<220> FEATURE:
<223> OTHER INFORMATION: CLONE# 3382 L1

<400> SEQUENCE: 27

```
Gln Asp Val Ser Ile Gly
1               5
```

```
<210> SEQ ID NO 28
<211> LENGTH: 9
<212> TYPE: PRT
<213> ORGANISM: Artificial Sequence
<220> FEATURE:
<223> OTHER INFORMATION: CLONE# 3382 L3

<400> SEQUENCE: 28

Gln Gln Tyr Tyr Ile Tyr Pro Ala Thr
1               5

<210> SEQ ID NO 29
<211> LENGTH: 3
<212> TYPE: PRT
<213> ORGANISM: Artificial Sequence
<220> FEATURE:
<223> OTHER INFORMATION: CLONE# 3382 L2

<400> SEQUENCE: 29

Ser Ala Ser
1

<210> SEQ ID NO 30
<211> LENGTH: 450
<212> TYPE: PRT
<213> ORGANISM: Artificial Sequence
<220> FEATURE:
<223> OTHER INFORMATION: CLONE# 5065 FULL

<400> SEQUENCE: 30

Gly Glu Val Gln Leu Val Glu Ser Gly Gly Leu Val Gln Pro Gly
1               5                   10                  15

Gly Ser Leu Arg Leu Ser Cys Ala Ala Ser Gly Phe Asn Ile Lys Asp
            20                  25                  30

Thr Tyr Ile His Trp Val Arg Gln Ala Pro Gly Lys Gly Leu Glu Trp
        35                  40                  45

Val Ala Arg Ile Tyr Pro Thr Asn Gly Tyr Thr Arg Tyr Ala Asp Ser
    50                  55                  60

Val Lys Gly Arg Phe Thr Ile Ser Ala Asp Thr Ser Lys Asn Thr Ala
65                  70                  75                  80

Tyr Leu Gln Met Asn Ser Leu Arg Ala Glu Asp Thr Ala Val Tyr Tyr
                85                  90                  95

Cys Ser Arg Trp Gly Gly Asp Gly Phe Tyr Ala Met Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Glu Val Thr Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Val Glu Pro Lys Ser Cys
    210                 215                 220

Asp Lys Thr His Thr Cys Pro Pro Cys Pro Ala Pro Glu Leu Leu Gly
225                 230                 235                 240
```

```
Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Val Tyr Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Tyr Lys Thr Thr Pro Pro
385                 390                 395                 400

Val Leu Asp Ser Asp Gly Ser Phe Ala Leu Val Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly
    450

<210> SEQ ID NO 31
<211> LENGTH: 1350
<212> TYPE: DNA
<213> ORGANISM: Artificial Sequence
<220> FEATURE:
<223> OTHER INFORMATION: CLONE# 5065 FULL

<400> SEQUENCE: 31
ggggaggtgc agctggtcga aagcggagga ggactggtgc agccaggagg gtcactgcga      60
ctgagctgcg cagcttccgg cttcaacatc aaggacacct acattcactg ggtccgccag     120
gctcctggaa aaggcctgga gtgggtggca cgaatctatc caactaatgg atacacccgg     180
tatgccgact ccgtgaaggg ccggttcacc atttctgcag atacaagtaa aaacactgcc     240
tacctgcaga tgaacagcct gcgagccgaa gatacagccg tgtactattg cagccgatgg     300
ggaggcgacg gcttctacgc tatggattat tgggggcagg gaaccctggt cacagtgagc     360
tccgcatcaa caaaggggcc tagcgtgttt ccactggccc cctctagtaa atccacctct     420
gggggaacag cagccctggg atgtgaggtg accgactact cccagagcc cgtcactgtg     480 agctggaact ccggcgccct gacatctggg gtccatactt ttcctgctgt gctgcagtca     540
agcggcctgt acagcctgtc ctctgtggtc actgtgccaa gttcaagcct ggggactcag     600
acctatatct gcaacgtgaa tcacaagcca tccaatacca agtcgacaa gaaagtggaa     660 cccaagtctt gtgataaaac acatacttgc cccccttgtc ctgcaccaga gctgctggga     720
ggaccaagcg tgttcctgtt tccacccaag cctaaagaca ccctgatgat tagtaggact     780
```

-continued

| | |
|---|---|
| ccagaagtca cctgcgtggt cgtggacgtg agccacgagg accccgaagt caagttcaac | 840 |
| tggtacgtgg atggcgtcga ggtgcataat gccaagacaa acccaggga ggaacagtac | 900 |
| aactccactt atcgcgtcgt gtctgtcctg accgtgctgc accaggactg gctgaacggc | 960 |
| aaggagtata agtgcaaagt gagcaataag gctctgcccg cacctatcga gaaacaatt | 1020 |
| tccaaggcta aagggcagcc tagagaacca caggtgtacg tgtaccctcc atctagggac | 1080 |
| gagctgacca agaaccaggt cagtctgaca tgtctggtga aagggttcta tcccagcgat | 1140 |
| atcgcagtgg agtgggaatc caatggacag cctgagaaca attacaagac cacacccct | 1200 |
| gtgctggact ctgatggaag tttcgccctg gtgagtaagc tgaccgtcga taaatcacgg | 1260 |
| tggcagcagg gcaacgtgtt cagctgttca gtgatgcacg aagcactgca caaccactac | 1320 |
| acccagaaaa gcctgtccct gtcccccggc | 1350 |

```
<210> SEQ ID NO 32
<211> LENGTH: 120
<212> TYPE: PRT
<213> ORGANISM: Artificial Sequence
<220> FEATURE:
<223> OTHER INFORMATION: CLONE# 5065 VH

<400> SEQUENCE: 32

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser
        115                 120

<210> SEQ ID NO 33
<211> LENGTH: 8
<212> TYPE: PRT
<213> ORGANISM: Artificial Sequence
<220> FEATURE:
<223> OTHER INFORMATION: CLONE# 5065, 720, 719 H1

<400> SEQUENCE: 33

Gly Phe Asn Ile Lys Asp Thr Tyr
1               5

<210> SEQ ID NO 34
<211> LENGTH: 13
<212> TYPE: PRT
<213> ORGANISM: Artificial Sequence
<220> FEATURE:
<223> OTHER INFORMATION: CLONE# 5065, 720, 719 H2

<400> SEQUENCE: 34

Ser Arg Trp Gly Gly Asp Gly Phe Tyr Ala Met Asp Tyr
1               5                   10
```

```
<210> SEQ ID NO 35
<211> LENGTH: 8
<212> TYPE: PRT
<213> ORGANISM: Artificial Sequence
<220> FEATURE:
<223> OTHER INFORMATION: CLONE# 5065, 720, 719 H3

<400> SEQUENCE: 35

Ile Tyr Pro Thr Asn Gly Tyr Thr
1               5

<210> SEQ ID NO 36
<211> LENGTH: 449
<212> TYPE: PRT
<213> ORGANISM: Artificial Sequence
<220> FEATURE:
<223> OTHER INFORMATION: CLONE# 6586 FULL

<400> SEQUENCE: 36

Gly Glu Val Gln Leu Val Glu Ser Gly Gly Leu Val Gln Pro Gly
1               5                   10                  15

Gly Ser Leu Arg Leu Ser Cys Ala Ala Ser Gly Phe Thr Phe Ala Asp
                20                  25                  30

Tyr Thr Met Asp Trp Val Arg Gln Ala Pro Gly Lys Gly Leu Glu Trp
            35                  40                  45

Val Gly Asp Val Asn Pro Asn Ser Gly Gly Ser Ile Tyr Asn Gln Arg
50                  55                  60

Phe Lys Gly Arg Phe Thr Phe Ser Val Asp Arg Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Arg Asn Leu Gly Pro Ser Phe Tyr Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
```

```
                290                 295                 300
Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
                340                 345                 350

Val Tyr Pro Ser Arg Asp Glu Leu Thr Lys Asn Gln Val Ser Leu
                355                 360                 365

Thr Cys Leu Val Lys Gly Phe Tyr Pro Ser Asp Ile Ala Val Glu Trp
                370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Ala Leu Val Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
                435                 440                 445

Gly

<210> SEQ ID NO 37
<211> LENGTH: 1347
<212> TYPE: DNA
<213> ORGANISM: Artificial Sequence
<220> FEATURE:
<223> OTHER INFORMATION: CLONE# 6586 FULL

<400> SEQUENCE: 37
ggcgaggtgc agctggtgga atcaggaggg ggcctggtgc agcccggagg gtctctgcga      60
ctgtcatgtg ccgcttctgg gttcactttc gcagactaca caatggattg ggtgcgacag     120
gcccccggaa agggactgga gtgggtgggc gatgtcaacc ctaattctgg cgggagtatc     180
tacaaccagc ggttcaaggg gagattcact ttttcagtgg acagaagcaa aaacaccctg     240
tatctgcaga tgaacagcct gagggccgaa gataccgctg tctactattg cgctcgcaat     300
ctgggcccca gtttctactt tgactattgg gggcagggaa ccctggtgac agtcagctcc     360
gctagcacta aggggccttc cgtgtttcca ctggctccct ctagtaaatc cacctctgga     420
ggcacagctg cactgggatg tctggtgaag gattacttcc ctgaaccagt cacagtgagt     480
tggaactcag ggctctgac aagtggagtc catactttc ccgcagtgct gcagtcaagc     540
ggactgtact ccctgtcctc tgtggtcacc gtgcctagtt caagcctggg cacccagaca     600
tatatctgca acgtgaatca caagccatca aatacaaaag tcgacaagaa agtggagccc     660
aagagctgtg ataaaactca tacctgccca ccttgtccgg cgccagaact gctgggagga     720
ccaagcgtgt tcctgtttcc acccaagcct aaagacaccc tgatgatttc ccggactcct     780
gaggtcacct gcgtggtcgt ggacgtgtct cacgaggacc ccgaagtcaa gttcaactgg     840
tacgtggatg gcgtcgaagt gcataatgcc aagaccaaac cccggggagga acagtacaac     900 tctacctata gagtcgtgag tgtcctgaca gtgctgcacc aggactggct gaatgggaag     960
gagtataagt gtaaagtgag caacaaagcc ctgcccgccc caatcgaaaa aacaatctct    1020
aaagcaaaag gacagcctcg cgaaccacag gtctacgtct accccccatc aagagatgaa    1080
ctgacaaaaa atcaggtctc tctgacatgc ctggtcaaag gattctaccc ttccgacatc    1140
```

```
gccgtggagt gggaaagtaa cggccagccc gagaacaatt acaagaccac accccctgtc    1200
ctggactctg atgggagttt cgctctggtg tcaaagctga ccgtcgataa aagccggtgg    1260
cagcagggca atgtgtttag ctgctccgtc atgcacgaag ccctgcacaa tcactacaca    1320
cagaagtccc tgagcctgag ccctggc                                        1347
```

<210> SEQ ID NO 38
<211> LENGTH: 119
<212> TYPE: PRT
<213> ORGANISM: Artificial Sequence
<220> FEATURE:
<223> OTHER INFORMATION: CLONE# 6586 VH

<400> SEQUENCE: 38

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ala Asp Tyr
            20                  25                  30

Thr Met Asp Trp Val Arg Gln Ala Pro Gly Lys Gly Leu Glu Trp Val
        35                  40                  45

Gly Asp Val Asn Pro Asn Ser Gly Gly Ser Ile Tyr Asn Gln Arg Phe
    50                  55                  60

Lys Gly Arg Phe Thr Phe Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Leu Gly Pro Ser Phe Tyr Phe Asp Tyr Trp Gly Gln Gly
            100                 105                 110

Thr Leu Val Thr Val Ser Ser
        115
```

<210> SEQ ID NO 39
<211> LENGTH: 8
<212> TYPE: PRT
<213> ORGANISM: Artificial Sequence
<220> FEATURE:
<223> OTHER INFORMATION: CLONE# 6586 H1

<400> SEQUENCE: 39

```
Gly Phe Thr Phe Ala Asp Tyr Thr
1               5
```

<210> SEQ ID NO 40
<211> LENGTH: 12
<212> TYPE: PRT
<213> ORGANISM: Artificial Sequence
<220> FEATURE:
<223> OTHER INFORMATION: CLONE# 6586 H3

<400> SEQUENCE: 40

```
Ala Arg Asn Leu Gly Pro Ser Phe Tyr Phe Asp Tyr
1               5                   10
```

<210> SEQ ID NO 41
<211> LENGTH: 8
<212> TYPE: PRT
<213> ORGANISM: Artificial Sequence
<220> FEATURE:
<223> OTHER INFORMATION: CLONE# 6586 H2

<400> SEQUENCE: 41

```
Val Asn Pro Asn Ser Gly Gly Ser
```

<210> SEQ ID NO 42
<211> LENGTH: 227
<212> TYPE: PRT
<213> ORGANISM: Artificial Sequence
<220> FEATURE:
<223> OTHER INFORMATION: CLONE# 3904 FULL

<400> SEQUENCE: 42

Gly Tyr Pro Tyr Asp Val Pro Asp Tyr Ala Thr Gly Ser Asp Ile Gln
1               5                   10                  15

Met Thr Gln Ser Pro Ser Ser Leu Ser Ala Ser Val Gly Asp Arg Val
            20                  25                  30

Thr Ile Thr Cys Lys Ala Ser Gln Asp Val Ser Ile Gly Val Ala Trp
        35                  40                  45

Tyr Gln Gln Lys Pro Gly Lys Ala Pro Lys Leu Leu Ile Tyr Ser Ala
    50                  55                  60

Ser Tyr Arg Tyr Thr Gly Val Pro Ser Arg Phe Ser Gly Ser Gly Ser
65                  70                  75                  80

Gly Thr Asp Phe Thr Leu Thr Ile Ser Ser Leu Gln Pro Glu Asp Phe
                85                  90                  95

Ala Thr Tyr Tyr Cys Gln Gln Tyr Tyr Ile Tyr Pro Tyr Thr Phe Gly
            100                 105                 110

Gln Gly Thr Lys Val Glu Ile Lys Arg Thr Val Ala Ala Pro Ser Val
        115                 120                 125

Phe Ile Phe Pro Pro Ser Asp Glu Leu Lys Ser Gly Thr Ala Ser
    130                 135                 140

Val Val Cys Leu Leu Asn Asn Phe Tyr Pro Arg Glu Ala Lys Val Gln
145                 150                 155                 160

Trp Lys Val Asp Asn Ala Leu Gln Ser Gly Asn Ser Glu Glu Ser Val
                165                 170                 175

Thr Glu Gln Asp Ser Lys Asp Ser Thr Tyr Ser Leu Ser Ser Thr Leu
            180                 185                 190

Glu Leu Ser Lys Ala Asp Tyr Glu Lys His Lys Val Tyr Ala Cys Glu
        195                 200                 205

Val Thr His Gln Gly Leu Ser Ser Pro Val Thr Lys Ser Phe Asn Arg
    210                 215                 220

Gly Glu Cys
225

<210> SEQ ID NO 43
<211> LENGTH: 681
<212> TYPE: DNA
<213> ORGANISM: Artificial Sequence
<220> FEATURE:
<223> OTHER INFORMATION: CLONE# 3904 FULL

<400> SEQUENCE: 43
gggtatccct acgatgtgcc tgactacgct actggctccg atatccagat gacccagtct      60
ccaagctccc tgagtgcatc agtgggggac cgagtcacca tcacatgcaa ggcttcccag     120
gatgtgtcta ttggagtcgc atggtaccag cagaagccag gcaaagcacc caagctgctg     180
atctacagcg cctcctaccg gtatactggg gtgccttcca gattctctgg cagtgggtca     240
ggaaccgact ttactctgac catctctagt ctgcagcccg aggatttcgc cacctactat     300
tgccagcagt actatatcta cccttatacc tttggccagg gacaaaagt ggagatcaag     360

```
aggacagtgg ccgctccaag tgtcttcatt tttccccctt ccgacgaaga gctgaaaagt    420
ggaactgctt cagtggtctg tctgctgaac aatttctacc cccgcgaagc caaagtgcag    480
tggaaggtcg ataacgctct gcagagcggc aattccgagg agtctgtgac agaacaggac    540
agtaaagatt caacttatag cctgtcaagc acactggagc tgtctaaggc agactacgag    600
aagcacaaag tgtatgcctg cgaagtcacc catcagggc tgtcctctcc cgtgacaaag    660
agctttaaca gaggagagtg t                                              681
```

```
<210> SEQ ID NO 44
<211> LENGTH: 107
<212> TYPE: PRT
<213> ORGANISM: Artificial Sequence
<220> FEATURE:
<223> OTHER INFORMATION: CLONE# 3904 VL

<400> SEQUENCE: 44

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ile Tyr Pro Tyr
                85                  90                  95

Thr Phe Gly Gln Gly Thr Lys Val Glu Ile Lys
            100                 105
```

```
<210> SEQ ID NO 45
<211> LENGTH: 482
<212> TYPE: PRT
<213> ORGANISM: Artificial Sequence
<220> FEATURE:
<223> OTHER INFORMATION: CLONE# 719 FULL

<400> SEQUENCE: 45

Gly Asp Ile Gln Met Thr Gln Ser Pro Ser Ser Leu Ser Ala Ser Val
1               5                   10                  15

Gly Asp Arg Val Thr Ile Thr Cys Arg Ala Ser Gln Asp Val Asn Thr
            20                  25                  30

Ala Val Ala Trp Tyr Gln Gln Lys Pro Gly Lys Ala Pro Lys Leu Leu
        35                  40                  45

Ile Tyr Ser Ala Ser Phe Leu Tyr Ser Gly Val Pro Ser Arg Phe Ser
    50                  55                  60

Gly Ser Arg Ser Gly Thr Asp Phe Thr Leu Thr Ile Ser Ser Leu Gln
65                  70                  75                  80

Pro Glu Asp Phe Ala Thr Tyr Tyr Cys Gln Gln His Tyr Thr Thr Pro
                85                  90                  95

Pro Thr Phe Gly Gln Gly Thr Lys Val Glu Ile Lys Gly Gly Ser Gly
            100                 105                 110

Gly Gly Ser Gly Gly Gly Ser Gly Gly Gly Ser Gly Gly Gly Ser Gly
        115                 120                 125

Glu Val Gln Leu Val Glu Ser Gly Gly Gly Leu Val Gln Pro Gly Gly
    130                 135                 140
```

Ser Leu Arg Leu Ser Cys Ala Ala Ser Gly Phe Asn Ile Lys Asp Thr
145                 150                 155                 160

Tyr Ile His Trp Val Arg Gln Ala Pro Gly Lys Gly Leu Glu Trp Val
            165                 170                 175

Ala Arg Ile Tyr Pro Thr Asn Gly Tyr Thr Arg Tyr Ala Asp Ser Val
        180                 185                 190

Lys Gly Arg Phe Thr Ile Ser Ala Asp Thr Ser Lys Asn Thr Ala Tyr
            195                 200                 205

Leu Gln Met Asn Ser Leu Arg Ala Glu Asp Thr Ala Val Tyr Tyr Cys
        210                 215                 220

Ser Arg Trp Gly Gly Asp Gly Phe Tyr Ala Met Asp Tyr Trp Gly Gln
225                 230                 235                 240

Gly Thr Leu Val Thr Val Ser Ser Ala Ala Glu Pro Lys Ser Ser Asp
            245                 250                 255

Lys Thr His Thr Cys Pro Pro Cys Pro Ala Pro Glu Leu Leu Gly Gly
            260                 265                 270

Pro Ser Val Phe Leu Phe Pro Pro Lys Pro Lys Asp Thr Leu Met Ile
            275                 280                 285

Ser Arg Thr Pro Glu Val Thr Cys Val Val Val Asp Val Ser His Glu
290                 295                 300

Asp Pro Glu Val Lys Phe Asn Trp Tyr Val Asp Gly Val Glu Val His
305                 310                 315                 320

Asn Ala Lys Thr Lys Pro Arg Glu Glu Gln Tyr Asn Ser Thr Tyr Arg
            325                 330                 335

Val Val Ser Val Leu Thr Val Leu His Gln Asp Trp Leu Asn Gly Lys
            340                 345                 350

Glu Tyr Lys Cys Lys Val Ser Asn Lys Ala Leu Pro Ala Pro Ile Glu
        355                 360                 365

Lys Thr Ile Ser Lys Ala Lys Gly Gln Pro Arg Glu Pro Gln Val Tyr
    370                 375                 380

Thr Tyr Pro Pro Ser Arg Asp Glu Leu Thr Lys Asn Gln Val Ser Leu
385                 390                 395                 400

Thr Cys Leu Val Lys Gly Phe Tyr Pro Ser Asp Ile Ala Val Glu Trp
            405                 410                 415

Glu Ser Asn Gly Gln Pro Glu Asn Asn Tyr Lys Thr Thr Pro Pro Val
            420                 425                 430

Leu Asp Glu Asp Gly Ser Phe Ala Leu Val Ser Lys Leu Thr Val Asp
        435                 440                 445

Lys Ser Arg Trp Gln Gln Gly Asn Val Phe Ser Cys Ser Val Met His
    450                 455                 460

Glu Ala Leu His Asn His Tyr Thr Gln Lys Ser Leu Ser Leu Ser Pro
465                 470                 475                 480

Gly Lys

<210> SEQ ID NO 46
<211> LENGTH: 1446
<212> TYPE: DNA
<213> ORGANISM: Artificial Sequence
<220> FEATURE:
<223> OTHER INFORMATION: CLONE# 719 FULL

<400> SEQUENCE: 46
ggagacatcc agatgaccca gtctccatcc tccctgtctg catctgtagg agacagagtc    60
accatcactt gccgggcaag tcaggacgtt aacaccgctg tagcttggta tcagcagaaa   120

```
ccagggaaag cccctaagct cctgatctat tctgcatcct ttttgtacag tggggtccca      180
tcaaggttca gtggcagtcg atctgggaca gatttcactc tcaccatcag cagtctgcaa      240
cctgaagatt ttgcaactta ctactgtcaa cagcattaca ctaccccacc cactttcggc      300
caagggacca aagtggagat caaagtggt tctggtggtg gttctggtgg tggttctggt       360
ggtggttctg gtggtggttc tggtgaagtg cagctggtgg agtctggggg aggcttggta      420
cagcctggcg ggtccctgag actctcctgt gcagcctctg gattcaacat taaagatact      480
tatatccact gggtccggca agctccaggg aagggcctgg agtgggtcgc acgtatttat      540
cccacaaatg gttacacacg gtatgcggac tctgtgaagg gccgattcac catctccgca      600
gacacttcca agaacaccgc gtatctgcaa atgaacagtc tgagagctga ggacacggcc      660
gtttattact gttcaagatg gggcggagac ggtttctacg ctatggacta ctggggccaa      720
gggaccctgg tcaccgtctc ctcagccgcc gagcccaaga gcagcgataa gacccacacc      780
tgcccctccc gtccagctcc agaactgctg gaggaccta gcgtgttcct gtttccccct       840
aagccaaaag acactctgat gatttccagg actcccgagg tgacctgcgt ggtggtggac      900
gtgtctcacg aggaccccga agtgaagttc aactggtacg tggatggcgt ggaagtgcat      960
aatgctaaga caaaaccaag agaggaacag tacaactcca cttatcgcgt cgtgagcgtg      1020
ctgaccgtgc tgcaccagga ctggctgaac gggaaggagt ataagtgcaa agtcagtaat      1080
aaggccctgc ctgctccaat cgaaaaaacc atctctaagg ccaaaggcca gccaagggag      1140
ccccaggtgt acacataccc acccagcaga gacgaactga ccaagaacca ggtgtccctg      1200
acatgtctgg tgaaaggctt ctatcctagt gatattgctg tggagtggga atcaaatgga      1260
cagccagaga caattacaa gaccacacct ccagtgctgg acgaggatgg cagcttcgcc       1320
ctggtgtcca agctgacagt ggataaatct cgatggcagc aggggaacgt gtttagttgt      1380
tcagtgatgc atgaagccct gcacaatcat tacactcaga gagcctgtc cctgtctccc       1440 ggcaaa                                                                 1446
```

<210> SEQ ID NO 47
<211> LENGTH: 107
<212> TYPE: PRT
<213> ORGANISM: Artificial Sequence
<220> FEATURE:
<223> OTHER INFORMATION: CLONE# 719 VL

<400> SEQUENCE: 47

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
            100                 105

```
<210> SEQ ID NO 48
<211> LENGTH: 120
<212> TYPE: PRT
<213> ORGANISM: Artificial Sequence
<220> FEATURE:
<223> OTHER INFORMATION: CLONE# 719 VH

<400> SEQUENCE: 48

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser
        115                 120

<210> SEQ ID NO 49
<211> LENGTH: 482
<212> TYPE: PRT
<213> ORGANISM: Artificial Sequence
<220> FEATURE:
<223> OTHER INFORMATION: CLONE# 720 FULL

<400> SEQUENCE: 49

Gly Asp Ile Gln Met Thr Gln Ser Pro Ser Ser Leu Ser Ala Ser Val
1               5                   10                  15

Gly Asp Arg Val Thr Ile Thr Cys Arg Ala Ser Gln Asp Val Asn Thr
            20                  25                  30

Ala Val Ala Trp Tyr Gln Gln Lys Pro Gly Lys Ala Pro Lys Leu Leu
        35                  40                  45

Ile Tyr Ser Ala Ser Phe Leu Tyr Ser Gly Val Pro Ser Arg Phe Ser
    50                  55                  60

Gly Ser Arg Ser Gly Thr Asp Phe Thr Leu Thr Ile Ser Ser Leu Gln
65                  70                  75                  80

Pro Glu Asp Phe Ala Thr Tyr Tyr Cys Gln Gln His Tyr Thr Thr Pro
                85                  90                  95

Pro Thr Phe Gly Gln Gly Thr Lys Val Glu Ile Lys Gly Gly Ser Gly
            100                 105                 110

Gly Gly Ser Gly Gly Gly Ser Gly Gly Gly Ser Gly Gly Gly Ser Gly
        115                 120                 125

Glu Val Gln Leu Val Glu Ser Gly Gly Gly Leu Val Gln Pro Gly Gly
            130                 135                 140

Ser Leu Arg Leu Ser Cys Ala Ala Ser Gly Phe Asn Ile Lys Asp Thr
145                 150                 155                 160

Tyr Ile His Trp Val Arg Gln Ala Pro Gly Lys Gly Leu Glu Trp Val
                165                 170                 175

Ala Arg Ile Tyr Pro Thr Asn Gly Tyr Thr Arg Tyr Ala Asp Ser Val
            180                 185                 190
```

```
Lys Gly Arg Phe Thr Ile Ser Ala Asp Thr Ser Lys Asn Thr Ala Tyr
            195                 200                 205

Leu Gln Met Asn Ser Leu Arg Ala Glu Asp Thr Ala Val Tyr Tyr Cys
    210                 215                 220

Ser Arg Trp Gly Gly Asp Gly Phe Tyr Ala Met Asp Tyr Trp Gly Gln
225                 230                 235                 240

Gly Thr Leu Val Thr Val Ser Ser Ala Ala Glu Pro Lys Ser Ser Asp
                245                 250                 255

Lys Thr His Thr Cys Pro Pro Cys Pro Ala Pro Glu Leu Leu Gly Gly
            260                 265                 270

Pro Ser Val Phe Leu Phe Pro Pro Lys Pro Lys Asp Thr Leu Met Ile
            275                 280                 285

Ser Arg Thr Pro Glu Val Thr Cys Val Val Val Asp Val Ser His Glu
290                 295                 300

Asp Pro Glu Val Lys Phe Asn Trp Tyr Val Asp Gly Val Glu Val His
305                 310                 315                 320

Asn Ala Lys Thr Lys Pro Arg Glu Glu Gln Tyr Asn Ser Thr Tyr Arg
            325                 330                 335

Val Val Ser Val Leu Thr Val Leu His Gln Asp Trp Leu Asn Gly Lys
            340                 345                 350

Glu Tyr Lys Cys Lys Val Ser Asn Lys Ala Leu Pro Ala Pro Ile Glu
            355                 360                 365

Lys Thr Ile Ser Lys Ala Lys Gly Gln Pro Arg Glu Pro Gln Val Tyr
            370                 375                 380

Thr Leu Pro Pro Ser Arg Asp Glu Leu Thr Lys Asn Gln Val Ser Leu
385                 390                 395                 400

Ile Cys Leu Val Lys Gly Phe Tyr Pro Ser Asp Ile Ala Val Glu Trp
                405                 410                 415

Glu Ser Asn Gly Gln Pro Glu Asn Arg Tyr Met Thr Trp Pro Pro Val
            420                 425                 430

Leu Asp Ser Asp Gly Ser Phe Phe Leu Tyr Ser Lys Leu Thr Val Asp
            435                 440                 445

Lys Ser Arg Trp Gln Gln Gly Asn Val Phe Ser Cys Ser Val Met His
450                 455                 460

Glu Ala Leu His Asn His Tyr Thr Gln Lys Ser Leu Ser Leu Ser Pro
465                 470                 475                 480

Gly Lys

<210> SEQ ID NO 50
<211> LENGTH: 1446
<212> TYPE: DNA
<213> ORGANISM: Artificial Sequence
<220> FEATURE:
<223> OTHER INFORMATION: CLONE# 720 FULL

<400> SEQUENCE: 50
ggagacatcc agatgaccca gtctccatcc tccctgtctg catctgtagg agacagagtc    60
accatcactt gccgggcaag tcaggacgtt aacaccgctg tagcttggta tcagcagaaa   120
ccagggaaag cccctaagct cctgatctat tctgcatcct ttttgtacag tggggtccca   180
tcaaggttca gtggcagtcg atctgggaca gatttcactc tcaccatcag cagtctgcaa   240
cctgaagatt ttgcaactta ctactgtcaa cagcattaca ctaccccacc cactttcggc   300
caagggacca aagtggagat caaaggtggt tctggtggtg gttctggtgg tggttctggt   360
ggtggttctg gtggtggttc tggtgaagtg cagctggtgg agtctggggg aggcttggta   420
```

```
cagcctggcg ggtccctgag actctcctgt gcagcctctg gattcaacat taaagatact    480
tatatccact gggtccggca agctccaggg aagggcctgg agtgggtcgc acgtatttat    540
cccacaaatg gttacacacg gtatgcggac tctgtgaagg gccgattcac catctccgca    600
gacacttcca agaacaccgc gtatctgcaa atgaacagtc tgagagctga ggacacggcc    660
gtttattact gttcaagatg gggcggagac ggtttctacg ctatggacta ctggggccaa    720
gggaccctgg tcaccgtctc ctcagccgcc gagcccaaga gcagcgataa gacccacacc    780
tgccctccct gtccagctcc agaactgctg gaggaccta gcgtgttcct gtttccccct    840
aagccaaaag acactctgat gatttccagg actcccgagg tgacctgcgt ggtggtggac    900
gtgtctcacg aggaccccga agtgaagttc aactggtacg tggatggcgt ggaagtgcat    960
aatgctaaga caaaaccaag agaggaacag tacaactcca cttatcgcgt cgtgagcgtg   1020
ctgaccgtgc tgcaccagga ctggctgaac gggaaggagt ataagtgcaa agtcagtaat   1080
aaggccctgc ctgctccaat cgaaaaaacc atctctaagg ccaaaggcca gccaagggag   1140
ccccaggtgt acacactgcc acccagcaga gacgaactga ccaagaacca ggtgtccctg   1200
atctgtctgg tgaaaggctt ctatcctagt gatattgctg tggagtggga atcaaatgga   1260
cagccagaga acagatacat gacctggcct ccagtgctgg acagcgatgg cagcttcttc   1320
ctgtattcca agctgacagt ggataaatct cgatggcagc aggggaacgt gtttagttgt   1380
tcagtgatgc atgaagccct gcacaatcat tacactcaga agagcctgtc cctgtctccc   1440
ggcaaa                                                              1446
```

<210> SEQ ID NO 51
<211> LENGTH: 107
<212> TYPE: PRT
<213> ORGANISM: Artificial Sequence
<220> FEATURE:
<223> OTHER INFORMATION: CLONE# 720 VL

<400> SEQUENCE: 51

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
            100                 105

<210> SEQ ID NO 52
<211> LENGTH: 120
<212> TYPE: PRT
<213> ORGANISM: Artificial Sequence
<220> FEATURE:
<223> OTHER INFORMATION: CLONE# 720 VH

<400> SEQUENCE: 52

Glu Val Gln Leu Val Glu Ser Gly Gly Gly Leu Val Gln Pro Gly Gly

-continued

```
1               5                   10                  15
Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
            35                  40                  45

Ala Arg Ile Tyr Pro Thr Asn Gly Tyr Thr Arg Tyr Ala Asp Ser Val
            50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
                100                 105                 110

Gly Thr Leu Val Thr Val Ser Ser
                115                 120

<210> SEQ ID NO 53
<211> LENGTH: 449
<212> TYPE: PRT
<213> ORGANISM: Artificial Sequence
<220> FEATURE:
<223> OTHER INFORMATION: CLONE# 3041 FULL

<400> SEQUENCE: 53

Gly Glu Val Gln Leu Val Glu Ser Gly Gly Gly Leu Val Gln Pro Gly
1               5                   10                  15

Gly Ser Leu Arg Leu Ser Cys Ala Ala Ser Gly Phe Thr Phe Thr Asp
            20                  25                  30

Tyr Thr Met Asp Trp Val Arg Gln Ala Pro Gly Lys Gly Leu Glu Trp
            35                  40                  45

Val Ala Asp Val Asn Pro Asn Ser Gly Gly Ser Ile Tyr Asn Gln Arg
            50                  55                  60

Phe Lys Gly Arg Phe Thr Leu Ser Val Asp Arg Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Arg Asn Leu Gly Pro Ser Phe Tyr Phe Asp Tyr Trp Gly Gln
                100                 105                 110

Gly Thr Leu Val Thr Val Ser Ser Ala Ser Thr Lys Gly Pro Ser Val
                115                 120                 125

Phe Pro Leu Ala Pro Ser Ser Lys Ser Thr Ser Gly Gly Thr Ala Ala
            130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Gln Thr Tyr Ile Cys Asn Val Asn His Lys
                195                 200                 205

Pro Ser Asn Thr Lys Val Asp Lys Lys Val Glu Pro Lys Ser Cys Asp
            210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
```

```
                   245                 250                 255
Ser Arg Thr Pro Glu Val Thr Cys Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
        340                 345                 350

Val Leu Pro Pro Ser Arg Asp Glu Leu Thr Lys Asn Gln Val Ser Leu
    355                 360                 365

Leu Cys Leu Val Lys Gly Phe Tyr Pro Ser Asp Ile Ala Val Glu Trp
370                 375                 380

Glu Ser Asn Gly Gln Pro Glu Asn Asn Tyr Leu Thr Trp Pro Pro Val
385                 390                 395                 400

Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
        420                 425                 430

Glu Ala Leu His Asn His Tyr Thr Gln Lys Ser Leu Ser Leu Ser Pro
    435                 440                 445

Gly

<210> SEQ ID NO 54
<211> LENGTH: 1347
<212> TYPE: DNA
<213> ORGANISM: Artificial Sequence
<220> FEATURE:
<223> OTHER INFORMATION: CLONE# 3041 FULL

<400> SEQUENCE: 54
ggggaagtgc agctggtcga atctggagga ggactggtgc agccaggagg gtccctgcgc    60
ctgtcttgcg ccgctagtgg cttcactttt accgactaca ccatggattg ggtgcgacag   120
gcacctggaa agggcctgga gtgggtcgcc gatgtgaacc caaatagcgg aggctccatc   180
tacaaccagc ggttcaaggg ccggttcacc ctgtcagtgg accggagcaa aaacaccctg   240
tatctgcaga tgaatagcct gcgagccgaa gatactgctg tgtactattg cgcccggaat   300
ctggggccct ccttctactt tgactattgg ggcagggaa ctctggtcac cgtgagctcc   360
gcctccacca agggaccttc tgtgttccca ctggctccct ctagtaaatc cacatctggg   420
ggaactgcag ccctgggctg tctggtgaag gactacttcc cagagcccgt cacagtgtct   480
tggaacagtg gcgctctgac ttctggggtc cacacctttc ctgcagtgct gcagtcaagc   540
gggctgtaca gcctgtcctc tgtggtcacc gtgccaagtt caagcctggg aacacagact   600
tatatctgca acgtgaatca caagccatcc aatacaaaag tcgacaagaa agtggaaccc   660
aagtcttgtg ataaaaccca tacatgcccc ccttgtcctg caccagagct gctgggagga   720
ccaagcgtgt tcctgtttcc acccaagcct aaagatacac tgatgattag taggacccca   780
gaagtcacat gcgtggtcgt ggacgtgagc acgaggacc ccgaagtcaa gtttaactgg   840
tacgtggacg gcgtcgaggt gcataatgcc aagactaaac ccagggagga acagtacaac   900
```

-continued

```
agtacctatc gcgtcgtgtc agtcctgaca gtgctgcatc aggattggct gaacgggaaa       960
gagtataagt gcaaagtgag caataaggct ctgcccgcac ctatcgagaa acaatttcc       1020 aaggcaaaag gacagcctag agaaccacag gtgtacgtgc tgcctccatc aagggatgag     1080
ctgacaaaga accaggtcag cctgctgtgt ctggtgaaag gattctatcc ctctgacatt     1140
gctgtggagt gggaaagtaa tggccagcct gagaacaatt acctgacctg gcccctgtg     1200 ctggactcag atggcagctt ctttctgtat agcaagctga ccgtcgacaa atcccggtgg     1260 cagcaggga atgtgtttag ttgttcagtc atgcacgagg cactgcacaa ccattacacc      1320
cagaagtcac tgtcactgtc accaggg                                         1347
```

<210> SEQ ID NO 55
<211> LENGTH: 119
<212> TYPE: PRT
<213> ORGANISM: Artificial Sequence
<220> FEATURE:
<223> OTHER INFORMATION: CLONE# 3041 VH

<400> SEQUENCE: 55

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Thr Met Asp Trp Val Arg Gln Ala Pro Gly Lys Gly Leu Glu Trp Val
        35                  40                  45

Ala Asp Val Asn Pro Asn Ser Gly Gly Ser Ile Tyr Asn Gln Arg Phe
    50                  55                  60

Lys Gly Arg Phe Thr Leu Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Leu Gly Pro Ser Phe Tyr Phe Asp Tyr Trp Gly Gln Gly
            100                 105                 110

Thr Leu Val Thr Val Ser Ser
        115
```

<210> SEQ ID NO 56
<211> LENGTH: 449
<212> TYPE: PRT
<213> ORGANISM: Artificial Sequence
<220> FEATURE:
<223> OTHER INFORMATION: CLONE# 3057 FULL

<400> SEQUENCE: 56

```
Gly Glu Val Gln Leu Val Glu Ser Gly Gly Gly Leu Val Gln Pro Gly
1               5                   10                  15

Gly Ser Leu Arg Leu Ser Cys Ala Ala Ser Gly Phe Thr Phe Thr Asp
            20                  25                  30

Tyr Thr Met Asp Trp Val Arg Gln Ala Pro Gly Lys Gly Leu Glu Trp
        35                  40                  45

Val Ala Asp Val Asn Pro Asn Ser Gly Gly Ser Ile Tyr Asn Gln Arg
    50                  55                  60

Phe Lys Gly Arg Phe Thr Leu Ser Val Asp Arg Ser Lys Asn Thr Leu
65                  70                  75                  80

Tyr Leu Gln Met Asn Ser Leu Arg Ala Glu Asp Thr Ala Val Tyr Tyr
                85                  90                  95
```

Cys Ala Arg Asn Leu Gly Pro Ser Phe Tyr Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
        180                 185                 190

Ser Ser Ser Leu Gly Thr Gln Thr Tyr Ile Cys Asn Val Asn His Lys
    195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
        260                 265                 270

Asp Pro Glu Val Lys Phe Asn Trp Tyr Val Asp Gly Val Glu Val His
    275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
        340                 345                 350

Val Tyr Pro Pro Ser Arg Asp Glu Leu Thr Lys Asn Gln Val Ser Leu
    355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Ala Leu Val Ser Lys Leu Thr Val Asp
                405                 410                 415

Lys Ser Arg Trp Gln Gln Gly Asn Val Phe Ser Cys Ser Val Met His
        420                 425                 430

Glu Ala Leu His Asn His Tyr Thr Gln Lys Ser Leu Ser Leu Ser Pro
    435                 440                 445

Gly

<210> SEQ ID NO 57
<211> LENGTH: 1347
<212> TYPE: DNA
<213> ORGANISM: Artificial Sequence
<220> FEATURE:
<223> OTHER INFORMATION: CLONE# 3057 FULL

<400> SEQUENCE: 57
ggggaagtgc agctggtcga atctggagga ggactggtgc agccaggagg gtccctgcgc      60

```
ctgtcttgcg ccgctagtgg cttcactttt accgactaca ccatggattg ggtgcgacag    120
gcacctggaa agggcctgga gtgggtcgcc gatgtgaacc caaatagcgg aggctccatc    180
tacaaccagc ggttcaaggg ccggttcacc ctgtcagtgg accggagcaa aaacaccctg    240
tatctgcaga tgaatagcct gcgagccgaa gatactgctg tgtactattg cgcccggaat    300
ctggggccct ccttctactt tgactattgg ggcagggaa ctctggtcac cgtgagctcc    360
gcctccacca agggaccttc tgtgttccca ctggctccct ctagtaaatc acatctgggg    420
ggaactgcag ccctgggctg tctggtgaag gactacttcc cagagcccgt cacagtgtct    480
tggaacagtg gcgctctgac ttctggggtc cacaccttc ctgcagtgct gcagtcaagc    540
gggctgtaca gcctgtcctc tgtggtcacc gtgccaagtt caagcctggg aacacagact    600
tatatctgca acgtgaatca caagccatcc aatacaaaag tcgacaagaa agtggaaccc    660
aagtcttgtg ataaaaccca tacatgcccc ccttgtcctg caccagagct gctgggagga    720
ccaagcgtgt tcctgtttcc acccaagcct aaagatacac tgatgattag taggaccccca   780 gaagtcacat gcgtggtcgt ggacgtgagc cacgaggacc ccgaagtcaa gtttaactgg    840
tacgtggacg gcgtcgaggt gcataatgcc aagactaaac caggagga acagtacaac    900 agtacctatc gcgtcgtgtc agtcctgaca gtgctgcatc aggattggct gaacgggaaa    960
gagtataagt gcaaagtgag caataaggct ctgcccgcac ctatcgagaa aacaatttcc   1020
aaggcaaaag acagcctag agaaccacag gtgtacgtgt atcctccatc aagggatgag   1080
ctgacaaaga accaggtcag cctgacttgt ctggtgaaag gattctatcc ctctgacatt   1140
gctgtggagt gggaaagtaa tggccagcct gagaacaatt acaagaccac accccctgtg   1200
ctggactcag atggcagctt cgcgctggtg agcaagctga ccgtcgacaa atcccggtgg   1260
cagcagggga atgtgtttag ttgttcagtc atgcacgagg cactgcacaa ccattacacc   1320
cagaagtcac tgtcactgtc accaggg                                       1347
```

<210> SEQ ID NO 58
<211> LENGTH: 119
<212> TYPE: PRT
<213> ORGANISM: Artificial Sequence
<220> FEATURE:
<223> OTHER INFORMATION: CLONE# 3057 VH

<400> SEQUENCE: 58

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Thr Met Asp Trp Val Arg Gln Ala Pro Gly Lys Gly Leu Glu Trp Val
        35                  40                  45

Ala Asp Val Asn Pro Asn Ser Gly Gly Ser Ile Tyr Asn Gln Arg Phe
    50                  55                  60

Lys Gly Arg Phe Thr Leu Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Leu Gly Pro Ser Phe Tyr Phe Asp Tyr Trp Gly Gln Gly
            100                 105                 110

Thr Leu Val Thr Val Ser Ser
        115

```
<210> SEQ ID NO 59
<211> LENGTH: 476
<212> TYPE: PRT
<213> ORGANISM: Artificial Sequence
<220> FEATURE:
<223> OTHER INFORMATION: CLONE# 3317 FULL

<400> SEQUENCE: 59

Gly Asp Ile Gln Met Thr Gln Ser Pro Ser Ser Leu Ser Ala Ser Val
1               5                   10                  15

Gly Asp Arg Val Thr Ile Thr Cys Lys Ala Ser Gln Asp Val Ser Ile
            20                  25                  30

Gly Val Ala Trp Tyr Gln Gln Lys Pro Gly Lys Ala Pro Lys Leu Leu
        35                  40                  45

Ile Tyr Ser Ala Ser Tyr Arg Tyr Thr Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gln Gln Tyr Tyr Ile Tyr Pro
                85                  90                  95

Tyr Thr Phe Gly Gln Gly Thr Lys Val Glu Ile Lys Gly Gly Gly Gly
            100                 105                 110

Ser Gly Gly Gly Gly Ser Gly Gly Gly Ser Glu Val Gln Leu Val
            115                 120                 125

Glu Ser Gly Gly Gly Leu Val Gln Pro Gly Gly Ser Leu Arg Leu Ser
130                 135                 140

Cys Ala Ala Ser Gly Phe Thr Phe Thr Asp Tyr Thr Met Asp Trp Val
145                 150                 155                 160

Arg Gln Ala Pro Gly Lys Gly Leu Glu Trp Val Ala Asp Val Asn Pro
                165                 170                 175

Asn Ser Gly Gly Ser Ile Tyr Asn Gln Arg Phe Lys Gly Arg Phe Thr
            180                 185                 190

Leu Ser Val Asp Arg Ser Lys Asn Thr Leu Tyr Leu Gln Met Asn Ser
        195                 200                 205

Leu Arg Ala Glu Asp Thr Ala Val Tyr Tyr Cys Ala Arg Asn Leu Gly
    210                 215                 220

Pro Ser Phe Tyr Phe Asp Tyr Trp Gly Gln Gly Thr Leu Val Thr Val
225                 230                 235                 240

Ser Ser Ala Ala Glu Pro Lys Ser Ser Asp Lys Thr His Thr Cys Pro
                245                 250                 255

Pro Cys Pro Ala Pro Glu Leu Leu Gly Gly Pro Ser Val Phe Leu Phe
            260                 265                 270

Pro Pro Lys Pro Lys Asp Thr Leu Met Ile Ser Arg Thr Pro Glu Val
        275                 280                 285

Thr Cys Val Val Val Asp Val Ser His Glu Asp Pro Glu Val Lys Phe
    290                 295                 300

Asn Trp Tyr Val Asp Gly Val Glu Val His Asn Ala Lys Thr Lys Pro
305                 310                 315                 320

Arg Glu Glu Gln Tyr Asn Ser Thr Tyr Arg Val Val Ser Val Leu Thr
                325                 330                 335

Val Leu His Gln Asp Trp Leu Asn Gly Lys Glu Tyr Lys Cys Lys Val
            340                 345                 350

Ser Asn Lys Ala Leu Pro Ala Pro Ile Glu Lys Thr Ile Ser Lys Ala
        355                 360                 365
```

```
Lys Gly Gln Pro Arg Glu Pro Gln Val Tyr Val Tyr Pro Pro Ser Arg
    370                 375                 380

Asp Glu Leu Thr Lys Asn Gln Val Ser Leu Thr Cys Leu Val Lys Gly
385                 390                 395                 400

Phe Tyr Pro Ser Asp Ile Ala Val Glu Trp Glu Ser Asn Gly Gln Pro
                405                 410                 415

Glu Asn Asn Tyr Lys Thr Thr Pro Pro Val Leu Asp Ser Asp Gly Ser
                420                 425                 430

Phe Ala Leu Val Ser Lys Leu Thr Val Asp Lys Ser Arg Trp Gln Gln
                435                 440                 445

Gly Asn Val Phe Ser Cys Ser Val Met His Glu Ala Leu His Asn His
    450                 455                 460

Tyr Thr Gln Lys Ser Leu Ser Leu Ser Pro Gly Lys
465                 470                 475

<210> SEQ ID NO 60
<211> LENGTH: 1428
<212> TYPE: DNA
<213> ORGANISM: Artificial Sequence
<220> FEATURE:
<223> OTHER INFORMATION: CLONE# 3317 FULL

<400> SEQUENCE: 60
ggggacattc agatgaccca gagccctagc tccctgagtg cctcagtcgg ggacagggtg      60
actatcacct gcaaggcttc acaggatgtc agcattggcg tggcatggta ccagcagaag     120
ccagggaaag cacccaagct gctgatctat agcgcctcct acaggtatac aggcgtgcca     180
tcccgcttct ctggcagtgg gtcaggaact gactttacac tgactatttc tagtctgcag     240
cccgaagatt tcgccacata ctattgccag cagtactata tctaccctta tacttttggc     300
caggggacca agtggagat taagggcgga ggaggctccg gaggaggagg gtctggagga     360
ggaggaagtg aggtccagct ggtggaatct ggaggaggac tggtgcagcc aggagggtcc     420
ctgaggctgt cttgtgccgc tagtggcttc acctttacag actacacaat ggattgggtg     480
cgccaggcac caggaaaggg actggaatgg gtcgctgatg tgaaccctaa tagcggaggc     540
tccatctaca accagcggtt caaaggacg ttcaccctgt cagtggaccg gagcaagaac     600
accctgtatc tgcagatgaa cagcctgaga gccgaggata ctgctgtgta ctattgcgcc     660
aggaatctgg gcccaagctt ctactttgac tattgggggc agggaacact ggtcactgtg     720
tcaagcgcag ccgaacccaa atcctctgat aagactcaca cctgcccacc ttgtccagct     780
ccagagctgc tgggaggacc tagcgtgttc ctgtttccac ccaagccaaa agacactctg     840
atgatttcta gaacccctga agtgacatgt gtggtcgtgg acgtcagtca cgaggacccc     900
gaagtcaaat tcaactggta cgtggatggc gtcgaggtgc ataatgccaa gaccaaaccc     960
cgagaggaac agtacaactc aacctatcgg gtcgtgagcg tcctgacagt gctgcatcag    1020
gactggctga acggcaagga gtataagtgc aaagtgagca caaggctct gcctgcacca    1080 atcgagaaga ccatttccaa ggctaaaggg cagccccgcg aacctcaggt ctacgtgtat    1140
cctccaagcc gagatgagct gacaaaaaac caggtctccc tgacttgtct ggtgaaggga    1200
ttttacccaa gtgacatcgc agtggagtgg gaatcaaatg ccagcccga aaacaattat    1260 aagaccacac cccctgtgct ggactctgat gggagtttcg cactggtctc caaactgacc    1320
gtggacaagt ctcggtggca gcagggaaac gtctttagct gttccgtgat gcacgaggcc    1380
ctgcacaatc attacacaca gaaatctctg agtctgtcac ctggcaag             1428
```

<210> SEQ ID NO 61
<211> LENGTH: 107
<212> TYPE: PRT
<213> ORGANISM: Artificial Sequence
<220> FEATURE:
<223> OTHER INFORMATION: CLONE# 3317 VL

<400> SEQUENCE: 61

```
Asp Ile Gln Met Thr Gln Ser Pro Ser Leu Ser Ala Ser Val Gly
1               5                   10                  15

Asp Arg Val Thr Ile Thr Cys Lys Ala Ser Gln Asp Val Ser Ile Gly
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ile Tyr Pro Tyr
                85                  90                  95

Thr Phe Gly Gln Gly Thr Lys Val Glu Ile Lys
            100                 105
```

<210> SEQ ID NO 62
<211> LENGTH: 119
<212> TYPE: PRT
<213> ORGANISM: Artificial Sequence
<220> FEATURE:
<223> OTHER INFORMATION: CLONE# 3317 VH

<400> SEQUENCE: 62

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Thr Met Asp Trp Val Arg Gln Ala Pro Gly Lys Gly Leu Glu Trp Val
        35                  40                  45

Ala Asp Val Asn Pro Asn Ser Gly Gly Ser Ile Tyr Asn Gln Arg Phe
    50                  55                  60

Lys Gly Arg Phe Thr Leu Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Leu Gly Pro Ser Phe Tyr Phe Asp Tyr Trp Gly Gln Gly
            100                 105                 110

Thr Leu Val Thr Val Ser Ser
        115
```

<210> SEQ ID NO 63
<211> LENGTH: 481
<212> TYPE: PRT
<213> ORGANISM: Artificial Sequence
<220> FEATURE:
<223> OTHER INFORMATION: CLONE# 5244 FULL

<400> SEQUENCE: 63

```
Gly Asp Ile Gln Met Thr Gln Ser Pro Ser Leu Ser Ala Ser Val
1               5                   10                  15

Gly Asp Arg Val Thr Ile Thr Cys Arg Ala Ser Gln Asp Val Asn Thr
```

-continued

```
             20                  25                  30
Ala Val Ala Trp Tyr Gln Gln Lys Pro Gly Lys Ala Pro Lys Leu Leu
            35                  40                  45
Ile Tyr Ser Ala Ser Phe Leu Tyr Ser Gly Val Pro Ser Arg Phe Ser
            50                  55                  60
Gly Ser Arg Ser Gly Thr Asp Phe Thr Leu Thr Ile Ser Ser Leu Gln
65                  70                  75                  80
Pro Glu Asp Phe Ala Thr Tyr Tyr Cys Gln Gln His Tyr Thr Thr Pro
                    85                  90                  95
Pro Thr Phe Gly Gln Gly Thr Lys Val Glu Ile Lys Gly Gly Ser Gly
                100                 105                 110
Gly Gly Ser Gly Gly Gly Ser Gly Gly Gly Ser Gly Gly Gly Ser Gly
            115                 120                 125
Glu Val Gln Leu Val Glu Ser Gly Gly Gly Leu Val Gln Pro Gly Gly
            130                 135                 140
Ser Leu Arg Leu Ser Cys Ala Ala Ser Gly Phe Asn Ile Lys Asp Thr
145                 150                 155                 160
Tyr Ile His Trp Val Arg Gln Ala Pro Gly Lys Gly Leu Glu Trp Val
                165                 170                 175
Ala Arg Ile Tyr Pro Thr Asn Gly Tyr Thr Arg Tyr Ala Asp Ser Val
                180                 185                 190
Lys Gly Arg Phe Thr Ile Ser Ala Asp Thr Ser Lys Asn Thr Ala Tyr
                195                 200                 205
Leu Gln Met Asn Ser Leu Arg Ala Glu Asp Thr Ala Val Tyr Tyr Cys
            210                 215                 220
Ser Arg Trp Gly Gly Asp Gly Phe Tyr Ala Met Asp Tyr Trp Gly Gln
225                 230                 235                 240
Gly Thr Leu Val Thr Val Ser Ser Ala Ala Glu Pro Lys Ser Ser Asp
                245                 250                 255
Lys Thr His Thr Cys Pro Pro Cys Pro Ala Pro Glu Leu Leu Gly Gly
                260                 265                 270
Pro Ser Val Phe Leu Phe Pro Pro Lys Pro Lys Asp Thr Leu Met Ile
            275                 280                 285
Ser Arg Thr Pro Glu Val Thr Cys Val Val Val Asp Val Ser His Glu
290                 295                 300
Asp Pro Glu Val Lys Phe Asn Trp Tyr Val Asp Gly Val Glu Val His
305                 310                 315                 320
Asn Ala Lys Thr Lys Pro Arg Glu Glu Gln Tyr Asn Ser Thr Tyr Arg
                325                 330                 335
Val Val Ser Val Leu Thr Val Leu His Gln Asp Trp Leu Asn Gly Lys
            340                 345                 350
Glu Tyr Lys Cys Lys Val Ser Asn Lys Ala Leu Pro Ala Pro Ile Glu
            355                 360                 365
Lys Thr Ile Ser Lys Ala Lys Gly Gln Pro Arg Glu Pro Gln Val Tyr
            370                 375                 380
Val Leu Pro Pro Ser Arg Asp Glu Leu Thr Lys Asn Gln Val Ser Leu
385                 390                 395                 400
Leu Cys Leu Val Lys Gly Phe Tyr Pro Ser Asp Ile Ala Val Glu Trp
                405                 410                 415
Glu Ser Asn Gly Gln Pro Glu Asn Asn Tyr Leu Thr Trp Pro Pro Val
            420                 425                 430
Leu Asp Ser Asp Gly Ser Phe Phe Leu Tyr Ser Lys Leu Thr Val Asp
            435                 440                 445
```

<210> SEQ ID NO 64
<211> LENGTH: 1443
<212> TYPE: DNA
<213> ORGANISM: Artificial Sequence
<220> FEATURE:
<223> OTHER INFORMATION: CLONE# 5244 FULL

<400> SEQUENCE: 64

```
ggagacattc agatgacaca gagccccagc tccctgagtg cttcagtcgg cgacagggtg      60
actatcacct gccgcgcatc ccaggatgtc aacaccgctg tggcatggta ccagcagaag     120
cctggaaaag ccccaaagct gctgatctac agcgcttcct tcctgtattc tggcgtgcca     180
agtcggtttt ctggaagtag atcaggcact gacttcacac tgactatctc tagtctgcag     240
cccgaagatt ttgccaccta ctattgccag cagcactata ccacccccc tacattcgga     300
cagggcacta aagtggagat aagggcgggt caggcggag ggagcggagg agggtccgga     360
ggagggtctg gaggagggag tggagaggtc cagctggtgg aatctggagg aggactggtg     420
cagcctggag gctcactgcg actgagctgt gccgcttccg gctttaacat caaagacaca     480
tacattcatt gggtcaggca ggcaccaggg aagggactgg aatgggtggc ccgcatctat     540
cccacaaatg gtacactcg atatgccgac agcgtgaaag gacggtttac catttctgct     600
gataccagta agaacacagc atacctgcag atgaacagcc tgcgcgcaga ggatacagcc     660
gtgtactatt gcagtcgatg ggggggagac ggcttctacg ccatggatta ttggggccag     720
gggactctgg tcaccgtgtc aagcgcagcc gaacctaaat cctctgacaa gacccacaca     780
tgcccaccct gtcctgctcc agagctgctg gaggaccat ccgtgttcct gtttcctcca     840
aagcctaaag atacactgat gattagccgc actcccgaag tcacctgtgt ggtcgtggac     900
gtgtcccacg aggacccccga agtcaagttc aactggtacg tggacggcgt cgaggtgcat     960
aatgccaaga ctaaaccaag agaggaacag tacaattcaa cctataggt cgtgagcgtc    1020
ctgacagtgc tgcatcagga ttggctgaac ggcaaggagt ataagtgcaa agtgtctaac    1080
aaggccctgc ccgctcctat cgagaagact attagcaagg caaagggca gccacgggaa    1140
cccagggtct acgtgctgcc ccctagcaga gacgagctga ccaaaaacca ggtctcctg    1200
ctgtgtctgg tgaagggctt ttatcctagt gatatcgctg tggagtggga atcaaatggg    1260
cagccagaaa acaattacct gacatggcca cccgtgctgg acagcgatgg gtccttcttt    1320
ctgtattcca aactgactgt ggacaagtct agatggcagc agggaaacgt cttcagctgt    1380
tccgtgatgc acgaggccct gcacaatcat tacacccaga agtctctgag tctgtcaccc    1440
ggc                                                                  1443
```

<210> SEQ ID NO 65
<211> LENGTH: 107
<212> TYPE: PRT
<213> ORGANISM: Artificial Sequence
<220> FEATURE:
<223> OTHER INFORMATION: CLONE# 5244 VL

<400> SEQUENCE: 65

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
            100                 105
```

<210> SEQ ID NO 66
<211> LENGTH: 120
<212> TYPE: PRT
<213> ORGANISM: Artificial Sequence
<220> FEATURE:
<223> OTHER INFORMATION: CLONE# 5244 VH

<400> SEQUENCE: 66

```
Glu Val Gln Leu Val Glu Ser Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser
        115                 120
```

<210> SEQ ID NO 67
<211> LENGTH: 6
<212> TYPE: PRT
<213> ORGANISM: Artificial Sequence
<220> FEATURE:
<223> OTHER INFORMATION: CLONE# 5244, 5034, 719, 720 L1

<400> SEQUENCE: 67

```
Gln Asp Val Asn Thr Ala
1               5
```

<210> SEQ ID NO 68
<211> LENGTH: 3
<212> TYPE: PRT
<213> ORGANISM: Artificial Sequence
<220> FEATURE:
<223> OTHER INFORMATION: CLONE# 5244, 5034, 719, 720 L2

<400> SEQUENCE: 68

Ser Ala Ser

```
<210> SEQ ID NO 69
<211> LENGTH: 9
<212> TYPE: PRT
<213> ORGANISM: Artificial Sequence
<220> FEATURE:
<223> OTHER INFORMATION: CLONE# 5244, 5034, 719, 720 L3

<400> SEQUENCE: 69

Gln Gln His Tyr Thr Thr Pro Pro Thr
1               5

<210> SEQ ID NO 70
<211> LENGTH: 8
<212> TYPE: PRT
<213> ORGANISM: Artificial Sequence
<220> FEATURE:
<223> OTHER INFORMATION: CLONE# 5244 H1

<400> SEQUENCE: 70

Gly Phe Asn Ile Lys Asp Thr Tyr
1               5

<210> SEQ ID NO 71
<211> LENGTH: 8
<212> TYPE: PRT
<213> ORGANISM: Artificial Sequence
<220> FEATURE:
<223> OTHER INFORMATION: CLONE# 5244 H2

<400> SEQUENCE: 71

Ile Tyr Pro Thr Asn Gly Tyr Thr
1               5

<210> SEQ ID NO 72
<211> LENGTH: 13
<212> TYPE: PRT
<213> ORGANISM: Artificial Sequence
<220> FEATURE:
<223> OTHER INFORMATION: CLONE# 5244 H3

<400> SEQUENCE: 72

Ser Arg Trp Gly Gly Asp Gly Phe Tyr Ala Met Asp Tyr
1               5                   10
```

METHODS OF USING A BISPECIFIC ANTIGEN-BINDING CONSTRUCT TARGETING HER2 IN COMBINATION WITH CDK4/6 INHIBITORS FOR THE TREATMENT OF BREAST CANCER

CROSS REFERENCE TO RELATED APPLICATIONS

This application claims the benefit under 35 U.S.C. § 119(e) of U.S. Provisional Application, 62/944,822, filed Dec. 6, 2019, of which is herein incorporated in its entirety by reference.

SEQUENCE LISTING

The instant application contains a Sequence Listing which will be submitted via EFS-Web and is hereby incorporated by reference in its entirety. Said ASCII copy, created on May 27, 2020, is named Zyme070US1_sequencelisting.txt, has 72 sequences and is 100,675 bytes in size.

BACKGROUND

Breast cancer presents a significant health burden worldwide. Globally, in 2018, over 2 million new cases were reported with over 600,000 deaths (GLOBOCAN. Breast cancer fact sheet. Global Cancer Observatory. Available from: gco.iarc.fr/today/data/factsheets/cancers/20-Breast-fact-sheet.pdf). The lifetime incidence rate of female invasive breast cancer in the United States (US) is approximately 12% (one in eight women), and it is estimated that over 271,270 new cases of locally advanced or metastatic breast cancer will be diagnosed in 2019 in both men and women. The 5- and 10-year relative survival rates for women with invasive breast cancer in the US are 90% and 83%, respectively. However, 5-year relative survival rates drop to 27% when metastases are present (American Cancer Society. Cancer Facts & FIGS. 2019. Available from: www.cancer.org/content/dam/cancer-org/research/cancer-facts-and-statistics/annual-cancer-facts-and-figures/2019/cancer-facts-and-figures-2019.pdf). The estimated number of breast cancer cases in both sexes and all ages in the European Union (EU) (28 countries) for 2018 is 404,920 with an estimated mortality of 98,755 cases (European Cancer Information System (ECIS). Measuring cancer burden and its time trends across Europe 2018. Available from: ecisjrc.ec.Europa.eu/).

There remains a need for treatments for breast cancers.

International Patent Publication No. WO2015/077891 describes bispecific anti-HER2 antibodies directed against two distinct HER2 epitopes in ECD4 and ECD2, the same epitopes bound by trastuzumab and pertuzumab.

SUMMARY

One aspect of the present disclosure provides a method of treating a patient with human epidermal growth factor receptor 2 (HER2)-positive, hormone receptor (HR)-positive breast cancer, the method comprising administering to the patient: I) a palbociclib 75 mg, 100 mg or 125 mg capsule administered orally (PO) once daily (QD) for the first 21 days of each 28-day cycle; II) about 15 mg/kg to 20 mg/kg of a bispecific anti-HER2 antigen-binding construct or antibody drug conjugate (ADC) thereof every 2 weeks (Q2W); and III) fulvestrant administered at 250 mg-500 mg Q2W for the first 3 doses, then once every 4 weeks (Q4W).

In one embodiment of the method, the breast cancer is resectable, partially resectable, or unresectable. In certain embodiments of the method of treating breast cancer, the breast cancer is locally advanced and/or metastatic. In another embodiment of the method, the breast cancer is HER2 3+, HER2 2+, or HER2 1+ as measured by immunohistochemistry (IHC) and gene amplified. In other embodiments of the method, the breast cancer is HER2 3+, HER2 2+, or HER2 1+ as measured by immunohistochemistry (IHC), without HER2 gene amplification. In certain other embodiments of the method, the bispecific anti-HER2 antigen-binding construct comprises a heavy chain H1, a heavy chain H2, and a light chain L1, wherein: a) heavy chain H1 comprises the CDR sequences set forth in SEQ ID NO:39, SEQ ID NO:40, and SEQ ID NO:41; b) heavy chain H2 comprises the CDR sequences set forth in SEQ ID NO:67, SEQ ID NO:68, SEQ ID NO:69, SEQ ID NO:70, SEQ ID NO:71, and SEQ ID NO:72; and c) heavy chain L1 comprises the CDR sequences set forth in SEQ ID NO:27, SEQ ID NO:28, and SEQ ID NO:29. In yet another embodiment of the method, the bispecific anti-HER2 antigen-binding construct comprises a heavy chain H1 comprising the amino acid sequence set forth in SEQ ID NO:36, a heavy chain H2 comprising the amino acid sequence set forth in SEQ ID NO:63, and a light chain L1 comprising the amino acid sequence set forth in SEQ ID NO:24. In one embodiment of the method of treating breast cancer, the effective amount of the bispecific anti-HER2 antigen-binding construct is 20 mg/kg every two weeks. In another embodiment, the effective amount of the bispecific anti-HER2 antigen-binding construct is 30 mg/kg every three weeks.

In certain embodiments of the methods of treating breast cancer, the administrations of I, II and III result in a complete response (CR), partial response (PR) or stable disease (SD) in the patient. In one embodiment, the disease control rate in a group of patients administered I, II and III is greater than 60%, 70%, or 80%. In another embodiment, the overall response rate in a group of patients administered I, II, and III is greater than 50%, 60%, 70%, or 80%. In certain embodiments of the methods, the administrations of I, II and III are administered following at least one, two, or three first-line therapies. In one embodiment, the patient has prior progression or intolerance following prior trastuzumab, pertuzumab and T-DM1 treatment. In another embodiment, the method further comprises administration of one or more chemotherapeutic agents. In this regard, the chemotherapeutic agent may be gemcitabine and/or cisplatin.

In certain embodiments, the method of treating breast cancer further comprises administration of gonadotropin-releasing hormone analogue.

Another aspect of the present disclosure provides palbociclib, a bispecific anti-HER2 antigen-binding construct or ADC thereof, and fulvestrant, for use in treating human epidermal growth factor receptor 2 (HER2)-positive, hormone receptor (HR)-positive breast cancer in a patient, wherein the palbociclib, the bispecific anti-HER2 antigen-binding construct or ADC thereof, and the fulvestrant is administered by a dosage regime comprising: I) one palbociclib 75 mg, 100 mg or 125 mg capsule administered orally (PO) once daily (QD) for the first 21 days of each 28-day cycle; II) about 15 mg/kg to 20 mg/kg of a bispecific anti-HER2 antigen-binding construct or antibody drug conjugate (ADC) thereof every 2 weeks (Q2W); and III) fulvestrant administered at 250 mg-500 mg Q2W for the first 3 doses, then once every 4 weeks (Q4W). In certain embodiments, the breast cancer is HER2 3+, HER2 2+, or HER2 1+ as measured by immunohistochemistry (IHC) and gene amplified. In another embodiment, the breast cancer is HER2 3+, HER2 2+, or HER2 1+ as measured by immunohistochemistry (IHC), without HER2 gene amplification. In yet another embodiment, the bispecific anti-HER2 antigen-binding construct comprises a heavy chain H1, a heavy chain H2, and a light chain L1, wherein: a) heavy chain H1 comprises the CDR sequences set forth in SEQ ID NO:39, SEQ ID NO:40, and SEQ ID NO:41; b) heavy chain H2 comprises the CDR sequences set forth in SEQ ID NO:67, SEQ ID NO:68, SEQ ID NO:69, SEQ ID NO:70, SEQ ID NO:71, and SEQ ID NO:72; and c) heavy chain L1 comprises the CDR sequences set forth in SEQ ID NO:27, SEQ ID NO:28, and SEQ ID NO:29. In still another embodiment, the bispecific anti-HER2 antigen-binding construct comprises a heavy chain H1 comprising the amino acid sequence set forth in SEQ ID NO:36, a heavy chain H2 comprising the amino acid sequence set forth in SEQ ID NO:63, and a light chain L1 comprising the amino acid sequence set forth in SEQ ID NO:24. In additional embodiments, the effective amount of the bispecific anti-HER2 antigen-binding construct is 20 mg/kg every two weeks or the effective amount of the bispecific anti-HER2 antigen-binding construct is 30 mg/kg every three weeks. In other embodiments, the dosage regimen results in a complete response (CR), partial response (PR) or stable disease (SD) in the subject. In certain embodiments of the uses described herein the disease control rate in a group of subjects treated with the dosage regiment is greater than 60%, 70%, or 80%. In another embodiment, the overall response rate in a group of subjects treated with the dosage regimen is greater than 50%, 60%, 70%, or 80%. In certain embodiments, the dosage regimen is administered following at least one, two, or three first-line therapies. In another embodiment, the patient has prior progression or intolerance following prior trastuzumab, pertuzumab and T-DM1 treatment. In still another embodiment, the dosage regimen is administered in conjunction with other chemotherapies.

One aspect of the present disclosure provides a method of treating a patient with human epidermal growth factor receptor 2 (HER2)-positive, hormone receptor (HR)-positive breast cancer, the method comprising administering to the patient: I) about 15 mg/kg to 20 mg/kg of a bispecific anti-HER2 antigen-binding construct or antibody drug conjugate (ADC) thereof every 2 weeks (Q2W); and one or both of: II) a palbociclib 75 mg, 100 mg or 125 mg capsule administered orally (PO) once daily (QD) for the first 21 days of each 28-day cycle; and III) fulvestrant administered at 250 mg-500 mg Q2W for the first 3 doses, then once every 4 weeks (Q4W). In one embodiment, the breast cancer is HER2 3+, HER2 2+, or HER2 1+ as measured by immunohistochemistry (IHC). In another embodiment, the breast cancer is HER2 1+ as measured by IHC.

DETAILED DESCRIPTION

Figure 1:
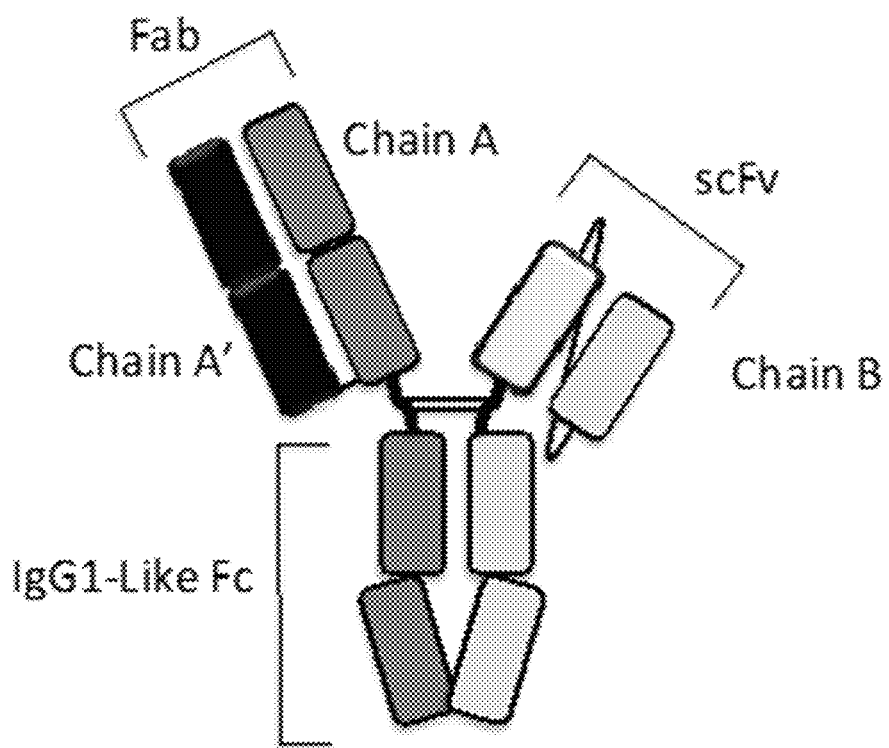
FIG. 1 depicts a representation of an exemplary bispecific anti-HER2 antigen-binding construct in a Fab/scFv format.

Described herein are methods of treating breast cancer comprising administering to a subject having breast cancer, a bispecific anti-HER2 antigen-binding construct or ADC as described herein, in combination with a CDK4/6 inhibitor and, in certain embodiments, further in combination with endocrine-based therapy, in an amount effective to treat, prevent or ameliorate this disease or disorder.

Human epidermal growth factor receptor 2 (HER2) is a member of the epidermal growth factor receptor (EGFR/ErbB) family comprising 4 structurally related receptors: HER1 (EGFR), HER2, HER3, and HER4. HER receptors are normally activated by binding to specific ligands, resulting in a conformational change that allows formation of receptor homodimers and heterodimers. Receptor dimerization triggers autophosphorylation of specific tyrosine residues and activation of intracellular signaling pathways (Moasser M M. The oncogene HER2: its signaling and transforming functions and its role in human cancer pathogenesis. Oncogene. 2007; 26(45):6469-87. doi: 10.1038/sj.onc.1210477). HER2 is unique among HER family members in that it has no known ligand and maintains a dimerization-ready conformation. HER2 is the preferred dimerization partner for other HER family members. HER2-containing heterodimers, particularly HER2/HER3, deliver the most potent growth signals (Pohlmann P R, Mayer I A, Mernaugh R. Resistance to Trastuzumab in Breast Cancer. Clin Cancer Res. 2009; 15(24):7479-91. doi: 10.1158/1078-0432.CCR-09-0636).

The oncogenic role of HER2 is best defined for breast cancers with HER2 gene amplification and high levels of HER2 protein expression, which historically have been associated with aggressive tumor growth and poor clinical outcomes. However, because HER2 is the preferred dimerization partner for all other HER family receptors and can interact synergistically with other receptor tyrosine kinase cell growth pathways (Moasser 2007), HER2-targeted therapy may be important even in the absence of gene amplification and/or in the setting of lower levels of expression.

Approximately 15% of patients with breast cancer have tumors that overexpress the HER2 protein, and these patients can benefit from HER2-targeted therapies. Approximately half of all HER2-positive breast cancers are also hormone receptor (HR) positive (Giordano 2014, American Society of Clinical Oncology clinical practice guideline. J Clin Oncol. 2014; 32(19):2078-99. doi: 10.1200/JCO.2013.54.0948). Identification of receptor expression offers options for individualized targeted therapies (Schramm 2015 Targeted Therapies in HER2-Positive Breast Cancer—a Systematic Review. Breast Care (Basel). 2015; 10(3):173-8).

Despite the gains obtained with current HER2-directed therapy, medical need remains for patients with all HER2-expressing cancers, particularly with recurrent or metastatic disease that has progressed after standard of care therapy. This includes HER2 overexpressing breast cancers, where patients may have primary or secondary resistance to current HER2-targeted treatments. Resistance may be due to a number of factors, including increased heterodimerization with other EGFR/ErbB family members as well as heterogeneity in levels of HER2 expression (Lee 2014; Rye 2018). HER2 expression levels can vary within a tumor and be discordant between the site of primary and metastatic disease. Increased heterogeneity and/or decreased levels of HER2 expression may be particularly important in development of resistance to T-DM1, which relies on receptor binding and internalization for its cytotoxic effect. In addition to a need for new targeted HER2 therapy that can overcome resistant disease, there is a need to develop less toxic treatment regimens, particularly in the adjuvant setting.

Definitions

Unless defined otherwise, all technical and scientific terms used herein have the same meaning as commonly understood by one of ordinary skill in the art.

As used herein, the term "about" refers to an approximately +/−10% variation from a given value, unless otherwise indicated. It is to be understood that such a variation is always included in any given value provided herein, whether or not it is specifically referred to.

The use of the word "a" or "an" when used herein in conjunction with the term "comprising" may mean "one," but it is also consistent in certain embodiments with the meaning of "one or more," "at least one" or "one or more than one."

As used herein, the terms "comprising," "having," "including" and "containing," and grammatical variations thereof, are inclusive or open-ended and do not exclude additional, unrecited elements and/or method steps. The term "consisting essentially of" when used herein in connection with a composition, use or method, denotes that additional elements and/or method steps may be present, but that these additions do not materially affect the manner in which the recited composition, method or use functions. The term "consisting of" when used herein in connection with a composition, use or method, excludes the presence of additional elements and/or method steps. A composition, use or method described herein as comprising certain elements and/or steps may also, in certain embodiments consist essentially of those elements and/or steps, and in other embodiments consist of those elements and/or steps, whether or not these embodiments are specifically referred to.

It is contemplated that any embodiment discussed herein can be implemented with respect to any method, use or composition disclosed herein.

Particular features, structures and/or characteristics described in connection with an embodiment disclosed herein may be combined with features, structures and/or characteristics described in connection with another embodiment disclosed herein in any suitable manner to provide one or more further embodiments.

It is also to be understood that the positive recitation of a feature in one embodiment, serves as a basis for excluding the feature in an alternative embodiment. For example, where a list of options is presented for a given embodiment or claim, it is to be understood that one or more option may be deleted from the list and the shortened list may form an alternative embodiment, whether or not such an alternative embodiment is specifically referred to.

Bispecific Antigen-Binding Constructs that Bind HER2

Bispecific antigen-binding constructs that bind HER2 (also referred to as bispecific anti-HER2 antigen-binding constructs) are described below.

The term "antigen-binding construct" refers to an agent, e.g., polypeptide or polypeptide complex capable of binding to an antigen. In some aspects an antigen-binding construct is a polypeptide that specifically binds to an antigen of interest. An antigen-binding construct can be a monomer, dimer, multimer, a protein, a peptide, or a protein or peptide complex; an antibody, an antibody fragment, or an antigen-binding fragment thereof; an scFv and the like. An antigen-binding construct can be a polypeptide construct that is monospecific, bispecific, or multispecific. In some aspects, an antigen-binding construct can include, e.g., one or more antigen-binding components (e.g., Fabs or scFvs) linked to one or more Fc. Further examples of antigen-binding constructs are described below and provided in the Examples.

The term "bispecific" is intended to include any agent, e.g., an antigen-binding construct, which has two antigen-binding moieties (e.g. antigen-binding polypeptide constructs), each with a unique binding specificity. For example, a first antigen-binding moiety binds to an epitope on a first antigen, and a second antigen-binding moiety binds to an epitope on a second antigen. The term "biparatopic" as used herein, refers to a bispecific antibody where the first antigen-binding moiety and the second antigen-binding moiety bind to different epitopes on the same antigen. A biparatopic bispecific antibody may bind to two epitopes on the same antigen molecule, or it may bind to epitopes on two different antigen molecules.

A monospecific antigen-binding construct refers to an antigen-binding construct with one binding specificity. In other words, both antigen-binding moieties bind to the same epitope on the same antigen. Examples of monospecific antigen-binding constructs include trastuzumab and pertuzumab, which bind to HER2.

An antigen-binding construct can be an antibody or antigen-binding portion thereof. As used herein, an "antibody" or "immunoglobulin" refers to a polypeptide substantially encoded by an immunoglobulin gene or immunoglobulin genes, or fragments thereof, which specifically bind and recognize an analyte (e.g., antigen). The recognized immunoglobulin genes include the kappa, lambda, alpha, gamma, delta, epsilon and mu constant region genes, as well as the myriad immunoglobulin variable region genes. Light chains are classified as either kappa or lambda. The "class" of an antibody or immunoglobulin refers to the type of constant domain or constant region possessed by its heavy chain. There are five major classes of antibodies: IgA, IgD, IgE, IgG, and IgM, and several of these may be further divided into subclasses (isotypes), e.g., $IgG_1$, $IgG_2$, $IgG_3$, $IgG_4$, $IgA_1$, and $IgA_2$. The heavy chain constant domains that correspond to the different classes of immunoglobulins are called α, δ, ε, γ, and μ, respectively.

An exemplary immunoglobulin (antibody) structural unit is composed of two pairs of polypeptide chains, each pair having one "light" (about 25 kD) and one "heavy" chain (about 50-70 kD). The N-terminal domain of each chain defines a variable region of about 100 to 110 or more amino acids primarily responsible for antigen recognition. The terms variable light chain (VL) and variable heavy chain (VH) refer to these light and heavy chain domains respectively. The IgG1 heavy chain comprises of the VH, CH1, CH2 and CH3 domains respectively from the N to C-terminus. The light chain comprises of the VL and CL domains from N to C terminus. The IgG1 heavy chain comprises a hinge between the CH1 and CH2 domains. In certain embodiments, the immunoglobulin constructs comprise at least one immunoglobulin domain from IgG, IgM, IgA, IgD, or IgE connected to a therapeutic polypeptide. In some embodiments, the immunoglobulin domain found in an antigen-binding construct provided herein, is from or derived from an immunoglobulin based construct such as a diabody, or a nanobody. In certain embodiments, the immunoglobulin constructs described herein comprise at least one immunoglobulin domain from a heavy chain antibody such as a camelid antibody. In certain embodiments, the immunoglobulin constructs provided herein comprise at least one immunoglobulin domain from a mammalian antibody such as a bovine antibody, a human antibody, a camelid antibody, a mouse antibody or any chimeric antibody.

A "complementarity determining region" or "CDR" is an amino acid sequence that contributes to antigen-binding specificity and affinity. "Framework" regions (FR) can aid in maintaining the proper conformation of the CDRs to promote binding between the antigen-binding region and an antigen. Structurally, framework regions can be located in antibodies between CDRs. The variable regions typically exhibit the same general structure of relatively conserved framework regions (FR) joined by three hyper variable regions, also known as CDRs. The CDRs from the variable domains of the heavy chain and light chain typically are aligned by the framework regions, which can enable binding to a specific epitope. From N-terminal to C-terminal, both light and heavy chain variable domains typically comprise the domains FR1, CDR1, FR2, CDR2, FR3, CDR3, and FR4. The assignment of amino acids to each domain is typically in accordance with the definitions of Kabat Sequences of Proteins of Immunological Interest (National Institutes of Health, Bethesda, Md. (1987 and 1991)), unless stated otherwise. Typically, there are three heavy chain and three light chain CDRs (or CDR regions) in the variable portion of an immunoglobulin. The three heavy chain CDRs are referred to herein as CDRH1, CDRH2, and CDRH3, while the three light chain CDRs are referred to as CDRL1, CDRL2, and CDRL3. Thus, "CDRs" as used herein may refer to all three heavy chain CDRs, or all three light chain CDRs (or both all heavy and all light chain CDRs, if appropriate). CDRs provide the majority of contact residues for the binding of the antibody to the antigen or epitope. Often, the three heavy chain CDRs and the three light chain CDRs are required to bind antigen. However, in some instances, even a single variable domain can confer binding specificity to the antigen. Furthermore, as is known in the art, in some cases, antigen-binding may also occur through a combination of a minimum of one or more CDRs selected from the VH and/or VL domains, for example CDRH3.

A number of different definitions of the CDR sequences are in common use, including those described by Kabat et al. (1983, *Sequences of Proteins of Immunological Interest*, NIH Publication No. 369-847, Bethesda, MD), by Chothia et al. (1987, *J Mol Biol*, 196:901-917), as well as the IMGT, AbM (University of Bath) and Contact (MacCallum R. M., and Martin A. C. R. and Thornton J. M, (1996), Journal of Molecular Biology, 262 (5), 732-745) definitions. By way of example, CDR definitions according to Kabat, Chothia, IMGT, AbM and Contact are provided in Table 1 below. Accordingly, as would be readily apparent to one skilled in the art, the exact numbering and placement of CDRs may differ based on the numbering system employed. However, it is to be understood that the disclosure herein of a VH includes the disclosure of the associated (inherent) heavy chain CDRs (HCDRs) as defined by any of the known numbering systems. Similarly, disclosure herein of a VL includes the disclosure of the associated (inherent) light chain CDRs (LCDRs) as defined by any of the known numbering systems.

TABLE 1

Common CDR Definitions[1]

| | Heavy Chain | | | Light Chain | | |
|---|---|---|---|---|---|---|
| Definition | CDR1[2] | CDR2 | CDR3 | CDR1 | CDR2 | CDR3 |
| Kabat | H31-H35B | H50-H65 | H95-H102 | L24-L34 | L50-L56 | L89-L97 |
| Chothia | H26-H32, H33 or H34 | H52-H56 | H95-H102 | L24-L34 | L50-L56 | L89-L97 |
| IMGT | H26-H33, H34, H35, H35A or H35B | H51-H57 | H93-H102 | L27-L32 | L50-L52 | L89-L97 |
| AbM | H26-H35B | H50-H58 | H95-H102 | L24-L34 | L50-L56 | L89-L97 |
| Contact | H30-H35B | H47-H58 | H93-H101 | L30-L36 | L46-L55 | L89-L96 |

[1]Either the Kabat or Chothia numbering system may be used for HCDR2, HCDR3 and the light chain CDRs for all definitions except Contact, which uses Chothia numbering
[2]Using Kabat numbering. The position in the Kabat numbering scheme that demarcates the end of the Chothia and IMGT CDR-H1 loop varies depending on the length of the loop because Kabat places insertions outside of those CDR definitions at positions 35A and 35B. However, the IMGT and Chothia CDR-H1 loop can be unambiguously defined using Chothia numbering. CDR-H1 definitions using Chothia numbering: Kabat H31-H35, Chothia H26-H32, AbM H26-H35, IMGT H26-H33, Contact H30-H35.

As used herein, the term "single-chain" refers to a molecule comprising amino acid monomers linearly linked by peptide bonds. In certain embodiments, one of the antigen-binding polypeptide constructs is a single-chain FIT molecule (scFv). As described in more detail herein, an scFv has a variable domain of light chain (VL) connected from its C-terminus to the N-terminal end of a variable domain of heavy chain (VH) by a polypeptide chain. Alternatively, the scFv may be a polypeptide chain wherein the C-terminal end of the VH is connected to the N-terminal end of VL by a polypeptide chain.

Antigen-Binding Polypeptide Construct

The bispecific anti-HER2 antigen-binding construct comprises two antigen-binding polypeptide constructs that each bind to a particular domain or epitope of HER2. In one embodiment, each antigen-binding polypeptide construct binds to an extracellular domain of HER2, e.g., ECD2, or ECD4. The antigen-binding polypeptide construct can be, e.g., a Fab, or an scFv, depending on the application.

The format of the bispecific anti-HER2 antigen-binding construct determines the functional characteristics of the bispecific anti-HER2 antigen-binding construct. In one embodiment, the bispecific anti-HER2 antigen-binding construct has an scFv-Fab format (i.e. one antigen-binding polypeptide construct is an scFv and the other antigen-binding polypeptide construct is a Fab, also referred to as Fab-scFv format). In another embodiment, the bispecific anti-HER2 antigen-binding construct has an scFv-scFv format (i.e. both antigen-binding polypeptide constructs are scFvs).

The "Fab fragment" (also referred to as fragment antigen-binding) contains the constant domain (CL) of the light chain and the first constant domain (CH1) of the heavy chain along with the variable domains VL and VH on the light and heavy chains respectively. The variable domains comprise the complementarity determining loops (CDR, also referred to as hypervariable region) that are involved in antigen-binding. Fab' fragments differ from Fab fragments by the addition of a few residues at the carboxy terminus of the heavy chain CH1 domain including one or more cysteines from the antibody hinge region.

The "Single-chain Fv" or "scFv" includes the VH and VL domains of an antibody, wherein these domains are present in a single polypeptide chain. In one embodiment, the Fv polypeptide further comprises a polypeptide linker between the VH and VL domains which enables the scFv to form the desired structure for antigen-binding. For a review of scFv see Pluckthun in *The Pharmacology of Monoclonal Antibodies*, vol. 113, Rosenburg and Moore eds., Springer-Verlag, New York, pp. 269-315 (1994). HER2 antibody scFv fragments are described in WO93/16185; U.S. Pat. Nos. 5,571,894; and 5,587,458.

Format and Function of Antigen-Binding Constructs

Provided herein are bispecific anti-HER2 antigen-binding constructs having two antigen-binding polypeptide constructs, the first of which specifically binds to HER2 ECD2, and the second of which specifically binds to HER2 ECD4. The format of the bispecific anti-HER2 antigen-binding construct is such that at least one of the first or the second antigen-binding polypeptide is an scFv. The format of the bispecific anti-HER2 antigen-binding construct may be scFv-scFv, or Fab-scFv or scFv-Fab (first antigen-binding polypeptide construct-second antigen-binding polypeptide respectively).

In certain embodiments, the bispecific anti-HER2 antigen-binding constructs exhibit anti-tumor activities in vitro, such as (i) the ability to inhibit cancer cell growth both in the presence or absence of stimulation by epidermal growth factor or heregulin, (ii) the ability to be internalized in cancer cells (through binding to the HER2 antigen and causing it to be internalized) and (iii) the ability to mediate antibody-directed effector cell killing (ADCC). These in vitro activities are observed both with the naked bispecific anti-HER2 antigen-binding construct, and with the bispecific anti-HER2 antigen-binding construct conjugated to an auristatin analogue, and at varying levels of HER2 expression (1+, 2+ and 3+).

The format (scFv/scFv, scFv/Fab or Fab/Fab) of the bispecific anti-HER2 antigen-binding constructs is important in determining its functional profile as described in International Patent Publication No. WO2015/077891. In certain embodiments, the anti-HER2 binding constructs exhibit an increased ability to be internalized by HER2-expressing tumor cells compared to a reference antigen-binding construct in which both the ECD2- and ECD4-binding polypeptide constructs are Fabs. It is contemplated that the degree of internalization of the bispecific anti-HER2 antigen-binding constructs can be further improved by increasing the affinity of one or both antigen-binding polypeptide construct for ECD2 or ECD4. In one embodiment in which the ECD2-binding polypeptide is a Fab and the ECD4-binding polypeptide is a scFv, the construct is internalized to a greater extent compared to constructs of equivalent affinity that have a Fab/Fab format, and is internalized to a similar extent as constructs of equivalent affinity that have a scFv/scFv format, by high and low HER2 expressing tumor cells. Embodiments that are readily internalized are good candidates for antibody-drug conjugates, which require internalization by a tumor cell to effect killing. Conversely, in certain embodiments, bispecific anti-HER2 antigen-binding constructs which are not as readily internalized exhibit an increased potency in ADCC killing of tumor cells that express low levels of HER2 compared to constructs of equivalent affinity that have a Fab/Fab format. In one embodiment, a bispecific anti-HER2 antigen-binding construct having a Fab/scFv format is more potent in ADCC killing of tumor cells expressing low levels of HER2 (HER2 0-1+ or 1+) than an anti-HER2 construct having a Fab/Fab format, which in turn is more potent than a bispecific anti-HER2 antigen-binding construct having a scFv/scFv format. The enhanced ADCC potency of some embodiments may be due to 1) their increased ability to avidly bind cells with low HER2 receptor density and subsequently to cluster the HER2 receptor on the target cell surface and mediate downstream cell-mediated killing; and/or 2) their increased ability to remain on the cell surface (rather than causing internalization); hence they are more available for cell-mediated effector killing.

HER2

The bispecific anti-HER2 antigen-binding constructs described herein comprise antigen-binding polypeptide constructs that bind to ECD2 and ECD4 of HER2.

The expressions "ErbB2" and "HER2" are used interchangeably herein and refer to human HER2 protein described, for example, in Semba et al., *PNAS (USA)* 82:6497-6501 (1985) and Yamamoto et al. *Nature* 319:230-234 (1986) (Genebank accession number X03363). The term "erbB2" and "neu" refers to the gene encoding human ErbB2 protein. p185 or p185neu refers to the protein product of the neu gene.

HER2 is a HER receptor. A "HER receptor" is a receptor protein tyrosine kinase which belongs to the human epidermal growth factor receptor (HER) family and includes EGFR, HER2, HER3 and HER4 receptors. A HER receptor will generally comprise an extracellular domain, which may bind an HER ligand; a lipophilic transmembrane domain; a conserved intracellular tyrosine kinase domain; and a carboxyl-terminal signaling domain harboring several tyrosine residues which can be phosphorylated. By "HER ligand" is meant a polypeptide which binds to and/or activates an HER receptor.

The extracellular (ecto) domain of HER2 comprises four domains, Domain I (ECD1, amino acid residues from about 1-195), Domain II (ECD2, amino acid residues from about 196-319), Domain III (ECD3, amino acid residues from about 320-488), and Domain IV (ECD4, amino acid residues from about 489-630) (residue numbering without signal peptide). See Garrett et al. *Mol. Cell.* 11: 495-505 (2003), Cho et al. *Nature* 421: 756-760 (2003), Franklin et al. *Cancer Cell* 5:317-328 (2004), Tse et al. Cancer Treat Rev.

2012 April; 38(2):133-42 (2012), or Plowman et al. *Proc. Natl. Acad. Sci.* 90:1746-1750 (1993).

The sequence of HER2 is as follows; ECD boundaries are Domain I: 1-165; Domain II: 166-322; Domain III: 323-488; Domain IV: 489-607.

moiety to an unrelated protein is less than about 10% of the binding of the bispecific anti-HER2 antigen-binding construct to the antigen as measured, e.g., by SPR. In certain embodiments, a bispecific anti-HER2 antigen-binding construct that binds to the antigen, or an antigen-binding mol-

```
                                                       (SEQ ID NO: 1)
  1 tqvctgtdmk lrlpaspeth ldmlrhlyqg cqvvqgnlel tylptnasls flgdigevqg 61 yvliahnqvr qvplqrlriv rgtqlfedny alavldngdp lnnttpvtga spgglrelql 121 rslteilkgg vliqrnpqlc yqdtilwkdi fhknnqlalt lidtnrsrac hpcspmckgs 181 rcwgessedc qsltrtvcag gcarckgplp tdccheqcaa gctgpkhsdc laclhfnhsg 241 icelhcpalv tyntdtfesm pnpegrytfg ascvtacpyn ylstdvgsct lvcplhngev 301 taedgtqrce kcskpcarvc yglgmehlre vravtsaniq efagckkifg slaflpesfd 361 gdpasntapl gpeqlqvfet leeitgylyi sawpdslpdl svfqnlqvir grilhngays 421 ltlqglgisw lglrslrelg sglalihhnt hlcfvhtvpw dqlfrnphqa llhtanrped 481 ecvgeglach qlcarghcwg pgptqcvncs qflrggecve ecrvlqglpr eyvnarhclp 541 chpecqpqng svtcfgpead qcvacahykd ppfcvarcps gvkpdlsymp iwkfpdeega 601 cqpcpin
```

The "epitope 2C4" is the region in the extracellular domain of HER2 to which the antibody 2C4 binds. Epitope 2C4 comprises residues from domain II in the extracellular domain of HER2. 2C4 and Pertuzumab bind to the extracellular domain of HER2 at the junction of domains I, II and III. Franklin et al. *Cancer Cell* 5:317-328 (2004). In order to screen for antibodies which bind to the 2C4 epitope, a routine cross-blocking assay such as that described in *Antibodies, A Laboratory Manual*, Cold Spring Harbor Laboratory, Ed Harlow and David Lane (1988), can be performed. Alternatively, epitope mapping can be performed to assess whether the antibody binds to the 2C4 epitope of HER2 using methods known in the art and/or one can study the antibody-HER2 structure (Franklin et al. *Cancer Cell* 5:317-328 (2004)) to see what domain(s) of HER2 is/are bound by the antibody.

The "epitope 4D5" is the region in the extracellular domain of HER2 to which the antibody 4D5 (ATCC CRL 10463) and Trastuzumab bind. This epitope is close to the transmembrane domain of HER2, and within Domain IV of HER2. To screen for antibodies which bind to the 4D5 epitope, a routine cross-blocking assay such as that described in *Antibodies, A Laboratory Manual*, Cold Spring Harbor Laboratory, Ed Harlow and David Lane (1988), can be performed. Alternatively, epitope mapping can be performed to assess whether the antibody binds to the 4D5 epitope of HER2 (e.g. any one or more residues in the region from about residue 529 to about residue 625, inclusive, see FIG. 1 of US Patent Publication No. 2006/0018899).

"Specifically binds", "specific binding" or "selective binding" means that the binding is selective for the antigen and can be discriminated from unwanted or non-specific interactions. The ability of a bispecific anti-HER2 antigen-binding construct to bind to a specific antigenic determinant can be measured either through an enzyme-linked immunosorbent assay (ELISA) or other techniques familiar to one of skill in the art, e.g. surface plasmon resonance (SPR) technique (analyzed on a BIAcore instrument) (Liljeblad et al, Glyco J 17, 323-329 (2000)), and traditional binding assays (Heeley, Endocr Res 28, 217-229 (2002)). In one embodiment, the extent of binding of an antigen-binding moiety to an unrelated protein is less than about 10% of the binding of the bispecific anti-HER2 antigen-binding construct to the antigen as measured, e.g., by SPR. In certain embodiments, a bispecific anti-HER2 antigen-binding construct that binds to the antigen, or an antigen-binding molecule comprising that antigen-binding moiety, has a dissociation constant ($K_D$) of <1 µM, <100 nM, <10 nM, <1 nM, <0.1 nM, <0.01 nM, or <0.001 nM (e.g. $10^{-8}$ M or less, e.g. from $10^{-8}$ M to $10^{-13}$ M, e.g., from $10^{-9}$ M to $10^{-13}$ M).

"Heregulin" (HRG) when used herein refers to a polypeptide encoded by the heregulin gene product as disclosed in U.S. Pat. No. 5,641,869 or Marchionni et al., Nature, 362:312-318 (1993). Examples of heregulins include heregulin-α, heregulin-β1, heregulin-β2 and heregulin-β3 (Holmes et al., Science, 256:1205-1210 (1992); and U.S. Pat. No. 5,641,869); neu differentiation factor (NDF) (Peles et al. Cell 69: 205-216 (1992)); acetylcholine receptor-inducing activity (ARIA) (Falls et al. Cell 72:801-815 (1993)); glial growth factors (GGFs) (Marchionni et al., Nature, 362:312-318 (1993)); sensory and motor neuron derived factor (SMDF) (Ho et al. J. Biol. Chem. 270:14523-14532 (1995)); γ-heregulin (Schaefer et al. Oncogene 15:1385-1394 (1997)). The term includes biologically active fragments and/or amino acid sequence variants of a native sequence HRG polypeptide, such as an EGF-like domain fragment thereof (e.g. HRGβ1177-244).

"HER activation" or "HER2 activation" refers to activation, or phosphorylation, of any one or more HER receptors, or HER2 receptors. Generally, HER activation results in signal transduction (e.g. that caused by an intracellular kinase domain of a HER receptor phosphorylating tyrosine residues in the HER receptor or a substrate polypeptide). HER activation may be mediated by HER ligand binding to a HER dimer comprising the HER receptor of interest. HER ligand binding to a HER dimer may activate a kinase domain of one or more of the HER receptors in the dimer and thereby results in phosphorylation of tyrosine residues in one or more of the HER receptors and/or phosphorylation of tyrosine residues in additional substrate polypeptides(s), such as Akt or MAPK intracellular kinases.

"Humanized" forms of non-human (e.g., rodent) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. For further details, see Jones et al., Nature 321:522-525 (1986); Riechmann et al., Nature 332:323-329 (1988); and Presta, Curr. Op. Struct. Biol. 2:593-596 (1992).

Fc of Bispecific Anti-HER2 Antigen-Binding Constructs.

In some embodiments, the bispecific anti-HER2 antigen-binding constructs described herein comprise an Fc, e.g., a dimeric Fc.

The term "Fc domain" or "Fc region" herein is used to define a C-terminal region of an immunoglobulin heavy chain that contains at least a portion of the constant region. The term includes native sequence Fc regions and variant Fc regions. Unless otherwise specified herein, numbering of amino acid residues in the Fc region or constant region is according to the EU numbering system, also called the EU index, as described in Kabat et al, Sequences of Proteins of Immunological Interest, 5th Ed. Public Health Service, National Institutes of Health, Bethesda, M D, 1991. An "Fc polypeptide" of a dimeric Fc as used herein refers to one of the two polypeptides forming the dimeric Fc domain, i.e. a polypeptide comprising C-terminal constant regions of an immunoglobulin heavy chain, capable of stable self-association. For example, an Fc polypeptide of a dimeric IgG Fc comprises an IgG CH2 and an IgG CH3 constant domain sequence.

An Fc domain comprises either a CH3 domain or a CH3 and a CH2 domain. The CH3 domain comprises two CH3 sequences, one from each of the two Fc polypeptides of the dimeric Fc. The CH2 domain comprises two CH2 sequences, one from each of the two Fc polypeptides of the dimeric Fc.

In some aspects, the Fc comprises at least one or two CH3 sequences. In some aspects, the Fc is coupled, with or without one or more linkers, to a first antigen-binding polypeptide construct and/or a second antigen-binding polypeptide construct. In some aspects, the Fc is a human Fc. In some aspects, the Fc is a human IgG or IgG1 Fc. In some aspects, the Fc is a heterodimeric Fc. In some aspects, the Fc comprises at least one or two CH2 sequences.

In some aspects, the Fc comprises one or more modifications in at least one of the CH3 sequences. In some aspects, the Fc comprises one or more modifications in at least one of the CH2 sequences. In some aspects, an Fc is a single polypeptide. In some aspects, an Fc is multiple peptides, e.g., two polypeptides.

In some aspects, an Fc is an Fc described in patent applications PCT/CA2011/001238, filed Nov. 4, 2011 or PCT/CA2012/050780, filed Nov. 2, 2012.

Modified CH3 Domains

In some aspects, the bispecific anti-HER2 antigen-binding construct described herein comprises a heterodimeric Fc comprising a modified CH3 domain that has been asymmetrically modified. The heterodimeric Fc can comprise two heavy chain constant domain polypeptides: a first Fc polypeptide and a second Fc polypeptide, which can be used interchangeably provided that Fc comprises one first Fc polypeptide and one second Fc polypeptide. Generally, the first Fc polypeptide comprises a first CH3 sequence and the second Fc polypeptide comprises a second CH3 sequence.

Two CH3 sequences that comprise one or more amino acid modifications introduced in an asymmetric fashion generally results in a heterodimeric Fc, rather than a homodimer, when the two CH3 sequences dimerize. As used herein, "asymmetric amino acid modifications" refers to any modification where an amino acid at a specific position on a first CH3 sequence is different from the amino acid on a second CH3 sequence at the same position, and the first and second CH3 sequence preferentially pair to form a heterodimer, rather than a homodimer. This heterodimerization can be a result of modification of only one of the two amino acids at the same respective amino acid position on each sequence; or modification of both amino acids on each sequence at the same respective position on each of the first and second CH3 sequences. The first and second CH3 sequence of a heterodimeric Fc can comprise one or more than one asymmetric amino acid modification.

Table 2 provides the amino acid sequence of the human IgG1 Fc sequence, corresponding to amino acids 231 to 447 of the full-length human IgG1 heavy chain. The CH3 sequence comprises amino acid 341-447 of the full-length human IgG1 heavy chain.

Typically an Fc can include two contiguous heavy chain sequences (A and B) that are capable of dimerizing. In some aspects, one or both sequences of an Fc include one or more mutations or modifications at the following locations: L351, F405, Y407, T366, K392, T394, T350, S400, and/or N390, using EU numbering. In some aspects, an Fc includes a variant sequence shown in Table 2. In some aspects, an Fc includes the mutations of Variant 1 A-B. In some aspects, an Fc includes the mutations of Variant 2 A-B. In some aspects, an Fc includes the mutations of Variant 3 A-B. In some aspects, an Fc includes the mutations of Variant 4 A-B. In some aspects, an Fc includes the mutations of Variant 5 A-B.

TABLE 2

| IgG1 Fc sequences | | |
|---|---|---|
| Human IgG1 Fc sequence 231-447 (EU-numbering) | | APELLGGPSVFLFPPKPKDTLMISRTPEVTCVVVDVSHE DPEVKFNWYVDGVEVHNAKTKPREEQYNSTYRVVSVLTV LHQDWLNGKEYKCKVSNKALPAPIEKTISKAKGQPREPQ VYTLPPSRDELTKNQVSLTCLVKGFYPSDIAVEWESNGQ PENNYKTTPPVLDSDGSFFLYSKLTVDKSRWQQGNVFSC SVMHEALHNHYTQKSLSLSPGK (SEQ ID NO: 2) |
| Variant IgG1 Fc sequence (231-447) | Chain | Mutations |
| 1 | A | L351Y_F405A_Y407V |
| 1 | B | T366L_K392M_T394W |
| 2 | A | L351Y_F405A_Y407V |
| 2 | B | T366L_K392L_T394W |
| 3 | A | T350V_L351Y_F405A_Y407V |
| 3 | B | T350V_T366L_K392L_T394W |

TABLE 2-continued

IgG1 Fc sequences

| | | |
|---|---|---|
| 4 | A | T350V_L351Y_F405A_Y407V |
| 4 | B | T350V_T366L_K392M_T394W |
| 5 | A | T350V_L351Y_S400E_F405A_Y407V |
| 5 | B | T350V_T366L_N390R_K392M_T394W |

The first and second CH3 sequences can comprise amino acid mutations as described herein, with reference to amino acids 231 to 447 of the full-length human IgG1 heavy chain. In one embodiment, the heterodimeric Fc comprises a modified CH3 domain with a first CH3 sequence having amino acid modifications at positions F405 and Y407, and a second CH3 sequence having amino acid modifications at position T394. In one embodiment, the heterodimeric Fc comprises a modified CH3 domain with a first CH3 sequence having one or more amino acid modifications selected from L351Y, F405A, and Y407V, and the second CH3 sequence having one or more amino acid modifications selected from T366L, T366I, K392L, K392M, and T394W.

In one embodiment, a heterodimeric Fc comprises a modified CH3 domain with a first CH3 sequence having amino acid modifications at positions L351, F405 and Y407, and a second CH3 sequence having amino acid modifications at positions T366, K392, and T394, and one of the first or second CH3 sequences further comprising amino acid modifications at position Q347, and the other CH3 sequence further comprising amino acid modification at position K360. In another embodiment, a heterodimeric Fc comprises a modified CH3 domain with a first CH3 sequence having amino acid modifications at positions L351, F405 and Y407, and a second CH3 sequence having amino acid modifications at position T366, K392, and T394, one of the first or second CH3 sequences further comprising amino acid modifications at position Q347, and the other CH3 sequence further comprising amino acid modification at position K360, and one or both of said CH3 sequences further comprise the amino acid modification T350V.

In one embodiment, a heterodimeric Fc comprises a modified CH3 domain with a first CH3 sequence having amino acid modifications at positions L351, F405 and Y407, and a second CH3 sequence having amino acid modifications at positions T366, K392, and T394 and one of said first and second CH3 sequences further comprising amino acid modification of D399R or D399K and the other CH3 sequence comprising one or more of T411E, T411D, K409E, K409D, K392E and K392D. In another embodiment, a heterodimeric Fc comprises a modified CH3 domain with a first CH3 sequence having amino acid modifications at positions L351, F405 and Y407, and a second CH3 sequence having amino acid modifications at positions T366, K392, and T394, one of said first and second CH3 sequences further comprises amino acid modification of D399R or D399K and the other CH3 sequence comprising one or more of T411E, T411D, K409E, K409D, K392E and K392D, and one or both of said CH3 sequences further comprise the amino acid modification T350V.

In one embodiment, a heterodimeric Fc comprises a modified CH3 domain with a first CH3 sequence having amino acid modifications at positions L351, F405 and Y407, and a second CH3 sequence having amino acid modifications at positions T366, K392, and T394, wherein one or both of said CH3 sequences further comprise the amino acid modification of T350V.

In one embodiment, a heterodimeric Fc comprises a modified CH3 domain comprising the following amino acid modifications, where "A" represents the amino acid modifications to the first CH3 sequence, and "B" represents the amino acid modifications to the second CH3 sequence: A:L351Y_F405A_Y407V, B:T366L_K392M_T394W, A:L351Y_F405A_Y407V, B:T366L_K392L_T394W, A:T350V_L351Y_F405A_Y407V, B:T350V_T366V_T366L_L392L_T394W, A3350V_L351Y_F405A_Y407V, B:1350V_T366L_K392M_T394W, A:T350V_L351Y_S400E_F405A_Y407V, and/or B1350V_T366L_N390R_K392M_T394W.

The one or more asymmetric amino acid modifications can promote the formation of a heterodimeric Fc in which the heterodimeric CH3 domain has a stability that is comparable to a wild-type homodimeric CH3 domain. In an embodiment, the one or more asymmetric amino acid modifications promote the formation of a heterodimeric Fc domain in which the heterodimeric Fc domain has a stability that is comparable to a wild-type homodimeric Fc domain. In an embodiment, the one or more asymmetric amino acid modifications promote the formation of a heterodimeric Fc domain in which the heterodimeric Fc domain has a stability observed via the melting temperature (Tm) in a differential scanning calorimetry study, and where the melting temperature is within 4° C. of that observed for the corresponding symmetric wild-type homodimeric Fc domain. In some aspects, the Fc comprises one or more modifications in at least one of the CH3 sequences that promote the formation of a heterodimeric Fc with stability comparable to a wild-type homodimeric Fc.

Exemplary Bispecific Anti-HER2 Antigen-Binding Constructs

In certain embodiments, the bispecific anti-HER2 antigen-binding construct is one of the biparatopic antibodies described in U.S. Patent Application Publication No. 2016/0289335 or International Patent Publication No. WO2015/077891. In some embodiments, the bispecific anti-HER2 antigen-binding construct is one of v5019, v5020, v7091, v10000, v6902, v6903 or v6717 (see Tables 3, 4, 5, and Sequence Tables). In some embodiments, one of the antigen-binding polypeptide constructs of the bispecific anti-HER2 antigen-binding construct comprises a VH sequence and a VL sequence from the ECD2-binding arm of one of v5019, v5020, v7091, v10000, v6902, v6903 or v6717. In some embodiments, one of the antigen-binding polypeptide constructs of the bispecific anti-HER2 antigen-binding construct comprises a VH sequence and a VL sequence from the ECD2-binding arm of one of v5019, v5020, v7091, v10000, v6902, v6903 or v6717, and the other antigen-binding polypeptide construct comprises a VH sequence and a VL sequence from the ECD4-binding arm of one of v5019, v5020, v7091, v10000, v6902, v6903 or v6717.

In some embodiments, one of the antigen-binding polypeptide constructs of the bispecific anti-HER2 antigen-binding construct comprises the CDR sequences from the ECD2-binding arm of one of v5019, v5020, v7091, v10000, v6902, v6903 or v6717. In some embodiments, one of the antigen-binding polypeptide constructs of the bispecific anti-HER2 antigen-binding construct comprises the CDR sequences from the ECD2-binding arm of one of v5019, v5020, v7091, v10000, v6902, v6903 or v6717, and the other antigen-binding polypeptide construct comprises the CDR sequences from the ECD4-binding arm of one of v5019, v5020, v7091, v10000, v6902, v6903 or v6717.

One skilled in the art will appreciate that a limited number of amino acid substitutions may be introduced into the CDR sequences or to the VH or VL sequences of known antibodies without the antibody losing its ability to bind its target. Candidate amino acid substitutions may be identified by computer modeling or by art-known techniques such as alanine scanning, with the resulting variants being tested for binding activity by standard techniques. Accordingly, in certain embodiments, one of the antigen-binding polypeptide constructs of the bispecific anti-HER2 antigen-binding construct comprises a set of CDRs (i.e. heavy chain CDR1, CDR2 and CDR3, and light chain CDR1, CDR2 and CDR3) that have 90% or greater, 95% or greater, 98% or greater, 99% or greater, or 100% sequence identity to a set of CDRs from the ECD2-binding arm of one of v5019, v5020, v7091, v10000, v6902, v6903 or v6717, wherein the antigen-binding polypeptide construct retains the ability to bind ECD2. In certain embodiments, one of the antigen-binding polypeptide constructs of the bispecific anti-HER2 antigen-binding construct comprises a variant of these CDR sequences comprising between 1 and 10 amino acid substitutions across the six CDRs (that is, the CDRs may be modified by including up to 10 amino acid substitutions with any combination of CDRs being modified), for example, between 1 and 7 amino acid substitutions, between 1 and 5 amino acid substitutions, between 1 and 4 amino acid substitutions, between 1 and 3 amino acid substitutions, between 1 and 2 amino acid substitutions, or 1 amino acid substitution, across the CDRs, wherein the variant retains the ability to bind ECD2. Typically, such amino acid substitutions will be conservative amino acid substitutions. In certain embodiments, one of the antigen-binding polypeptide constructs of the bispecific anti-HER2 antigen-binding construct comprises a set of CDRs (i.e. heavy chain CDR1, CDR2 and CDR3, and light chain CDR1, CDR2 and CDR3) that have 90% or greater, 95% or greater, 98% or greater, 99% or greater, or 100% sequence identity to a set of CDRs from the ECD2-binding arm of v10000, wherein the antigen-binding polypeptide construct retains the ability to bind ECD2.

In certain embodiments, one of the antigen-binding polypeptide constructs of the bispecific anti-HER2 antigen-binding construct comprises a VH sequence that is at least 80%, at least 85%, at least 90%, at least 91%, at least 92%, at least 93%, at least 94%, at least 95%, at least 96%, at least 97%, at least 98%, at least 99%, or 100% identical to the VH sequence from the ECD2-binding arm of one of v5019, v5020, v7091, v10000, v6902, v6903 or v6717, wherein the antigen-binding polypeptide construct retains the ability to bind ECD2. In some embodiments, one of the antigen-binding polypeptide constructs of the bispecific anti-HER2 antigen-binding construct comprises a VL sequence that is at least 80%, at least 85%, at least 90%, at least 91%, at least 92%, at least 93%, at least 94%, at least 95%, at least 96%, at least 97%, at least 98%, at least 99%, or 100% identical to the VL sequence from the ECD2-binding arm of one of v5019, v5020, v7091, v10000, v6902, v6903 or v6717, wherein the antigen-binding polypeptide construct retains the ability to bind ECD2.

In certain embodiments, one of the antigen-binding polypeptide constructs of the bispecific anti-HER2 antigen-binding construct comprises a VH sequence that is at least 80%, at least 85%, at least 90%, at least 91%, at least 92%, at least 93%, at least 94%, at least 95%, at least 96%, at least 97%, at least 98%, at least 99%, or 100% identical to the VH sequence from the ECD2-binding arm of v10000, wherein the antigen-binding polypeptide construct retains the ability to bind ECD2. In some embodiments, one of the antigen-binding polypeptide constructs of the bispecific anti-HER2 antigen-binding construct comprises a VL sequence that is at least 80%, at least 85%, at least 90%, at least 91%, at least 92%, at least 93%, at least 94%, at least 95%, at least 96%, at least 97%, at least 98%, at least 99%, or 100% identical to the VL sequence from the ECD2-binding arm of v10000, wherein the antigen-binding polypeptide construct retains the ability to bind ECD2.

In certain embodiments, one of the antigen-binding polypeptide constructs of the bispecific anti-HER2 antigen-binding construct comprises a set of CDRs (i.e. heavy chain CDR1, CDR2 and CDR3, and light chain CDR1, CDR2 and CDR3) that have 90% or greater, 95% or greater, 98% or greater, 99% or greater, or 100% sequence identity to a set of CDRs from the ECD4-binding arm of one of v5019, v5020, v7091, v10000, v6902, v6903 or v6717, wherein the antigen-binding polypeptide construct retains the ability to bind ECD4. In certain embodiments, one of the antigen-binding polypeptide constructs of the bispecific anti-HER2 antigen-binding construct comprises a variant of these CDR sequences comprising between 1 and 10 amino acid substitutions across the six CDRs (that is, the CDRs may be modified by including up to 10 amino acid substitutions with any combination of CDRs being modified), for example, between 1 and 7 amino acid substitutions, between 1 and 5 amino acid substitutions, between 1 and 4 amino acid substitutions, between 1 and 3 amino acid substitutions, between 1 and 2 amino acid substitutions, or 1 amino acid substitution, across the CDRs, wherein the variant retains the ability to bind ECD4. Typically, such amino acid substitutions will be conservative amino acid substitutions. In certain embodiments, one of the antigen-binding polypeptide constructs of the bispecific anti-HER2 antigen-binding construct comprises a set of CDRs (i.e. heavy chain CDR1, CDR2 and CDR3, and light chain CDR1, CDR2 and CDR3) that have 90% or greater, 95% or greater, 98% or greater, 99% or greater, or 100% sequence identity to a set of CDRs from the ECD4-binding arm of v10000, wherein the antigen-binding polypeptide construct retains the ability to bind ECD4.

In certain embodiments, one of the antigen-binding polypeptide constructs of the bispecific anti-HER2 antigen-binding construct comprises a VH sequence that is at least 80%, at least 85%, at least 90%, at least 91%, at least 92%, at least 93%, at least 94%, at least 95%, at least 96%, at least 97%, at least 98%, at least 99%, or 100% identical to the VH sequence from the ECD4-binding arm of one of v5019, v5020, v7091, v10000, v6902, v6903 or v6717, wherein the antigen-binding polypeptide construct retains the ability to bind ECD4. In some embodiments, one of the antigen-binding polypeptide constructs of the bispecific anti-HER2 antigen-binding construct comprises a VL sequence that is at least 80%, at least 85%, at least 90%, at least 91%, at least 92%, at least 93%, at least 94%, at least 95%, at least 96%, at least 97%, at least 98%, at least 99%, or 100% identical to the VL sequence from the ECD4-binding arm of one of v5019, v5020, v7091, v10000, v6902, v6903 or v6717, wherein the antigen-binding polypeptide construct retains the ability to bind ECD4.

In certain embodiments, one of the antigen-binding polypeptide constructs of the bispecific anti-HER2 antigen-binding construct comprises a VH sequence that is at least 80%, at least 85%, at least 90%, at least 91%, at least 92%, at least 93%, at least 94%, at least 95%, at least 96%, at least 97%, at least 98%, at least 99%, or 100% identical to the VH sequence from the ECD4-binding arm of v10000, wherein the antigen-binding polypeptide construct retains the ability to bind ECD4. In some embodiments, one of the antigen-binding polypeptide constructs of the bispecific anti-HER2 antigen-binding construct comprises a VL sequence that is at least 80%, at least 85%, at least 90%, at least 91%, at least 92%, at least 93%, at least 94%, at least 95%, at least 96%, at least 97%, at least 98%, at least 99%, or 100% identical to the VL sequence from the ECD4-binding arm of v10000, wherein the antigen-binding polypeptide construct retains the ability to bind ECD4.

TABLE 3

Exemplary bispecific anti-HER2 antigen-binding constructs

| Variant | | Chain A | Chain B |
|---|---|---|---|
| 5019 | Domain containing target epitope | ECD2 | ECD4 |
| | Format | Fab | scFv |
| | Antibody name | Pertuzumab | Trastuzumab |
| | CH3 sequence substitutions§ | T350V_L351Y_F405A_Y407V | T366I_N390R_K392M_T394W |
| 5020 | Domain containing target epitope | ECD4 | ECD2 |
| | Format | scFv | Fab |
| | Antibody name | Trastuzumab | Pertuzumab |
| | CH3 sequence substitutions | L351Y_S400E_F405A_Y407V | T350V_T366L_K392L_T394W |
| 7091 | Domain containing target epitope | ECD2 | ECD4 |
| | Format | Fab | scFv |
| | Antibody name | Pertuzumab | Trastuzumab |
| | CH3 sequence substitutions | T350V_L351Y_F405A_Y407V | T350V_T366L_K392L_T394W |
| 10000 | Domain containing target epitope | ECD2 | ECD4 |
| | Format | Fab | scFv |
| | Antibody name | Pertuzumab | Trastuzumab |
| | Fab sequence substitutions* | HC: T30A_A49G_L69F LC: Y96A | |
| | CH3 sequence substitutions | T350V_L351Y_F405A_Y407V | T350V_T366L_K392L_T394W |
| 6902 | Domain containing target epitope | ECD4 | ECD2 |
| | Format | Fab | Fab |
| | Antibody name | Trastuzumab | Pertuzumab |
| | Fab sequence substitutions | HC: L143E_K145T LC: Q124R | HC: D146G_Q179K LC: Q124E Q160E T180E |
| | CH3 sequence substitutions | T350V_L351Y_F405A_Y407V | T350V_T366L_K392L_T394W |
| 6903 | Domain containing target epitope | ECD4 | ECD2 |
| | Format | Fab | Fab |
| | Fab sequence substitutions | HC: L143E_K145T LC: Q124R Q1160K T178R | HC: D146G_Q179K LC: Q124E Q160E T180E |
| | Antibody name | Trastuzumab | Pertuzumab |
| | CH3 sequence substitutions | T350V_L351Y_F405A_Y407V | T350V_T366L_K392L_T394W |
| 6717 | Domain containing target epitope | ECD2 | ECD4 |
| | Format | scFv | scFv |
| | Antibody name | Pertuzumab | Trastuzumab |
| | CH3 sequence substitutions | T350V_L351Y_F405A_Y407V | T366I_N390R_K392M_T394W |

*Fab or variable domain numbering according to Kabat (Kabat et al., Sequences of proteins of immunological interest, 5th Edition, US Department of Health and Human Services, NIH Publication No. 91-3242, p. 647, 1991)
§CH3 numbering according to EU index as in Kabat (Edelman et al., 1969, PNAS USA, 63: 78-85)

TABLE 4

CDR Sequences of the ECD2-Binding Arm of Variants v5019, v5020, v7091, v10000, v6902, v6903 and v6717 (identified using IMGT method[1])

| Variant | HC CDRs | SEQ ID NO | LC CDRs | SEQ ID NO |
|---|---|---|---|---|
| 5019, 5020, 7091, 6902, 6903 & 6717 | H1: GFTFTDYT | 6 | L1: QDVSIG | 12 |
|  | H2: VNPNSGGS | 8 | L2: SAS | 14 |
|  | H3: ARNLGPSFYFDY | 7 | L3: QQYYIYPYT | 13 |
| 10000 | H1: GFTFADYT | 39 | L1: QDVSIG | 27 |
|  | H2: VNPNSGGS | 41 | L2: SAS | 29 |
|  | H3: ARNLGPSFYFDY | 40 | L3: QQYYIYPAT | 28 |

[1]Lefranc M-P, Pommié C, Ruiz M, Giudicelli V, Foulquier E, Truong L, Thouvenin-Contet V, Lefranc G. 2003. IMGT unique numbering for immunoglobulin and T cell receptor variable domains and Ig superfamily V-like domains. Dev Comp Immunol 27: 55-77

TABLE 5

CDR Sequences of the ECD4-Binding Arm of Variants v5019, v5020, v7091, v10000, v6902, v6903 and v6717 (identified using IMGT method[1])

| HC CDRs | SEQ ID NO | LC CDRs | SEQ ID NO |
|---|---|---|---|
| H1: GFNIKDTY | 33 | L1: QDVNTA | 67 |
| H2: IYPTNGYT | 35 | L2: SAS | 68 |
| H3: SRWGGDGFYAMDY | 34 | L3: QQHYTTPPT | 69 |

[1]Lefranc M-P, et al, Supra.

Preparation of Bispecific Anti-HER2 Antigen-Binding Constructs

Bispecific anti-HER2 antigen-binding constructs described herein may be produced using recombinant methods and compositions, e.g., as described in U.S. Pat. No. 4,816,567 or International Patent Publication No. WO2015/077891.

In one embodiment, isolated nucleic acid encoding a bispecific anti-HER2 antigen-binding construct described herein is provided. Such nucleic acid may encode an amino acid sequence comprising the VL and/or an amino acid sequence comprising the VH of the bispecific anti-HER2 antigen-binding construct (e.g., the light and/or heavy chains of the antigen-binding construct). In a further embodiment, one or more vectors (e.g., expression vectors) comprising such nucleic acid are provided. As is known in the art, because many amino acid acids are encoded by more than one codon, multiple nucleic acids may encode a single polypeptide sequence. An exemplary nucleic acid is provided herein for each polypeptide of the bispecific anti-HER2 antigen-binding construct; however it is understood that other nucleic acids may be used to prepare the bispecific anti-HER2 antigen-binding construct described herein.

In one embodiment, the nucleic acid is provided in a multicistronic vector. In a further embodiment, a host cell comprising such nucleic acid is provided. In one such embodiment, a host cell comprises (e.g., has been transformed with): (1) a vector comprising a nucleic acid that encodes an amino acid sequence comprising the VL of the bispecific anti-HER2 antigen-binding construct and an amino acid sequence comprising the VH of the antigen-binding polypeptide construct, or (2) a first vector comprising a nucleic acid that encodes an amino acid sequence comprising the VL of the antigen-binding polypeptide construct and a second vector comprising a nucleic acid that encodes an amino acid sequence comprising the VH of the antigen-binding polypeptide construct. In one embodiment, the host cell is eukaryotic, e.g. a Chinese Hamster Ovary (CHO) cell, or human embryonic kidney (HEK) cell, or lymphoid cell (e.g., Y0, NS0, Sp20 cell). In one embodiment, a method of making a bispecific anti-HER2 antigen-binding construct is provided, wherein the method comprises culturing a host cell comprising nucleic acid encoding the bispecific anti-HER2 antigen-binding construct, as provided above, under conditions suitable for expression of the bispecific anti-HER2 antigen-binding construct, and optionally recovering the bispecific anti-HER2 antigen-binding construct from the host cell (or host cell culture medium).

For recombinant production of the bispecific anti-HER2 antigen-binding construct, nucleic acid encoding a bispecific anti-HER2 antigen-binding construct, e.g., as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the bispecific anti-HER2 antigen-binding construct).

The term "substantially purified" refers to a construct described herein, or variant thereof that may be substantially or essentially free of components that normally accompany or interact with the protein as found in its naturally occurring environment, i.e. a native cell, or host cell in the case of recombinantly produced bispecific anti-HER2 antigen-binding construct that in certain embodiments, is substantially free of cellular material includes preparations of protein having less than about 30%, less than about 25%, less than about 20%, less than about 15%, less than about 10%, less than about 5%, less than about 4%, less than about 3%, less than about 2%, or less than about 1% (by dry weight) of contaminating protein. When the bispecific anti-HER2 antigen-binding construct is recombinantly produced by the host cells, the protein in certain embodiments is present at about 30%, about 25%, about 20%, about 15%, about 10%, about 5%, about 4%, about 3%, about 2%, or about 1% or less of the dry weight of the cells. When the bispecific anti-HER2 antigen-binding construct is recombinantly produced by the host cells, the protein, in certain embodiments, is present in the culture medium at about 5 g/L, about 4 g/L, about 3 g/L, about 2 g/L, about 1 g/L, about 750 mg/L, about 500 mg/L, about 250 mg/L, about 100 mg/L, about 50 mg/L, about 10 mg/L, or about 1 mg/L or less of the dry weight of the cells. In certain embodiments, "substantially purified" bispecific anti-HER2 antigen-binding construct produced by the methods described herein, has a purity level of at least about 30%, at least about 35%, at least about 40%, at least about 45%, at least about 50%, at least about 55%, at least about 60%, at least about 65%, at least about 70%, specifically, a purity level of at least about 75%, 80%, 85%, and more specifically, a purity level of at least about 90%, a purity level of at least about 95%, a purity level of at least about 99% or greater as determined by appropriate methods such as SDS/PAGE analysis, RP-HPLC, SEC, and capillary electrophoresis.

Suitable host cells for cloning or expression of bispecific anti-HER2 antigen-binding construct-encoding vectors include prokaryotic or eukaryotic cells described herein.

A "recombinant host cell" or "host cell" refers to a cell that includes an exogenous polynucleotide, regardless of the method used for insertion, for example, direct uptake, transduction, f-mating, or other methods known in the art to create recombinant host cells. The exogenous polynucleotide may be maintained as a nonintegrated vector, for example, a plasmid, or alternatively, may be integrated into the host genome.

As used herein, the term "eukaryote" refers to organisms belonging to the phylogenetic domain Eucarya such as animals (including but not limited to, mammals, insects, reptiles, birds, etc.), ciliates, plants (including but not limited to, monocots, dicots, algae, etc.), fungi, yeasts, flagellates, microsporidia, protists, etc.

As used herein, the term "prokaryote" refers to prokaryotic organisms. For example, a non-eukaryotic organism can belong to the Eubacteria (including but not limited to, *Escherichia coli, Thermus thermophilus, Bacillus stearothermophilus, Pseudomonas fluorescens, Pseudomonas aeruginosa, Pseudomonas putida*, etc.) phylogenetic domain, or the Archaea (including but not limited to, *Methanococcus jannaschii, Methanobacterium thermoautotrophicum, Halobacterium* such as *Haloferax volcanii* and *Halobacterium* species NRC-1, *Archaeoglobus fulgidus, Pyrococcus furiosus, Pyrococcus horikoshii, Aeuropyrum pernix*, etc.) phylogenetic domain.

For example, bispecific anti-HER2 antigen-binding construct may be produced in bacteria, in particular when glycosylation and Fc effector function are not needed. For expression of bispecific anti-HER2 antigen-binding construct fragments and polypeptides in bacteria, see, e.g., U.S. Pat. Nos. 5,648,237, 5,789,199, and 5,840,523. (See also Charlton, *Methods in Molecular Biology*, Vol. 248 (B. K. C. Lo, ed., Humana Press, Totowa, N.J., 2003), pp. 245-254, describing expression of antibody fragments in *E. coli*) After expression, the bispecific anti-HER2 antigen-binding construct may be isolated from the bacterial cell paste in a soluble fraction and can be further purified.

In addition to prokaryotes, eukaryotic microbes such as filamentous fungi or yeast are suitable cloning or expression hosts for bispecific anti-HER2 antigen-binding construct-encoding vectors, including fungi and yeast strains whose glycosylation pathways have been "humanized," resulting in the production of a bispecific anti-HER2 antigen-binding construct with a partially or fully human glycosylation pattern. See Gerngross, *Nat. Biotech.* 22:1409-1414 (2004), and Li et al., *Nat. Biotech.* 24:210-215 (2006).

Suitable host cells for the expression of glycosylated bispecific anti-HER2 antigen-binding constructs are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells.

Plant cell cultures can also be utilized as hosts. See, e.g., U.S. Pat. Nos. 5,959,177, 6,040,498, 6,420,548, 7,125,978, and 6,417,429 (describing PLANTIBODIES™ technology for producing antigen-binding constructs in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al., *J. Gen Virol.* 36:59 (1977)); baby hamster kidney cells (BHK); mouse sertoli cells (TM4 cells as described, e.g., in Mather, *Biol. Reprod.* 23:243-251 (1980)); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather et al., *Annals N.Y. Acad. Sci.* 383:44-68 (1982); MRC 5 cells; and FS4 cells. Other useful mammalian host cell lines include Chinese hamster ovary (CHO) cells, including DHFR$^-$ CHO cells (Urlaub et al., *Proc. Natl. Acad. Sci. USA* 77:4216 (1980)); and myeloma cell lines such as Y0, NS0 and Sp2/0. For a review of certain mammalian host cell lines suitable for antigen-binding construct production, see, e.g., Yazaki and Wu, *Methods in Molecular Biology*, Vol. 248 (B. K. C. Lo, ed., Humana Press, Totowa, N.J.), pp. 255-268 (2003).

In one embodiment, the bispecific anti-HER2 antigen-binding constructs described herein are produced in stable mammalian cells, by a method comprising: transfecting at least one stable mammalian cell with: nucleic acid encoding the bispecific anti-HER2 antigen-binding construct, in a predetermined ratio; and expressing the nucleic acid in the at least one mammalian cell. In some embodiments, the predetermined ratio of nucleic acid is determined in transient transfection experiments to determine the relative ratio of input nucleic acids that results in the highest percentage of the bispecific anti-HER2 antigen-binding construct in the expressed product.

In some embodiments the bispecific anti-HER2 antigen-binding construct is produced in stable mammalian cells wherein the expression product of the at least one stable mammalian cell comprises a larger percentage of the desired glycosylated bispecific anti-HER2 antigen-binding construct as compared to the monomeric heavy or light chain polypeptides, or other antibodies. In some embodiments, identification of the glycosylated bispecific anti-HER2 antigen-binding construct is by one or both of liquid chromatography and mass spectrometry.

If required, the bispecific anti-HER2 antigen-binding constructs can be purified or isolated after expression. Proteins may be isolated or purified in a variety of ways known to those skilled in the art. Standard purification methods include chromatographic techniques, including ion exchange, hydrophobic interaction, affinity, sizing or gel filtration, and reversed-phase, carried out at atmospheric pressure or at high pressure using systems such as FPLC and HPLC. Purification methods also include electrophoretic, immunological, precipitation, dialysis, and chromatofocusing techniques. Ultrafiltration and diafiltration techniques, in conjunction with protein concentration, are also useful. As is well known in the art, a variety of natural proteins bind Fc and antibodies, and these proteins can find use for purification of bispecific anti-HER2 antigen-binding constructs described herein. For example, the bacterial proteins A and G bind to the Fc region. Likewise, the bacterial protein L binds to the Fab region of some antibodies. Purification can often be enabled by a particular fusion partner. For example, antibodies may be purified using glutathione resin if a GST fusion is employed, Ni$^{+2}$ affinity chromatography if a His-tag is employed, or immobilized anti-flag antibody if a flag-tag is used. For general guidance in suitable purification techniques, see, e.g. Protein Purification: Principles and Practice, 3$^{rd}$Ed., Scopes, Springer-Verlag, NY, 1994. The degree of purification necessary will vary depending on the use of the bispecific anti-HER2 antigen-binding constructs. In some instances no purification is necessary.

In certain embodiments the bispecific anti-HER2 antigen-binding constructs are purified using Anion Exchange Chromatography including, but not limited to, chromatography on Q-sepharose, DEAE sepharose, poros HQ, poros DEAF, Toyopearl Q, Toyopearl QAE, Toyopearl DEAE, Resource/Source Q and DEAE, Fractogel Q and DEAE columns.

In specific embodiments the bispecific anti-HER2 antigen-binding construct described herein are purified using Cation Exchange Chromatography including, but not limited to, SP-sepharose, CM sepharose, poros HS, poros CM, Toyopearl SP, Toyopearl CM, Resource/Source S and CM, Fractogel S and CM columns and their equivalents and comparables.

In addition, bispecific anti-HER2 antigen-binding constructs described herein can be chemically synthesized using techniques known in the art (e.g., see Creighton, 1983, Proteins: Structures and Molecular Principles, W. H. Freeman & Co., N.Y and Hunkapiller et al., Nature, 310:105-111 (1984)). For example, a polypeptide corresponding to a fragment of a polypeptide can be synthesized by use of a peptide synthesizer. Furthermore, if desired, nonclassical amino acids or chemical amino acid analogs can be introduced as a substitution or addition into the polypeptide sequence. Non-classical amino acids include, but are not limited to, the D-isomers of the common amino acids, 2,4diaminobutyric acid, alpha-amino isobutyric acid, 4aminobutyric acid, Abu, 2-amino butyric acid, γ-Abu, ε-Ahx, 6amino hexanoic acid, Aib, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, β-alanine, fluoro-amino acids, designer amino acids such as β-methyl amino acids, Ca-methyl amino acids, N α-methyl amino acids, and amino acid analogs in general. Furthermore, the amino acid can be D (dextrorotary) or L (levorotary).

Post-Translational Modifications:

In certain embodiments bispecific anti-HER2 antigen-binding constructs described herein are differentially modified during or after translation.

The term "modified," as used herein refers to any changes made to a given polypeptide, such as changes to the length of the polypeptide, the amino acid sequence, chemical structure, co-translational modification, or post-translational modification of a polypeptide. The form "(modified)" term means that the polypeptides being discussed are optionally modified, that is, the polypeptides of the bispecific anti-HER2 antigen-binding construct can be modified or unmodified.

The term "post-translationally modified" refers to any modification of a natural or non-natural amino acid that occurs to such an amino acid after it has been incorporated into a polypeptide chain. The term encompasses, by way of example only, co-translational in vivo modifications, co-translational in vitro modifications (such as in a cell-free translation system), post-translational in vivo modifications, and post-translational in vitro modifications.

In some embodiments, the modification is at least one of: glycosylation, acetylation, phosphorylation, amidation, derivatization by known protecting/blocking groups, proteolytic cleavage and linkage to an antibody molecule or bispecific anti-HER2 antigen-binding construct or other cellular ligand. In some embodiments, the bispecific anti-HER2 antigen-binding construct is chemically modified by known techniques, including but not limited, to specific chemical cleavage by cyanogen bromide, trypsin, chymotrypsin, papain, V8 protease, $NaBH_4$; acetylation, formylation, oxidation, reduction; and metabolic synthesis in the presence of tunicamycin.

Additional post-translational modifications of bispecific anti-HER2 antigen-binding constructs include, for example, N-linked or O-linked carbohydrate chains, processing of N-terminal or C-terminal ends), attachment of chemical moieties to the amino acid backbone, chemical modifications of N-linked or O-linked carbohydrate chains, and addition or deletion of an N-terminal methionine residue as a result of prokaryotic host cell expression. The bispecific anti-HER2 antigen-binding constructs described herein are modified with a detectable label, such as an enzymatic, fluorescent, isotopic or affinity label to allow for detection and isolation of the protein. In certain embodiments, examples of suitable enzyme labels include horseradish peroxidase, alkaline phosphatase, beta-galactosidase, or acetylcholinesterase; examples of suitable prosthetic group complexes include streptavidin biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include iodine, carbon, sulfur, tritium, indium, technetium, thallium, gallium, palladium, molybdenum, xenon, fluorine.

In specific embodiments, bispecific anti-HER2 antigen-binding constructs described herein are attached to macrocyclic chelators that associate with radiometal ions.

In some embodiments, the bispecific anti-HER2 antigen-binding constructs described herein are modified by either natural processes, such as post-translational processing, or by chemical modification techniques which are well known in the art. In certain embodiments, the same type of modification may be present in the same or varying degrees at several sites in a given polypeptide. In certain embodiments, polypeptides from bispecific anti-HER2 antigen-binding constructs described herein are branched, for example, as a result of ubiquitination, and in some embodiments are cyclic, with or without branching. Cyclic, branched, and branched cyclic polypeptides are a result from posttranslation natural processes or made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristylation, oxidation, pegylation, proteolytic processing, phosphorylation, prenylation, racemization, selenoylation, sulfation, transfer-RNA mediated addition of amino acids to proteins such as arginylation, and ubiquitination. (See, for instance, PROTEINS—STRUCTURE AND MOLECULAR PROPERTIES, 2nd Ed., T. E. Creighton, W.H. Freeman and Company, New York (1993); POST-TRANSLATIONAL COVALENT MODIFICATION OF PROTEINS, B. C. Johnson, Ed., Academic Press, New York, pgs. 1-12 (1983); Seifter et al., Meth. Enzymol. 182:626-646 (1990); Rattan et al., Ann. N.Y. Acad. Sci. 663:48-62 (1992)).

Antibody Drug Conjugates (ADCs)

Certain embodiments relate to a method of treating BREAST CANCER using an antibody-drug conjugate (ADC) comprising a bispecific anti-HER2 antigen-binding construct conjugated to an auristatin analogue at a low average drug-to-antibody ratio (DAR). "Low average DAR," as used herein, refers to an average DAR of <3.9. Of particular use in the described methods are ADCs comprising a bispecific anti-HER2 antigen-binding construct conjugated to an auristatin analogue having an average DAR of about 2.5 or less, such as between about 1.8 and 2.5. In certain embodiments, the bispecific anti-HER2 antigen-binding construct included in the ADCs is v10000.

In certain embodiments, the auristatin analogue comprised by the ADCs for use in the methods described herein may be an auristatin analogue as described in International Patent Application Publication No. WO 2016/041082. In certain embodiments, the auristatin analogue comprised by the ADCs for use in the methods described herein is a compound of general Formula (I):

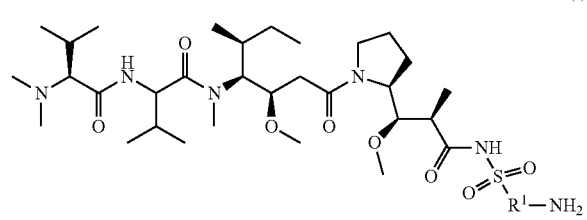

(I)

wherein $R^1$ is selected from:

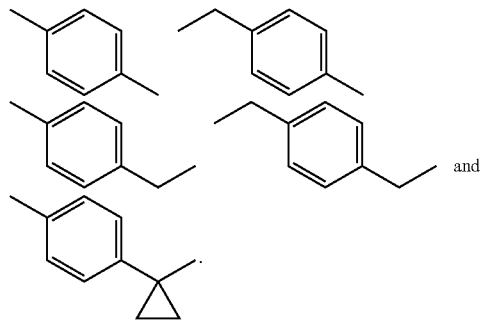

and

In certain embodiments, in compounds of Formula (I), $R^1$ is:

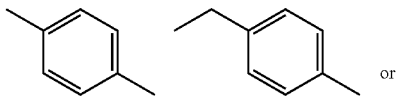

or

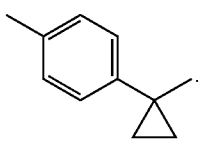

In certain embodiments, in compounds of Formula (I), $R^1$ is:

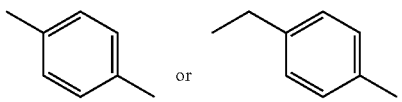

or

In certain embodiments, in compounds of Formula (I), $R^1$ is:

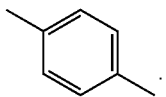

In certain embodiments, the compound of Formula (I) is selected from:

Compound 16

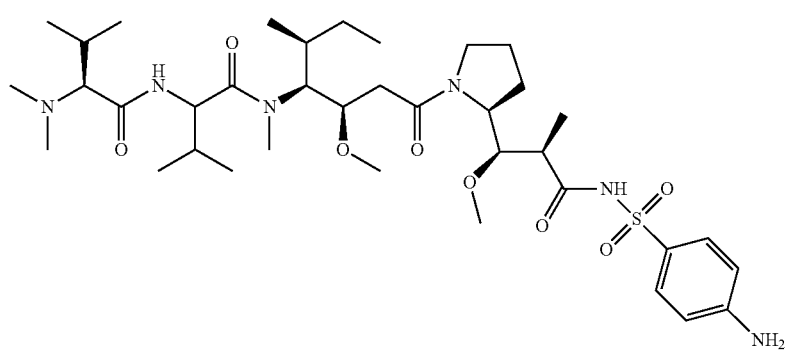

Compound 17

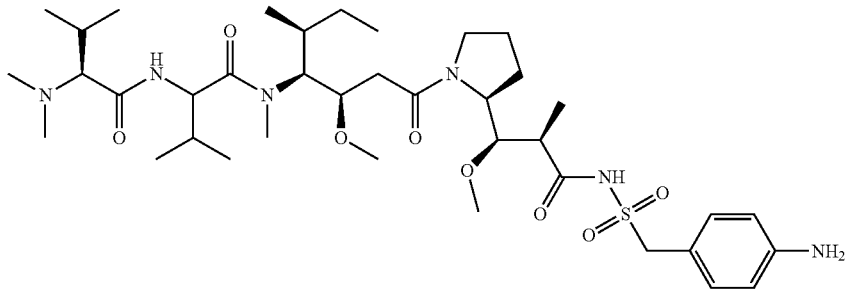

Compound 18

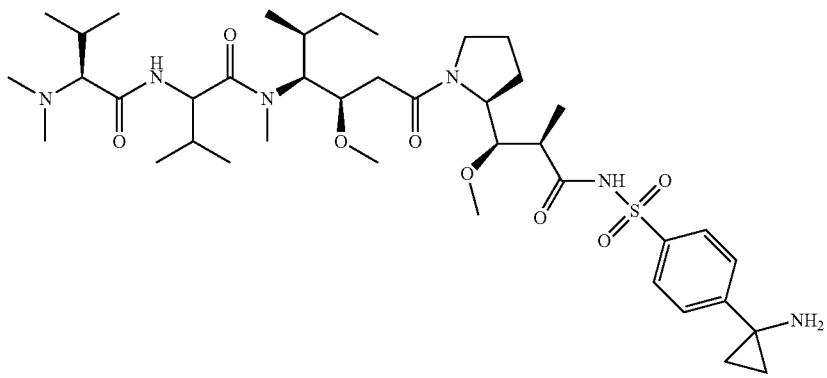

Compounds of general Formula (I) may be prepared by standard synthetic organic chemistry protocols from commercially available starting materials. Exemplary methods of synthesis are provided in International Patent Application Publication No. WO 2016/041082.

In certain embodiments, the ADC for use in the methods described herein comprises the bispecific anti-HER2 antigen-binding construct conjugated to an auristatin analogue (toxin) via a linker (L), in which the linker-toxin has general Formula (II):

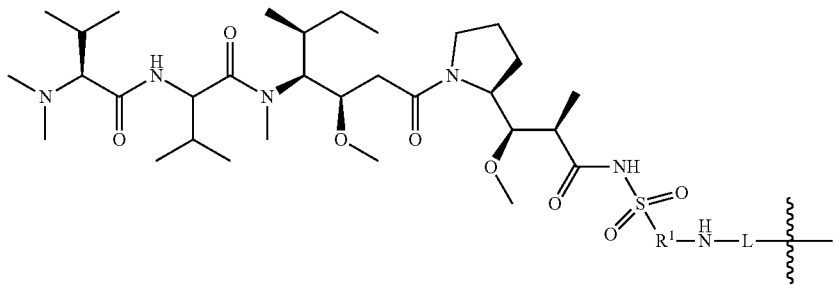

(II)

wherein:
$R^1$ is selected from:

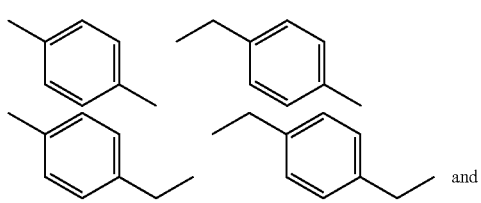

and

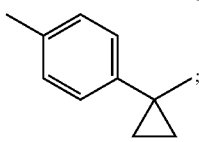

;

L is a cleavable linker, and
⸸ represents the point of attachment of the linker-toxin to the bispecific anti-HER2 antigen-binding construct.

In some embodiments, in the linker-toxin of general Formula (II), R¹ is:

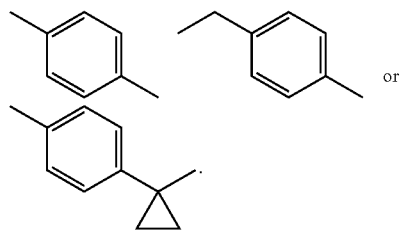 or

In some embodiments, in the linker-toxin of general Formula (II), R¹ is:

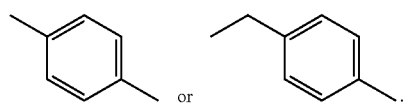 or

In some embodiments, in the linker-toxin of Formula (II), R¹ is:

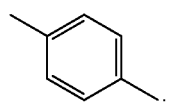

In some embodiments, in the linker-toxin of general Formula (II), L is a peptide-containing linker.

In some embodiments, in the linker-toxin of general Formula (II), L is a protease-cleavable linker.

In certain embodiments, the ADC for use in the methods described herein comprises the bispecific anti-HER2 antigen-binding construct conjugated to an auristatin analogue (toxin) via a linker (L) and has general Formula (III):

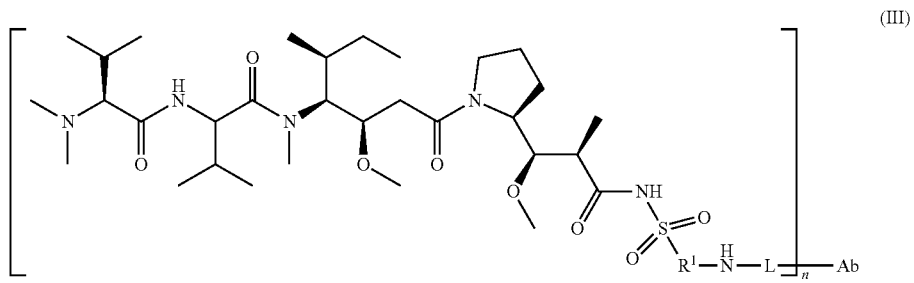

wherein:

R¹ and L are as defined for general Formula (II);

n is the average drug-to-antibody ratio (DAR) and is less than 3.9, and

Ab is the bispecific anti-HER2 antigen-binding construct.

In some embodiments, in the ADC of general Formula (III), R¹ is:

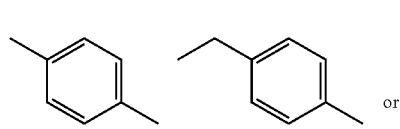 or

-continued

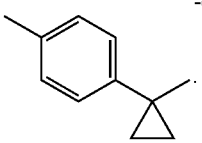

In some embodiments, in the ADC of general Formula (III), R¹ is:

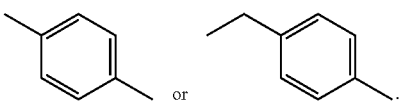 or

In some embodiments, in the ADC of general Formula (III), $R^1$ is:

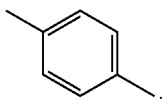

In some embodiments, in the ADC of general Formula (III), L is a peptide-containing linker.

In some embodiments, in the ADC of general Formula (III), L is a protease-cleavable linker.

In some embodiments, in the ADC of general Formula (III), n is between 0.5 and 3.8.

In some embodiments, in the ADC of general Formula (III), n is between about 1.0 and 3.8, between about 1.0 and 3.5, between about 1.0 and 3.0, or between about 1.0 and 2.5.

In some embodiments, in the ADC of general Formula (III), n is between about 1.5 and 3.8, between about 1.5 and 3.5, between about 1.5 and 3.0, or between about 1.5 and 2.5.

In some embodiments, in the ADC of general Formula (III), n is between about 1.8 and 2.8, or between about 1.8 and 2.5.

In some embodiments, in the ADC of general Formula (III), Ab is v10000.

Combinations of any of the foregoing embodiments for ADCs of general Formula (III) are also contemplated and each combination forms a separate embodiment for the purposes of the present disclosure.

In the ADCs described herein, the bispecific anti-HER2 antigen-binding construct is linked to the auristatin analogue (toxin) by a linker. Linkers are bifunctional or multifunctional moieties capable of linking one or more toxin molecules to an antibody. A bifunctional (or monovalent) linker links a single drug to a single site on the antibody, whereas a multifunctional (or polyvalent) linker links more than one toxin molecule to a single site on the antibody. Linkers capable of linking one toxin molecule to more than one site on the antibody may also be considered to be multifunctional.

Attachment of a linker to an antibody can be accomplished in a variety of ways, such as through surface lysines on the antibody, reductive-coupling to oxidized carbohydrates on the antibody, or through cysteine residues on the antibody liberated by reducing interchain disulfide linkages. Alternatively, attachment of a linker to an antibody may be achieved by modification of the antibody to include additional cysteine residues (see, for example, U.S. Pat. Nos. 7,521,541; 8,455,622 and 9,000,130) or non-natural amino acids that provide reactive handles, such as selenomethionine, p-acetylphenylalanine, formylglycine or p-azidomethyl-L-phenylalanine (see, for example, Hofer et al., Biochemistry, 48:12047-12057 (2009); Axup et al., PNAS, 109:16101-16106 (2012); Wu et al., PNAS, 106:3000-3005 (2009); Zimmerman et al., Bioconj. Chem., 25:351-361 (2014)), to allow for site-specific conjugation.

Linkers include a functional group capable of reacting with the target group or groups on the antibody, and one or more functional groups capable of reacting with a target group on the toxin. Suitable functional groups are known in the art and include those described, for example, in *Bioconjugate Techniques* (G. T. Hermanson, 2013, Academic Press).

Non-limiting examples of functional groups for reacting with free cysteines or thiols include maleimide, haloacetamide, haloacetyl, activated esters such as succinimide esters, 4-nitrophenyl esters, pentafluorophenyl esters, tetrafluorophenyl esters, anhydrides, acid chlorides, sulfonyl chlorides, isocyanates and isothiocyanates. Also useful in this context are "self-stabilizing" maleimides as described in Lyon et al., Nat. Biotechnol., 32:1059-1062 (2014).

Non-limiting examples of functional groups for reacting with surface lysines on an antibody or free amines on a toxin include activated esters such as N-hydroxysuccinamide (NETS) esters, sulfo-NHS esters, imido esters such as Traut's reagent, isothiocyanates, aldehydes and acid anhydrides such as diethylenetriaminepentaacetic anhydride (DTPA). Other examples include succinimido-1,1,3,3-tetramethyluroniumtetrafluoroborate (TSTU) and benzotriazol-1-yl-oxytripyrrolidinophosphonium hexafluorophosphate (PyBOP).

Non-limiting examples of functional groups capable of reacting with an electrophilic group on the antibody or toxin (such as an aldehyde or ketone carbonyl group) include hydrazide, oxime, amino, hydrazine, thiosemicarbazone, hydrazine carboxylate and arylhydrazide.

Other linkers include those having a functional group that allows for bridging of two interchain cysteines on the antibody, such as a ThioBridge™ linker (Badescu et al., Bioconjug. Chem., 25:1124-1136 (2014)), a dithiomaleimide (DTM) linker (Behrens et al., Mol. Pharm., 12:3986-3998 (2015)), a dithioaryl(TCEP)pyridazinedione based linker (Lee et al., Chem. Sci., 7:799-802 (2016)), a dibromopyridazinedione based linker (Maruani et al., Nat. Commun., 6:6645 (2015)) and others known in the art.

A linker may comprise various linker components. Typically, a linker will comprise two or more linker components. Exemplary linker components include functional groups for reaction with the antibody, functional groups for reaction with the toxin, stretchers, peptide components, self-immolative groups, self-elimination groups, hydrophilic moieties, and the like. Various linker components are known in the art, some of which are described below.

Certain useful linker components can be obtained from various commercial sources, such as Pierce Biotechnology, Inc. (now Thermo Fisher Scientific, Waltham, MA) and Molecular Biosciences Inc. (Boulder, Colo.), or may be synthesized in accordance with procedures described in the art (see, for example, Toki et al., J. Org. Chem., 67:1866-1872 (2002); Dubowchik, et al., Tetrahedron Letters, 38:5257-60 (1997); Walker, M. A., J. Org. Chem., 60:5352-5355 (1995); Frisch, et al., Bioconjugate Chem., 7:180-186 (1996); U.S. Pat. Nos. 6,214,345 and 7,553,816, and International Patent Application Publication No. WO 02/088172).

The linker employed in the ADCs described herein is a cleavable linker. A cleavable linker is typically susceptible to cleavage under intracellular conditions, for example, through lysosomal processes. Examples include linkers that are protease-sensitive, acid-sensitive, reduction-sensitive or photolabile.

Suitable cleavable linkers include, for example, linkers comprising a peptide component that includes two or more amino acids and is cleavable by an intracellular protease, such as lysosomal protease or an endosomal protease. A peptide component may comprise amino acid residues that occur naturally and/or minor amino acids and/or non-naturally occurring amino acid analogues, such as citrulline. Peptide components may be designed and optimized for enzymatic cleavage by a particular enzyme, for example, a tumour-associated protease, cathepsin B, C or D, or a plasmin protease.

In certain embodiments, the linker included in the ADCs may be a dipeptide-containing linker, such as a linker containing valine-citrulline (Val-Cit) or phenylalanine-lysine (Phe-Lys). Other examples of suitable dipeptides for inclusion in linkers include Val-Lys, Ala-Lys, Me-Val-Cit, Phe-homoLys, Phe-Cit, Leu-Cit, Ile-Cit, Trp-Cit, Phe-Arg, Ala-Phe, Val-Ala, Met-Lys, Asn-Lys, Ile-Pro, Ile-Val, Asp-Val, His-Val, Met-(D)Lys, Asn-(D)Lys, Val-(D)Asp, NorVal-(D)Asp, Ala-(D)Asp, Me$_3$Lys-Pro, PhenylGly-(D)Lys, Met-(D)Lys, Asn-(D)Lys, Pro-(D)Lys and Met-(D)Lys. Cleavable linkers may also include longer peptide components such as tripeptides, tetrapeptides or pentapeptides. Examples include, but are not limited to, the tripeptides Met-Cit-Val, Gly-Cit-Val, (D)Phe-Phe-Lys and (D)Ala-Phe-Lys, and the tetrapeptides Gly-Phe-Leu-Gly and Ala-Leu-Ala-Leu.

Additional examples of cleavable linkers include disulfide-containing linkers, such as, for example, N-succinimydyl-4-(2-pyridyldithio) butanoate (SPBD) and N-succinimydyl-4-(2-pyridyldithio)-2-sulfo butanoate (sulfo-SPBD). Disulfide-containing linkers may optionally include additional groups to provide steric hindrance adjacent to the disulfide bond in order to improve the extracellular stability of the linker, for example, inclusion of a geminal dimethyl group. Other suitable linkers include linkers hydrolyzable at a specific pH or within a pH range, such as hydrazone linkers. Linkers comprising combinations of these functionalities may also be useful, for example, linkers comprising both a hydrazone and a disulfide are known in the art.

A further example of a cleavable linker is a linker comprising a β-glucuronide, which is cleavable by β-glucuronidase, an enzyme present in lysosomes and tumour interstitium (see, for example, De Graaf et al., Curr. Pharm. Des., 8:1391-1403 (2002)).

Cleavable linkers may optionally further comprise one or more additional components such as self-immolative and self-elimination groups, stretchers or hydrophilic moieties.

Self-immolative and self-elimination groups that find use in linkers include, for example, p-aminobenzyloxycarbonyl (PABC) and p-aminobenzyl ether (PABE) groups, and methylated ethylene diamine (MED). Other examples of self-immolative groups include, but are not limited to, aromatic compounds that are electronically similar to the PABC or PABE group such as heterocyclic derivatives, for example 2-aminoimidazol-5-methanol derivatives as described in U.S. Pat. No. 7,375,078. Other examples include groups that undergo cyclization upon amide bond hydrolysis, such as substituted and unsubstituted 4-aminobutyric acid amides (Rodrigues et al., Chemistry Biology, 2:223-227 (1995)) and 2-aminophenylpropionic acid amides (Amsberry, et al., J. Org. Chem., 55:5867-5877 (1990)).

Stretchers that find use in linkers for ADCs include, for example, alkylene groups and stretchers based on aliphatic acids, diacids, amines or diamines, such as diglycolate, malonate, caproate and caproamide. Other stretchers include, for example, glycine-based stretchers, polyethylene glycol (PEG) stretchers and monomethoxy polyethylene glycol (mPEG) stretchers. PEG and mPEG stretchers also function as hydrophilic moieties.

In certain embodiments, the linker comprised by the ADCs for use in the methods described herein are peptide-based linkers having general Formula (IV):

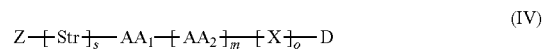

wherein:
Z is a functional group capable of reacting with the target group on the bispecific anti-HER2 antigen-binding construct;
Str is a stretcher;
AA$_1$ and AA$_2$ are each independently an amino acid, wherein AA$_1$-[AA$_2$]$_m$ forms a protease cleavage site;
X is a self-immolative group;
D is the point of attachment to the auristatin analogue;
s is 0 or 1;
m is an integer between 1 and 4, and
o is 0, 1 or 2.

In some embodiments, in general Formula (IV), Z is:

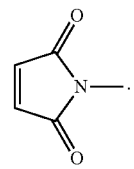

In some embodiments, in general Formula (IV), Str is selected from:

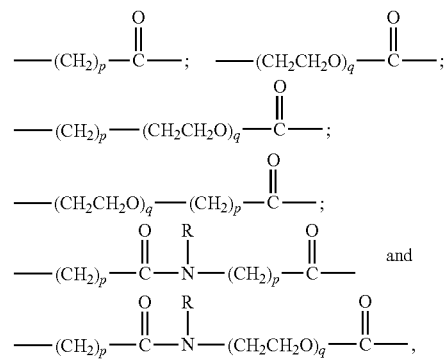

wherein:
R is H or C$_1$-C$_6$ alkyl;
p is an integer between 2 and 10, and
q is an integer between 1 and 10.

In some embodiments, in general Formula (IV), Str is:

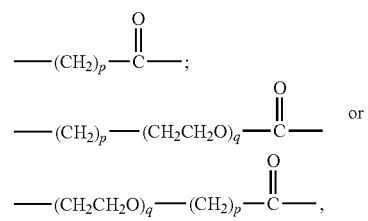

wherein p and q are as defined above.

In some embodiments, in general Formula (IV), Str is:

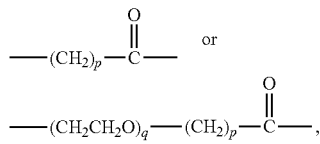

wherein p is an integer between 2 and 6, and
q is an integer between 2 and 8.

In some embodiments, in general Formula (IV), AA$_1$-[AA$_2$]$_m$ is selected from Val-Lys, Ala-Lys, Phe-Lys, Val-Cit, Phe-Cit, Leu-Cit, Ile-Cit, Trp-Cit, Phe-Arg, Ala-Phe, Val-Ala, Met-Lys, Asn-Lys, Ile-Pro, Ile-Val, Asp-Val, His-Val, Met-(D)Lys, Asn-(D)Lys, Val-(D)Asp, NorVal-(D)Asp, Ala-(D)Asp, Me$_3$Lys-Pro, PhenylGly-(D)Lys, Met-(D)Lys, Asn-(D)Lys, Pro-(D)Lys, Met-(D)Lys, Met-Cit-Val, Gly-Cit-Val, (D)Phe-Phe-Lys, (D)Ala-Phe-Lys, Gly-Phe-Leu-Gly and Ala-Leu-Ala-Leu.

In some embodiments, in general Formula (IV), m is 1 (i.e. AA$_1$-[AA$_2$]$_m$ is a dipeptide).

In some embodiments, in general Formula (IV), AA$_1$-[AA$_2$]$_m$ is a dipeptide selected from Val-Lys, Ala-Lys, Phe-Lys, Val-Cit, Phe-Cit, Leu-Cit, Ile-Cit and Trp-Cit.

In some embodiments, in general Formula (IV), m is 1, 2 or 3.

In some embodiments, in general Formula (IV), s is 1.

In some embodiments, in general Formula (IV), o is 0.

In some embodiments, in general Formula (IV):
Z is

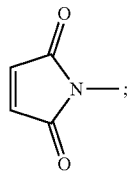

Str is

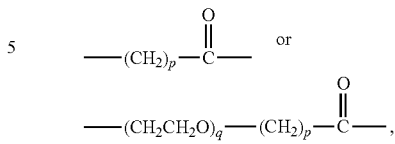

wherein p is an integer between 2 and 6, and q is an integer between 2 and 8;
m is 1 and AA$_1$-[AA$_2$]$_m$ is a dipeptide selected from Val-Lys, Ala-Lys, Phe-Lys, Val-Cit, Phe-Cit, Leu-Cit, Ile-Cit and Trp-Cit;
s is 1, and
o is 0.

In certain embodiments, the linker included in the ADCs for use in the methods described herein has general Formula (V):

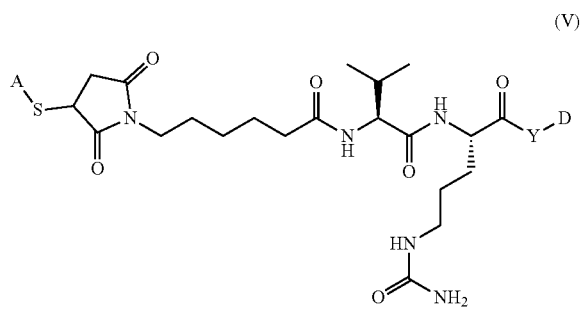

wherein:
A-S- is the point of attachment to the bispecific anti-HER2 antigen-binding construct;
Y is one or more additional linker components, or is absent, and
D is the point of attachment to the auristatin analogue.

In certain embodiments, the linker included in the ADCs for use in the methods described herein has general Formula (VI):

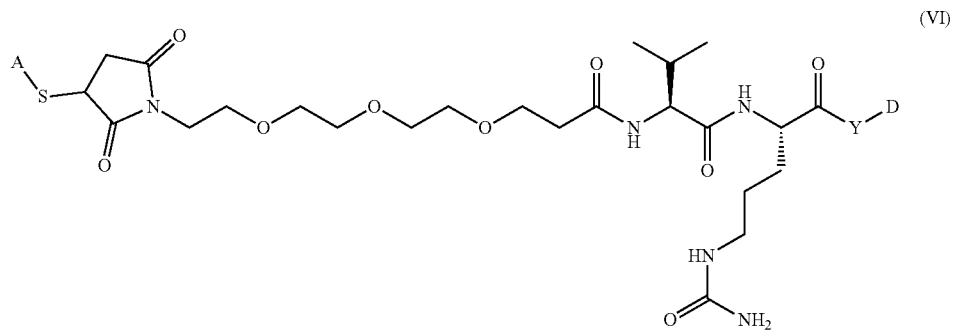

wherein:
A-S- is the point of attachment to the bispecific anti-HER2 antigen-binding construct;
Y is one or more additional linker components, or is absent, and
D is the point of attachment to the auristatin analogue.

In certain embodiments, the ADC for use in the methods described herein comprises an auristatin analogue of general Formula (I) conjugated to v10000 at a low average DAR via a linker having general Formula (IV), (V) or (VI).

In certain embodiments, the ADC for use in the methods described herein comprises v10000 conjugated at a low average DAR to a linker-toxin of general Formula (II) ni which the linker (L) has general Formula (IV), (V) or (VI).

In certain embodiments, the ADC for use in the methods described herein comprises v10000 and has general Formula (III) shown above in which the linker (L) has general Formula (IV), (V) or (VI).

In certain embodiments, the ADC for use in the methods described herein comprises an auristatin analogue conjugated to v10000 at a low average DAR via a linker having general Formula (IV), (V) or (VI), in which the auristatin analogue is Compound 16, Compound 17 or Compound 18.

In certain embodiments, the ADC for use in the methods described herein comprises a linker-toxin having the structure:

cysteine residues or non-natural amino acids that provide reactive handles, such as selenomethionine, p-acetylphenylalanine, formylglycine or p-azidomethyl-L-phenylalanine. Such modifications are well-known in the art (see, for example, U.S. Pat. Nos. 7,521,541; 8,455,622 and 9,000,130; Hofer et al., Biochemistry, 48:12047-12057 (2009); Axup et al., PNAS, 109:16101-16106 (2012); Wu et al., PNAS, 106:3000-3005 (2009); Zimmerman et al., Bioconj. Chem., 25:351-361 (2014)).

In certain embodiments, the ADCs for use in the methods described herein comprise an auristatin analogue conjugated via an appropriate linker to cysteine residues on the bispecific anti-HER2 antigen-binding construct that have been liberated by reducing one or more interchain disulfide linkages.

In the ADCs described herein, the bispecific anti-HER2 antigen-binding construct is conjugated to the toxin via a linker at a low average drug-to-antibody ratio (DAR), specifically an average DAR of less than 3.9 but more than 0.5, for example, between about 1.5 and about 2.5 in certain embodiments.

Various methods are known in the art to prepare ADCs with a low average DAR (see, for example, review by McCombs and Owen, The AAPS Journal, 17(2):339-351 (2015) and references therein; Boutureira & Bernardes, Chem. Rev., 115:2174-2195 (2015)).

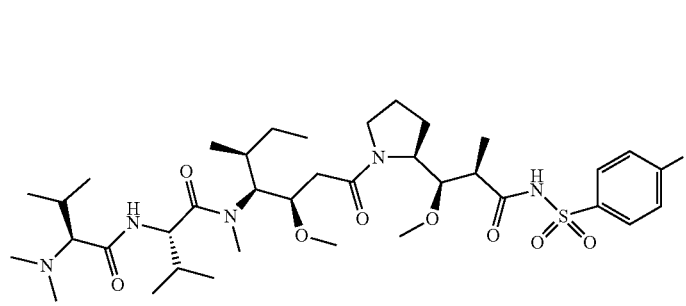
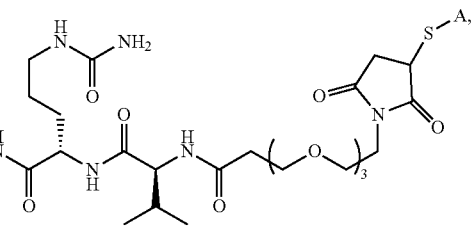

wherein A-S- is the point of attachment to the bispecific anti-HER2 antigen-binding construct.

Preparation of Antibody Drug Conjugates

The ADCs for use in the methods described herein may be prepared by one of several routes known in the art, employing organic chemistry reactions, conditions, and reagents known to those skilled in the art (see, for example, *Bioconjugate Techniques* (G. T. Hermanson, 2013, Academic Press, and the Examples provided herein). For example, conjugation may be achieved by (1) reaction of a nucleophilic group or an electrophilic group of an antibody with a bifunctional linker to form an antibody-linker intermediate Ab-L, via a covalent bond, followed by reaction with an activated auristatin analogue (D), or (2) reaction of a nucleophilic group or an electrophilic group of an auristatin analogue with a linker to form linker-toxin D-L, via a covalent bond, followed by reaction with a nucleophilic group or an electrophilic group of an antibody.

As described above, the auristatin analogue may be conjugated via an appropriate linker to various groups on the antibody to provide the ADC. For example, conjugation may be through surface lysines, through oxidized carbohydrates or through cysteine residues that have been liberated by reducing one or more interchain disulfide linkages. Alternatively, the antibody may be modified to include additional For example, for conjugation to cysteine residues, a partial reduction of the antibody interchain disulfide bonds may be conducted followed by conjugation to linker-toxin. Partial reduction can be achieved by limiting the amount of reducing agent used in the reduction reaction (see, for example, Lyon et al., Methods in Enzymology, 502:123-138 (2012), and examples therein, and the Examples provided herein). Suitable reducing agents are known in the art and include, for example, dithiothreitol (DTT), tris(2-carboxyethyl)phosphine (TCEP), 2-mercaptoethanol, cysteamine and a number of water soluble phosphines. Alternatively, or in addition, fewer equivalents of linker-toxin may be employed in order to obtain a low average DAR.

Alternatively, an engineered antibody may be employed in which one or more of the cysteine residues that make up the interchain disulfide bonds is replaced with a serine residue resulting in fewer available cysteine residues for conjugation (see McDonagh et al., Protein Eng. Des. Sel. PEDS, 19(7):299-307). The engineered antibody can then be treated with reducing agent and conjugated to linker-toxin.

Another approach is to employ a bis-thiol linker that bridges two cysteines that normally make up an interchain disulfide bond. Use of a bis-thiol linker that carries only one toxin molecule would produce an ADC with a maximum DAR4 for a full-size antibody, if all four interchain disulfide bonds are reduced and replaced with the bis-thiol linker. Partial reduction of the interchain disulfide bonds and/or fewer equivalents of linker may be used in conjunction with a bis-thiol linker in order to further reduce the DAR. Various bis-thiol linkers are known in the art (see, for example, Badescu et al., Bioconjug. Chem., 25(6):1124-1136 (2014); Behrens et al., Mol. Pharm., 12:3986-3998 (2015); Lee et al., Chem. Sci., 7:799-802 (2016); Maruani et al., Nat. Commun., 6:6645 (2015)).

Cysteine engineering approaches may also be employed in order to generate ADCs with a low average DAR. Such approaches involve engineering solvent-accessible cysteines into the antibody in order to provide a site-specific handle for conjugation. A number of appropriate sites for introduction of a cysteine residue have been identified with the IgG structure, and include those described in Junutula, et al., J. Immunol Methods, 332(1-2):41-52 (2008); Junutula, et al., Nat. Biotechnol., 26(8), 925-932 (2008), and U.S. Pat. Nos. 9,315,581; 9,000,130; 8,455,622; 8,507,654 and 7,521,541.

Low average DAR ADCs may also be prepared by lysine conjugation employing limiting amounts of activated linker-toxin. Selective reaction at the antibody N-terminal amino acids may also be employed. For example, N-terminal serine may be oxidized to an aldehyde with periodate, then reacted with linker-toxin (see, for example, Thompson, et al., Bioconjug. Chem., 26(10):2085-2096 (2015)). Similarly, N-terminal cysteine residues can be selectively reacted with aldehydes to give thiazolidinones (see, for example, Bernardes, et al., Nature Protocols, 8:2079-2089).

Additional approaches include engineering the antibody to include one or more unnatural amino acids, such as p-acetylphenylalanine (pAcPhe) or selenocysteine (Sec). The keto group in pAcPhe can be reacted with a linker-toxin comprising a terminal alkoxyamine or hydrazide to form an oxime or hydrazone bond (see, for example, Axup, et al., PNAS USA, 109:16101-16106 (2012)). Sec-containing antibodies can be reacted with maleimide- or iodoacetamide containing linker-toxins to form a selenoether conjugate (see, for example, Hofer, et al., Biochemistry, 48:12047-12057 (2009)).

Antibodies may also be engineered to include peptide tags recognized by certain enzymes to allow for enzyme-catalyzed conjugation. For example, Sortase-A (SortA) recognizes the sequence LPXTG. This pentapeptide may be engineered into the N- or C-terminus of the antibody to allow for SortA-mediated conjugation (see, for example, U.S. Patent Application Publication No. 2016/0136298; Kornberger and Skerra, mAbs, 6(2):354-366 (2014)). Trans-glutaminases have also been employed to generate DAR2 ADCs by using antibodies that have been deglycosylated at position N297 (which exposes Q295 for enzymatic conjugation) or by engineering antibodies to include a "glutamine tag" (LLQG) (Jeger, et al., Angew. Chem., 49:9995-9997 (2010); Strop, et al., Chem. Biol., 20(2):161-167 (2013)). In another approach, a formylglycine residue can be introduced into an antibody by engineering an appropriate consensus sequence into the antibody and co-expressing the engineered antibody with formylglycine-generating enzyme (FGE). The aldehyde functionality of the introduced formylglycine may then be used as a handle for conjugation of toxin (see, for example, Drake, et al., Bioconjug. Chem., 25(7):1331-1341 (2014)).

Another approach used to generate DAR2 ADCs is by conjugation of linker-toxin to the native sugars found on glycosylated antibodies. Conjugation to glycosylated antibodies may be achieved, for example, by periodate oxidation of terminal sugar residues to yield aldehydes, which may then be conjugated to an appropriate linker-toxin, or by glycoengineering approaches in which native sugars are modified with terminal sialic acid residues, which can then be oxidized to yield aldehydes for conjugation to linker-toxin (Zhou, et al., Bioconjug. Chem., 25(3):510-520 (2014)).

The use of UV cross-linking for conjugation of active moieties to antibodies has also been reported. This method uses the nucleotide binding site (NBS) for site-specific covalent functionalization of antibodies with reactive thiol moieties. An indole-3-butyric acid (IBA) conjugated version of cysteine was used to site-specifically photo-cross-link a reactive thiol moiety to antibodies at the NBS. The thiol moiety may then be used to conjugate linker-toxin having a thiol reactive group (Alves, et al., Bioconjug. Chem., 25(7): 1198-1202 (2014)).

Alternatively, ADCs with a low average DAR may be isolated from an ADC preparation containing a mixture of DAR species using chromatographic separation techniques, such as hydrophobic interaction chromatography (see, for example, Hamblett, et al., Clin. Cancer Res., 10:7063-7070 (2004); Sun, et al., Bioconj Chem., 28:1371-81 (2017); U.S. Patent Application Publication No. 2014/0286968).

ADCs with a low average DAR may also be generated by adding unconjugated (i.e. DAR0) antibody to preparations of ADC having an average DAR≥3.9. As is known in the art, the majority of conjugation methods yield an ADC preparation that includes various DAR species, with the reported DAR being the average of the individual DAR species. In certain embodiments, ADCs that include a proportion of DAR0 species may be advantageous. In some embodiments, the ADC for use in the methods described herein having an average DAR of less than 3.9 includes at least 5% DAR0 species. In some embodiments, the ADC for use in the methods described herein includes at least 10% DAR0 species, for example, at least 15% DAR0 species or at least 20% DAR0 species. In some embodiments, the ADC for use in the methods described herein includes between about 5% and about 50% DAR0 species, for example, between about 10% and about 50% DAR0 species, between about 10% and about 40%, or between about 10% and about 30% DAR0 species.

The average DAR for the ADCs may be determined by standard techniques such as UV/VIS spectroscopic analysis, ELISA-based techniques, chromatography techniques such as hydrophobic interaction chromatography (HIC), UV-MALDI mass spectrometry (MS) and MALDI-TOF MS. In addition, distribution of drug-linked forms (for example, the fraction of DAR0, DAR1, DAR2, etc. species) may also be analyzed by various techniques known in the art, including MS (with or without an accompanying chromatographic separation step), hydrophobic interaction chromatography, reverse-phase HPLC or iso-electric focusing gel electrophoresis (IEF) (see, for example, Sun et al., Bioconj Chem., 28:1371-81 (2017); Wakankar et al., mAbs, 3:161-172 (2011)).

In certain embodiments, the average DAR of the ADCs is determined by hydrophobic interaction chromatography (HIC) techniques.

Following conjugation, the ADCs may be purified and separated from unconjugated reactants and/or any conjugate aggregates by purification methods known in the art. Such methods include, but are not limited to, size exclusion chromatography (SEC), hydrophobic interaction chromatography (HIC), ion exchange chromatography, chromatofocusing, ultrafiltration, centrifugal ultrafiltration, and combinations thereof.

Cell Cycle Inhibitors

Also provided herein are compositions comprising cell cycle inhibitors. In certain embodiments, the cell cycle inhibitor is a cyclin-dependent kinase 4/6 (CDK4/6) inhibitor. In this regard, in certain embodiments, the CDK4/6 inhibitor is selected from the group of palbociclib, abemaciclib, and ribociclib.

In various embodiments, the methods of treatment described herein comprise administering an effective amount of the bispecific antigen-binding constructs described herein in combination with an effective amount of a cell cycle inhibitor. In certain embodiments, the cell cycle inhibitor comprises a cyclin-dependent kinase 4/6 (CDK4/6) inhibitor. In some embodiments, the CDK4/6 inhibitor is selected from the group of palbociclib, abemaciclib, and ribociclib.

Palbociclib is an inhibitor of CDK4 and CDK6, has the molecular formula $C_{24}H_{29}N_7O_2$ and has the structure shown below (National Center for Biotechnology Information. PubChem Database. Palbociclib, CID=5330286).

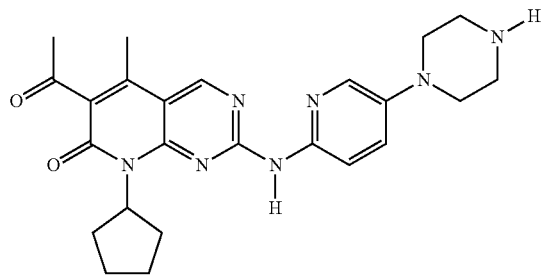 [SMILES: CC(=O)c1c(C)c2cnc(Nc3ccc(N4CCNCC4)cn3)nc2n(C2CCCC2)c1=O]

Cyclin D1 and CDK4/6 are downstream of signaling pathways which lead to cellular proliferation. In vitro, palbociclib reduced cellular proliferation of estrogen receptor (ER)-positive breast cancer cell lines by blocking progression of the cell from G1 into S phase of the cell cycle. Palbociclib is approved for the treatment of hormone receptor (HR)-positive, HER2-negative advanced or metastatic breast cancer in combination with fulvestrant in patients with disease progression following endocrine therapy. The addition of a CDK4/6 inhibitor to endocrine therapy has demonstrated improved clinical outcomes, with delayed onset of tumor progression. The combination of endocrine therapy and a CDK4/6 inhibitor is now included in the treatment guidelines for advanced HR-positive breast cancer (Sammons 2017, Curr Cancer Drug Targets. 2017; 17(7): 637-49).

Abemaciclib is a cyclin-dependent kinase (CDK) inhibitor that targets the CDK4 (cyclin D1) and CDK6 (cyclin D3) cell cycle pathway, has the molecular formula $C_{27}H_{32}F_2N_8$ and the chemical structure shown below (National Center for Biotechnology Information. PubChem Database. Abemaciclib, CID=46220502).

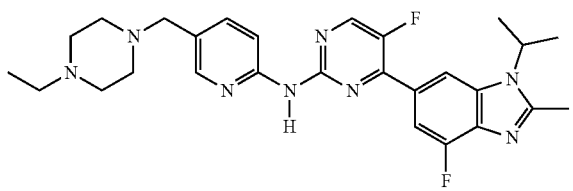 [SMILES: CCN1CCN(Cc2ccc(Nc3ncc(F)c(-c4cc(F)c5nc(C)n(C(C)C)c5c4)n3)nc2)CC1]

Ribociclib is a cyclin D1/CDK4 and CDK6 inhibitor, has the molecular formula $C_{23}H_{30}N_8O$ and has the molecular structure shown below (National Center for Biotechnology Information. PubChem Database. Ribociclib, CID=44631912).

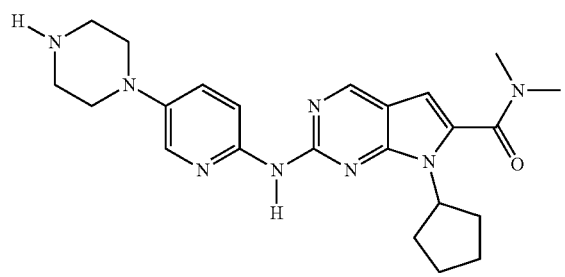 [SMILES: CN(C)C(=O)c1cc2cnc(Nc3ccc(N4CCNCC4)cn3)nc2n1C1CCCC1]

Endocrine-Based Therapy

Art recognized endocrine based therapies can be used in the compositions and methods of treatment described herein. Exemplary endocrine based therapies include non-steroidal aromatase inhibitors (e.g., letrozole, anostrozole) and selective estrogen receptor degraders (e.g., fulvestrant, brilanestrant, elacestrant).

An exemplary endocrine based therapy is letrozole. Letrozole (trade name FEMARA) is a nonsteroidal aromatase inhibitor (inhibitor of estrogen synthesis). Letrozole inhibits the aromatase enzyme by competitively binding to the heme of the cytochrome P450 subunit of the enzyme, resulting in a reduction of estrogen biosynthesis in all tissues. It is chemically described as 4,4'-(1H-1,2,4-Triazol-1-ylmethylene)dibenzonitrile and its structural formula is:

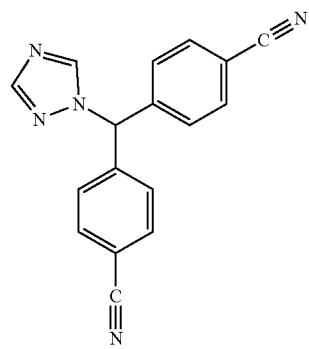 [SMILES: N#Cc1ccc(C(c2ccc(C#N)cc2)n2cncn2)cc1]

Another exemplary endocrine based therapy is anastrozole (trade name ARIMIDEX). ARIMIDEX (anastrozole) is an orally available aromatase inhibitor which competitively blocks the conversion of androgens to estrogens in peripheral (extra-gonadal) tissues. The chemical name is a,a,a',a'-Tetramethyl-5-(1H-1,2,4-triazol-1-ylmethyl)-1,3-benzenediacetonitrile. The molecular formula is $C_{17}H_{19}N_5$ and its structural formula is:

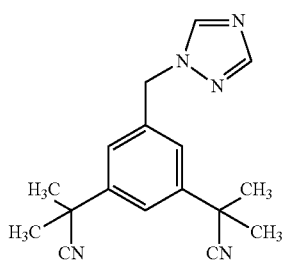

Another exemplary endocrine based therapy is fulvestrant (trade name FASLODEX). FASLODEX (fulvestrant) injection for intramuscular administration is an estrogen receptor antagonist. The chemical name is 7-alpha-[9-(4,4,5,5,5-penta fluoropentylsulphinyl) nonyl]estra-1,3,5-(10)-triene-3,17beta-diol. The molecular formula is $C_{32}H_{47}F_5O_3S$ and its structural formula is:

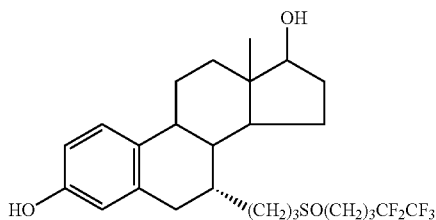

Fulvestrant is an estrogen receptor (ER) antagonist that binds to the ER in a competitive manner with affinity comparable to that of estradiol and downregulates the ER protein in human breast cancer cells. Fulvestrant is approved for the treatment of HR-positive, HER2-negative advanced or metastatic breast cancer in combination with palbociclib in patients with disease progression after endocrine therapy.

Pharmaceutical Compositions

Also provided herein are pharmaceutical compositions comprising a bispecific anti-HER2 antigen-binding construct described herein, the cell cycle inhibitors described herein and the endrocrine therapies described herein. Pharmaceutical compositions comprise the bispecific anti-HER2 antigen-binding construct and a pharmaceutically acceptable carrier. In certain embodiments, the bispecific anti-HER2 antigen-binding construct described herein, the cell cycle inhibitors described herein and the endrocrine-based therapies described herein are each provided in a separate pharmaceutical composition. In other embodiments, the bispecific anti-HER2 antigen-binding construct described herein, the cell cycle inhibitors described herein and the endrocrine-based therapies may be combined in a single pharmaceutical composition. In certain embodiments, the bispecific anti-HER2 antigen-binding construct described herein and the cell cycle inhibitors described herein may be combined in the same pharmaceutical composition, or the bispecific anti-HER2 antigen-binding construct described herein and the endrocrine-based therapies described herein may be combined in the same pharmaceutical compositions or the cell cycle inhibitors described herein and the endrocrine-based therapies described herein may be combined in the same pharmaceutical composition.

The term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. In some aspects, the carrier is a man-made carrier not found in nature. Water can be used as a carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the bispecific anti-HER2 antigen-binding construct, preferably in purified form, together with a suitable amount of carrier so as to provide the form for proper administration to the patient. The formulation should suit the mode of administration.

In certain embodiments, the composition herein (e.g., compositions comprising a bispecific anti-HER2 antigen-binding construct, compositions comprising a cell cycle inhibitor as described herein or compositions comprising an endrocrine-based therapy described herein) is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

In certain embodiments, the compositions described herein are formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxide isopropylamine, triethylamine, 2-ethylamino ethanol, histidine, procaine, etc.

Methods of Treating Breast Cancer

Described herein are methods of treating breast cancer comprising administering to a subject having breast cancer, a bispecific anti-HER2 antigen-binding construct or ADC as described herein, in combination with a CDK4/6 inhibitor and endocrine-based therapy, in an amount effective to treat, prevent or ameliorate this disease or disorder. Such treatment regimens comprising a bispecific anti-HER2 antigen-binding construct or ADC, in combination with a CDK4/6 inhibitor and endocrine-based therapy are also referred to herein as a "combination treatment" or "combination regimen" as a shorthand. Note that in certain embodiments, the "combination regimen" comprising a bispecific anti-HER2 antigen-binding construct or ADC, in combination with a CDK4/6 inhibitor and endocrine-based therapy may be used in conjunction or combination with (i.e., before, at the same time or after) other treatments, such as radiation, surgery, chemotherapies, and other cancer treatments.

"Disorder" or "disease" refers to any condition that would benefit from treatment with a bispecific anti-HER2 antigen-binding construct or method and the combination regimens described herein. This includes chronic and acute disorders or diseases including those pathological conditions which predispose the mammal to the disorder in question. In the embodiments described herein, the disorder or disease is breast cancer, and in certain embodiments, epidermal growth factor receptor 2 (HER2)-positive, hormone receptor (HR)-positive breast cancer described in more detail below.

The term "subject" or "patient" refers to an animal, in some embodiments a mammal, which is the object of treatment, observation or experiment. An animal may be a human, a non-human primate, a companion animal (e.g., dogs, cats, and the like), farm animal (e.g., cows, sheep, pigs, horses, and the like) or a laboratory animal (e.g., rats, mice, guinea pigs, and the like).

The term "mammal" as used herein includes but is not limited to humans, non-human primates, canines, felines, murines, bovines, equines, and porcines.

"Treatment" refers to clinical intervention in an attempt to alter the natural course of the individual or cell being treated and can be performed during the course of clinical pathology. Desirable effects of treatment include, but are not limited to, preventing recurrence of disease, alleviation of symptoms, diminishing of any direct or indirect pathological consequences of the disease, preventing metastasis, decreasing the rate of disease progression, amelioration or palliation of the disease state, and remission or improved prognosis. In some embodiments, the combination regimens described herein may be used to delay development of a disease or to slow the progression of a disease. In some embodiments, the combination treatments herein may be used to delay development of a breast cancer. In one embodiment, the combination regimen and methods described herein may effect inhibition of breast cancer tumor/cancer growth. In another embodiment, the combination regimen may be used to slow the progression of a breast cancer.

The term "effective amount" as used herein refers to that amount of bispecific anti-HER2 antigen-binding construct, CDK4/6 inhibitor and/or endocrine-based therapy being administered, which will accomplish the goal of the recited method, e.g., relieve to some extent one or more of the symptoms of the disease, condition or disorder being treated. The amount of the bispecific anti-HER2 antigen-binding construct, CDK4/6 inhibitor and hormone therapy which will be effective in the treatment, or inhibition of the disease or disorder can be determined by standard clinical techniques. In addition, in vitro assays may optionally be employed to help identify optimal dosage ranges. The precise dose to be employed in the formulation will also depend on the route of administration, and the seriousness of the breast cancer, and should be decided according to the judgment of the practitioner and each patient's circumstances. Effective doses can be extrapolated from dose-response curves derived from in vitro or animal model test systems.

The term "first-line therapy," "first-line treatment" or "primary therapy" is a treatment regimen that is generally accepted as the initial treatment for a patient, taking into account the type and stage of a cancer. The term "second-line therapy" or "second-line treatment" is a treatment regimen that is typically administered if the first-line therapy does not provide the desired efficacy.

The term "neoadjuvant therapy" refers to treatment given as a first step to shrink a tumor before the main treatment, usually surgery, is given. Examples of neoadjuvant therapy include, but are not limited to, chemotherapy, radiation therapy, and hormone therapy. Neoadjuvant therapy may be considered as a first-line therapy.

The term "adjuvant therapy" refers to an additional cancer treatment given after the first-line treatment to lower the risk that the cancer will come back. Adjuvant therapies may include, but are not limited to, chemotherapy, radiation therapy, hormone therapy, targeted therapy (typically small molecule drugs or antibodies that target specific types of cancer cells rather than normal cells), or biological therapy (such as vaccines, cytokines, antibodies, or gene therapy, for example).

An "advanced cancer" is a cancer that has developed to the point where it cannot be safely removed or where a cure or long-term remission is highly unlikely. Cancers become advanced by growing adjacent to structures that prevent their removal or by spreading from where they started, crossing tissue lines, or to other parts of the body such as lymph nodes or other organs. Advanced cancers may be locally advanced, meaning that they have spread outside the organ of the primary site, but have not yet spread to distant sites. Advanced cancers may also be metastatic, meaning that the cancer cells have spread from the site were the cancer started (the primary site) to other more distant parts of the body (secondary sites).

A "resectable" cancer is one that can be treated by surgery. An "unresectable" cancer is one that cannot be treated by surgery, typically because the cancer has spread to the tissues surrounding the main tumor. Certain cancers may be assessed by a medical practitioner as "partially resectable" based on the degree of spread to surrounding tissues.

The compositions herein (e.g., compositions comprising a bispecific anti-HER2 antigen-binding construct, compositions comprising a cell cycle inhibitor as described herein or compositions comprising an endocrine-based therapy described herein) may be administered to the subject according to known methods. Various delivery systems are known and can be used to administer a bispecific anti-HER2 antigen-binding construct formulation described herein, e.g., encapsulation in liposomes, microparticles, microcapsules, recombinant cells capable of expressing the compound, receptor-mediated endocytosis (see, e.g., Wu and Wu, J. Biol. Chem. 262:4429-4432 (1987)), construction of a nucleic acid as part of a retroviral or other vector, etc. Methods of introduction include but are not limited to intradermal, intramuscular, intraperitoneal, intravenous, subcutaneous, intranasal, epidural, and oral routes. The compositions comprising a bispecific anti-HER2 antigen-binding construct, compositions comprising a cell cycle inhibitor as described herein or compositions comprising an endocrine-based therapy described herein may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, in certain embodiments, it may be desirable to introduce the bispecific anti-HER2 antigen-binding constructs described herein into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent. In specific embodiments, the bispecific anti-HER2 antigen-binding construct or ADC may be administered intravenously (IV).

In a specific embodiment, it may be desirable to administer the compositions comprising a bispecific anti-HER2 antigen-binding construct, compositions comprising a cell cycle inhibitor as described herein or compositions comprising an endocrine-based therapy described herein locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. Preferably, when administering a protein, such as a bispecific anti-HER2 antigen-binding construct, care must be taken to use materials to which the protein does not absorb.

In another embodiment, the bispecific anti-HER2 antigen-binding constructs or ADCs can be delivered in a vesicle, in particular a liposome (see Langer, Science 249:1527-1533 (1990); Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid.)

In yet another embodiment, the bispecific anti-HER2 antigen-binding constructs or ADCs, or compositions comprising a cell cycle inhibitor as described herein or compositions comprising an endocrine-based therapy described herein, can be delivered in a controlled release system. In one embodiment, a pump may be used (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989)). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, J., Macromol. Sci. Rev. Macromol. Chem. 23:61 (1983); see also Levy et al., Science 228:190 (1985); During et al., Ann. Neurol. 25:351 (1989); Howard et al., J. Neurosurg. 71:105 (1989)). In yet another embodiment, a controlled release system can be placed in proximity of the therapeutic target, thus requiring only a fraction of the systemic dose (see, e.g., Goodson, in Medical Applications of Controlled Release, vol. 2, pp. 115-138 (1984)).

In certain embodiments, the bispecific anti-HER2 antigen-binding construct or ADC is administered as follows: 20 mg/kg IV; dosing Q2W (every 2 weeks) on Days 1 and 15 of each 28-day cycle. Up to 1 step-down dose level may also be used, such as 15 mg/kg Q2W or other dose not lower than 15 mg/kg Q2W. In certain embodiments, the bispecific anti-HER2 antigen-binding construct or ADC is administered in a dose level from 10-50 mg/kg IV. The dose may be administered In certain embodiments, the dose of the cell cycle inhibitor is palbociclib in a 125 mg capsule taken orally with food once daily (QD) for 21 consecutive days (Days 1 through 21) followed by 7 days off treatment (Days 22 through 28) in a 28-day cycle. In another embodiment, palbociclib may be administered at a dose of 75, 80, 85, 90, 95, 100, 125, 150, 175, or 200 mgs taken orally with food once daily, every two days, every three days, every four days, every five days, every six days, or once weekly. In one embodiment, the dose of fulvestrant is a 500 mg IM injection into the buttocks (two 5-mL injections, one per buttock, with each injection being administered over 1 to 2 minutes) Q2W for 3 doses and Q4W (every 4 weeks) thereafter. In a 28-day cycle, this means fulvestrant injections on Cycle 1 Day 1, Cycle 1 Day 15, Cycle 2 Day 1, and then Day 1 of all subsequent cycles. In certain embodiments, the dose of fulvestrant is at 100, 125, 150, 175, 200, 225, 250, 275, 300, 325, 350, 375, 400, 425 or 450 mg injections. In another embodiment, fulvestrant may be administered twice a week, weekly, Q2W, Q3W, Q4W, Q5W, Q6W or Q8W.

The present disclosure also provides a method of treating a patient with human epidermal growth factor receptor 2 (HER2)-positive, hormone receptor (HR)-positive breast cancer, the method comprising administering to the patient: I) about 15 mg/kg to 20 mg/kg of a bispecific anti-HER2 antigen-binding construct or antibody drug conjugate (ADC) thereof every 2 weeks (Q2W); and one or both of: II) a palbociclib 75 mg, 100 mg or 125 mg capsule administered orally (PO) once daily (QD) for the first 21 days of each 28-day cycle; and III) fulvestrant administered at 250 mg-500 mg Q2W for the first 3 doses, then once every 4 weeks (Q4W). In one embodiment, the breast cancer is HER2 3+, HER2 2+, or HER2 1+ as measured by immunohistochemistry (IHC). In another embodiment, the breast cancer is HER2 1+ as measured by IHC.

In one embodiment, the present disclosure provides a method of treating a patient with human epidermal growth factor receptor 2 (HER2)-positive, hormone receptor (HR)-positive breast cancer, the method comprising administering to the patient: I) about 15 mg/kg to 20 mg/kg of a bispecific anti-HER2 antigen-binding construct or antibody drug conjugate (ADC) thereof every 2 weeks (Q2W); and II) a palbociclib 75 mg, 100 mg or 125 mg capsule administered orally (PO) once daily (QD) for the first 21 days of each 28-day cycle. In one embodiment, the breast cancer is HER2 3+, HER2 2+, or HER2 1+ as measured by immunohistochemistry (IHC). In another embodiment, the breast cancer is HER2 1+ as measured by IHC.

In another embodiment, the present disclosure also provides a method of treating a patient with human epidermal growth factor receptor 2 (HER2)-positive, hormone receptor (HR)-positive breast cancer, the method comprising administering to the patient: I) about 15 mg/kg to 20 mg/kg of a bispecific anti-HER2 antigen-binding construct or antibody drug conjugate (ADC) thereof every 2 weeks (Q2W); and II) fulvestrant administered at 250 mg-500 mg Q2W for the first 3 doses, then once every 4 weeks (Q4W). In one embodiment, the breast cancer is HER2 3+, HER2 2+, or HER2 1+ as measured by immunohistochemistry (IHC). In another embodiment, the breast cancer is HER2 1+ as measured by IHC.

The combination treatment methods described herein may be administered alone or in conjunction with other types of treatments (e.g., radiation therapy, chemotherapy, additional hormonal therapy, immunotherapy and anti-tumor agents). Generally, administration of products of a species origin or species reactivity (in the case of antibodies) that is the same species as that of the patient is preferred. Thus, in an embodiment, human or humanized bispecific anti-HER2 antigen-binding constructs, fragments derivatives, analogs, or nucleic acids, are administered to a human patient for therapy or prophylaxis.

In one embodiment, the combination treatments described herein may be used in a method of treating breast cancer. In one embodiment, the combination regimens described herein may be used in a method of treating advanced unresectable breast cancer. In one embodiment, the combination regimens described herein may be used in a method of treating patients with hormone receptor (HR)-positive breast cancer. In another embodiment, the combination regimens described herein may be used in a method of treating patients (HER2)-positive breast cancer. In other embodiments, the combination regimens described herein may be used in a method of treating patients with locally advanced (unresectable) and/or metastatic human epidermal growth factor receptor 2 (HER2)-positive, hormone receptor (HR)-positive breast cancer. In one embodiment, HR+ is defined as estrogen-receptor positive (ER+) and/or progesterone-receptor positive (PgR+) disease based on the ASCO/ CAP Guideline Recommendations for Immunohistochemical Testing of Estrogen and Progesterone Receptors in Breast Cancer (Hammond 2010, J Oncol Pract. 2010; 6(4): 195-7). In certain embodiments, a breast cancer which is HR+ is one which, in a diagnostic test, demonstrates the presence of the estrogen and/or the progesterone receptor in breast cancer cells. Such presence of ER and/or PR can be determined directly (e.g. by measuring the presence of the protein by immunohistochemical staining) or indirectly (e.g. by gene expression profiling). In certain embodiments, a breast cancer is considered ER+ and/or PgR+ if there are at least 1% positive invasive tumor nuclei in the sample on testing. The percentage can be arrived at by estimation, by quantification, by manually counting or by using image analysis. In certain embodiments, the intensity of ER and/or PgR staining of a breast cancer can also be categorized as weak, moderate or strong.

In one embodiment, the combination treatments described herein may be used to treat a subject having a breast cancer that displays HER2 expression, amplification, or activation. A breast cancer which "displays HER2 expression, amplification, or activation" is one which, in a diagnostic test, expresses (including overexpresses) a HER2 receptor, has amplified HER2 gene, and/or otherwise demonstrates activation or phosphorylation of a HER2 receptor.

A breast cancer which "displays HER2 activation" is one which, in a diagnostic test, demonstrates activation or phosphorylation of a HER2 receptor. Such activation can be determined directly (e.g. by measuring HER2 phosphorylation by ELISA) or indirectly (e.g. by gene expression profiling). In one embodiment, the combination treatments described herein may be used to treat a subject having a breast cancer that displays HER2 expression.

A breast cancer with "HER2 receptor overexpression or amplification" is one which has significantly higher levels of a HER2 receptor protein or gene compared to a noncancerous cell of the same tissue type. Such overexpression may be caused by gene amplification or by increased transcription or translation. HER2 receptor overexpression or amplification may be determined in a diagnostic or prognostic assay by evaluating increased levels of the HER2 protein present on the surface of a cell (e.g. via an immunohistochemistry assay; IHC). In one embodiment, HER2 overexpression may be analyzed by IHC, e.g. using the HERCEPTEST® (Dako). Paraffin embedded tissue sections from a tumor biopsy may be subjected to the IHC assay and accorded a HER2 protein staining intensity criteria as follows:

Score 0: no staining is observed or membrane staining is observed in less than 10% of tumor cells.

Score 1+: a faint/barely perceptible membrane staining is detected in more than 10% of the tumor cells. The cells are only stained in part of their membrane.

Score 2+: a weak to moderate complete membrane staining is observed in more than 10% of the tumor cells.

Score 3+: a moderate to strong complete membrane staining is observed in more than 10% of the tumor cells.

Those tumors with 0 or 1+ scores for HER2 overexpression assessment may be characterized as not overexpressing HER2, whereas those tumors with 2+ or 3+ scores may be characterized as overexpressing HER2. In one embodiment, the combination treatments described herein may be used to treat a subject having a breast cancer that displays HER2 overexpression and/or amplification.

Alternatively, or additionally, one may measure levels of HER2-encoding nucleic acid in the cell, e.g. via in situ hybridization (ISH), including fluorescent in situ hybridization (FISH; see WO98/45479 published October, 1998) and chromogenic in situ hybridization (CISH; see, e.g. Tanner et al., Am. J. Pathol. 157(5): 1467-1472 (2000); Bella et al., J. Clin. Oncol. 26: (May 20 suppl; abstr 22147) (2008)), southern blotting, polymerase chain reaction (PCR) techniques, such as quantitative real time PCR (qRT-PCR), or next-generation sequencing (NGS). Assessment of HER2 gene amplification using these methods is typically reported as positive (+) or negative (−), for example FISH+ for HER2 gene amplified cancers or FISH− for cancers that are not HER2 gene amplified. Assessment of HER2 gene amplification by NGS may also be reported with regard to the number of HER2 gene copies. In normal cells, there are two copies of the HER2 gene. Accordingly, a cancer may be considered to be a HER2 gene amplified cancer if it has more than two copies of the HER2 gene.

Described herein are methods of treating a subject having a breast cancer that displays HER2 expression, amplification or activation, comprising providing to the subject an effective amount of a bispecific anti-HER2 antigen-binding construct or ADC thereof in combination with CDK4/6 inhibitors and endocrine-based therapy as described herein. In some embodiments, the combination treatments described herein may be used in the treatment of a subject having a HER2 3+, gene amplified breast cancer. In other embodiments, the combination treatment regimens described herein may be used in the treatment of a HER2 2+, gene amplified breast cancer. In other embodiments, the combination treatments described herein may be used in the treatment of a HER2 1+, gene amplified breast cancer. In other embodiments, the combination treatments described herein may be used in the treatment of a breast cancer assessed as HER2 3+, without HER2 gene amplification. In other embodiments, the combination treatments described herein may be used in the treatment of a breast cancer assessed as HER2 2+, without HER2 gene amplification. In other embodiments, the combination treatments described herein may be used in the treatment of a breast cancer assessed as HER2 1+, without HER2 gene amplification.

In some embodiments, the subject being treated may have had no prior treatment for breast cancer and the combination regimen is administered as a first-line treatment. In some embodiments, the combination treatments described herein may be used as adjuvant or neoadjuvant therapy to treat subjects having resectable or partially resectable cancer. In other embodiments, the subject being treated may have had one or more prior treatments for breast cancer and the combination regimen is administered as a second-line treatment. In certain embodiments, the combination treatments described herein are administered to a breast cancer patient who has progressed or has developed intolerance following one or more or all of pertuzumab, trastuzumab and T-DM1. In certain embodiments, a patient may have received one or more prior treatments for breast cancer, including but not limited to a chemotherapy such as a taxane (docetaxel, paclitaxel), capecitabine, anthracyclines (including but not limited to doxorubicin, epirubicin, pegylated liposomal doxorubicin), optionally in combination with cyclophosphamide or fluorouracil or both; nabpaclitaxel, vinorelbine, tamoxifen, abraxane, epothilones, an mTOR inhibitor (e.g., everolimus, sirolimus, temsirolimus), gemcitabine, cisplatin, oxaliplatin, leucovorin, a fluoropyrimidine drug (e.g., fluorouracil (5-FU), capecitabine or gemcitabine), a platinum-based drug, a PI3 kinase inhibitor (e.g., Piqray (alpelisib)), an immune checkpoint inhibitor such as the anti-PD1 antibody pembrolizumab (Keytruda™) or the anti-PD-L1 antibody atezolizumab (TECENTRIQ®), A PARP inhibitor (such as Olaparib and Talazoparib), or hormone treatments; or a combination of one or more of the preceding treatments.

Exemplary effective amounts of the bispecific anti-HER2 antigen-binding construct or ADC that may be administered to a subject with breast cancer can be between 0.1 mg/kg and 100 mg/kg body weight of the subject. In some embodiments, the bispecific anti-HER2 antigen-binding construct or ADC is administered at 1, 2, 3, 4, 5, 6, 7, 8, 9, 10, 20, 30, 40, 50, 60, 70, 80, 90, or 100 mg/kg body weight.

In some embodiments, the bispecific anti-HER2 antigen-binding construct is administered weekly, biweekly (Q2W), every three weeks (Q3W), or every 4 weeks (Q4W). Exemplary effective amounts for weekly dosing of the bispecific anti-HER2 antigen-binding construct range between about 1 mg/kg to about 30 mg/kg. Exemplary effective amounts for biweekly dosing of the bispecific anti-HER2 antigen-binding construct range between about 10 mg/kg to about 50 mg/kg. Exemplary effective amounts for dosing of the bispecific anti-HER2 antigen-binding construct every three weeks range between about 15 mg/kg to about 50 mg/kg. Exemplary effective amounts for dosing of the bispecific anti-HER2 antigen-binding construct every four weeks range between about 40 mg/kg to about 70 mg/kg.

In some embodiments the effective amount of the bispecific anti-HER2 antigen-binding construct is 5, 10, or 15 mg/kg weekly. In some embodiments the effective amount of the bispecific anti-HER2 antigen-binding construct is 10 mg/kg weekly. In some embodiments the effective amount of the bispecific anti-HER2 antigen-binding construct is 20, 25, or 30 mg/kg every two weeks. In other embodiments, the effective amount of the bispecific anti-HER2 antigen-binding construct is 20 mg/kg every two weeks. In alternate embodiments, the effective amount of the bispecific anti-HER2 antigen-binding construct is 20 mg/kg every three weeks. In still other embodiments, the effective amount of the bispecific anti-HER2 antigen-binding construct is 30 mg/kg every three weeks. In further embodiments, the effective amount of the bispecific anti-HER2 antigen-binding construct is 40 mg/kg every four weeks. In some embodiments the effective amount of the bispecific anti-HER2 antigen-binding construct is an initial dose of 20, 25, or 30 mg/kg, followed by a lower dose of the bispecific anti-HER2 antigen-binding construct.

As is known in the art, ADCs may be administered to subjects in doses that are lower than the doses used for the bispecific anti-HER2 antigen-binding construct. In some embodiments, the ADC described herein (i.e. a bispecific anti-HER2 antigen-binding construct linked to an auristatin analogue) is administered weekly, biweekly (Q2W), every three weeks (Q3W), or every 4 weeks (Q4W). In some embodiments the effective amount of the ADC that may be administered to a subject with breast cancer is between about 1 to about 15 mg/kg weekly, every two weeks, or every three weeks.

As indicated above, in specific embodiments, the bispecific anti-HER2 antigen-binding construct or ADC may be administered intravenously. In one embodiment, the bispecific anti-HER2 antigen-binding construct may be administered by IV infusion in 0.9% saline over 120 to 150 minutes. In one embodiment, the bispecific anti-HER2 antigen-binding construct may be administered by IV infusion in 0.9% saline over 90 minutes. In one embodiment, the bispecific anti-HER2 antigen-binding construct may be administered by IV infusion in 0.9% saline over 60 minutes. In related embodiments, the infusion rate may not exceed 250 mL of normal saline per hour.

Also provided herein are methods of treating a subject having a breast cancer comprising administering an effective amount of the combination regimen described herein in conjunction with additional anti-tumor treatments. The additional anti-tumor treatments may be selected from one or more treatments for breast cancer including chemotherapy such as taxanes (docetaxel, paclitaxel) and capecitabine. In certain embodiments, the additional treatments may comprise anthracyclines (including but not limited to doxorubicin, epirubicin, pegylated liposomal doxorubicin), optionally in combination with cyclophosphamide or fluorouracil or both. In other embodiments, the treatments described herein may include nabpaclitaxel, vinorelbine, tamoxifen, abraxane, epothilones, an mTOR inhibitor (e.g., everolimus, sirolimus, temsirolimus), or gemcitabine alone or with a platinum-based chemotherapeutic. In certain embodiments, the combination regimen described herein may be combined with a chemotherapy as noted and/or may be combined with radiotherapy without additional chemotherapy and/or other investigational agents (i.e. those currently undergoing clinical trials but that have not yet been approved by the FDA). In one embodiment, the method of treating a subject having breast cancer comprises administering an effective amount of the combination regimen described herein in conjunction with gemcitabine and cisplatin, or in conjunction with gemcitabine and oxaliplatin. In one embodiment, the bispecific anti-HER2 antigen-binding construct or ADC may be administered in conjunction with a fluoropyrimidine drug and a platinum-based drug. Examples of fluoropyrimidine drugs include but are not limited to fluorouracil (5-FU), capecitabine or gemcitabine. Examples of platinum-based drugs include but are not limited to cisplatin or oxaliplatin. In other embodiments, the combination treatments described herein may be administered in conjunction with 5-FU, oxaliplatin, and leucovorin. In still other embodiments, the combination treatment may be administered in conjunction with an immune checkpoint inhibitor such as an anti-PD1 antibody (e.g., pembrolizumab (Keytruda™)) or an anti-PD-L1 antibody (e.g., atezolizumab (TECENTRIQ®)). In other embodiments, for breast cancer patients having BRCA mutated breast cancers, the combination regimens here may be administered in conjunction with PARP inhibitors (Olaparib and Talazoparib). In some embodiments, breast cancer patients having hormone receptor positive disease are also treated with hormone treatments.

Additional anti-tumor treatments for breast cancer are known in the art. One of skill in the art would be able to identify which of these treatments may be administered in conjunction with the combination treatments described herein.

The additional anti-tumor treatments described in the preceding paragraphs may be administered concurrently with the combination treatments or may be administered sequentially.

In some embodiments, the result of providing an effective amount of the combination treatments as described herein to a subject having a breast cancer is shrinking the lesion(s), inhibiting growth of the lesion(s), increasing time to progression of the lesion(s), prolonging disease-free survival of the subject, decreasing metastases, increasing the progression-free survival of the subject, or increasing overall survival of the subject or increasing the overall survival of a group of subjects receiving the treatment. In related embodiments, the result of providing an effective amount of the combination treatments herein to a subject is a partial response (PR) or stable disease (SD) in the subject, as measured by the revised Response Evaluation Criteria in Solid Tumors (RECIST) guideline (version 1.1) [Eur J Ca 45:228-247, 2009]. In subjects having metastatic disease and either a CR or PR, duration of response may also be measured.

As used herein, the term "progressive disease" (PD) refers to the appearance of one or more new lesions and/or unequivocal progression of existing non-target lesions. PD may be declared on the basis of "unequivocal progression" in cases where the overall tumor burden increases significantly enough to require a change in therapy; in most cases, a modest increase in the size of one or more non-target lesions is not sufficient to qualify (especially in the presence of SD or PR in target disease).

As used herein, the term "partial response," (PR) refers to at least a 30% decrease in the sum of the diameters of target lesions (including the short axes of any target lymph nodes), taking as reference the baseline sum diameter.

As used herein, the term "complete response" (CR) refers to the disappearance of all non-target lesions, the normalization of the tumor marker level (if tumor markers are measured and are initially above the upper limit of normal, those must normalize for a patient to be considered in complete clinical response). All lymph nodes must be <10 mm (short axis).

As used herein, the term "stable disease" (SD) refers to neither sufficient shrinkage to qualify for PR nor sufficient increase to qualify for PD, taking as reference the smallest sum diameter since the treatment started.

As used herein, the term "objective response rate" (ORR) is the proportion of all randomized patients who receive any amount of study medication with PR or CR according to RECIST v 1.1 from the start of the treatment until disease progression/recurrence (taking as reference for PD the smallest measurements recorded since the treatment started).

As used herein, the term "overall survival" (OS) refers to the time from the date of randomization to the date of death from any cause.

As used herein, the term "progression-free survival" (PFS) refers to the patient remaining alive without the cancer progressing or getting worse. In one embodiment, PFS is defined as the time from randomization in the Study until the first radiographic documentation of objective progression as defined by RECIST (Version 1.1), or death from any cause. Patients who die without a reported prior progression will be considered to have progressed on the day of their death. Patients who did not progress or are lost to follow-up will be censored at the day of their last radiographic tumor assessment.

As used herein, the term "disease-free survival" (DFS) refers to the length of time after primary treatment for a cancer ends that the patient survives without any signs or symptoms of that cancer. DFS may also be referred to as "relapse-free survival" (RFS).

As used herein, the term "time to progression" (TTP) refers to the length of time from the date of diagnosis or the start of treatment for a cancer until the cancer starts to get worse or spread to other parts of the body.

As used herein, the term "disease control rate" (DCR) refers to lack of disease progression and rate thereof. It refers to the group of patients with a best overall response categorized as CR, PR or SD (specifically excluding the patients with PD), wherein the best overall response is the best response recorded from the start of treatment until PD.

As used herein, the term "duration of overall response" (DOR) refers to the period measured from the time that measurement criteria are met for complete or partial response (whichever status is recorded first) until the first date that recurrent or progressive disease is objectively documented, taking as reference the smallest measurements recorded since treatment started.

In some embodiments, the result of providing an effective amount of the combination treatments herein to a subject having a breast cancer is increasing the disease control rate (DCR) in a group of subjects. DCR may be useful to measure the efficacy of therapies that have tumoristatic effects rather than tumoricidal effects. The DCR is calculated as the percentage of patients having breast cancer exhibiting CR, PR or SD after the combination treatment. In one embodiment, administration of an effective amount of the combination treatment to subjects results in a DCR greater than 10%, 15%, 20%, 25%, 30%, 35%, 40%, 45%, 50%, 55%, 60%, 65%, 70%, 75%, 80%, 85%, 90%, or 95%. In other embodiments, administration of an effective amount of the combination treatment to subjects results in a DCR greater than 20%, 25%, 30%, 35%, 40%, 45%, 50%, 55%, 60%, 65%, 70%, 75%, 80%, 85%, 90%, or 95%.

PFS (progression-free survival) and ORR (overall response rate) may also be used to determine the efficacy of the combination treatments and are measured according to the revised RECIST 1.1 guidelines noted above. PFS is defined as the time from randomization until objective tumor progression or death. ORR is defined as the proportion of subjects having breast cancer who have a partial or complete response to therapy with the combination regimen described herein. ORR may be used as a measure of drug tumoricidal activity. In some embodiments, the result of providing an effective amount of the combination treatment to a subject having breast cancer is increasing the progression-free survival (PFS) in a group of subjects. In some embodiments, the result of providing an effective amount of a combination treatment as described herein to a subject having breast cancer is increasing the overall response rate (ORR). In one embodiment, administration of an effective amount of the combination treatment to subjects results in an ORR greater than 10%, 15%, 20%, 25%, 30%, 35%, 40%, 45%, 50%, 55%, 60%, 65%, 70%, 75%, 80%, 85%, 90%, or 95%. In yet another embodiment, administration of an effective amount of the combination treatment to subjects results in an ORR greater than 20%, 25%, 30%, 35%, 40%, 45%, 50%, 55%, 60%, 65%, 70%, 75%, 80%, 85%, 90%, or 95%.

Overall survival, time to progression, duration of response (DOR) (may also be used to determine the efficacy of the combination treatment.

When the combination treatment is administered as an adjuvant or neoadjuvant therapy, disease-free survival may also be measured to determine the efficacy of the therapy.

In some embodiments, the bispecific antigen-binding construct targeting HER2 is linked to an auristatin analogue (referred to herein as an antibody-drug conjugate or ADC). In some embodiments, the bispecific antigen-binding construct targeting HER2 or ADCs thereof, may be used in a combination regimen as described herein for a method of treating, in particular, patients with locally advanced (unresectable) and/or metastatic human epidermal growth factor receptor 2 (HER2)-positive, hormone receptor (HR)-positive breast cancer. In other embodiments, the combination treatment, when administered to a subject with breast cancer may result in a decrease in the size of tumors or lesions in the subject. In yet other embodiments, administration of the combination treatment may result in a complete response (CR), partial response (PR) or stable disease (SD) in a subject as measured by RECIST 1.1 guidelines.

Also described herein is a method of treating breast cancer comprising administering a bispecific antigen-binding construct targeting HER2 to a subject in conjunction with a cell cycle inhibitor. In certain embodiments, the cell cycle inhibitor is a cyclin-dependent kinase 4/6 (CDK4/6) inhibitor. In this regard, in certain embodiments, the CDK4/6 inhibitor is selected from the group of palbociclib, abemaciclib, and ribociclib. In certain embodiments of the present disclosure, the methods further include administration to the breast cancer patient an endocrine based therapy, such as letrozole or fulvestrant.

In specific embodiments of the methods described herein, the bispecific anti-HER2 antigen-binding construct is v10000. In other specific embodiments of the methods described herein, the ADC is v10000 linked to an auristatin analogue. In specific embodiments of the methods described herein, the bispecific anti-HER2 antigen-binding construct is v10000 or an ADC thereof and the CDK4/6 inhibitor is selected from the group of palbociclib, abemaciclib, and ribociclib. In another embodiment of the methods described herein, the bispecific anti-HER2 antigen-binding construct is v10000 or an ADC thereof and the CDK4/6 inhibitor is selected from the group of palbociclib, abemaciclib, and ribociclib; and the endocrine-based therapy is a non-steroidal aromatase inhibitors or a selective estrogen receptor degrader. In another embodiment of the methods herein, the bispecific anti-HER2 antigen-binding construct is v10000 or an ADC thereof, the CDK4/6 inhibitor is palbociclib and the endocrine-based therapy is fulvestrant. In certain embodiments, the method of treating breast cancer comprises the following regimen: I) administering to the breast cancer patient: palbociclib between about 40 mg-150 mg oral capsules daily for 21 days of each 28 day cycle; II) about 10 mg/kg to 25 mg/kg of a bispecific anti-HER2 antigen-binding construct or antibody drug conjugate (ADC) thereof every 2 weeks (Q2W); and III) fulvestrant administered at about 200 mg-500 mg Q2W for the first 3 doses, then once every 4 weeks (Q4W).

In one particular embodiment, the method of treating breast cancer comprises the following treatment regimen: I) one palbociclib 75 mg, 100 mg or 125 mg capsule administered orally (PO) once daily (QD) for the first 21 days of each 28-day cycle; II) about 15 mg/kg to 20 mg/kg of a bispecific anti-HER2 antigen-binding construct or antibody drug conjugate (ADC) thereof every 2 weeks (Q2W); and III) fulvestrant administered at 250 mg-500 mg Q2W for the first 3 doses, then once every 4 weeks (Q4W).

Kits and Articles of Manufacture

Also described herein are kits comprising one or more bispecific anti-HER2 antigen-binding constructs or ADCs, one or more cell cycle inhibitors as described herein or one or more endocrine-based therapy as described herein. Individual components of the kit would be packaged in separate containers and, associated with such containers, can be a notice in the form prescribed by a governmental agency regulating the manufacture, use or sale of pharmaceuticals or biological products, which notice reflects approval by the agency of manufacture, use or sale. The kit may optionally contain instructions or directions outlining the method of use or administration regimen for the bispecific anti-HER2 antigen-binding construct or ADC, the cell cycle inhibitors and the endocrine-based therapy.

When one or more components of the kit are provided as solutions, for example an aqueous solution, or a sterile aqueous solution, the container means may itself be an inhalant, syringe, pipette, eye dropper, or other such like apparatus, from which the solution may be administered to a subject or applied to and mixed with the other components of the kit.

The components of the kit may also be provided in dried or lyophilized form and the kit can additionally contain a suitable solvent for reconstitution of the lyophilized components. Irrespective of the number or type of containers, the kits described herein also may comprise an instrument for assisting with the administration of the composition to a patient. Such an instrument may be an inhalant, nasal spray device, syringe, pipette, forceps, measured spoon, eye dropper or similar medically approved delivery vehicle.

In another aspect described herein, an article of manufacture containing materials useful for the treatment, prevention and/or diagnosis of breast cancers is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper pierceable by a hypodermic injection needle). The label or package insert indicates that the composition is used for treating the condition of choice. Moreover, the article of manufacture may comprise (a) a first container with a composition contained therein, wherein the composition comprises a bispecific anti-HER2 antigen-binding construct or ADC described herein; (b) a second container with a composition contained therein, wherein the composition comprises a cell cycle inhibitor such as palbociclib, abemaciclib, or ribociclib; (c) a third container with a composition contained therein, wherein the composition comprises an endocrine based therapy (such as but not limited to a non-steroidal aromatase inhibitors (e.g., letrozole, anostrozole) or a selective estrogen receptor degrader (e.g., fulvestrant, brilanestrant, elacestrant); and in certain embodiments, (d) a fourth container comprising a further cytotoxic or otherwise therapeutic agent. The article of manufacture in this embodiment described herein may further comprise a package insert indicating that the compositions can be used to treat breast cancers. Alternatively, or additionally, the article of manufacture may further comprise another container comprising a pharmaceutically acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

Polypeptides and Polynucleotides

The bispecific anti-HER2 antigen-binding constructs described herein comprise at least one polypeptide. Also described are polynucleotides encoding the polypeptides described herein. The bispecific anti-HER2 antigen-binding constructs are typically isolated.

As used herein, "isolated" means an agent (e.g., a polypeptide or polynucleotide) that has been identified and separated and/or recovered from a component of its natural cell culture environment. Contaminant components of its natural environment are materials that would interfere with diagnostic or therapeutic uses for the bispecific anti-HER2 antigen-binding construct, and may include enzymes, hormones, and other proteinaceous or non-proteinaceous solutes. Isolated also refers to an agent that has been synthetically produced, e.g., via human intervention.

The terms "polypeptide," "peptide" and "protein" are used interchangeably herein to refer to a polymer of amino acid residues. That is, a description directed to a polypeptide applies equally to a description of a peptide and a description of a protein, and vice versa. The terms apply to naturally occurring amino acid polymers as well as amino acid polymers in which one or more amino acid residues is a non-naturally encoded amino acid. As used herein, the terms encompass amino acid chains of any length, including full length proteins, wherein the amino acid residues are linked by covalent peptide bonds.

The term "amino acid" refers to naturally occurring and non-naturally occurring amino acids, as well as amino acid analogs and amino acid mimetics that function in a manner similar to the naturally occurring amino acids. Naturally encoded amino acids are the 20 common amino acids (alanine, arginine, asparagine, aspartic acid, cysteine, glutamine, glutamic acid, glycine, histidine, isoleucine, leucine, lysine, methionine, phenylalanine, praline, serine, threonine, tryptophan, tyrosine, and valine) and pyrrolysine and selenocysteine. Amino acid analogs refers to compounds that have the same basic chemical structure as a naturally occurring amino acid, i.e., an a carbon that is bound to a hydrogen, a carboxyl group, an amino group, and an R group, such as, homoserine, norleucine, methionine sulfoxide, methionine methyl sulfonium. Such analogs have modified R groups (such as, norleucine) or modified peptide backbones, but retain the same basic chemical structure as a naturally occurring amino acid. Reference to an amino acid includes, for example, naturally occurring proteogenic L-amino acids; D-amino acids, chemically modified amino acids such as amino acid variants and derivatives; naturally occurring non-proteogenic amino acids such as β-alanine, ornithine, etc.; and chemically synthesized compounds having properties known in the art to be characteristic of amino acids. Examples of non-naturally occurring amino acids include, but are not limited to, α-methyl amino acids (e.g. α-methyl alanine), D-amino acids, histidine-like amino acids (e.g., 2-amino-histidine, β-hydroxy-histidine, homohistidine), amino acids having an extra methylene in the side chain ("homo" amino acids), and amino acids in which a carboxylic acid functional group in the side chain is replaced with a sulfonic acid group (e.g., cysteic acid). The incorporation of non-natural amino acids, including synthetic non-native amino acids, substituted amino acids, or one or more D-amino acids into the proteins described herein may be advantageous in a number of different ways. D-amino acid-containing peptides, etc., exhibit increased stability in vitro or in vivo compared to L-amino acid-containing counterparts. Thus, the construction of peptides, etc., incorporating D-amino acids can be particularly useful when greater intracellular stability is desired or required. More specifically, D-peptides, etc., are resistant to endogenous peptidases and proteases, thereby providing improved bioavailability of the molecule, and prolonged lifetimes in vivo when such properties are desirable. Additionally, D-peptides, etc., cannot be processed efficiently for major histocompatibility complex class II-restricted presentation to T helper cells, and are therefore, less likely to induce humoral immune responses in the whole organism.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

Also described herein are polynucleotides encoding polypeptides of the bispecific anti-HER2 antigen-binding constructs. The term "polynucleotide" or "nucleotide sequence" is intended to indicate a consecutive stretch of two or more nucleotide molecules. The nucleotide sequence may be of genomic, cDNA, RNA, semisynthetic or synthetic origin, or any combination thereof.

The term "nucleic acid" refers to deoxyribonucleotides, deoxyribonucleosides, ribonucleosides, or ribonucleotides and polymers thereof in either single- or double-stranded form. Unless specifically limited, the term encompasses nucleic acids containing known analogues of natural nucleotides which have similar binding properties as the reference nucleic acid and are metabolized in a manner similar to naturally occurring nucleotides. Unless specifically limited otherwise, the term also refers to oligonucleotide analogs including PNA (peptidonucleic acid), analogs of DNA used in antisense technology (phosphorothioates, phosphoroamidates, and the like). Unless otherwise indicated, a particular nucleic acid sequence also implicitly encompasses conservatively modified variants thereof (including but not limited to, degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260:2605-2608 (1985); Rossolini et al., Mol. Cell. Probes 8:91-98 (1994)).

"Conservatively modified variants" applies to both amino acid and nucleic acid sequences. With respect to particular nucleic acid sequences, "conservatively modified variants" refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of ordinary skill in the art will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of ordinary skill in the art will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the deletion of an amino acid, addition of an amino acid, or substitution of an amino acid with a chemically similar amino acid. Conservative substitution tables providing functionally similar amino acids are known to those of ordinary skill in the art. Such conservatively modified variants are in addition to and do not exclude polymorphic variants, interspecies homologs, and alleles described herein.

Conservative substitution tables providing functionally similar amino acids are known to those of ordinary skill in the art. The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and [0139] 8) Cysteine (C), Methionine (M) (see, e.g., Creighton, Proteins: Structures and Molecular Properties (W H Freeman & Co.; 2nd edition (December 1993)

The terms "identical" or percent "identity," in the context of two or more nucleic acids or polypeptide sequences, refer to two or more sequences or subsequences that are the same. Sequences are "substantially identical" if they have a percentage of amino acid residues or nucleotides that are the same (i.e., about 60% identity, about 65%, about 70%, about 75%, about 80%, about 85%, about 90%, or about 95% identity over a specified region), when compared and aligned for maximum correspondence over a comparison window, or designated region as measured using one of the following sequence comparison algorithms (or other algorithms available to persons of ordinary skill in the art) or by manual alignment and visual inspection. This definition also refers to the complement of a test sequence. The identity can exist over a region that is at least about 50 amino acids or nucleotides in length, or over a region that is 75-100 amino acids or nucleotides in length, or, where not specified, across the entire sequence of a polynucleotide or polypeptide. A polynucleotide encoding a polypeptide described herein, including homologs from species other than human, may be obtained by a process comprising the steps of screening a library under stringent hybridization conditions with a labeled probe having a polynucleotide sequence described herein or a fragment thereof, and isolating full-length cDNA and genomic clones containing said polynucleotide sequence. Such hybridization techniques are well known to the skilled artisan.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are known to those of ordinary skill in the art. Optimal alignment of sequences for comparison can be conducted, including but not limited to, by the local homology algorithm of Smith and Waterman (1970) Adv. Appl. Math. 2:482c, by the homology alignment algorithm of Needleman and Wunsch (1970) J. Mol. Biol. 48:443, by the search for similarity method of Pearson and Lipman (1988) Proc. Nat'l. Acad. Sci. USA 85:2444, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Ausubel et al., Current Protocols in Molecular Biology (1995 supplement)).

One example of an algorithm that is suitable for determining percent sequence identity and sequence similarity are the BLAST and BLAST 2.0 algorithms, which are described in Altschul et al. (1997) Nuc. Acids Res. 25:3389-3402, and Altschul et al. (1990) J. Mol. Biol. 215:403-410, respectively. Software for performing BLAST analyses is publicly available through the National Center for Biotechnology Information available at the World Wide Web at ncbi.nlm.nih.gov. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff and Henikoff (1992) Proc. Natl. Acad. Sci. USA 89:10915) alignments (B) of 50, expectation (E) of 10, M=5, N=−4, and a comparison of both strands. The BLAST algorithm is typically performed with the "low complexity" filter turned off.

The BLAST algorithm also performs a statistical analysis of the similarity between two sequences (see, e.g., Karlin and Altschul (1993) Proc. Natl. Acad. Sci. USA 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, or less than about 0.01, or less than about 0.001.

The phrase "selectively (or specifically) hybridizes to" refers to the binding, duplexing, or hybridizing of a molecule only to a particular nucleotide sequence under stringent hybridization conditions when that sequence is present in a complex mixture (including but not limited to, total cellular or library DNA or RNA).

The phrase "stringent hybridization conditions" refers to hybridization of sequences of DNA, RNA, or other nucleic acids, or combinations thereof under conditions of low ionic strength and high temperature as is known in the art. Typically, under stringent conditions a probe will hybridize to its target subsequence in a complex mixture of nucleic acid (including but not limited to, total cellular or library DNA or RNA) but does not hybridize to other sequences in the complex mixture. Stringent conditions are sequence-dependent and will be different in different circumstances. Longer sequences hybridize specifically at higher temperatures. An extensive guide to the hybridization of nucleic acids is found in Tijssen, Laboratory Techniques in Biochemistry and Molecular Biology—Hybridization with Nucleic Probes, "Overview of principles of hybridization and the strategy of nucleic acid assays" (1993).

As used herein, the terms "engineer, engineered, engineering", are considered to include any manipulation of the peptide backbone or the post-translational modifications of a naturally occurring or recombinant polypeptide or fragment thereof. Engineering includes modifications of the amino acid sequence, of the glycosylation pattern, or of the side chain group of individual amino acids, as well as combinations of these approaches. The engineered proteins are expressed and produced by standard molecular biology techniques.

By "isolated nucleic acid molecule or polynucleotide" is intended a nucleic acid molecule, DNA or RNA, which has been removed from its native environment. For example, a recombinant polynucleotide encoding a polypeptide contained in a vector is considered isolated. Further examples of an isolated polynucleotide include recombinant polynucleotides maintained in heterologous host cells or purified (partially or substantially) polynucleotides in solution. An isolated polynucleotide includes a polynucleotide molecule contained in cells that ordinarily contain the polynucleotide molecule, but the polynucleotide molecule is present extra-chromosomally or at a chromosomal location that is different from its natural chromosomal location. Isolated RNA molecules include in vivo or in vitro RNA transcripts, as well as positive and negative strand forms, and double-stranded forms. Isolated polynucleotides or nucleic acids described herein, further include such molecules produced synthetically, e.g., via PCR or chemical synthesis. In addition, a polynucleotide or a nucleic acid, in certain embodiments, include a regulatory element such as a promoter, ribosome binding site, or a transcription terminator.

The term "polymerase chain reaction" or "PCR" generally refers to a method for amplification of a desired nucleotide sequence in vitro, as described, for example, in U.S. Pat. No. 4,683,195. In general, the PCR method involves repeated cycles of primer extension synthesis, using oligonucleotide primers capable of hybridising preferentially to a template nucleic acid.

By a nucleic acid or polynucleotide having a nucleotide sequence at least, for example, 95% "identical" to a reference nucleotide sequence of the present invention, it is intended that the nucleotide sequence of the polynucleotide is identical to the reference sequence except that the polynucleotide sequence may include up to five point mutations per each 100 nucleotides of the reference nucleotide sequence. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These alterations of the reference sequence may occur at the 5' or 3' terminal positions of the reference nucleotide sequence or anywhere between those terminal positions, interspersed either individually among residues in the reference sequence or in one or more contiguous groups within the reference sequence. As a practical matter, whether any particular polynucleotide sequence is at least 80%, 85%, 90%, 95%, 96%, 97%, 98% or 99% identical to a nucleotide sequence of the present invention can be determined conventionally using known computer programs, such as the ones discussed above for polypeptides (e.g. ALIGN-2).

A derivative, or a variant of a polypeptide is said to share "homology" or be "homologous" with the peptide if the amino acid sequences of the derivative or variant has at least 50% identity with a 100 amino acid sequence from the original peptide. In certain embodiments, the derivative or variant is at least 75% the same as that of either the peptide or a fragment of the peptide having the same number of amino acid residues as the derivative. In certain embodiments, the derivative or variant is at least 85% the same as that of either the peptide or a fragment of the peptide having the same number of amino acid residues as the derivative. In certain embodiments, the amino acid sequence of the derivative is at least 90% the same as the peptide or a fragment of the peptide having the same number of amino acid residues as the derivative. In some embodiments, the amino acid sequence of the derivative is at least 95% the same as the peptide or a fragment of the peptide having the same number of amino acid residues as the derivative. In certain embodiments, the derivative or variant is at least 99% the same as that of either the peptide or a fragment of the peptide having the same number of amino acid residues as the derivative.

The term "modified," as used herein refers to any changes made to a given polypeptide, such as changes to the length of the polypeptide, the amino acid sequence, chemical structure, co-translational modification, or post-translational modification of a polypeptide. The form "(modified)" term means that the polypeptides being discussed are optionally modified, that is, the polypeptides under discussion can be modified or unmodified.

In some aspects, a bispecific anti-HER2 antigen-binding construct comprises an amino acid sequence that is at least 80, 85, 90, 91, 92, 93, 94, 95, 96, 97, 98, 99, or 100% identical to a relevant amino acid sequence or fragment thereof set forth in the Table(s) or accession number(s) disclosed herein. In some aspects, an isolated bispecific anti-HER2 antigen-binding construct comprises an amino acid sequence encoded by a polynucleotide that is at least 80, 85, 90, 91, 92, 93, 94, 95, 96, 97, 98, 99, or 100% identical to a relevant nucleotide sequence or fragment thereof set forth in the Table(s) or accession number(s) disclosed herein.

It is to be understood that the disclosure is not limited to the particular protocols; cell lines, constructs, and reagents described herein and as such may vary. It is also to be understood that the terminology used herein is for the purpose of describing particular embodiments only, and is not intended to limit the scope of the present disclosure All publications and patents mentioned herein are incorporated herein by reference for the purpose of describing and disclosing, for example, the constructs and methodologies that are described in the publications, which might be used in connection with the constructs described herein. The publications discussed herein are provided solely for their disclosure prior to the filing date of the present application. Nothing herein is to be construed as an admission that the inventors are not entitled to antedate such disclosure by virtue of prior invention or for any other reason.

Sequence Tables

TABLE 6

Clone Numbers for Variants v5019, v5020, v7091, v10000, v6903, v6902 and v6717

| Variant | H1 clone # | H2 clone # | L1 clone # | L2 clone # |
|---------|------------|------------|------------|------------|
| 5019 | 3057 | 720 | 1811 | — |
| 5020 | 719 | 3041 | — | 1811 |
| 7091 | 3057 | 5244 | 1811 | — |
| 10000 | 6586 | 5244 | 3382 | — |
| 6903 | 5065 | 3468 | 5037 | 3904 |
| 6902 | 5065 | 3468 | 5034 | 3904 |
| 6717 | 3317 | 720 | — | — |

TABLE 7

Sequence for Variants v5019, v5020, v7091, v10000, v6903, v6902 and v6717 by Clone Number

| SEQ ID NO. | Clone # | Desc | Sequence (amino acid or DNA) |
|---|---|---|---|
| 3 | 3468 | Full | GEVQLVESGGGLVQPGGSLRLSCAASGFTFTDYTMDWVRQAPGKGLEWV ADVNPNSGGSIYNQRFKGRFTLSVDRSKNTLYLQMNSLRAEDTAVYYCAR NLGPSFYFDYWGQGTLVTVSSASTKGPSVFPLAPSSKSTSGGTAALGCLVK GYFPEPVTVSWNSGALTSGVHTFPAVLKSSGLYSLSSVVTVPSSSLGTQTYI CNVNHKPSNTKVDKKVEPKSCDKTHTCPPCPAPELLGGPSVFLFPPKPKDT LMISRTPEVTCVVVDVSHEDPEVKFNWYVDGVEVHNAKTKPREEQYNSTY RVVSVLTVLHQDWLNGKEYKCKVSNKALPAPIEKTISKAKGQPREPQVYV LPPSRDELTKNQVSLLCLVKGFYPSDIAVEWESNGQPENNYLTWPPVLDSD GSFFLYSKLTVDKSRWQQGNVFSCSVMHEALHNHYTQKSLSLSPG |
| 4 | 3468 | Full | GGGGAAGTGCAGCTGGTCGAATCTGGAGGAGGACTGGTGCAGCCAGGA GGGTCCCTGCGCCTGTCTTGCGCCGCTAGTGGCTTCACTTTTACCGACTA CACCATGGATTGGGTGCGACAGGCACCTGGAAAGGGCCTGGAGTGGGT CGCCGATGTGAACCCAAATAGCGGAGGCTCCATCTACAACCAGCGGTTC AAGGGGCCGGTTCACCCTGTCAGTGGACCGGAGCAAAAACACCCTGTAT CTGCAGATGAATAGCCTGCGAGCCGAAGATACTGCTGTGTACTATTGCG CCCCGGAATCTGGGGCCCTCCTTCTACTTTGACTATTGGGGGCAGGGAAC TCTGGTCACCGTGAGCTCCGCCTCCACCAAGGGACCTTCTGTGTTCCCA CTGGCTCCCTCTAGTAAATCCACATCTGGGGGAACTGCAGCCCTGGGCT GTCTGGTGAAGGGCTACTTCCCAGAGCCCGTCACAGTGTCTTGGAACAG TGGCGCTCTGACTTCTGGGGTCCACACCTTTCCTGCAGTGCTGAAGTCA AGCGGGCTGTACAGCCTGTCCTCTGTGGTCACCGTGCCAAGTTCAAGCC TGGGAACACAGACTTATATCTGCAACGTGAATCACAAGCCATCCAATAC AAAAGTCGACAAGAAAGTGGAACCCAAGTCTTGTGATAAAACCCATAC ATGCCCCCCTTGTCCTGCACCAGAGCTGCTGGGAGGACCAAGCGTGTTC CTGTTTCCACCCAAGCCTAAAGATACACTGATGATTAGTAGGACCCCAG AAGTCACATGCGTGGTCGTGGACGTGAGCCACGAGGACCCCGAAGTCA AGTTTAACTGGTACGTGGACGGCGTCGAGGTGCATAATGCCAAGACTA AACCCAGGGAGGAACAGTACAACAGTACCTATCGCGTCGTGTCAGTCCT GACAGTGCTGCATCAGGATTGGCTGAACGGGAAAGAGTATAAGTGCAA AGTGAGCAATAAGGCTCTGCCCGCACCTATCGAGAAAACAATTTCCAA GGCAAAAGGACAGCCTAGAGAACCACAGGTGTACGTGCTGCCTCCATC AAGGGATGAGCTGACAAAGAACCAGGTCAGCCTGCTGTGTCTGGTGAA AGGATTCTATCCCTCTGACATTGCTGTGGAGTGGGAAAGTAATGGCCAG CCTGAGAACAATTACCTGACCTGGCCCCCTGTGCTGGACTCAGATGGCA GCTTCTTTCTGTATAGCAAGCTGACCGTCGACAAATCCCGGTGGCAGCA GGGGAATGTGTTTAGTTGTTCAGTCATGCACGAGGCACTGCACAACCAT TACACCCAGAAGTCACTGTCACTGTCACCAGGG |
| 5 | 3468 | VH | EVQLVESGGGLVQPGGSLRLSCAASGFTFTDYTMDWVRQAPGKGLEWVA DVNPNSGGSIYNQRFKGRFTLSVDRSKNTLYLQMNSLRAEDTAVYYCARN LGPSFYFDYWGQGTLVTVSS |
| 6 | 3468, 3057, 3041, 3317 | H1 | GFTFTDYT |
| 7 | 3468, 3057, 3041, 3317 | H3 | ARNLGPSFYFDY |

TABLE 7-continued

Sequence for Variants v5019, v5020, v7091, v10000, v6903, v6902 and v6717 by Clone Number

| SEQ ID NO. | Clone # | Desc | Sequence (amino acid or DNA) |
|---|---|---|---|
| 8 | 3468, 3057, 3041, 3317 | H2 | VNPNSGGS |
| 9 | 1811 | Full | GDIQMTQSPSSLSASVGDRVTITCKASQDVSIGVAWYQQKPGKAPKLLIYS ASYRYTGVPSRFSGSGSGTDFTLTISSLQPEDFATYYCQQYYIYPYTFGQGT KVEIKRTVAAPSVFIFPPSDEQLKSGTASVVCLLNNFYPREAKVQWKVDNA LQSGNSQESVTEQDSKDSTYSLSSTLTLSKADYEKHKVYACEVTHQGLSSP VTKSFNRGEC |
| 10 | 1811 | Full | GGGGATATTCAGATGACCCAGTCCCCAAGCTCCCTGAGTGCCTCAGTGG GCGACCGAGTCACCATCACATGCAAGGCTTCCCAGGATGTGTCTATTGG AGTCGCATGGTACCAGCAGAAGCCAGGCAAAGCACCCAAGCTGCTGAT CTATAGCGCCTCCTACCGGTATACCGGCGTGCCCTCTAGATTCTCTGGC AGTGGGTCAGGAACAGACTTTACTCTGACCATCTCTAGTCTGCAGCCTG AGGATTTCGCTACCTACTATTGCCAGCAGTACTATATCTACCCATATACC TTTGGCCAGGGGACAAAAGTGGAGATCAAGAGGACTGTGGCCGCTCCC TCCGTCTTCATTTTTCCCCCTTCTGACGAACAGCTGAAAAGTGGCACAG CCAGCGTGGTCTGTCTGCTGAACAATTTCTACCCTCGCGAAGCCAAAGT GCAGTGGAAGGTCGATAACGCTCTGCAGAGCGGCAACAGCCAGGAGTC TGTGACTGAACAGGACAGTAAAGATTCAACCTATAGCCTGTCAAGCAC ACTGACTCTGAGCAAGGCAGACTACGAGAAGCACAAAGTGTATGCCTG CGAAGTCACACATCAGGGGCTGTCCTCTCCTGTGACTAAGAGCTTTAAC AGAGGAGAGTGT |
| 11 | 1811 | VL | DIQMTQSPSSLSASVGDRVTITCKASQDVSIGVAWYQQKPGKAPKLLIYSAS YRYTGVPSRFSGSGSGTDFTLTISSLQPEDFATYYCQQYYIYPYTFGQGTKV EIK |
| 12 | 1811, 3904, 3317 | L1 | QDVSIG |
| 13 | 1811, 3904, 3317 | L3 | QQYYIYPYT |
| 14 | 1811, 3904, 3317 | L2 | SAS |
| 15 | 5034 | Full | GDYKDDDDKDIQMTQSPSSLSASVGDRVTITCRASQDVNTAVAWYQQKP GKAPKLLIYSASFLYSGVPSRFSGSRSGTDFTLTISSLQPEDFATYYCQQHYT TPPTFGQGTKVEIKRTVAAPSVFIFPPSDERLKSGTASVVCLLNNFYPREAK VQWKVDNALQSGNSQESVTEQDSKDSTYSLSSTLTLSKADYEKHKVYACE VTHQGLSSPVTKSFNRGEC |
| 16 | 5034 | Full | GGGGACTACAAAGACGACGATGACAAAGATATCCAGATGACCCAGTCC CCTAGCTCCCTGTCCGCTTCTGTGGGCGATAGGGTCACTATTACCTGCCG CGCATCTCAGGACGTGAACACCGCAGTCGCCTGGTACCAGCAGAAGCC TGGGAAAGCTCCAAAGCTGCTGATCTACAGTGCATCATTCCTGTATTCA GGAGTGCCCAGCCGGTTTAGCGGCAGCAGATCTGGCACCGATTTCACAC TGACTATTTCTAGTCTGCAGCCTGAGGACTTTGCCACATACTATTGCCAG CAGCACTATACCACACCCCCTACTTTCGGCCAGGGGACCAAAGTGGAG ATCAAGCGAACTGTGGCCGCTCCAAGTGTCTTCATTTTTCCACCCAGCG ATGAAAGACTGAAGTCCGGCACAGCTTCTGTGGTCTGTCTGCTGAACAA TTTTTACCCCAGAGAGGCCAAGTGCAGTGGAAGGTCGACAACGCTCTG CAGAGTGGCAACAGCCAGGAGAGCGTGACAGAACAGGATTCCAAAGAC TCTACTTATAGTCTGTCAAGCACCCTGACACTGAGCAAGGCAGACTACG AAAAGCATAAAGTGTATGCCTGTGAGGTCACACATCAGGGGCTGTCATC ACCAGTCACCAAATCATTCAATCGGGGGAGTGC |
| 17 | 5034 | VL | DIQMTQSPSSLSASVGDRVTITCRASQDVNTAVAWYQQKPGKAPKLLIYSA SFLYSGVPSRFSGSRSGTDFTLTISSLQPEDFATYYCQQHYTTPPTFGQGTKV EIK |
| 18 | 5037 | Full | GDYKDDDDKDIQMTQSPSSLSASVGDRVTITCRASQDVNTAVAWYQQKP GKAPKLLIYSASFLYSGVPSRFSGSRSGTDFTLTISSLQPEDFATYYCQQHYT TPPTFGQGTKVEIKRTVAAPSVFIFPPSDERLKSGTASVVCLLNNFYPREAK VQWKVDNALQSGNSKESVTEQDSKDSTYSLSSRLTLSKADYEKHKVYACE VTHQGLSSPVTKSFNRGEC |

TABLE 7-continued

Sequence for Variants v5019, v5020, v7091, v10000, v6903, v6902 and v6717 by Clone Number

| SEQ ID NO. | Clone # | Desc | Sequence (amino acid or DNA) |
|---|---|---|---|
| 19 | 5037 | Full | GGGGACTACAAAGACGACGATGACAAAGATATCCAGATGACCCAGTCC<br>CCTAGCTCCCTGTCCGCTTCTGTGGGCGATAGGGTCACTATTACCTGCCG<br>CGCATCTCAGGACGTGAACACCGCAGTCGCCTGGTACCAGCAGAAGCC<br>TGGGAAAGCTCCAAAGCTGCTGATCTACAGTGCATCATTCCTGTATTCA<br>GGAGTGCCCAGCCGGTTTAGCGGCAGCAGATCTGGCACCGATTTCACAC<br>TGACTATTTCTAGTCTGCAGCCTGAGGACTTTGCCACATACTATTGCCAG<br>CAGCACTATACCACACCCCCTACTTTCGGCCAGGGGACCAAAGTGGAG<br>ATCAAGCGAACTGTGGCCGCTCCAAGTGTCTTCATTTTTCCACCCAGCG<br>ATGAAAGACTGAAGTCCGGCACAGCTTCGTGGTCTGTCTGCTGAACAA<br>TTTTTACCCCAGAGAGGCCAAAGTGCAGTGGAAGGTCGACAACGCTCTG<br>CAGAGTGGCAACAGCAAGGAGAGCGTGACAGAACAGGATTCCAAAGA<br>CTCTACTTATAGTCTGTCAAGCAGACTGACACTGAGCAAGGCAGACTAC<br>GAAAAGCATAAAGTGTATGCCTGTGAGGTCACACATCAGGGGCTGTCA<br>TCACCAGTCACCAAATCATTCAATCGGGGGGAGTGC |
| 20 | 5037 | VL | DIQMTQSPSSLSASVGDRVTITCRASQDVNTAVAWYQQKPGKAPKLLIYSA<br>SFLYSGVPSRFSGSRSGTDFTLTISSLQPEDFATYYCQQHYTTPPTFGQGTKV<br>EIK |
| 21 | 5037 | L1 | QDVNTA |
| 22 | 5037 | L3 | QQHYTTPPT |
| 23 | 5037 | L2 | SAS |
| 24 | 3382 | Full | GDIQMTQSPSSLSASVGDRVTITCKASQDVSIGVAWYQQKPGKAPKLLIYS<br>ASYRYTGVPSRFSGSGSGTDFTLTISSLQPEDFATYYCQQYYIYPATFGQGT<br>KVEIKRTVAAPSVFIFPP SDEQLKSGTASVVCLLNNFYPREAKVQWKVDNA<br>LQSGNSQESVTEQDSKDSTYSLSSTLTLSKADYEKHKVYACEVTHQGLSSP<br>VTKSFNRGEC |
| 25 | 3382 | Full | GGGGATATTCAGATGACCCAGTCCCCAAGCTCCCTGAGTGCCTCAGTGG<br>GCGACCGAGTCACCATCACATGCAAGGCTTCCCAGGATGTGTCTATTGG<br>AGTCGCATGGTACCAGCAGAAGCCAGGCAAAGCACCCAAGCTGCTGAT<br>CTATAGCGCCTCCTACCGGTATACCGGCGTGCCCTCTAGATTCTCTGGC<br>AGTGGGTCAGGAACAGACTTTACTCTGACCATCTCTAGTCTGCAGCCTG<br>AGGATTTCGCTACCTACTATTGCCAGCAGTACTATATCTACCCAGCCAC<br>CTTTGGCCAGGGGACAAAAGTGGAGATCAAGAGGACTGTGGCCGCTCC<br>CTCCGTCTTCATTTTTCCCCCTTCTGACGAACAGCTGAAAAGTGGCACA<br>GCCAGCGTGGTCTGTCTGCTGAACAATTTCTACCCTCGCGAAGCCAAAG<br>TGCAGTGGAAGGTCGATAACGCTCTGCAGAGCGGCAACAGCCAGGAGT<br>CTGTGACTGAACAGGACAGTAAAGATTCAACCTATAGCCTGTCAAGCAC<br>ACTGACTCTGAGCAAGGCAGACTACGAGAAGCACAAAGTGTATGCCTG<br>CGAAGTCACACATCAGGGGCTGTCCTCTCCTGTGACTAAGAGCTTTAAC<br>AGAGGAGAGTGT |
| 26 | 3382 | VL | DIQMTQSPSSLSASVGDRVTITCKASQDVSIGVAWYQQKPGKAPKLLIYSAS<br>YRYTGVPSRFSGSGSGTDFTLTISSLQPEDFATYYCQQYYIYPATFGQGTKV<br>EIK |
| 27 | 3382 | L1 | QDVSIG |
| 28 | 3382 | L3 | QQYYIYPAT |
| 29 | 3382 | L2 | SAS |
| 30 | 5065 | Full | GEVQLVESGGGLVQPGGSLRLSCAASGFNIKDTYIHWVRQAPGKGLEWVA<br>RIYPTNGYTRYADSVKGRFTISADTSKNTAYLQMNSLRAEDTAVYYCSRW<br>GGDGFYAMDYWGQGTLVTVSSASTKGPSVFPLAPSSKSTSGGTAALGCEV<br>TDYFPEPVTVSWNSGALTSGVHTFPAVLQSSGLYSLSSVVTVPSSSLGTQTY<br>ICNVNHKPSNTKVDKKVEPKSCDKTHTCPPCPAPELLGGPSVFLFPPKPKDT<br>LMISRTPEVTCVVVDVSHEDPEVKFNWYVDGVEVHNAKTKPREEQYNSTY<br>RVVSVLTVLHQDWLNGKEYKCKVSNKALPAPIEKTISKAKGQPREPQVYV<br>YPPSRDELTKNQVSLTCLVKGFYPSDIAVEWESNGQPENNYKTTPPVLDSD<br>GSFALVSKLTVDKSRWQQGNVFSCSVMHEALHNHYTQKSLSLSPG |
| 31 | 5065 | Full | GGGGAGGTGCAGCTGGTCGAAAGCGGAGGAGGACTGGTGCAGCCAGG<br>AGGGTCACTGCGACTGAGCTGCGCAGCTTCCGGCTTCAACATCAAGGAC<br>ACCTACATTCACTGGGTCCGCCAGGCTCCTGGAAAAGGCCTGGAGTGG<br>TGGCACGAATCTATCCAACTAATGGATACACCCGGTATGCCGACTCCGT<br>GAAGGGCCGGTTCACCATTTCTGCAGATACAAGTAAAAACACTGCCTAC<br>CTGCAGATGAACAGCCTGCGAGCCGAAGATACAGCCGTGTACTATTGC<br>AGCCGATGGGGAGGCGACGGCTTCTACGCTATGGATTATTGGGGCCAG |

TABLE 7-continued

Sequence for Variants v5019, v5020, v7091, v10000, v6903, v6902 and v6717 by Clone Number

| SEQ ID NO. | Clone # | Desc | Sequence (amino acid or DNA) |
|---|---|---|---|
| | | | GGAACCCTGGTCACAGTGAGCTCCGCATCAACAAAGGGGCCTAGCGTG
TTTCCACTGGCCCCCTCTAGTAAATCCACCTCTGGGGGAACAGCAGCCC
TGGGATGTGAGGTGACCGACTACTTCCCAGAGCCCGTCACTGTGAGCTG
GAACTCCGGCGCCCTGACATCTGGGGTCCATACTTTTCCTGCTGTGCTGC
AGTCAAGCGGCCTGTACAGCCTGTCCTCTGTGGTCACTGTGCCAAGTTC
AAGCCTGGGGACTCAGACCTATATCTGCAACGTGAATCACAAGCCATCC
AATACCAAAGTCGACAAGAAAGTGGAACCCAAGTCTTGTGATAAAACA
CATACTTGCCCCCCTTGTCCTGCACCAGAGCTGCTGGGAGGACCAAGCG
TGTTCCTGTTTCCACCCAAGCCTAAAGACACCCTGATGATTAGTAGGAC
TCCAGAAGTCACCTGCGTGGTCGTGGACGTGAGCCACGAGGACCCCGA
AGTCAAGTTCAACTGGTACGTGGATGGCGTCGAGGTGCATAATGCCAA
GACAAAACCCAGGGAGGAACAGTACAACTCCACTTATCGCGTCGTGTCT
GTCCTGACCGTGCTGCACCAGGACTGGCTGAACGGCAAGGAGTATAAG
TGCAAAGTGAGCAATAAGGCTCTGCCCGCACCTATCGAGAAACAATTT
CCAAGGCTAAAGGGCAGCCTAGAGAACCACAGGTGTACGTGTACCCTC
CATCTAGGGACGAGCTGACCAAGAACCAGGTCAGTCTGACATGTCTGGT
GAAAGGGTTCTATCCCAGCGATATCGCAGTGGAGTGGGAATCCAATGG
ACAGCCTGAGAACAATTACAAGACCACACCCCCTGTGCTGGACTCTGAT
GGAAGTTTCGCCCTGGTGAGTAAGCTGACCGTCGATAAATCACGGTGGC
AGCAGGGCAACGTGTTCAGCTGTTCAGTGATGCACGAAGCACTGCACA
ACCACTACACCCAGAAAAGCCTGTCCCTGTCCCCCGGC |
| 32 | 5065 | VH | EVQLVESGGGLVQPGGSLRLSCAASGFNIKDTYIHWVRQAPGKGLEWVAR
IYPTNGYTRYADSVKGRFTISADTSKNTAYLQMNSLRAEDTAVYYCSRWG
GDGFYAMDYWGQGTLVTVSS |
| 33 | 5065, 720, 719 | H1 | GFNIKDTY |
| 34 | 5065, 720, 719 | H3 | SRWGGDGFYAMDY |
| 35 | 5065, 720, 719 | H2 | IYPTNGYT |
| 36 | 6586 | Full | GEVQLVESGGGLVQPGGSLRLSCAASGFTFADYTMDWVRQAPGKGLEWV
GDVNPNSGGSIYNQRFKGRFTFSVDRSKNTLYLQMNSLRAEDTAVYYCAR
NLGPSFYFDYWGQGTLVTVSSASTKGPSVFPLAPSSKSTSGGTAALGCLVK
DYFPEPVTVSWNSGALTSGVHTFPAVLQSSGLYSLSSVVTVPSSSLGTQTYI
CNVNHKPSNTKVDKKVEPKSCDKTHTCPPCPAPELLGGPSVFLFPPKPKDT
LMISRTPEVTCVVVDVSHEDPEVKFNWYVDGVEVHNAKTKPREEQYNSTY
RVVSVLTVLHQDWLNGKEYKCKVSNKALPAPIEKTISKAKGQPREPQVYV
YPPSRDELTKNQVSLTCLVKGFYPSDIAVEWESNGQPENNYKTTPPVLDSD
GSFALVSKLTVDKSRWQQGNVFSCSVMHEALHNHYTQKSLSLSPG |
| 37 | 6586 | Full | GGCGAGGTGCAGCTGGTGGAATCAGGAGGGGGCCTGGTGCAGCCCGGA
GGGTCTCTGCGACTGTCATGTGCCGCTTCTGGGTTCACTTTCGCAGACTA
CACAATGGATTGGGTGCGACAGGCCCCCGGAAAGGGACTGGAGTGGGT
GGGCGATGTCAACCCTAATTCTGGCGGGAGTATCTACAACCAGCGGTTC
AAGGGGGAGATTCACTTTTTCAGTGGACAGAAGCAAAAACACCCTGTATC
TGCAGATGAACAGCCTGAGGGCCGAAGATACCGCTGTCTACTATTGCGC
TCGCAATCTGGGCCCCAGTTTCTACTTTGACTATTGGGGGCAGGGAACC
CTGGTGACAGTCAGCTCCGCTAGCACTAAGGGGCCTTCCGTGTTTCCAC
TGGCTCCCTCTAGTAAATCCACCTCTGGAGGCACAGCTGCACTGGGATG
TCTGGTGAAGGATTACTTCCCTGAACCAGTCACAGTGAGTTGGAACTCA
GGGGCTCTGACAAGTGGAGTCCATACTTTTCCCGCAGTGCTGCAGTCAA
GCGGACTGTACTCCCTGTCCTCTGTGGTCACCGTGCCTAGTTCAAGCCTG
GGCACCCAGACATATATCTGCAACGTGAATCACAAGCCATCAAATACA
AAAGTCGACAAGAAAGTGGAGCCCAAGAGCTGTGATAAAACTCATACC
TGCCCACCTTGTCCGGCGCCAGAACTGCTGGGAGGACCAAGCGTGTTCC
TGTTTCCACCCAAGCCTAAAGACACCCTGATGATTTCCCGGACTCCTGA
GGTCACCTGCGTGGTCGTGGACGTGTCTCACGAGGACCCCGAAGTCAAG
TTCAACTGGTACGTGGATGGCGTCGAAGTGCATAATGCCAAGACCAAA
CCCCGGGAGGAACAGTACAACTCTACCTATAGAGTCGTGAGTGTCCTGA
CAGTGCTGCACCAGGACTGGCTGAATGGAAGGAGTATAAGTGTAAAG
TGAGCAACAAAGCCCTGCCCGCCCCAATCGAAAAACAATCTCTAAAG
CAAAAGGACAGCCTCGCGAACCACAGGTCTACGTCTACCCCCCATCAA
GAGATGAACTGACAAAAAATCAGGTCTCTCTGACATGCCTGGTCAAAG
GATTCTACCCTTCCGACATCGCCGTGGAGTGGGAAAGTAACGGCCAGCC
CGAGAACAATTACAAGACCACACCCCCTGTCCTGGACTCTGATGGGAGT |

TABLE 7-continued

Sequence for Variants v5019, v5020, v7091, v10000, v6903, v6902 and v6717 by Clone Number

| SEQ ID NO. | Clone # | Desc | Sequence (amino acid or DNA) |
|---|---|---|---|
| | | | TTCGCTCTGGTGTCAAAGCTGACCGTCGATAAAAGCCGGTGGCAGCAGG GCAATGTGTTTAGCTGCTCCGTCATGCACGAAGCCCTGCACAATCACTA CACACAGAAGTCCCTGAGCCTGAGCCCTGGC |
| 38 | 6586 | VH | EVQLVESGGGLVQPGGSLRLSCAASGFTFADYTMDWVRQAPGKGLEWVG DVNPNSGGSIYNQRFKGRFTFSVDRSKNTLYLQMNSLRAEDTAVYYCARN LGPSFYFDYWGQGTLVTVSS |
| 39 | 6586 | H1 | GFTFADYT |
| 40 | 6586 | H3 | ARNLGPSFYFDY |
| 41 | 6586 | H2 | VNPNSGGS |
| 42 | 3904 | Full | GYPYDVPDYATGSDIQMTQSPSSLSASVGDRVTITCKASQDVSIGVAWYQQ KPGKAPKLLIYSASYRYTGVPSRFSGSGSGTDFTLTISSLQPEDFATYYCQQ YYIYPYTFGQGTKVEIKRTVAAPSVFIFPPSDEELKSGTASVVCLLNNFYPRE AKVQWKVDNALQSGNSEESVTEQDSKDSTYSLSSTLELSKADYEKHKVYA CEVTHQGLSSPVTKSFNRGEC |
| 43 | 3904 | Full | GGGTATCCCTACGATGTGCCTGACTACGCTACTGGCTCCGATATCCAGA TGACCCAGTCTCCAAGCTCCCTGAGTGCATCAGTGGGGGACCGAGTCAC CATCACATGCAAGGCTTCCCAGGATGTGTCTATTGGAGTCGCATGGTAC CAGCAGAAGCCAGGCAAAGCACCCAAGCTGCTGATCTACAGCGCCTCC TACCGGTATACTGGGGTGCCTTCCAGATTCTCTGGCAGTGGGTCAGGAA CCGACTTTACTCTGACCATCTCTAGTCTGCAGCCCGAGGATTTCGCCACC TACTATTGCCAGCAGTACTATATCTACCCTTATACCTTTGGCCAGGGGA CAAAAGTGGAGATCAAGAGGACAGTGGCCGCTCCAAGTGTCTTCATTTT TCCCCCTTCCGACGAAGAGCTGAAAAGTGGAACTGCTTCAGTGGTCTGT CTGCTGAACAATTTCTACCCCCGCGAAGCCAAAGTGCAGTGGAAGGTCG ATAACGCTCTGCAGAGCGGCAATTCCGAGGAGTCTGTGACAGAACAGG ACAGTAAAGATTCAACTTATAGCCTGTCAAGCACACTGGAGCTGTCTAA GGCAGACTACGAGAAGCACAAAGTGTATGCCTGCGAAGTCACCCATCA GGGGCTGTCCTCTCCCGTGACAAAGAGCTTTAACAGAGGAGAGTGT |
| 44 | 3904 | VL | DIQMTQSPSSLSASVGDRVTITCKASQDVSIGVAWYQQKPGKAPKLLIYSAS YRYTGVPSRFSGSGSGTDFTLTISSLQPEDFATYYCQQYYIYPYTFGQGTKV EIK |
| 45 | 719 | Full | GDIQMTQSPSSLSASVGDRVTITCRASQDVNTAVAWYQQKPGKAPKLLIYS ASFLYSGVPSRFSGSRSGTDFTLTISSLQPEDFATYYCQQHYTTPPTFGQGTK VEIKGGSGGGSGGGSGGGSGGGSGEVQLVESGGGLVQPGGSLRLSCAASG FNIKDTYIHWVRQAPGKGLEWVARIYPTNGYTRYADSVKGRFTISADTSKN TAYLQMNSLRAEDTAVYYCSRWGGDGFYAMDYWGQGTLVTVSSAAEPK SSDKTHTCPPCPAPELLGGPSVFLFPPKPKDTLMISRTPEVTCVVVDVSHED PEVKFNWYVDGVEVHNAKTKPREEQYNSTYRVVSVLTVLHQDWLNGKE YKCKVSNKALPAPIEKTISKAKGQPREPQVYTYPPSRDELTKNQVSLTCLV KGFYPSDIAVEWESNGQPENNYKTTPPVLDEDGSFALVSKLTVDKSRWQQ GNVFSCSVMHEALHNHYTQKSLSLSPGK |
| 46 | 719 | Full | GGAGACATCCAGATGACCCAGTCTCCATCCTCCCTGTCTGCATCTGTAG GAGACAGAGTCACCATCACTTGCCGGGCAAGTCAGGACGTTAACACCG CTGTAGCTTGGTATCAGCAGAAACCAGGGAAAGCCCCTAAGCTCCTGAT CTATTCTGCATCCTTTTTGTACAGTGGGGTCCCATCAAGGTTCAGTGGCA GTCGATCTGGGACAGATTTCACTCTCACCATCAGCAGTCTGCAACCTGA AGATTTTGCAACTTACTACTGTCAACAGCATTACACTACCCCACCCACTT TCGGCCAAGGGACCAAAGTGGAGATCAAGGTGGTTCTGGTGGTGGTT CTGGTGGTGGTTCTGGTGGTGGTTCTGGTGGTGGTTCTGGTGAAGTGCA GCTGGTGGAGTCTGGGGGAGGCTTGGTACAGCCTGGCGGGTCCCTGAG ACTCTCCTGTGCAGCCTCTGGATTCAACATTAAAGATACTTATATCCACT GGGTCCGGCAAGCTCCAGGGAAGGGCCTGGAGTGGGTCGCACGTATTT ATCCCACAAATGGTTACACACGGTATGCGGACTCTGTGAAGGGCCGATT CACCATCTCCGCAGACACTTCCAAGAACACCGCGTATCTGCAAATGAAC AGTCTGAGAGCTGAGGACACGGCCGTTTATTACTGTTCAAGATGGGGCG GAGACGGTTTCTACGCTATGGACTACTGGGGCCAAGGGACCCTGGTCAC GTCTCCTCAGCCGCCGAGCCCAAGAGCAGCGATAAGACCCACACCTG CCCTCCCTGTCCAGCTCCAGAACTGCTGGGAGGACCTAGCGTGTTCCTG TTTCCCCCTAAGCCAAAGACACTCTGATGATTTCCAGGACTCCCGAGG TGACCTGCGTGGTGGTGGACGTGTCTCACGAGGACCCCGAAGTGAAGTT CAACTGGTACGTGGATGGCGTGGAAGTGCATAATGCTAAGACAAAACC AAGAGAGGAACAGTACAACTCCACTTATCGCGTCGTGAGCGTGCTGAC CGTGCTGCACCAGGACTGGCTGAACGGGAAGGAGTATAAGTGCAAAGT CAGTAATAAGGCCCTGCCTGCTCCAATCGAAAAAACCATCTCTAAGGCC |

TABLE 7-continued

Sequence for Variants v5019, v5020, v7091, v10000, v6903, v6902 and v6717 by Clone Number

| SEQ ID NO. | Clone # | Desc | Sequence (amino acid or DNA) |
|---|---|---|---|
| | | | AAAGGCCAGCCAAGGGAGCCCCAGGTGTACACATACCCACCCAGCAGA GACGAACTGACCAAGAACCAGGTGTCCCTGACATGTCTGGTGAAAGGC TTCTATCCTAGTGATATTGCTGTGGAGTGGGAATCAAATGGACAGCCAG AGAACAATTACAAGACCACACCTCCAGTGCTGGACGAGGATGGCAGCT TCGCCCTGGTGTCCAAGCTGACAGTGGATAAATCTCGATGGCAGCAGGG GAACGTGTTTAGTTGTTCAGTGATGCATGAAGCCCTGCACAATCATTAC ACTCAGAAGAGCCTGTCCCTGTCTCCCGGCAAA |
| 47 | 719 | VL | DIQMTQSPSSLSASVGDRVTITCRASQDVNTAVAWYQQKPGKAPKLLIYSA SFLYSGVPSRFSGSRSGTDFTLTISSLQPEDFATYYCQQHYTTPPTFGQGTKV EIK |
| 48 | 719 | VH | EVQLVESGGGLVQPGGSLRLSCAASGFNIKDTYIHWVRQAPGKGLEWVAR IYPTNGYTRYADSVKGRFTISADTSKNTAYLQMNSLRAEDTAVYYCSRWG GDGFYAMDYWGQGTLVTVSS |
| 49 | 720 | Full | GDIQMTQSPSSLSASVGDRVTITCRASQDVNTAVAWYQQKPGKAPKLLIYS ASFLYSGVPSRFSGSRSGTDFTLTISSLQPEDFATYYCQQHYTTPPTFGQGTK VEIKGGSGGGSGGGSGGGSGGGSGEVQLVESGGGLVQPGGSLRLSCAASG FNIKDTYIHWVRQAPGKGLEWVARTYPTNGYTRYADSVKGRFTISADTSKN TAYLQMNSLRAEDTAVYYCSRWGGDGFYAMDYWGQGTLVTVSSAAEPK SSDKTHTCPPCPAPELLGGPSVFLFPPKPKDTLMISRTPEVTCVVVDVSHED PEVKFNWYVDGVEVHNAKTKPREEQYNSTYRVVSVLTVLHQDWLNGKE YKCKVSNKALPAPIEKTISKAKGQPREPQVYTLPPSRDELTKNQVSLICLVK GFYPSDIAVEWESNGQPENRYMTWPPVLDSDGSFFLYSKLTVDKSRWQQG NVFSCSVMHEALHNHYTQKSLSLSPGK |
| 50 | 720 | Full | GGAGACATCCAGATGACCCAGTCTCCATCCTCCCTGTCTGCATCTGTAG GAGACAGAGTCACCATCACTTGCCGGGCAAGTCAGGACGTTAACACCG CTGTAGCTTGGTATCAGCAGAAACCAGGGAAAGCCCCTAAGCTCCTGAT CTATTCTGCATCCTTTTTGTACAGTGGGGTCCCATCAAGGTTCAGTGGCA GTCGATCTGGGACAGATTTCACTCTCACCATCAGCAGTCTGCAACCTGA AGATTTTGCAACTTACTACTGTCAACAGCATTACACTACCCCACCCACTT TCGGCCAAGGGACCAAAGTGGAGATCAAAGGTGGTTCTGGTGGTGGTT CTGGTGGTGGTTCTGGTGGTGGTTCTGGTGGTGGTTCTGGTGAAGTGCA GCTGGTGGAGTCTGGGGGAGGCTTGGTACAGCCTGGCGGGTCCCTGAG ACTCTCCTGTGCAGCCTCTGGATTCAACATTAAAGATACTTATATCCACT GGGTCCGGCAAGCTCCAGGGAAGGGCCTGGAGTGGGTCGCACGTATTT ATCCCACAAATGGTTACACACGGTATGCGGACTCTGTGAAGGGCCGATT CACCATCTCCGCAGACACTTCCAAGAACACCGCGTATCTGCAAATGAAC AGTCTGAGAGCTGAGGACACGGCCGTTTATTACTGTTCAAGATGGGGCG GAGACGGTTTCTACGCTATGGACTACTGGGGCCAAGGGACCCTGGTCAC CGTCTCCTCAGCCGCCGAGCCCAAGAGCAGCGATAAGACCCACACCTG CCCTCCCTGTCCAGCTCCAGAACTGCTGGGAGGACCTAGCGTGTTCCTG TTTCCCCCTAAGCCAAAAGACACTCTGATGATTTCCAGGACTCCCGAGG TGACCTGCGTGGTGGTGGACGTGTCTCACGAGGACCCCGAAGTGAAGTT CAACTGGTACGTGGATGGCGTGGAAGTGCATAATGCTAAGACAAAACC AAGAGAGGAACAGTACAACTCCACTTATCGCGTCGTGAGCGTGCTGAC CGTGCTGCACCAGGACTGGCTGAACGGGAAGGAGTATAAGTGCAAAGT CAGTAATAAGGCCCTGCCTGCTCCAATCGAAAAAACCATCTCTAAGGCC AAAGGCCAGCCAAGGGAGCCCCAGGTGTACACACTGCCACCCAGCAGA GACGAACTGACCAAGAACCAGGTGTCCCTGATCTGTCTGGTGAAAGGCT TCTATCCTAGTGATATTGCTGTGGAGTGGGAATCAAATGGACAGCCAGA GAACAGATACATGACCTGGCCTCCAGTGCTGGACAGCGATGGCAGCTTC TTCCTGTATTCCAAGCTGACAGTGGATAAATCTCGATGGCAGCAGGGGA ACGTGTTTAGTTGTTCAGTGATGCATGAAGCCCTGCACAATCATTACAC TCAGAAGAGCCTGTCCCTGTCTCCCGGCAAA |
| 51 | 720 | VL | DIQMTQSPSSLSASVGDRVTITCRASQDVNTAVAWYQQKPGKAPKLLIYSA SFLYSGVPSRFSGSRSGTDFTLTISSLQPEDFATYYCQQHYTTPPTFGQGTKV EIK |
| 52 | 720 | VH | EVQLVESGGGLVQPGGSLRLSCAASGFNIKDTYIHWVRQAPGKGLEWVAR IYPTNGYTRYADSVKGRFTISADTSKNTAYLQMNSLRAEDTAVYYCSRWG GDGFYAMDYWGQGTLVTVSS |
| 53 | 3041 | Full | GEVQLVESGGGLVQPGGSLRLSCAASGFTFTDYTMDWVRQAPGKGLEWV ADVNPNSGGSIYNQRFKGRFTLSVDRSKNTLYLQMNSLRAEDTAVYYCAR NLGPSFYFDYWGQGTLVTVSSASTKGPSVFPLAPSSKSTSGGTAALGCLVK DYFPEPVTVSWNSGALTSGVHTFPAVLQSSGLYSLSSVVTVPSSSLGTQTYI CNVNHKPSNTKVDKKVEPKSCDKTHTCPPCPAPELLGGPSVFLFPPKPKDT LMISRTPEVTCVVVDVSHEDPEVKFNWYVDGVEVHNAKTKPREEQYNSTY RVVSVLTVLHQDWLNGKEYKCKVSNKALPAPIEKTISKAKGQPREPQVYV |

TABLE 7-continued

Sequence for Variants v5019, v5020, v7091, v10000, v6903, v6902 and v6717 by Clone Number

| SEQ ID NO. | Clone # | Desc | Sequence (amino acid or DNA) |
|---|---|---|---|
| | | | LPPSRDELTKNQVSLLCLVKGFYPSDIAVEWESNGQPENNYLTWPPVLDSD GSFFLYSKLTVDKSRWQQGNVFSCSVMHEALHNHYTQKSLSLSPG |
| 54 | 3041 | Full | GGGGAAGTGCAGCTGGTCGAATCTGGAGGAGGACTGGTGCAGCCAGGA GGGTCCCTGCGCCTGTCTTGCGCCGCTAGTGGCTTCACTTTTACCGACTA CACCATGGATTGGGTGCGACAGGCACCTGGAAAGGGCCTGGAGTGGGT CGCCGATGTGAACCCAAATAGCGGAGGCTCCATCTACAACCAGCGGTTC AAGGGGCCGGTTCACCCTGTCAGTGGACCGGAGCAAAAACACCCTGTAT CTGCAGATGAATAGCCTGCGAGCCGAAGATACTGCTGTGTACTATTGCG CCCCGGAATCTGGGGCCCTCCTTCTACTTTGACTATTGGGGGCAGGGAAC TCTGGTCACCGTGAGCTCCGCCTCCACCAAGGGACCTTCTGTGTTCCCA CTGGCTCCCTCTAGTAAATCCACATCTGGGGGAACTGCAGCCCTGGGCT GTCTGGTGAAGGACTACTTCCCAGAGCCCGTCACAGTGTCTTGGAACAG TGGCGCTCTGACTTCTGGGGTCCACACCTTTCCTGCAGTGCTGCAGTCA AGCGGGCTGTACAGCCTGTCCTCTGTGGTCACCGTGCCAAGTTCAAGCC TGGGAACACAGACTTATATCTGCAACGTGAATCACAAGCCATCCAATAC AAAAGTCGACAAGAAAGTGGAACCCAAGTCTTGTGATAAAACCCATAC ATGCCCCCTTGTCCTGCACCAGAGCTGCTGGGAGGACCAAGCGTGTTC CTGTTTCCACCCAAGCCTAAAGATACACTGATGATTAGTAGGACCCCAG AAGTCACATGCGTGGTCGTGGACGTGAGCCACGAGGACCCCGAAGTCA AGTTTAACTGGTACGTGGACGGCGTCGAGGTGCATAATGCCAAGACTA AACCCAGGGAGGAACAGTACAACAGTACCTATCGCGTCGTGTCAGTCCT GACAGTGCTGCATCAGGATTGGCTGAACGGGAAAGAGTATAAGTGCAA AGTGAGCAATAAGGCTCTGCCCGCACCTATCGAGAAAACAATTTCCAA GGCAAAAGGACAGCCTAGAGAACCACAGGTGTACGTGCTGCCTCCATC AAGGGGATGAGCTGACAAAGAACCAGGTCAGCCTGACTTGTCTGGTGAA AGGATTCTATCCCTCTGACATTGCTGTGGAGTGGGAAAGTAATGGCCAG CCTGAGAACAATTACCTGACCTGGCCCCCTGTGCTGGACTCAGATGGCA GCTTCTTTCTGTATAGCAAGCTGACCGTCGACAAATCCCGGTGGCAGCA GGGGAATGTGTTTAGTTGTTCAGTCATGCACGAGGCACTGCACAACCAT TACACCCAGAAGTCACTGTCACTGTCACCAGGG |
| 55 | 3041 | VH | EVQLVESGGGLVQPGGSLRLSCAASGFTFTDYTMDWVRQAPGKGLEWVA DVNPNSGGSIYNQRFKGRFTLSVDRSKNTLYLQMNSLRAEDTAVYYCARN LGPSFYFDYWGQGTLVTVSS |
| 56 | 3057 | Full | GEVQLVESGGGLVQPGGSLRLSCAASGFTFTDYTMDWVRQAPGKGLEWV ADVNPNSGGSIYNQRFKGRFTLSVDRSKNTLYLQMNSLRAEDTAVYYCAR NLGPSFYFDYWGQGTLVTVSSASTKGPSVFPLAPSSKSTSGGTAALGCLVK DYFPEPVTVSWNSGALTSGVHTFPAVLQSSGLYSLSSVVTVPSSSLGTQTYI CNVNHKPSNTKVDKKVEPKSCDKTHTCPPCPAPELLGGPSVFLFPPKPKDT LMISRTPEVTCVVVDVSHEDPEVKFNWYVDGVEVHNAKTKPREEQYNSTY RVVSVLTVLHQDWLNGKEYKCKVSNKALPAPIEKTISKAKGQPREPQVYV YPPSRDELTKNQVSLTCLVKGFYPSDIAVEWESNGQPENNYKTTPPVLDSD GSFALVSKLTVDKSRWQQGNVFSCSVMHEALHNHYTQKSLSLSPG |
| 57 | 3057 | Full | GGGGAAGTGCAGCTGGTCGAATCTGGAGGAGGACTGGTGCAGCCAGGA GGGTCCCTGCGCCTGTCTTGCGCCGCTAGTGGCTTCACTTTTACCGACTA CACCATGGATTGGGTGCGACAGGCACCTGGAAAGGGCCTGGAGTGGGT CGCCGATGTGAACCCAAATAGCGGAGGCTCCATCTACAACCAGCGGTTC AAGGGGCCGGTTCACCCTGTCAGTGGACCGGAGCAAAAACACCCTGTAT CTGCAGATGAATAGCCTGCGAGCCGAAGATACTGCTGTGTACTATTGCG CCCCGGAATCTGGGGCCCTCCTTCTACTTTGACTATTGGGGGCAGGGAAC TCTGGTCACCGTGAGCTCCGCCTCCACCAAGGGACCTTCTGTGTTCCCA CTGGCTCCCTCTAGTAAATCCACATCTGGGGGAACTGCAGCCCTGGGCT GTCTGGTGAAGGACTACTTCCCAGAGCCCGTCACAGTGTCTTGGAACAG TGGCGCTCTGACTTCTGGGGTCCACACCTTTCCTGCAGTGCTGCAGTCA AGCGGGCTGTACAGCCTGTCCTCTGTGGTCACCGTGCCAAGTTCAAGCC TGGGAACACAGACTTATATCTGCAACGTGAATCACAAGCCATCCAATAC AAAAGTCGACAAGAAAGTGGAACCCAAGTCTTGTGATAAAACCCATAC ATGCCCCCTTGTCCTGCACCAGAGCTGCTGGGAGGACCAAGCGTGTTC CTGTTTCCACCCAAGCCTAAAGATACACTGATGATTAGTAGGACCCCAG AAGTCACATGCGTGGTCGTGGACGTGAGCCACGAGGACCCCGAAGTCA AGTTTAACTGGTACGTGGACGGCGTCGAGGTGCATAATGCCAAGACTA AACCCAGGGAGGAACAGTACAACAGTACCTATCGCGTCGTGTCAGTCCT GACAGTGCTGCATCAGGATTGGCTGAACGGGAAAGAGTATAAGTGCAA AGTGAGCAATAAGGCTCTGCCCGCACCTATCGAGAAAACAATTTCCAA GGCAAAAGGACAGCCTAGAGAACCACAGGTGTACGTGTATCCTCCATC AAGGGGATGAGCTGACAAAGAACCAGGTCAGCCTGACTTGTCTGGTGAA AGGATTCTATCCCTCTGACATTGCTGTGGAGTGGGAAAGTAATGGCCAG CCTGAGAACAATTACAAGACCACACCCCCTGTGCTGGACTCAGATGGCA |

TABLE 7-continued

Sequence for Variants v5019, v5020, v7091, v10000, v6903, v6902 and v6717 by Clone Number

| SEQ ID NO. | Clone # | Desc | Sequence (amino acid or DNA) |
|---|---|---|---|
| | | | GCTTCGCGCTGGTGAGCAAGCTGACCGTCGACAAATCCCGGTGGCAGC AGGGGAATGTGTTTAGTTGTTCAGTCATGCACGAGGCACTGCACAACCA TTACACCCAGAAGTCACTGTCACTGTCACCAGGG |
| 58 | 3057 | VH | EVQLVESGGGLVQPGGSLRLSCAASGFTFTDYTMDWVRQAPGKGLEWVA DVNPNSGGSIYNQRFKGRFTLSVDRSKNTLYLQMNSLRAEDTAVYYCARN LGPSFYFDYWGQGTLVTVSS |
| 59 | 3317 | Full | GDIQMTQSPSSLSASVGDRVTITCKASQDVSIGVAWYQQKPGKAPKLLIYS ASYRYTGVPSRFSGSGSGTDFTLTISSLQPEDFATYYCQQYYIYPYTFGQGT KVEIKGGGGSGGGGSGGGGSEVQLVESGGGLVQPGGSLRLSCAASGFTFT DYTMDWVRQAPGKGLEWVADVNPNSGGSIYNQRFKGRFTLSVDRSKNTL YLQMNSLRAEDTAVYYCARNLGPSFYFDYWGQGTLVTVSSAAEPKSSDKT HTCPPCPAPELLGGPSVFLFPPKPKDTLMISRTPEVTCVVVDVSHEDPEVKF NWYVDGVEVHNAKTKPREEQYNSTYRVVSVLTVLHQDWLNGKEYKCKV SNKALPAPIEKTISKAKGQPREPQVYVYPPSRDELTKNQVSLTCLVKGFYPS DIAVEWESNGQPENNYKTTPPVLDSDGSFALVSKLTVDKSRWQQGNVFSC SVMHEALHNHYTQKSLSLSPGK |
| 60 | 3317 | Full | GGGGACATTCAGATGACCCAGAGCCCTAGCTCCCTGAGTGCCTCAGTCG GGGACAGGGTGACTATCACCTGCAAGGCTTCACAGGATGTCAGCATTG GCGTGGCATGGTACCAGCAGAAGCCAGGGAAAGCACCCAAGCTGCTGA TCTATAGCGCCTCCTACAGGTATACAGGCGTGCCATCCCGCTTCTCTGG CAGTGGGTCAGGAACTGACTTTACACTGACTATTTCTAGTCTGCAGCCC GAAGATTTCGCCACATACTATTGCCAGCAGTACTATATCTACCCTTATA CTTTTGGCCAGGGGACCAAAGTGGAGATTAAGGGCGGAGGAGGCTCCG GAGGAGGAGGGTCTGGAGGAGGAGGAAGTGAGGTCCAGCTGGTGGAA TCTGGAGGAGGACTGGTGCAGCCAGGAGGGTCCCTGAGGCTGTCTTGTG CCGCTAGTGGCTTCACCTTTACAGACTACACAATGGATTGGGTGCGCCA GGCACCAGGAAAGGGACTGGAATGGGTCGCTGATGTGAACCCTAATAG CGGAGGCTCCATCTACAACCAGCGGTTCAAAGGACGGTTCACCCTGTCA GTGGACCGGAGCAAGAACACCCTGTATCTGCAGATGAACAGCCTGAGA GCCGAGGATACTGCTGTGTACTATTGCGCCAGGAATCTGGGCCCAAGCT TCTACTTTGACTATTGGGGCAGGGAACACTGGTCACTGTGTCAAGCGC AGCCGAACCCAAATCCTCTGATAAGACTCACACCTGCCCACCTTGTCCA GCTCCAGAGCTGCTGGGAGGACCTAGCGTGTTCCTGTTTCCACCCAAGC CAAAAGACACTCTGATGATTTCTAGAACCCCTGAAGTGACATGTGTGGT CGTGGACGTCAGTCACGAGGACCCCGAAGTCAAATTCAACTGGTACGT GGATGGCGTCGAGGTGCATAATGCCAAGACCAAACCCCGAGAGGAACA GTACAACTCAACCTATCGGGTCGTGAGCGTCCTGACAGTGCTGCATCAG GACTGGCTGAACGGCAAGGAGTATAAGTGCAAAGTGAGCAACAAGGCT CTGCCTGCACCAATCGAGAAGACCATTTCCAAGGCTAAAGGGCAGCCC CGCGAACCTCAGGTCTACGTGTATCCTCCAAGCCGAGATGAGCTGACAA AAAACCAGGTCTCCCTGACTTGTCTGGTGAAGGGATTTTACCCAAGTGA CATCGCAGTGGAGTGGGAATCAAATGGCCAGCCCGAAAACAATTATAA GACCACACCCCTGTGCTGGACTCTGATGGGAGTTTCGCACTGGTCTCC AAACTGACCGTGGACAAGTCTCGGTGGCAGCAGGGAAACGTCTTTAGC TGTTCCGTGATGCACGAGGCCCTGCACAATCATTACACACAGAAATCTC TGAGTCTGTCACCTGGCAAG |
| 61 | 3317 | VL | DIQMTQSPSSLSASVGDRVTITCKASQDVSIGVAWYQQKPGKAPKLLIYSAS YRYTGVPSRFSGSGSGTDFTLTISSLQPEDFATYYCQQYYIYPYTFGQGTKV EIK |
| 62 | 3317 | VH | EVQLVESGGGLVQPGGSLRLSCAASGFTFTDYTMDWVRQAPGKGLEWVA DVNPNSGGSIYNQRFKGRFTLSVDRSKNTLYLQMNSLRAEDTAVYYCARN LGPSFYFDYWGQGTLVTVSS |
| 63 | 5244 | Full | GDIQMTQSPSSLSASVGDRVTITCRASQDVNTAVAWYQQKPGKAPKLLIYS ASFLYSGVPSRFSGSRSGTDFTLTISSLQPEDFATYYCQQHYTTPPTFGQGTK VEIKGGSGGGSGGGGSGGGSGGGSGEVQLVESGGGLVQPGGSLRLSCAASG FNIKDTYIHWVRQAPGKGLEWVARIYPTNGYTRYADSVKGRFTISADTSKN TAYLQMNSLRAEDTAVYYCSRWGGDGFYAMDYWGQGTLVTVSSAAEPK SSDKTHTCPPCPAPELLGGPSVFLFPPKPKDTLMISRTPEVTCVVVDVSHED PEVKFNWYVDGVEVHNAKTKPREEQYNSTYRVVSVLTVLHQDWLNGKE YKCKVSNKALPAPIEKTISKAKGQPREPQVYVLPPSRDELTKNQVSLLCLV KGFYPSDIAVEWESNGQPENNYLTWPPVLDSDGSFFLYSKLTVDKSRWQQ GNVFSCSVMHEALHNHYTQKSLSLSPG |
| 64 | 5244 | Full | GGAGACATTCAGATGACACAGAGCCCCAGCTCCCTGAGTGCTTCAGTCG GCGACAGGGTGACTATCACCTGCCGCGCATCCCAGGATGTCAACACCGC TGTGGCATGGTACCAGCAGAAGCCTGGAAAAGCCCCCAAAGCTGCTGAT CTACAGCGCTTCCTTCCTGTATTCTGGCGTGCCAAGTCGGTTTTCTGGAA |

TABLE 7-continued

Sequence for Variants v5019, v5020, v7091, v10000, v6903, v6902 and v6717 by Clone Number

| SEQ ID NO. | Clone # | Desc | Sequence (amino acid or DNA) |
|---|---|---|---|
| | | | GTAGATCAGGCACTGACTTCACACTGACTATCTCTAGTCTGCAGCCCGA AGATTTTGCCACCTACTATTGCCAGCAGCACTATACCACACCCCCTACA TTCGGACAGGGCACTAAAGTGGAGATTAAGGGCGGGTCAGGCGGAGGG AGCGGAGGAGGGTCCGGAGGAGGGTCTGGAGGAGGGAGTGGAGAGGT CCAGCTGGTGGAATCTGGAGGAGGACTGGTGCAGCCTGGAGGCTCACT GCGACTGAGCTGTGCCGCTTCCGGCTTTAACATCAAAGACACATACATT CATTGGGTCAGGCAGGCACCAGGGAAGGGACTGGAATGGGTGGCCCGC ATCTATCCCACAAATGGGTACACTCGATATGCCGACAGCGTGAAAGGA CGGTTTACCATTTCTGCTGATACCAGTAAGAACACAGCATACCTGCAGA TGAACAGCCTGCGCGCAGAGGATACAGCCGTGTACTATTGCAGTCGATG GGGGGGAGACGGCTTCTACGCCATGGATTATTGGGGCCAGGGGACTCT GGTCACCGTGTCAAGCGCAGCCGAACCTAAATCCTCTGACAAGACCCAC ACATGCCCACCCTGTCCTGCTCCAGAGCTGCTGGGAGGACCATCCGTGT TCCTGTTTCCTCCAAAGCCTAAAGATACACTGATGATTAGCCGCACTCC CGAAGTCACCTGTGTGGTCGTGGACGTGTCCCACGAGGACCCCGAAGTC AAGTTCAACTGGTACGTGGACGGCGTCGAGGTGCATAATGCCAAGACT AAACCAAGAGAGGAACAGTACAATTCAACCTATAGGGTCGTGAGCGTC CTGACAGTGCTGCATCAGGATTGGCTGAACGGCAAGGAGTATAAGTGC AAAGTGTCTAACAAGGCCCTGCCCGCTCCTATCGAGAAGACTATTAGCA AGGCAAAAGGGCAGCCACGGGAACCCCAGGTCTACGTGCTGCCCCCTA GCAGAGACGAGCTGACCAAAAACCAGGTCTCCCTGCTGTGTCTGGTGA AGGGCTTTTATCCTAGTGATATCGCTGTGGAGTGGGAATCAAATGGGCA GCCAGAAAACAATTACCTGACATGGCCACCCGTGCTGGACAGCGATGG GTCCTTCTTTCTGTATTCCAAACTGACTGTGGACAAGTCTAGATGGCAG CAGGGAAACGTCTTCAGCTGTTCCGTGATGCACGAGGCCCTGCACAATC ATTACACCCAGAAGTCTCTGAGTCTGTCACCCGGC |
| 65 | 5244 | VL | DIQMTQSPSSLSASVGDRVTITCRASQDVNTAVAWYQQKPGKAPKLLIYSA SFLYSGVPSRFSGSRSGTDFTLTISSLQPEDFATYYCQQHYTTPPTFGQGTKV EIK |
| 66 | 5244 | VH | EVQLVESGGGLVQPGGSLRLSCAASGFNIKDTYIHWVRQAPGKGLEWVAR IYPTNGYTRYADSVKGRFTISADTSKNTAYLQMNSLRAEDTAVYYCSRWG GDGFYAMDYWGQGTLVTVSS |
| 67 | 5244, 5034, 719, 720 | L1 | QDVNTA |
| 68 | 5244, 5034, 719, 720 | L2 | SAS |
| 69 | 5244, 5034, 719, 720 | L3 | QQHYTTPPT |
| 70 | 5244 | H1 | GFNIKDTY |
| 71 | 5244 | H2 | IYPTNGYT |
| 72 | 5244 | H3 | SRWGGDGFYAMDY |

EXAMPLES

Below are examples of specific embodiments for making and using the bispecific anti-HER2 antigen-binding construct and ADCs described herein. The examples are offered for illustrative purposes only and are not intended to limit the scope of the disclosure in any way. Efforts have been made to ensure accuracy with respect to numbers used (e.g., amounts, temperatures, etc.), but some experimental error and deviation should, of course, be allowed for.

The constructs and methods described herein can be prepared and carried out employing, unless otherwise indicated, conventional methods of protein chemistry, biochemistry, recombinant DNA techniques and pharmacology, within the skill of the art. Such techniques are explained fully in the literature. See, e.g., T. E. Creighton, *Proteins: Structures and Molecular Properties* (W.H. Freeman and Company, 1993); A. L. Lehninger, Biochemistry (Worth Publishers, Inc., current addition); Sambrook, et al., *Molecular Cloning: A Laboratory Manual* (2nd Edition, 1989); *Methods In Enzymology* (S. Colowick and N. Kaplan eds., Academic Press, Inc.); *Remington's Pharmaceutical Sciences,* 18th Edition (Easton, Pennsylvania: Mack Publishing Company, 1990); Carey and Sundberg *Advanced Organic Chemistry* 3rd Ed. (Plenum Press) Vols A and B(1992).

Example 1: Description and Preparation of Variant 10000 (v10000)

v10000 is a humanized bispecific antibody that recognizes 2 non-overlapping epitopes of the ECD of the human HER2 antigen. The IgG1-like Fc region of v 10000 contains complementary mutations in each CH3 domain that impart preferential pairing to generate a heterodimeric molecule and correspondingly disfavor formation of homodimers. FIG. 1 depicts a representation of the format of v10000 where heavy chain A and light chain A' form the ECD2 binding portion of the antibody and heavy chain B comprises the scFv that forms the ECD4 binding portion of the antibody. Variant 10000 comprises a heavy chain H1 (corresponding to heavy chain A in FIG. 1) comprising the sequence set forth in SEQ ID NO:36, a heavy chain H2 (corresponding to heavy chain B in FIG. 1) comprising the sequence set forth in SEQ ID NO:63, and a light chain L1 (corresponding to light chain A') comprising the sequence set forth in SEQ ID NO:24. Methods of preparing v10000 are described in detail in International Patent Publication No. WO 2015/077891.

v10000 was manufactured according to the relevant regulatory requirements for human trials and formulated at 15 mg/mL in biocompatible aqueous buffer, for IV infusion at ambient temperature. v10000 was supplied in a vial containing 300 mg v10000 in 20 mL buffer. Vials of v10000 were shipped frozen and stored at −20° C. (+/−5° C.) until ready for use. Vials were thawed at ambient temperature prior to use. Thawed solutions in vials were stored for up to 24 hours at ambient temperatures or up to 72 hours at refrigerated conditions (2° C. to 8° C.) and used before the labeled expiration date.

Example 2: Pre-Clinical Evaluation of v10000 in Combination with Palbociclib or Fulvestrant or Both Demonstrates Additive or Synergistic Effects in Cancer Cell Lines In Vitro Study 1: Growth Inhibitory Activity of v10000 Combined with Palbociclib or Fulvestrant in HER2-expressing Breast Cancer Cell Lines This experiment was performed to measure whether v10000 has additive, synergistic and antagonistic interactions in combination with palbociclib or fulvestrant in representative HER2-expressing breast cancer cell lines.

The growth-inhibition effects of v10000 in combination with palbociclib or fulvestrant were tested in 7 breast cancer cell lines in dose matrices of 9 concentrations vs. 9 concentrations of each chemotherapeutic. Twenty-four hours after cells were plated, cells were incubated for 120 hours in 384-well plates with v10000 (300 to 0 nM) and the chemotherapeutics agents as single agents or in combination as 9-point concentration dilution of fulvestrant or palbociclib (10 to 0 Cell viability was assessed using the ATPLite Luminescence Assay System (Perkin Elmer, Waltham, Massachusetts), and luminescence was measured with an EnVision™ plate reader (Perkin Elmer). Cell viability was analyzed to determine additive, synergistic and antagonistic interactions using the Loewe Additivity model (Horizon Discovery, Cambridge, UK).

Growth Inhibition (GI) was used as a measure of cell viability and calculated by applying the following test and equation:

$$\text{If } T < V_0: 100*(1-(T-V_0)/V_0)$$

$$\text{If } T \geq V_0: 100*(1-(T-V_0)/(V-V_0))$$

where T is the signal measure for a test article, V is the vehicle-treated control measure, and $V_0$ is the vehicle control measure at time zero. The cell viability of vehicle is measured at the time of dosing (To) and after one hundred twenty hours (Tim). This formula is derived from the Growth Inhibition calculation used in the National Cancer Institute's NCI-60 high throughput screen, where a GI reading of 0% represents no growth inhibition, a GI of 100% represents complete growth inhibition and a GI 200% represents complete death of all cells in the culture well (Rickles et al. Glob J Cancer Ther 2015; 1: 009-017).

Additive, synergistic and antagonistic interactions were determined using the Loewe Additivity model. The Loewe Additivity model defines additivity as a non-synergistic combination interaction where the combination dose matrix surface should be indistinguishable from either drug crossed with itself. The calculation for additivity is:

$$I_{Loewe} \text{ that satisfies } (X/X_1)+(Y/Y_1)=1$$

where $X_1$ and $Y_1$ are the single agent effective concentrations for the observed combination effect I is dose-based and applies only to the activity levels achieved by the single agents.

TABLE 8

Summary of Synergistic, Additive and Antagonsitic Interaction Scores for Viability of Human Epidermal Growth Factor Receptor 2-expressing Breast Cancer Cell Lines Treated with v10000 in Combination with Palbociclib or Fulvestrant

| Breast Cancer Cell Line | HER2 Receptor Score (IHC) | ER[g] | PR[g] | Interaction Scores* v10000 + Chemotherapeutic | |
|---|---|---|---|---|---|
| | | | | Palbociclib | Fulvestrant |
| BT-474 | 3+[c] | + | + | + | + |
| SK-BR-3 | 3+[a, c] | − | − | + | + |
| JIMT-1 | 2+[f] | − | − | + | + |
| ZR-75-1 | 2+[a, c] | + | +/− | + | + |
| MDA-MB-175-VII | 1+[b] | + | − | ++ | ++ |

TABLE 8-continued

Summary of Synergistic, Additive and Antagonsitic Interaction Scores for
Viability of Human Epidermal Growth Factor Receptor 2-expressing Breast Cancer
Cell Lines Treated with v10000 in Combination with Palbociclib or Fulvestrant

| Breast Cancer Cell Line | HER2 Receptor Score (IHC) | ER$^g$ | PR$^g$ | Interaction Scores* v10000 + Chemotherapeutic | |
|---|---|---|---|---|---|
| | | | | Palbociclib | Fulvestrant |
| BT-20 | 0/1$^c$ | − | − | + | + |
| HCC38 | low$^d$ | − | − | + | + |

*Interaction Scores:
+ = indicates additive interactions;
++ = synergistic interactions (antagonistic interactions were not observed);
HER2 = human epidermal growth factor receptor 2;
ER = Estrogen receptor;
PR = Progesterone receptor
$^a$Bunn et al, Clinical Cancer Research 2001; 7: 3239-3250
$^b$Wilson et al. Cancer Cell 2011; 20: 158-72 2010; 4: 35-41
$^c$Subik et al. Breast Cancer: Basic and Clinical Research
$^d$Wu et al. Cancer Biology & Therapy 2014; 15: 1593-99
$^e$Yi et al. Sci Rep 2014; 4: 7592
$^f$Turini et al. Oncotarget. 2014; 5: 5304-19
$^g$Dai et al. Journal of Cancer 2017; 8: 3131-3141

To identify whether palbociclib or fulvestrant could result in synergistic, additive, or antagonistic inhibition of cancer cell growth when combined with v10000, palbociclib or fulvestrant were screened in pair-wise combinations with v10000 across 7 HER2 expressing cancer cell lines. The results of v10000 in pair-wise combinations with palbociclib or fulvestrant is shown in Table 8. Growth inhibition data were analyzed for synergistic additive, and antagonistic interactions based on the Loewe Additivity model (Tallarida, Genes Cancer 2011; 2:1003-1008).

V10000 demonstrated synergistic (++; Table 8) or additive interactions (+; Table 8) with palbociclib or fulvestrant in breast cancer cell lines expressing low to high (HER 3+) HER2 (Table 8). Synergistic inhibition of cell growth was observed with v10000 in combination with palbociclib in MDA-MB-175-VII (HER2 1+, ER+, PR−) breast cancer, and with v10000 in combination with fluvestrant in MDA-MB-175-VII (HER2 1+, ER+, PR−) breast cancer (Table 8). Additive inhibition of cell growth was observed with v10000 in combination with palbociclib or fulvestrant in BT-474, SK-BR-3, JIMT-1, ZR-75-1, BT-20, and HCC38 breast cancer cell lines. No antagonistic interactions were observed for v10000 in combination with palbociclib or fulvestrant in any of the 7 breast cancer cell lines.

Study 2: Growth Inhibitory Activity of v10000 in Combination with Palbociclib and Fulvestrant in Estrogen Receptor Positive HER2-Expressing Breast Cancer Cell Lines This experiment was performed to identify whether v10000 has additive, synergistic and antagonistic interactions in combination with palbociclib and fulvestrant in representative ER-positive HER2 expressing cancer cell lines.

The growth-inhibition effects of v10000 in combination with palbociclib and fulvestrant were tested in 5 ER-positive breast cancer cell lines in dose matrices of 6-point concentration dilution of v10000 and a 7-point concentration dilution of a fixed 5:2 molar ratio of "single agent" palbociclib plus fulvestrant. Twenty-four hours after cells were plated in 96-well plates, cells were incubated for 72 hours with v10000 (160 to 0 nM) and palbociclib (12.5 to 0 μM) plus fulvestrant (5 to 0 μM) as single agents and combinations. Cell viability was assessed using MTT reagent (30 μl, Sigma Aldrich) added at 37° C. for 4 h, the supernatant aspirated and MTT salt dissolved in DMSO (100 μL). Plates were read at 570 nm absorbance (Ospedale, San Raffaele). Cell viability was analyzed to determine additive, synergistic and antagonistic interactions using the Loewe Additivity model (Zymeworks Inc., Vancouver).

Growth Inhibition (GI) was used as a measure of cell viability. Percent growth inhibition was normalized according to the equation below, where C is the mean absorbance of untreated cells on the same plate, and T is the absorbance of a treated sample.

$$GI = C\text{-}TC \cdot 100\% \quad GI = C\text{-}TC \cdot 100\%$$

Additive, synergistic and antagonistic interactions were determined using the Loewe Additivity model as described in Study 1 shown above.

The results of v10000 in pair-wise combinations with palbociclib and fulvestrant are shown in Table 9. Growth inhibition data were analyzed for synergistic additive, and antagonistic interactions based on the Loewe Additivity model (Tallarida, Genes Cancer 2011; 2:1003-1008). V10000 demonstrated additive interactions (+; Table 9) with palbociclib plus fulvestrant in each of the 5 ER-positive HER2-expressing breast cancer cell lines (Table 9). Additive inhibition of cancer cell growth was observed with v10000 in combination with palbociclib and fulvestrant in BT-474, ZR-75-30, MDA-MB-361, MCF7 and T47D breast cancer cell lines. No antagonistic or synergistic interactions were observed for v10000 in combination with palbociclib and fulvestrant in any of the 5 ER-postive HER2-expressing breast cancer cell lines.

These results show that v10000 combined with palbociclib or fulvestrant results in additive or synergistic growth inihibiton of ER-positive and ER-negative HER2-expressing breast cancer cells. These results also show that v10000 combined with palbociclib and fulvestrant results in additive growth inhibition of ER-positive HER2-expressing breast cancer cells.

TABLE 9

Summary of Synergistic, Additive and Antagonsitic Interaction Scores for Viability of Estrogen Receptor Positive and Human Epidermal Growth Factor Receptor 2-expressing Breast Cancer Cell Lines Treated with ZW25 in Combination with Palbociclib and Fulvestrant

| Breast Cancer Cell Line | HER2 Receptor Score (IHC) | $ER^d$ | $PR^d$ | Interaction Scores[a] V10000 + Chemotherapeutic Palbociclib + Fulvestrant |
|---|---|---|---|---|
| BT-474 | $3+^{a, b}$ | + | + | + |
| ZR-75-30 | $3+^a$ | + | − | + |
| MDA-MB-361 | $3^a$ | + | + | + |
| MCF7 | $0/1+^b$ | + | + | + |
| T47D | $low^c$ | + | + | + |

[a]Interaction Scores:
+ = indicates additive interactions; (antagonistic nor synergistic interactions were not observed);
HER2 = human epidermal growth factor receptor 2;
ER = Estrogen receptor;
PR = Progesterone receptor
[a]Ginestier et al. Oncogene 2007; 26: 7163-7169
[b]Subik et al. Breast Cancer: Basic and Clinical Research 2010; 4: 35-41
[c]Neve et al. Cancer Cell. Dec. 10, 2006(6): 515-527.
[d]Dai et al. Journal of Cancer 2017; 8: 3131-3141

Example 3: Summary of Ongoing v10000 Clinical Study

A first-in-human clinical study of V10000 was initiated in September 2016. This ongoing, multi-part, Phase 1 study is evaluating the safety, pharmacokinetics (PK), immunogenicity, and anti-tumor activity of v10000 as a single agent and in combination with selected chemotherapy agents in patients with locally advanced (unresectable) and/or metastatic HER2-expressing tumors.

Part 1 of the v100000 study is using a standard 3+3 dose-escalation design to determine the maximum-tolerated dose (MTD), optimal biological dose (OBD), or recommended dose(s) (RDs) of v10000 monotherapy administered weekly (QW), once every 2 weeks (Q2W), and/or once every 3 weeks (Q3W) in patients with any HER2-expressing cancer that has progressed after receipt of all therapies known to confer clinical benefit. Part 2 of the study is characterizing the safety, tolerability, and preliminary anti-tumor activity of v10000 monotherapy administered at the Part 1 MTD, OBD, or RD in patients with selected HER2-expressing locally advanced (unresectable) and/or metastatic cancers in up to 5 disease-specific expansion cohorts, including HER2-high breast cancer (immunohistochemistry (IHC) 3+, or IHC 2+/fluorescent in situ hybridization (FISH+), HER2-intermediate breast cancer (IHC 2+/FISH-negative [FISH-]), HER2-high gastroesophageal adenocarcinoma (GEA), HER2-intermediate GEA, and other HER2-high cancers. The recommended single-agent dose for further study was identified in Part 1 of the study as 10 mg/kg QW or 20 mg/kg Q2W. Part 3 of the study is evaluating the safety, tolerability and preliminary anti-tumor activity of v10000 administered in combination with selected chemotherapy agents, including paclitaxel, capecitabine and vinorelbine, in patients with HER2-expressing breast and GEA.

Table 10 below shows the patient characteristics of the dose escalation and expansion cohorts (enrollment ongoing—interim analysis is from unlocked database 18 Apr. 2018 and subject to change). Patients are heavily pretreated, with median 5 prior systemic regimens. Prior HER2 agents include: trastuzumab (93%), pertuzumab (48%), and T-DM1 (43%).

TABLE 10

Patient Characteristics: Dose Escalation and Expansion Cohorts (April 18, 2018)

| | Total | 5 mg/kg QW | 10 mg/kg QW | 15 mg/kg QW | 20 mg/kg Q2W |
|---|---|---|---|---|---|
| | N = 42[1] | n = 3 | n = 13 | 11 = 7 | n = 19 |
| Male/Female (n) | 15/27 | ½ | 5/8 | 3/4 | 6/13 |
| Median age (range) | 63 (27-79) | 61 (58-64) | 62 (31-77) | 52 (36-70) | 67 (27-79) |
| Median prior systemic regimens (range) | 5 (0-17) | 4 (4-8) | 4 (2-17) | 6 (2-7) | 5 (0-10) |
| Cancer Diagnosis (n) | | | | | |
| Breast | 20 (48%) | 2 | 6 | 4 | 8 |
| Gastroesophageal | 13 (31%) | 1 | 5 | 2 | 5 |
| Colorectal | 5 (12%) | — | 1 | 1 | 3 |
| Other | 4 (9%) | — | 1 | — | 3 |

Safety overview (n=42 patients receiving <1 to 15+ treatment cycles (1 cycle=28 days): There were no dose-limiting toxicities; Treatment-related AEs were all Grade 1 or 2 except in one patient who experienced revisable Grade 3 hypophosphatemia, arthralgia and fatigue (10 mg/kg QW); There were no treatment-related serious adverse events or discontinuations; There were no LVEF decreases ≥10% during treatment and no new detectable anti-drug antibodies. Table 11 summarizes the incidence of most common treatment emergent adverse events.

TABLE 11

Incidence of Most Common Treatment Emergent Adverse Events

| | | | | | QW | | | | | | | |
|---|---|---|---|---|---|---|---|---|---|---|---|---|
| | Total (n = 42) | | | | 5 mg/kg (n = 3) | | | | 10 mg/kg (n = 13) | | | |
| Grade | Any | 1 | 2 | 3 | Any | 1 | 2 | 3 | Any | 1 | 2 | 3 |
| Adverse Event | n (%) | | | | | | | | | | | |
| Infusion Reaction | 23 (55%) | 2 | 21 | — | 1 (33%) | — | 1 | — | 8 (62%) | — | 8 | — |
| Diarrhea | 22 (52%) | 15 | 7 | — | 1 (33%) | 1 | — | — | 8 (62%) | 7 | 1 | — |
| Fatigue | 16 (38%) | 6 | 9 | 1 | 3 (100%) | 2 | 1 | — | 5 (39%) | — | 4 | 1 |
| Nausea | 11 (26%) | 7 | 4 | — | 0 (0%) | — | — | — | 4 (31%) | 3 | 1 | — |
| Anorexia | 10 (24%) | 7 | 3 | — | 2 (67%) | 1 | 1 | — | 2 (15%) | 2 | — | — |
| Rash | 9 (21%) | 9 | — | — | 0 (0%) | — | — | — | 3 (23%) | 3 | — | — |

| | | QW | | | | Q2W | | |
|---|---|---|---|---|---|---|---|---|
| | 15 mg/kg (n = 7) | | | | 20 mg/kg (n = 19) | | | |
| Grade | Any | 1 | 2 | 3 | Any | 1 | 2 | 3 |
| Adverse Event | | | | | | | | |
| Infusion Reaction | 3 (43%) | 2 | 1 | — | 11 (58%) | — | 11 | — |
| Diarrhea | 2 (29%) | 1 | 1 | — | 11 (58%) | 6 | 5 | — |
| Fatigue | 3 (43%) | 2 | 1 | — | 5 (38%) | 2 | 3 | — |
| Nausea | 3 (43%) | 1 | 2 | — | 4 (21%) | 3 | 1 | — |
| Anorexia | 0 (0%) | — | — | — | 6 (32%) | 4 | 2 | — |
| Rash | 1 (14%) | 1 | — | — | 5 (26%) | 5 | — | — |

Treatment emergent adverse events reported in ≥ 20% of patients regardless of relationship to study drug

TABLE 12 summarizes the best RECIST 1.1 response to single agent v10000.
Best RECIST 1.1 Response to Single Agent v10000

| | Response-Evaluable Patients[1] | Disease Control Rate | Partial Response | Stable Disease | Progressive Disease |
|---|---|---|---|---|---|
| Total (n = 42) | 33 | 18 (55%) | 12 (36%) | 6 (18%) | 15 (45%) |
| Breast cancer (n = 20) | 18 | 9 (50%) | 6 (33%) | 3 (17%) | 9 (50%) |
| Gastroesophageal cancer (n = 13) | 9 | 5 (56%) | 4 (44%) | 1 (12%) | 4 (44%) |
| Other cancers (n = 9) | 6 | 4 (67%) | 2 (33%) | 2 (33%) | 2 (33%) |
| Colorectal (n = 5) | 3 | 2 (67%) | 1 (33%) | 1 (33%) | 1 (33%) |
| Other (n = 4) | 3 | 2 (67%) | 1 (33%) | 1 (33%) | 1 (33%) |

Figure 2:
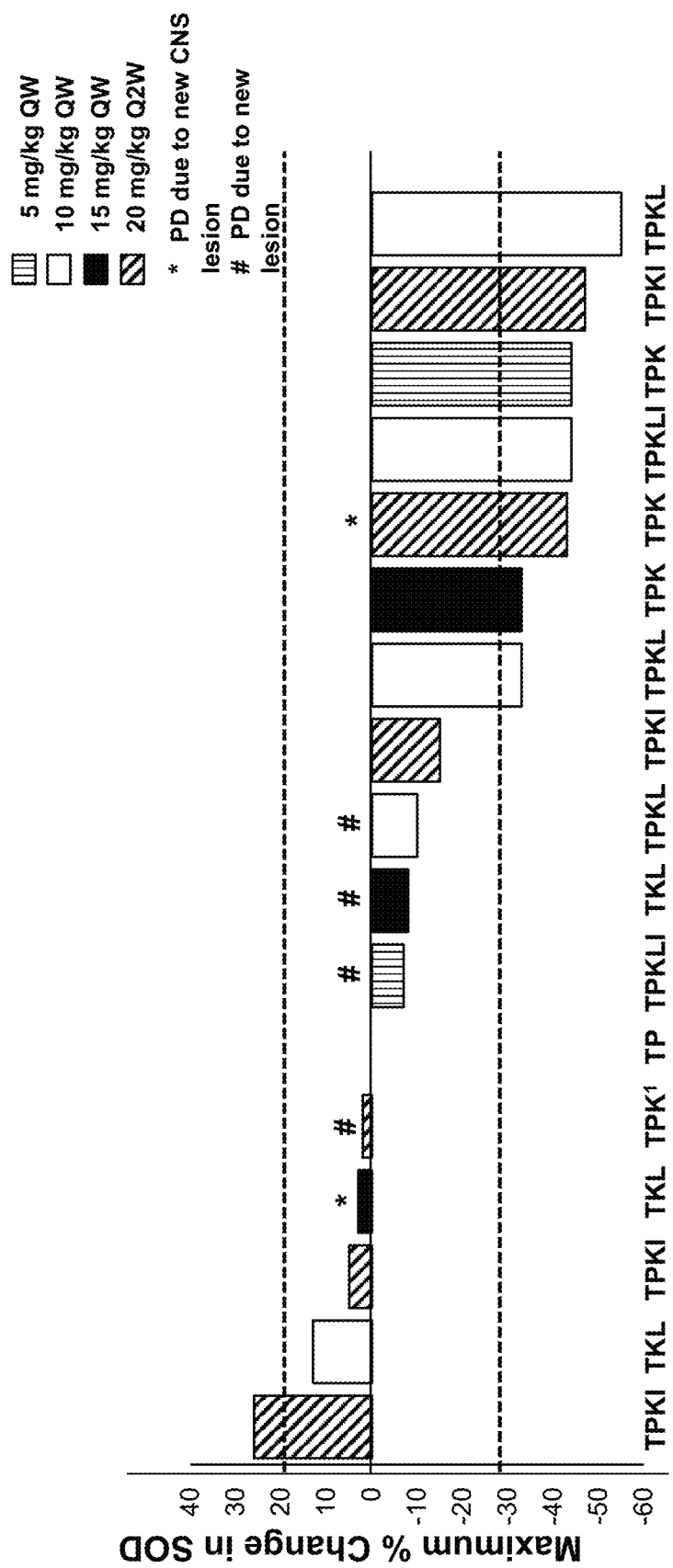
FIG. 2 is a waterfall plot showing maximum % change in sum of diameters for breast cancer patients in a first-in-human clinical study of V10000 as described in Example 3. All 20 patients with history of HER2 High breast cancer, and median 5 prior HER2-targeted regimens for metastatic disease; Prior trastuzumab (T)=100%; T-DM1 (K)=95%; pertuzumab (P)=85%; lapatinib (L)=50%; investigational agent (I)=35%; [1]HER2 negative liver biopsy obtained at study entry; progressive disease in liver. *PD due to new CNS lesion. #PD due to new lesion. Maximum change regardless of best response. SOD=sum of diameters. 3/20 breast cancer patients not evaluable for change in SOD: no measurable disease (n=2); clinical progression on Day 21 (n=1). T: trastuzumab; P: pertuzumab; K: T-DM1; L: lapatinib; I: investigational agent.
Figure 3:
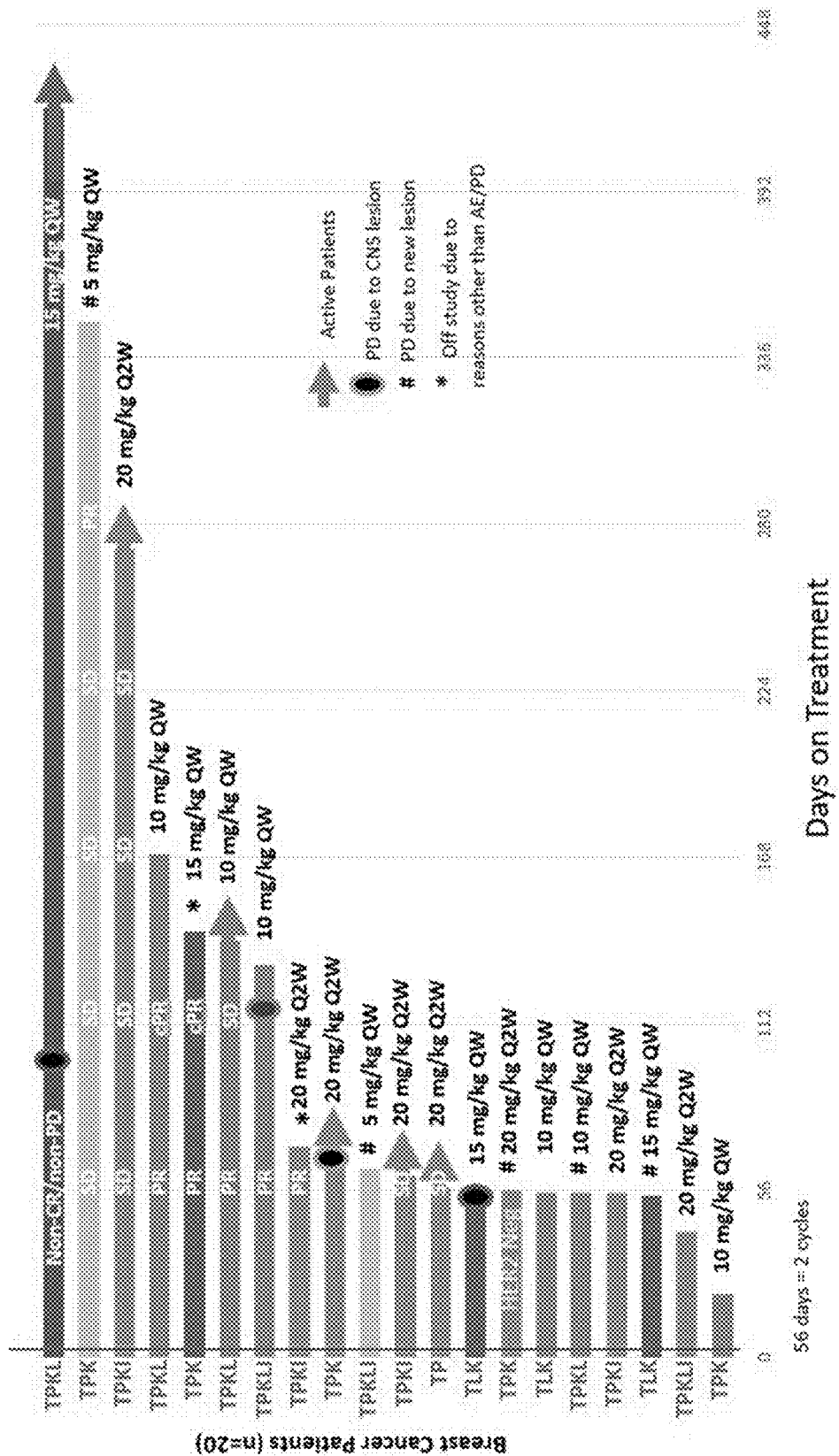
FIG. 3 is a graph showing patient time on treatment for breast cancer patients in a first-in-human clinical study of V10000 as described in Example 3. Lines ending in arrow indicate active patients; filled oval indicates PD due to CNS lesion; #:PD due to new lesion *:Off study due to reasons other than AE/PD; T: trastuzumab; P: pertuzumab; K: T-DM1; L: lapatinib; I: investigational agent. ASCO Data cut-off date of 18 Apr. 2018.

[1]Response evaluable = measurable disease per RECIST 1.1 and at least one tumor restaging or unequivocal clinical progression.
Not evaluable n = 9, including: too early (n = 3); no target lesions (n = 4); withdrawal of consent (n = 1); unrelated SAE (n = 1). Data cut-off date Apr. 18, 2018.
DCR: Disease control rate = best response of stable disease or partial response at any time Breast Cancer: Single Agent Anti-tumor Activity: The waterfall plot for breast cancer patients in the study is shown in FIG. 2, including all 20 patients with history of HER2 High breast cancer, and median 5 prior HER2-targeted regimens for metastatic disease. FIG. 3 shows patient time on treatment for breast cancer patients. Lines ending in arrow indicate active patients; filled oval indicates PD due to CNS lesion; #:PD due to new lesion *:Off study due to reasons other than AE/PD; T: trastuzumab; P: pertuzumab; K: T-DM1; L: lapatinib; I: investigational agent. ASCO Data cut-off date of 18 Apr. 2018.

Summary of v10000 single agent experience: v10000 was well tolerated at all dose levels/schedules in heavily pretreated patients. The recommended dose was found to be 20 mg/kg every two weeks. Cytotoxin-free anti-tumor activity was seen across multiple cancers:

HER2 High breast cancer with median 5 prior HER2-targeted regimens

HER2 High and HER2 Intermediate gastroesophageal cancers after prior trastuzumab HER2 High colorectal, gall bladder and salivary gland cancers This data indicates clinical responses to treatment with v10000 in patients who have PD after treatment with multiple prior HER2 targeted therapies.

Example 4: Phase 2a Study of v10000 in Combination with Palbociclib Plus Fulvestrant Based upon the activity of v10000 as a single agent, as well as the safety profile observed to date, v10000 has the potential to provide clinical benefit to patients with advanced breast cancer. This study will evaluate the safety and preliminary anti-tumor activity of v10000 in combination with palbociclib plus fulvestrant in the treatment of patients with advanced HER2-positive/HR-positive breast cancer that has progressed on or been refractory to prior treatment with trastuzumab, pertuzumab, and T-DM1. Premenopausal women and perimenopausal women will also be treated with a luteinizing hormone-releasing hormone (LHRH) analogue (also known as gonadotropin-releasing hormone analogue) per institutional guidelines.

The v10000 combination study is a multicenter, Phase 2a, open-label, 2-part study to investigate the safety, tolerability, and anti-tumor activity of v10000 in combination with palbociclib (IBRANCE®, an inhibitor of cyclin-dependent kinases 4 and 6 [CDK4 and CDK6] plus fulvestrant (FASLODEX®, an estrogen receptor antagonist) in patients with locally advanced (unresectable) and/or metastatic HER2-positive, HR-positive breast cancer that has progressed on or been refractory to prior treatment with trastuzumab, pertuzumab, and T-DM1.

The primary objective of Part 1 is to characterize the safety and tolerability of v10000 at a monotherapy RD derived from a Phase 1 Study of v10000 (20 mg/kg Q2W) when administered with palbociclib (125 mg per oral (PO) QD for the first 21 days of each 4-week cycle) plus fulvestrant (500 mg intramuscularly [IM] Q2W for the first 3 doses, then Q4W thereafter) and to confirm the RD of v10000 in combination with palbociclib plus fulvestrant. Part 2 of the study will evaluate the anti-tumor activity of the recommended dose level of the combination of v10000 with palbociclib plus fulvestrant in this population (patients with HER2+, HR+ breast cancer).

The clinical trial will be conducted in compliance with the protocol, GCP and all the applicable regulatory requirements.

Objectives

The primary objective of Part 1 is to evaluate the safety and tolerability of v10000 in combination with palbociclib plus fulvestrant in patients with locally advanced (unresectable) and/or metastatic HER2+, HR+ breast cancer. In addition, Part 1 will confirm the recommended doses for all the drugs in this combination; will evaluate the pharmacokinetics (PK) of v10000 in combination with palbociclib plus fulvestrant and; will evaluate the immunogenicity of v10000 in combination with palbociclib plus fulvestrant.

The primary objective of Part 2 of the study is to evaluate the anti-tumor activity of v10000 in combination with palbociclib plus fulvestrant in patients with locally advanced (unresectable) and/or metastatic HER2+, HR+ breast cancer. The secondary objectives are: to evaluate the safety and tolerability of v10000 in combination with palbociclib plus fulvestrant; to evaluate the PK of v10000 in combination with palbociclib plus fulvestrant and; to evaluate the immunogenicity of v10000 in combination with palbociclib plus fulvestrant.

Patients i. Inclusion Criteria

Patients must meet all of the following inclusion criteria.

1. Pathologically-confirmed diagnosis of breast cancer with evidence of locally advanced (unresectable) and/or metastatic disease. All patients in both Parts 1 and 2 must have HER2-positive and HR-positive disease as follows:

HER2+ based on the HER2 Testing in Breast Cancer: ASCO/CAP Clinical Practice Guidelines (Wolff A C, et al. J Clin Oncol. 2018; 36(20):2105-22).

HR+ defined as ER+ and/or PgR+ disease based on the ASCO/CAP Guideline Recommendations for Immunohistochemical Testing of Estrogen and Progesterone Receptors in Breast Cancer (Hammond M E, et al., J Oncol Pract. 2010; 6(4):195-7).

2. Able to provide a new formalin-fixed, paraffin-embedded (FFPE) tumor sample (preferred) or archived tumor tissue (most recent sample available) for retrospective central review of HER2 status.

Local assessments performed on a new tumor sample or archived tumor tissue in a Clinical Laboratory Improvements Amendments (CLIA)-certified lab using a combination of IHC and ISH/FISH methods may be used to determine HER2 and HR status for study eligibility. IHC must be used to determine HR status. Unless otherwise approved by the sponsor medical monitor, specimens should be provided for centralized retrospective review of HER2 status.

3. Disease that has progressed on or been refractory to prior treatment with trastuzumab, pertuzumab, AND ado-trastuzumab emtansine (T-DM1). Patients in any part of the study who did not receive pertuzumab or T-DM1 because of lack of access (e.g., due to insurance coverage or because they were treated prior to regulatory agency approval of the agent in a relevant indication) or due to medical ineligibility for treatment with T-DM1 (e.g., history of severe infusion reactions to trastuzumab, Grade 2 peripheral neuropathy, or platelet count <100×10$^9$/L) may be eligible for the study after discussion with and approval from the sponsor medical monitor. Prior treatment with endocrine therapy in the neoadjuvant, adjuvant, and/or metastatic setting is permitted.

4. Sites of disease assessible per Response Evaluation Criteria in Solid Tumors (RECIST) version 1.1 (both measurable and non-measurable disease allowed)

5. Male and female patients aged 18 years or older

6. An Eastern Cooperative Oncology Group (ECOG) Performance Status score of 0 or 1

7. Life expectancy of at least 3 months in the opinion of the investigator
8. The following baseline laboratory data:
   Absolute neutrophil count (ANC)≥1.5×10$^9$/L
   Platelet count ≥75×10$^9$/L
   Hemoglobin ≥9 g/dL
   Prothrombin time (PT) and/or International Normalized Ratio (INR) and partial thromboplastin time (PTT) ≤1.5×ULN, unless on medication known to alter the INR or PTT
   Total bilirubin≤1.5×ULN per institutional values (patients with known Gilbert's Syndrome may enroll with 2.5× ULN provided the direct bilirubin is ≤1.5 mg/dL)
   ALT≤3.0×ULN per institutional values (if liver metastases are present, 5.0×ULN)
   AST≤3.0×ULN per institutional values (if liver metastases are present, 5.0×ULN)
   Serum creatinine 1.5×ULN or calculated glomerular filtration rate 50 mL/min
9. Adequate cardiac left ventricular function, as defined by LVEF institutional standard of normal
10. All toxicity related to prior cancer therapies must have resolved to Grade 1, with the exception of alopecia or Grade 2 neuropathy
11. If female and of child-bearing potential, must have a negative pregnancy test 3 days prior to the first dose of v10000
12. For female patients who are not surgically sterile or post-menopausal and for male patients with a partner of child-bearing potential, willingness to use 2 methods of birth control with a failure rate of less than 1% per year during the study and for 12 months after the last dose of study drug (v10000, palbociclib, and/or fulvestrant). These include, but are not limited to, established use of oral, implanted, or injected hormonal contraceptives; placement of intra-uterine device or intra-uterine system; or use of barrier methods, such as condom or diaphragm together with a spermicidal product.
13. Female patients must agree not to breastfeed or donate ova starting at screening and throughout the study period, and for at least 12 months after the last dose of study drug (v10000, palbociclib, and/or fulvestrant)
14. Male patients must not donate sperm starting at screening and throughout the study period, and for at least 12 months after the last dose of study drug (v10000, palbociclib, and/or fulvestrant)
15. Signed informed consent prior to any study procedures not considered standard of care ii. Exclusion Criteria Patients will be excluded from the study if 1 or more of the following criteria are applicable:

Prior treatment with trastuzumab, pertuzumab, lapatinib, T-DM1, or other anti-HER2-targeted therapy ≤3 weeks before the first dose of v10000

Prior treatment with chemotherapy, other anti-cancer therapy not otherwise specified, or hormonal cancer therapy ≤3 weeks before the first dose of v10000

Prior treatment with experimental biologic and non-biologic therapies ≤4 weeks before the first dose of v10000

Prior treatment with radiation therapy other than for central nervous system (CNS) disease ≤3 weeks before the first dose of v10000

Treatment with anthracyclines within 90 days before first dose of v10000 and/or total lifetime load exceeding 360 mg/m$^2$ Adriamycin® or equivalent Use of any medications or substances that are strong inhibitors or inducers of CYP3A isoenzymes within 7 days of first dose of any study drug History of life-threatening hypersensitivity to monoclonal antibodies, recombinant proteins, or excipients in the drug formulation Prior Treatment with Palbociclib or any Other CDK4/6 Inhibitors, Including Experimental Agents Use of corticosteroids administered at doses equivalent to >15 mg per day of prednisone within 2 weeks of first v10000 dosing unless otherwise approved by the sponsor medical monitor. Topical, ocular, intra-articular, intranasal, and/or inhalational corticosteroids are permitted.

History of myocardial infarction or unstable angina within 6 months prior to enrollment, troponin levels consistent with myocardial infarction, or clinically significant cardiac disease, such as ventricular arrhythmia requiring therapy, uncontrolled hypertension, or any history of symptomatic congestive heart failure (CHF)

QTc Fridericia (QTcF)>450 ms

Grade 2 or greater pneumonitis and/or interstitial lung disease, including pulmonary fibrosis, or other clinically significant infiltrative pulmonary disease not related to lung metastases Active hepatitis B or hepatitis C infection Acute or chronic uncontrolled renal disease, pancreatitis, or severe liver disease (Child-Pugh Class C)

Known infection with Human Immunodeficiency Virus (HIV)-1 or HIV-2 (Exception: patients with well-controlled HIV [e.g., cluster of differentiation 4 (CD4)-positive T cell count >350/mm$^3$ and undetectable viral load] are eligible.)

Major surgery ≤3 weeks prior to the first dose of v10000

Prior or concurrent malignancy whose natural history or treatment has the potential to interfere with the safety or efficacy assessment of the investigational regimen Any other medical, social, or psychosocial factors that, in the opinion of the investigator, could impact safety or compliance with study procedures Females who are breastfeeding or pregnant, and females and males planning a pregnancy Brain metastases: Untreated CNS metastases, symptomatic CNS metastases, or radiation treatment for CNS metastases within 4 weeks of start of study treatment. Stable, treated brain metastases are allowed (defined as patients who are off steroids and anticonvulsants and are neurologically stable for at least 1 month at the time of screening).

Poorly-controlled seizures

Known leptomeningeal disease (LIVID). If LMD has been reported radiographically on baseline MRI, but is not suspected clinically by the investigator, the patient must be free of neurological symptoms of LMD.

Grade 3 or greater peripheral neuropathy

Treatment

In this study, patients will be treated with open-label v10000 in combination with palbociclib plus fulvestrant. In case of conflict between these instructions and the most recent local prescribing information for these approved drugs, Investigators should follow the most recent local prescribing information.

Part 1:

v10000 will be administered IV at the initial dose of 20 mg/kg Q2W, which is a single-agent recommended dose (RD) identified in Study NCT02892123. Palbociclib will be administered per oral (PO) with food at 125 mg QD for the first 21 days of each 28-day cycle. Fulvestrant will be administered as an IM injection at 500 mg Q2W for the first 3 doses, then Q4W thereafter. A step-down dose level of V10000 (e.g., 15 mg/kg [or other dose level not lower than 15 mg/kg] Q2W) and/or palbociclib (e.g., 100 mg PO and/or 75 mg PO QD) may be allowed if recommended by the safety monitoring committee (SMC). Patients will also receive LHRH analogue treatment per institutional guidelines. The dose-limiting toxicities (DLT)-evaluation period will be the initial 28 days of treatment beginning on Cycle 1 Day 1.

The dose level (evaluated dose of V10000 plus evaluated dose of palbociclib and fulvestrant) will be considered not tolerated if ≥2 of 6 evaluable patients experience a DLT. If DLTs are observed in ≥2 patients, the SMC may recommend a step-down dose level of 15 mg/kg Q2W or other dose not lower than 15 mg/kg Q2W for evaluation in up to 6 additional evaluable patients. Additionally, the SMC may recommend evaluation of step-down doses of palbociclib of 100 mg PO QD and/or 75 mg PO QD with or without recommending evaluation of a step-down dose of V10000. There is no step-down dose for fulvestrant at a cohort or study population level; however, individual patients who develop moderate hepatic impairment (Child-Pugh Class B) while on study treatment will have their fulvestrant dose reduced to 250 mg. Additional safety experiences in later cycles may be considered when confirming the recommended dose level (v10000 in combination with palbociclib plus fulvestrant) for Part 2.

Part 2:

The primary objective of Part 2 of the study is to evaluate the potential anti-tumor activity of the recommended dose level of the combination of v10000 with palbociclib plus fulvestrant in patients with a diagnosis of HER2-positive, HR-positive breast cancer that is locally advanced (unresectable) and/or metastatic.

Enrollment for Part 2 will begin once the recommended doses of v10000 and the other drugs of the combination therapy have been confirmed in Part 1. The treatment and blood collection schedules, treatment cycle duration and imaging evaluation intervals are the same as in Part 1. Patients must undergo at least one response assessment to be considered evaluable.

Part 2 of the study will utilize a Simon 2-stage Optimum design to evaluate the preliminary anti-tumor activity. All patients will be assessed for safety and anti-tumor response. Patients treated at the RD from Part 1 of the study and efficacy evaluable will be included in Stage 1. The primary efficacy endpoint will be PFS6 (defined as the % of efficacy evaluable patients with PFS of ≥24 weeks); secondary efficacy endpoints include ORR, DOR, DCR, and PFS. Stage 1 will include 15 efficacy evaluable patients (N1). If at least 6 of 15 efficacy evaluable patients achieve PFS6, then Stage 2 will be initiated and enroll an additional 31 efficacy evaluable patients (N2) for a total sample size of 46 efficacy evaluable patients across the entire study.

If possible, an additional optional tumor biopsy may be obtained at the time of disease progression from an accessible site to allow for assessment of changes in HER2 expression as well as the presence of other exploratory biomarkers. Biomarkers of response may be evaluated.

Efficacy Assessments

Tumor response will be evaluated based on CT and/or Mill scans (using the same methodology [decided by the investigator at baseline] for each scan of the same patient throughout the study) of the chest, abdomen, and pelvis plus additional areas of known or suspected tumor involvement (e.g., brain [MRI] and/or bone [scintigraphy with targeted assessment by X-ray, CT scan with bone windows, or MM to confirm findings as needed).

Bone scan (scintigraphy): For patients with new lesions identified by post-baseline bone scintigraphy, targeted assessment by X ray, CT scan with bone windows, or MRI will be performed to confirm findings.

Brain scan (MRI): After screening, brain scans will be required per protocol only for patients with findings on the screening brain scan; for patients without findings on the screening brain scan, subsequent brain scans will be done per institutional standard of care.

The radiological assessment(s) will be performed at the visits according to the description provided in the assessment schedule of the protocol.

Objective responses and tumor progression will be evaluated by the investigator using revised RECIST version 1.1 as outlined below (Eisenhauer E A, et al. Eur J Cancer. 2009; 45(2):228-47). Initial responses should be confirmed, if feasible, with a repeat scan 4 weeks (+1-week window) following initial documentation of objective response.

Scans from patients will be collected and may undergo centralized review at the discretion of the sponsor. The investigator assessment will be used for all treatment-related decisions.

Patients' clinical data must be available for CRF source verification. Copies of tumor images must be made available for review by the sponsor (or its designee), upon request.

Measurement of Effect

Antitumor Effect—Solid Tumors

For the purposes of this study, patients should be re-evaluated for response every 8 weeks. In addition to a baseline scan, confirmatory scans should also be obtained not less than 4 weeks following initial documentation of objective response.

Response and progression will be evaluated in this study using the new international criteria proposed by the revised Response Evaluation Criteria in Solid Tumors (RECIST) guideline (version 1.1) (Eisenhauer E A, et al. Eur J Cancer. 2009; 45(2):228-47). Changes in the largest diameter (uni-dimensional measurement) of the tumor lesions and the shortest diameter in the case of malignant lymph nodes are used in the RECIST version 1.1 criteria.

Definitions

Evaluable for toxicity: All patients will be evaluable for toxicity from the time of their first treatment with v10000.

Evaluable for objective response: Only those patients who have measurable disease present at baseline, have received at least 1 cycle of therapy, and have had their disease re-evaluated will be considered evaluable for response. These patients will have their response classified according to the definitions stated below. (Note: Patients who exhibit objective disease progression prior to the end of Cycle 1 will also be considered evaluable.)

Evaluable Non-Target Disease Response: Patients who have lesions present at baseline that are evaluable but do not meet the definitions of measurable disease, have received at least 1 cycle of therapy, and have had their disease re-evaluated will be considered evaluable for non-target disease. The response assessment is based on the presence, absence, or unequivocal progression of the lesions.

Disease Parameters

Measurable disease: Measurable lesions are defined as those that can be accurately measured in at least one dimension (longest diameter to be recorded) as >20 mm by chest x-ray, as >10 mm with CT scan, or ≥10 mm with calipers by clinical exam. All tumor measurements must be recorded in millimeters (or decimal fractions of centimeters).

Malignant lymph nodes: To be considered pathologically enlarged and measurable, a lymph node must be >15 mm in short axis when assessed by CT scan (CT scan slice thickness recommended to be no greater than 5 mm). At baseline and at follow-up, only the short axis will be measured and followed.

Non-measurable disease: All other lesions (or sites of disease), including small lesions (longest diameter <10 mm or pathological lymph nodes with ≥10 to <15 mm short axis), are considered non-measurable disease. B one lesions, leptomeningeal disease, ascites, pleural/pericardial effusions, lymphangitis cutis/pulmonitis, inflammatory breast disease, and abdominal masses (not followed by CT or MRI), are considered as non-measurable.

Note: Cystic lesions that meet the criteria for radiographically defined simple cysts should not be considered as malignant lesions (neither measurable nor non-measurable) since they are, by definition, simple cysts.

"Cystic lesions" thought to represent cystic metastases can be considered as measurable lesions, if they meet the definition of measurability described above. However, if non-cystic lesions are present in the same patient, these are preferred for selection as target lesions.

Target lesions: All measurable lesions up to a maximum of 2 lesions per organ and 5 lesions in total, representative of all involved organs, should be identified as target lesions and recorded and measured at baseline. Target lesions should be selected on the basis of their size (lesions with the longest diameter), be representative of all involved organs, but in addition should be those that lend themselves to reproducible repeated measurements. It may be the case that, on occasion, the largest lesion does not lend itself to reproducible measurement in which circumstance the next largest lesion which can be measured reproducibly should be selected. A sum of the diameters (longest for non-nodal lesions, short axis for nodal lesions) for all target lesions will be calculated and reported as the baseline sum diameters. If lymph nodes are to be included in the sum, then only the short axis is added into the sum. The baseline sum diameters will be used as reference to further characterize any objective tumor regression in the measurable dimension of the disease.

Non-target lesions: All other lesions (or sites of disease) including any measurable lesions over and above the 5 target lesions should be identified as non-target lesions and should also be recorded at baseline. Measurements of these lesions are not required, but the presence, absence, or in rare cases unequivocal progression of each should be noted throughout follow-up.

Methods for Evaluation of Measurable Disease

All measurements should be taken and recorded in metric notation using a ruler or calipers. All baseline evaluations should be performed as closely as possible to the beginning of treatment and never more than 4 weeks before the beginning of the treatment.

The same method of assessment and the same technique should be used to characterize each identified and reported lesion at baseline and during follow-up. Imaging-based evaluation is preferred to evaluation by clinical examination unless the lesion(s) being followed cannot be imaged but are assessable by clinical exam.

Clinical lesions: Clinical lesions will only be considered measurable when they are superficial (e.g., skin nodules and palpable lymph nodes) and 10 mm diameter as assessed using calipers (e.g., skin nodules). In the case of skin lesions, documentation by color photography, including a ruler to estimate the size of the lesion, is recommended.

Chest x-ray: Lesions on chest x-ray are acceptable as measurable lesions when they are clearly defined and surrounded by aerated lung. However, CT is preferable.

Conventional CT and MRI: This guideline has defined measurability of lesions on CT scan based on the assumption that CT slice thickness is 5 mm or less. If CT scans have slice thickness greater than 5 mm, the minimum size for a measurable lesion should be twice the slice thickness. Magnetic resonance imaging is also acceptable in certain situations (e.g., for body scans).

Response Criteria

Evaluation of Target Lesions

Complete Response (CR): Disappearance of all target lesions. Any pathological lymph nodes (whether target or non-target) must have reduction in short axis to <10 mm.

Partial Response (PR): At least a 30% decrease in the sum of the diameters of target lesions, taking as reference the baseline sum diameters Progressive Disease (PD): At least a 20% increase in the sum of the diameters of target lesions, taking as reference the smallest sum on study (this includes the baseline sum if that is the smallest on study). In addition to the relative increase of 20%, the sum must also demonstrate an absolute increase of at least 5 mm. (Note: the appearance of one or more new lesions is also considered progressions).

Stable Disease (SD): Neither sufficient shrinkage to qualify for PR nor sufficient increase to qualify for PD, taking as reference the smallest sum diameters while on study Evaluation of Non-Target Lesions Complete Response (CR): Disappearance of all non-target lesions and normalization of tumor marker level. All lymph nodes must be non-pathological in size (<10 mm short axis)

Note: If tumor markers are initially above the upper normal limit, they must normalize for a patient to be considered in complete clinical response.

Non-CR/Non-PD: Persistence of one or more non-target lesion(s) and/or maintenance of tumor marker level above the normal limits Progressive Disease (PD): Appearance of one or more new lesions and/or unequivocal progression of existing non-target lesions. Unequivocal progression should not normally trump target lesion status. It must be representative of overall disease status change, not a single lesion increase.

Although a clear progression of "non-target" lesions only is exceptional, the opinion of the treating physician should prevail in such circumstances, and the progression status should be confirmed at a later time by the review panel (or principal investigator).

Evaluation of Best Overall Response

The best overall response is the best response recorded from the start of the treatment until disease progression/recurrence (taking as reference for progressive disease the smallest measurements recorded since the treatment started). The patient's best response assignment will depend on the achievement of both measurement and confirmation criteria.

TABLE 13

For Patients with Measurable Disease (i.e., Target Disease)

| Target Lesions | Non-Target Lesions | New Lesions | Overall Response | Best Overall Response when Confirmation is Required[a] |
|---|---|---|---|---|
| CR | CR | No | CR | >4 wks. Confirmation[b] |
| CR | Non-CR/Non-PD | No | PR | >4 wks. Confirmation[b] |
| CR | Not evaluated | No | PR | |
| PR | Non-CR/Non-PD/not evaluated | No | PR | |
| SD | Non-CR/Non-PD/not evaluated | No | SD | documented at least once >4 wks. from baseline[b] |
| PD | Any | Yes or No | PD | no prior SD, PR or CR |
| Any | PD[c] | Yes or No | PD | |
| Any | Any | Yes | PD | |

CR = complete response;
PD = progressive disease;
SD = stable disease;
wks = weeks.
[a]See RECIST version 1.1 manuscript for further details on what is evidence of a new lesion.
[b]Only for non-randomized trials with response as primary endpoint.
[c]In exceptional circumstances, unequivocal progression in non-target lesions may be accepted as disease progression.
Note: Patients with a global deterioration of health status requiring discontinuation of treatment without objective evidence of disease progression at that time should be reported as "symptomatic deterioration." Every effort should be made to document the objective progression even after discontinuation of treatment.

TABLE 14

For Patients with Non-Measurable Disease (i.e., Non-Target Disease)

| Non-Target Lesions | New Lesions | Overall Response |
|---|---|---|
| CR | No | CR |
| Non-CR/non-PD | No | Non-CR/non-PD[a] |
| Not all evaluated | No | not evaluated |
| Unequivocal PD | Yes or No | PD |
| Any | Yes | PD |

CR = complete response;
PD = progressive disease;
SD = stable disease.
[a]"Non-CR/non-PD" is preferred over "stable disease" for non-target disease since SD is increasingly used as an endpoint for assessment of efficacy in some trials so to assign this category when no lesions can be measured is not advised.

Duration of Response

Duration of overall response: The duration of overall response is measured from the time measurement criteria are met for CR or PR (whichever is first recorded) until the first date that recurrent or progressive disease is objectively documented (taking as reference for progressive disease the smallest measurements recorded since the treatment started).

The duration of overall CR is measured from the time measurement criteria are first met for CR until the first date that progressive disease is objectively documented.

Duration of stable disease: Stable disease is measured from the start of the treatment until the criteria for progression are met, taking as reference the smallest measurements recorded since the treatment started, including the baseline measurements.

Progression-Free Survival

PFS is defined as the duration of time from start of treatment to time of progression or death, whichever occurs first.

Example 5: Preparation of Linker-Toxin 001

Linker-Toxin 001 was prepared as described below. Linker-Toxin 001 may also be prepared as described in International Patent Application Publication No. WO 2016/041082.

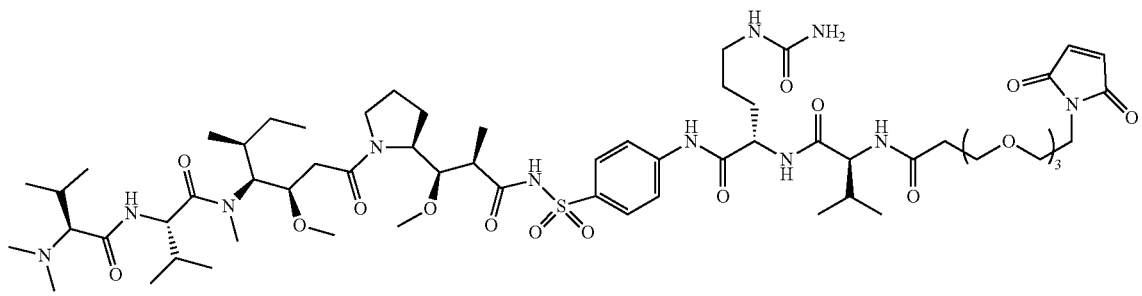

Linker-Toxin 001

A. Ethyl (2R,3R)-3-methoxy-2-methyl-3-((S)-pyrrolidin-2-yl)propanoate (Compound 1)

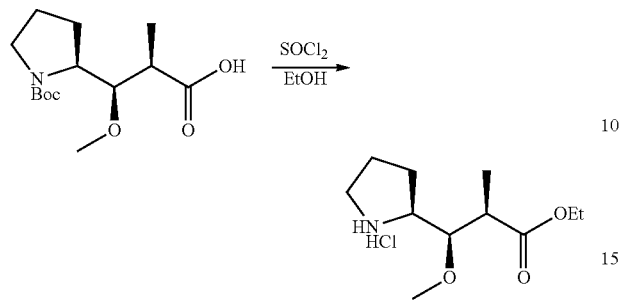

To a stirred solution of (2R,3R)-3-((S)-1-(tert-butoxycarbonyl)pyrrolidin-2-yl)-3-methoxy-2-methylpropanoic acid (Boc-Dap-OH, 4.31 g, 15.0 mmol) in absolute ethanol (27.0 mL) at 0° C. was added thionyl chloride (3.0 mL) in a dropwise fashion. The resulting solution was allowed to warm to room temperature and progress was monitored by HPLC-MS. After 18 h, no remaining starting material was detected and the solution was concentrated to dryness under reduced pressure. The resulting oil was suspended in toluene (10 mL) and concentrated under reduced pressure two times, then suspended in diethyl ether (5 mL) and concentrated under reduced pressure two times to afford a white solid foam (3.78 g, quant yield %). MS m/z obs.=216.5 (M+1).

B. (3R,4S,5S)-4-((S)-2-(((benzyloxy)carbonyl)amino)-N,3-dimethylbutanamido)-3-methoxy-5-methylheptanoic acid (Compound 3)

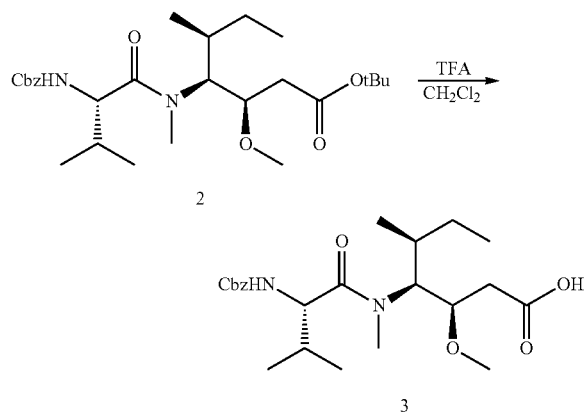

Compound 2 was prepared as described in International Patent Application Publication No. WO 2016/041082.

To a stirred solution of Compound 2 (6.965 g, 14.14 mmol) in dichloromethane (20 mL) was added trifluoroacetic acid (5.0 mL). The reaction was monitored for completion by HPLC-MS and after 40 h no starting material remained. The reaction was concentrated under reduced pressure, co-evaporated with toluene (2×10 mL) and dichloromethane (2×10 mL) to obtain a foamy white solid (6.2 g, quant yield with residual TFA). This material was dissolved in 200 mL of hot 1:3 EtOAc:hexanes and allowed to cool to room temperature. During cooling, a precipitate formed as well as some small crystals. 5 mL EtOAc was added and the suspension was heated once again to fully dissolve the precipitate. More crystals formed on cooling to room temperature and the flask was placed at −30° C. overnight. The following morning the mother liquor was decanted and the crystals rinsed with 2×50 mL hexanes and dried under high vacuum. Recovered 5.67 g of crystalline product. MS m/z obs.=405.7 (M+1).

C. Ethyl (2R,3R)-3-((S)-1-((3R,4S,5S)-4-((S)-2-(((benzyloxy)carbonyl)amino)-N,3-dimethylbutanamido)-3-methoxy-5-methylheptanoyl)pyrrolidin-2-yl)-3-methoxy-2-methylpropanoate (Compound 4)

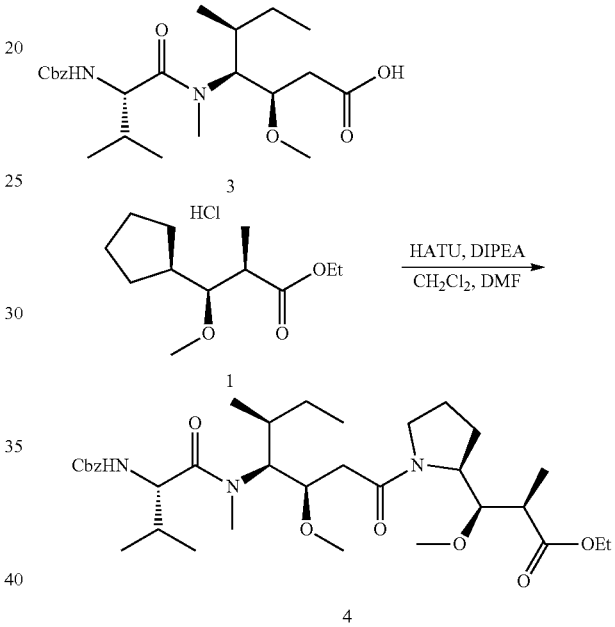

To a stirred solution of Compound 3 (6.711 g, 15.37 mmol, 1.025 equiv) in a mixture of dichloromethane (5.0 mL) and N,N-dimethylformamide (5.0 mL) at room temperature was added HATU (5.732 g, 15.07 mmol, 1.005 equiv) and N,N-diisopropylethylamine (7.84 mL, 3 equiv). After stirring for 30 minutes at room temperature, a solution of Compound 1 (3.776 g, 15.00 mmol, 1.0 equiv) in a mixture of dichloromethane (1.0 mL) and N,N-dimethylformamide (1.0 mL) was added dropwise, rinsed in residual Compound 1 with an additional 3 mL of 1:1 dichloromethane:N,N-dimethylformamide. The reaction was monitored by HPLC-MS and no remaining Compound 1 was observed after 15 minutes. The reaction was concentrated under reduced pressure, diluted with ethyl acetate (~125 mL) and the organic phase was extracted with 1 M HCl (2×50 mL), 1×dH$_2$O (1×50 mL), saturated NaHCO$_3$ (3×50 mL), brine (25 mL). Acidic and basic aqueous layers were both washed with 25 mL EtOAc. All organics were then pooled and dried over MgSO$_4$, filtered and concentrated to give a red oil. The residue was dissolved in a minimal amount of dichloromethane (~10 mL), loaded on to a Biotage® SNAP Ultra 360 g silica gel column (Isolera™ Flash System; Biotage AB, Sweden) for purification (20-100% EtOAc in hexanes over 10 column volumes). Fractions containing pure product were pooled to recover 7.9 g of foamy white solid. Impure fractions were subjected to a second purification on a Biotage® SNAP Ultra 100 g silica gel column and pooled with pure product to recover a white foam solid (8.390 g, 88.3%). MS m/z obs.=634.7 (M+1).

D. (2R,3R)-3-((S)-1-((3R,4S,5S)-4-((S)-2-(((benzyloxy)carbonyl)amino)-N,3-dimethyl butanamido)-3-methoxy-5-methylheptanoyl)pyrrolidin-2-yl)-3-methoxy-2-methylpropanoic acid (Compound 5)

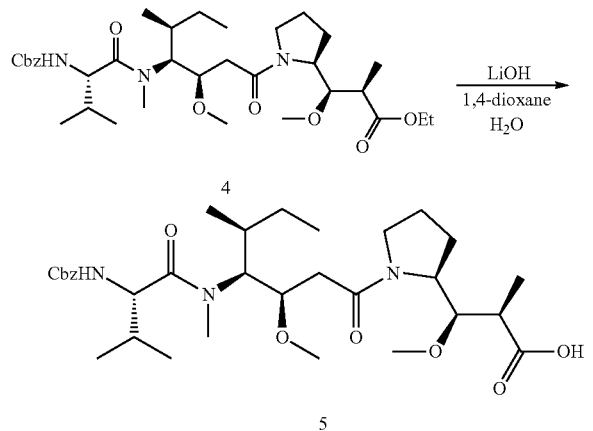

To a stirred solution of Compound 4 (8.390 g, 13.24 mmol) in 1,4-dioxane (158 mL) was added dH$_2$O (39.7 ml) and lithium hydroxide monohydrate (1 M in H$_2$O, 39.7 mL, 3 equiv). The reaction was stirred at 4° C. and monitored by HPLC-MS for consumption of starting material, which took 3 days until only trace Compound 4 remained. During the course of the reaction, a new product, corresponding to loss of methanol (β-elimination, <2%) formed in small percentages in addition to the desired material. The reaction was acidified with the addition of 1 M aqueous HCl (50 mL) and concentrated under reduced pressure to remove the dioxane. The remaining reaction mixture was extracted with ethyl acetate (4×50 mL) and the organic phase was pooled, washed with brine (15 mL+2 mL 2 M HCl), dried over MgSO$_4$, filtered and concentrated under reduced pressure to yield a light coloured oil. The oil was re-dissolved in diethyl ether (~50 mL) and concentrated under reduced pressure (3×) to facilitate the removal of residual dioxane, affording the title product as a stiff oil (7.81 g 97% yield with some residual dioxane and Compound 4). MS m/z obs.=606.7 (M+1).

E. Benzyl ((S)-1-((3R,4S,5S)-3-methoxy-1-((S)-2-((1R,2R)-1-methoxy-2-methyl-3-oxo-3-((4-(2,2,2-trifluoroacetamido)phenyl)sulfonamido)propyl)pyrrolidin-1-yl)-5-methyl-1-oxoheptan-4-yl)(methyl)amino)-3-methyl-1-oxobutan-2-yl)carbamate (Compound 7)

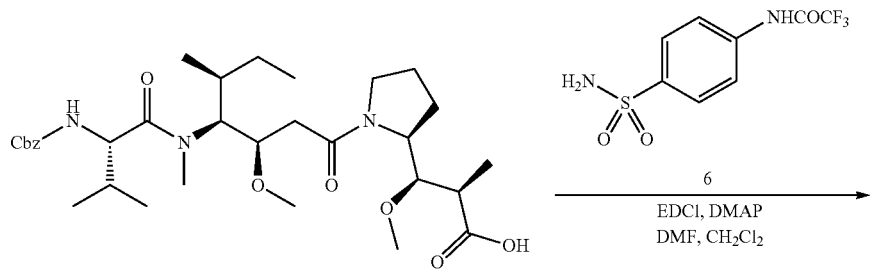

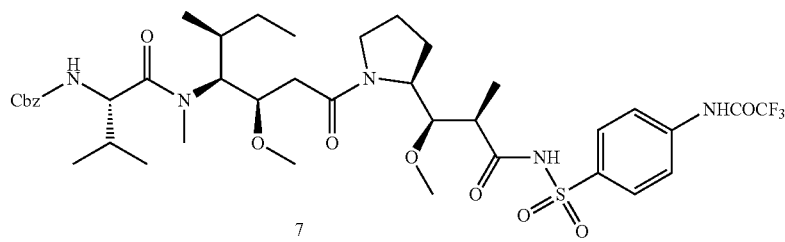

Compound 6 was prepared as described in International Patent Application Publication No. WO 2016/041082).

To a stirred solution of Compound 5 (7.12 g, 11.754 mmol) in dichloromethane (20 mL) was added 2,2,2-trifluoro-N-(4-sulfamoylphenyl)acetamide (Compound 6, 4.095 g, 1.3 equiv, dissolved in 3 mL DMF), N,N-dimethylpyridine (1.867 g, 1.3 equiv) and N,N-dimethylformamide (1.5 mL) to generate a light yellow suspension. Further addition of 5 mL of DMF did not clarify solution. IV-(3-Dimethylaminopropyl)-N'-ethylcarbodiimide hydrochloride (EDCI) (2.817 g, 1.25 equiv) was added in a single portion and the reaction was monitored by HPLC-MS. After 48 hr, reaction was no longer progressing and an additional 400 mg of EDCI was added. After 18 hr, no remaining starting material was observed and the reaction was concentrated under reduced pressure to give a yellow oil. The oil was dissolved in ethyl acetate (~150 mL) and 1 M HCl (20 mL), and the organic phase was washed with cold 2 M HCl (2×10 mL), saturated NaHCO$_3$ (1×10 mL), brine (20 mL+5 mL 2 M HCl). Acidic and basic aqueous fractions were extracted with EtOAc (1×20 mL), all organic fractions were pooled, dried over MgSO$_4$ and concentrated under reduced pressure to yield an oily crude solid (13 g). The residue was dissolved in dichloromethane (~10 mL), loaded on to a Biotage® SNAP Ultra 360 g silica gel column and purified under a 10-100% EtOAc (2% AcOH) in hexanes gradient over 12 column volumes with a 3-column volume plateau at 50% EtOAc. Fractions containing the pure product were pooled, concentrated under reduced pressure, dissolved and concentrated from toluene (2×10 mL) and diethyl ether (2×10 mL) to afford the desired product, 7.1 g of white foam solid. Impure fractions were subjected to repeat purification under shallower gradient conditions using a Biotage® SNAP Ultra 100 g silica gel column on an Isolera™ instrument. All pure fractions were pooled to recover pure product as a white foam solid (8.60 g, 86%). MS m/z obs.=856.7 (M+1).

F. (S)-2-amino-N-((3R,4S,5S)-3-methoxy-1-((S)-2-((1R,2R)-1-methoxy-2-methyl-3-oxo-3-((4-(2,2,2-trifluoroacetamido)phenyl)sulfonamido)propyl)pyrrolidin-1-yl)-5-methyl-1-oxoheptan-4-yl)-N,3-dimethylbutanamide (Compound 7a)

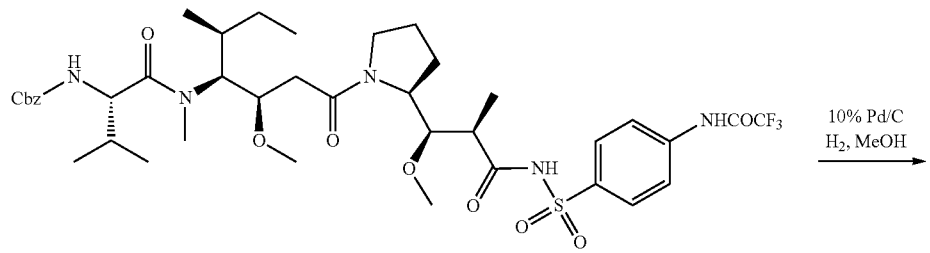

7

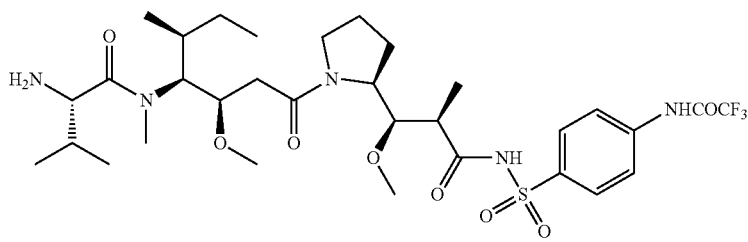

7a

Compound 7 (3.71 g, 4.33 mmol) was dissolved in 10% N,N-dimethylformamide in ethyl acetate (30 mL) in a round bottom flask containing a magnetic stirrer and fitted with a 3-way gas line adapter. The vessel was twice evacuated under reduced pressure and charged with nitrogen gas. 10% palladium on carbon (0.461 g, 0.1 equiv) was added in a single portion, the 3-way adapter was fitted to the flask, a hydrogen balloon was fitted to the adapter and the vessel twice evacuated under reduced pressure and charged with hydrogen. The reaction was allowed to stir for 2 days, over which time the hydrogen balloon was occasionally recharged. After approximately 48 h, HPLC-MS analysis indicated that no starting material remained. The reaction was diluted with methanol (20 mL) and filtered through a plug of celite. The celite was washed with methanol (2×50 mL). All filtrates were pooled and concentrated under reduced pressure and the resulting oil dissolved and concentrated from dichloromethane. After drying under reduced pressure, the title compound was isolated as a colourless powder (3.10 g, 99%). MS m/z obs.=722.6 (M+1).

G. (S)-2-((S)-2-(dimethylamino)-3-methylbutanamido)-N-((3R,4S,5S)-3-methoxy-1-((S)-2-((1R,2R)-1-methoxy-2-methyl-3-oxo-3-((4-(2,2,2-trifluoroacetamido)phenyl)sulfonamido) propyl)pyrrolidin-1-yl)-5-methyl-1-oxoheptan-4-yl)-N,3-dimethylbutanamide (Compound 8)

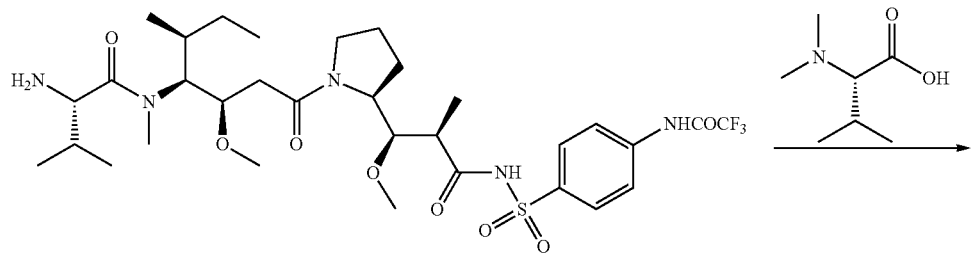

7a

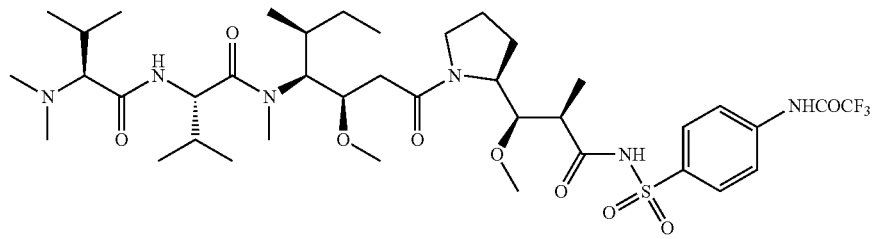

8

To a stirred solution of N,N-(L)-dimethylvaline (1.696 g, 9.35 mmol) in N,N-dimethylformamide (10 mL) was added HATU (3.216 g, 8.46 mmol) and di-isopropylethylamine (3.10 mL, 17.8 mmol). A clear yellow solution resulted after 5 minutes. Stirring was continued for an additional 10 minutes, then Compound 7a (3.213 g, 4.45 mmol) was added in a single portion. After an additional 1 h of stirring, HPLC-MS indicated that trace amounts of Compound 7a remained and the reaction was for 16 h. The reaction was then concentrated under reduced pressure, diluted with ethyl acetate (120 mL) and 40 mL 1:1 NaHCO₃ (sat.): 5% LiCl and transferred to a separating funnel. The aqueous layer was removed and the organic phase was washed with LiCl (1×20 mL), NaHCO₃ (sat., 2×20 mL). Aqueous layers were pooled and extracted with EtOAc (3×50 mL). Organic layers were pooled and washed with brine (1×20 mL), dried over sodium sulfate, filtered and concentrated to give a DMF-laden oil which was concentrated via rotary evaporator to remove residual DMF, yielding 7 g of crude straw coloured oil. The oil was dissolved in a minimal amount of 10% methanol in dichloromethane (~11 mL) and loaded onto a Biotage® SNAP Ultra 360 g silica gel column for purification (2-20% MeOH in CH₂Cl₂ over 15 column volumes, product eluting around 10-13%). The fractions containing the desired product were pooled and concentrated under reduced pressure to afford the title compound as a colourless foam. Impure fractions were combined, evaporated and subjected to repeat purification on a Biotage® SNAP Ultra 100 g silica gel column on an Isolera™ instrument and combined with the pure product from the first column to yield a colourless foam solid (3.78 g). MS m/z obs.=850.6 (M+1).

H. (S)—N-((3R,4S,5R)-1-((S)-2-((1R,2R)-3-(4-aminophenyl)sulfonamido)-1-methoxy-2-methyl-3-oxopropyl)pyrrolidin-1-yl)-3-methoxy-5-methyl-1-oxoheptan-4-yl)-2-((S)-2-(dimethylamino)-3-methylbutanamido)-N,3-dimethylbutanamide (Compound 9)

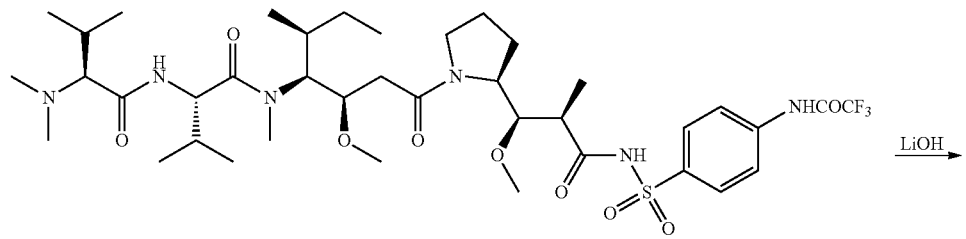

8

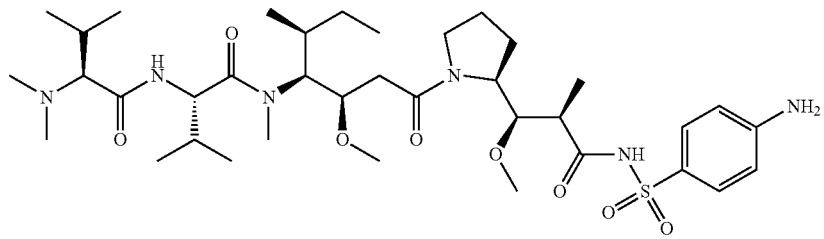

9

To a stirred solution of Compound 8 (0.980 g, 1.154 mmol) in 1,4-dioxanes (15 mL) was added water (3.5 mL) and 1 M lithium hydroxide monohydrate (3 equiv., 3.46 mL). The resulting light suspension was allowed to stir at 4° C. and was monitored by HPLC-MS for consumption of the starting material. When the conversion was complete (~5 days), the reaction was neutralized with 3.46 mL of 1 M HCl and concentrated under reduced pressure to remove dioxane. The resulting aqueous phase was diluted with 60 mL EtOAc and 5 mL brine, then extracted with ethyl acetate (2×30 mL). The organic fractions were pooled, dried over Na$_2$SO$_4$, filtered and evaporated to yield the title compound as a tan solid (0.930 g). R$_f$=0.5 (8% MeOH in CH$_2$Cl$_2$). MS m/z obs.=753.7 (M+1).

I. 2,3,5,6-tetrafluorophenyl 3-(2-(2-(2-(2,5-dioxo-2, 5-dihydro-1H-pyrrol-1-yl)ethoxy)ethoxy)ethoxy) propanoate (Compound 15)

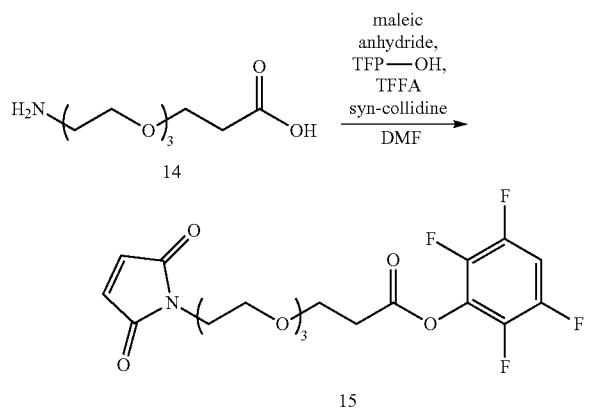

In a dried 50 mL conical flask, 3-(2-(2-(2-aminoethoxy) ethoxy)ethoxy)propanoic acid (Compound 14, 1.000 g, 4.52 mmol) and maleic anhydride (0.443 g, 4.52 mmol) were dissolved in anhydrous N,N-dimethylformamide (5 mL). The reaction was stirred at room temperature for 6 hr under N$_2$, at which point it was cooled to 0° C. and syn-collidine (1.263 mL, 2.1 eq) was added dropwise. In a separate dried 50 mL conical flask, tetrafluorophenol (3.002 g, 4 eq) was dissolved in anhydrous N,N-dimethylformamide (10 mL). The flask was cooled to 0° C. in an ice bath and trifluoroacetic anhydride (2.548 mL, 4 eq) was added dropwise. This flask was stirred for 15 minutes, at which point syn-collidine (2.407 mL, 4 eq) was added dropwise. The flask was allowed to stir for another 15 minutes, and then the contents were added to the first flask dropwise, via syringe. The reaction was allowed to warm to room temperature and stirring was continued under N$_2$. The reaction was monitored by HPLC-MS for the consumption of starting materials. After 6 days, the reaction was complete with the total consumption of Compound 14, leaving only Compound 15 and a small amount (~5%) of the bis-TFP maleic amide intermediate. The reaction was transferred to a separating funnel, diluted with diethyl ether (75 ml) and washed with 5% LiCl (1×20 mL), 1 M HCl (2×20 mL), sat. NaHCO$_3$ (5×20 mL) and brine (1×20 mL). The organic layer was dried over Na$_2$SO$_4$, filtered and evaporated to give brown crude oil with residual DMF. Crude oil was dissolved in 8 mL of 1:1 DMF:H$_2$O+ 0.1% TFA, loaded onto a 60 g Biotage® SNAP Ultra C18 column (Biotage AB, Uppsala, Sweden) and purified under a linear 30-100% gradient of ACN/H$_2$O+0.1% TFA over 8 column volumes. Pure fractions were pooled and diluted with brine (20 mL), then extracted 3×50 mL Et$_2$O. Pooled organics were dried over MgSO$_4$, filtered and evaporated to recover a light-yellow oil (1.34 g, 66% yield).

J. Tert-butyl ((S)-1-(((S)-1-((4-(N-((2R,3R)-3-((S)-1-((3R,4S,5S)-4-((S)-2-((S)-2-(dimethylamino)-3-methylbutanamido)-N,3-dimethylbutanamido)-3-methoxy-5-methylheptanoyl)pyrrolidin-2-yl)-3-methoxy-2-methylpropanoyl)sulfamoyl)phenyl) amino)-1-oxo-5-ureidopentan-2-yl)amino)-3-methyl-1-oxobutan-2-yl)carbamate (Compound 12)

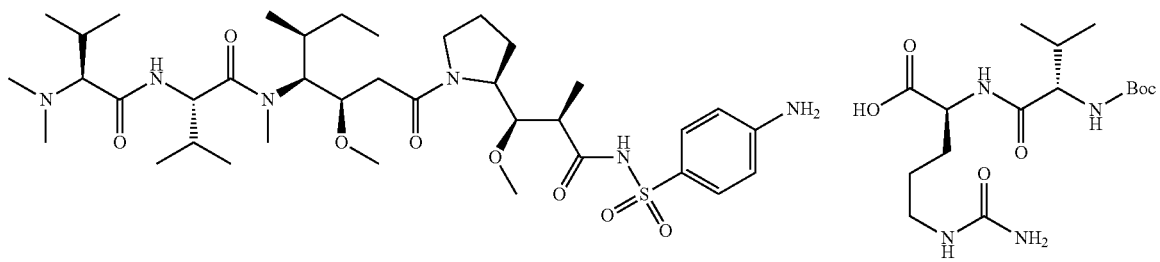

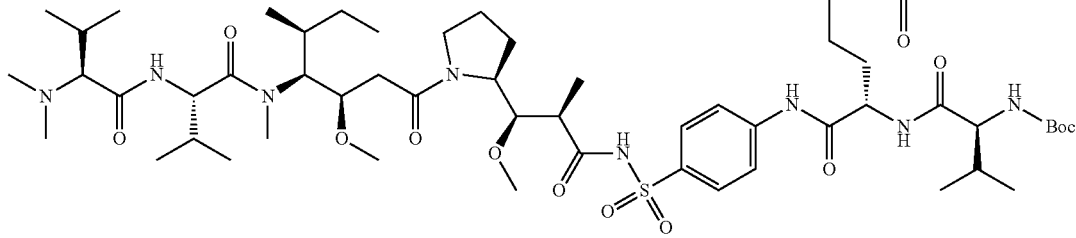

12

Compound 11 was prepared as described in International Patent Application Publication No. WO 2016/041082.

To an empty 25 mL pear shaped flask, was added Compound 11 (1.342 g, 3.58 mmol, 3.0 equiv), 1-ethyl-3-(3-dimethylaminopropyl)carbodiimide hydrochloride (0.664 g, 3.46 mmol, 2.9 equiv) and 7-hydroxy-azabenzotriazole (HOAT) (0.472 g, 3.46 mmol, 2.9 equiv). These solids were dissolved in a mixture of N,N-dimethylformamide (0.5 mL) and dichloromethane (4.5 mL) with stirring at room temperature over 30 minutes. Separately, Compound 9 (0.900 g, 1.20 mmol) was dissolved in a mixture of N,N-dimethylformamide (0.2 mL) and dichloromethane (1.8 mL) and added to the pear shaped flask, rinsing with dichloromethane (1.0 mL). Stirring rate was increased to 1000 rpm, producing a vortex. Within 2 minutes of adding Compound 9, copper (II) chloride (0.514 g, 3.83 mmol, 3.2 equiv) was added in one portion directly into the center of the vortex through a narrow powder funnel. The initially light-yellow solution turned to a dark-brown suspension which changed over 10 minutes to a dark-green suspension. The reaction was monitored for completion by HPLC-MS and no change to reaction progress was observed between the samples taken at 30 minutes and 1 h (~95% complete). The reaction was allowed to stir overnight at room temperature, then 2-(2-aminoethylamino)ethanol (0.483 mL, 4.781 mmol, 4 equiv), EtOAc (10 mL) and dH$_2$O (5 mL) were added to the stirred suspension, which underwent a colour change to deep blue. The suspension was stirred vigorously for 4 hr as the suspended solids gradually dissolved into the biphasic mixture. This mixture was transferred to a separating funnel and diluted with EtOAc (100 mL) and brine (10 mL), and the aqueous layer was extracted 10% IpOH/EtOAc (4×50 mL). The organic layers were pooled and washed with brine (10 mL), dried over Na$_2$SO$_4$, and evaporated to yield a faintly blue crude solid. This crude solid was dissolved in a mixture of methanol (0.5 mL) and dichloromethane (6 mL) and purified on a Biotage® SNAP Ultra 100 g silica gel column (2-20% MeOH in CH$_2$Cl$_2$ over 10 column volumes, followed by an 8-column volume plateau at 20% MeOH). The product eluted as a broad peak after 1-2 column volumes at ~20% MeOH in CH$_2$Cl$_2$. Fractions containing the desired material were pooled and concentrated under reduced pressure to give the title compound as a white solid (1.105 g, 83%). MS m/z obs.=555.9 ((M+2)/2), 1109.8 (M+1).

K. (S)-2-((S)-2-amino-3-methylbutanamido)-N-(4-(N-((2R,3R)-3-((S)-1-((3R,4S,5R)-4-((S)-2-((S)-2-(dimethylamino)-3-methylbutanamido)-N,3-dimethylbutanamido)-3-methoxy-5-methylheptanoyl) pyrrolidin-2-yl)-3-methoxy-2-methylpropanoyl) sulfamoyl)phenyl)-5-ureidopentanamide (Compound 13)

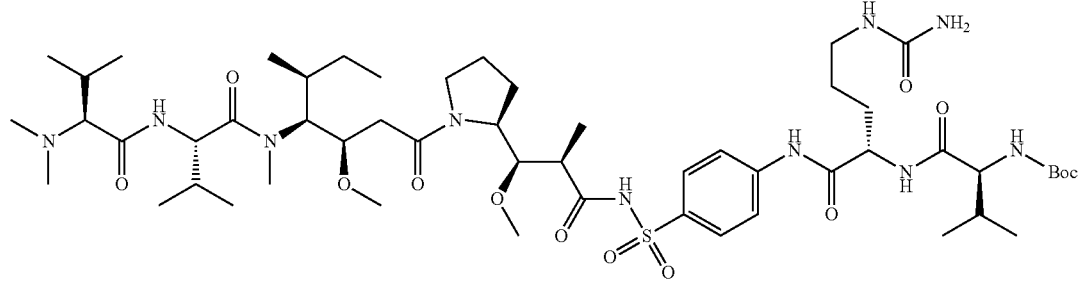

12

| TFA
| CH$_2$Cl$_2$
↓

-continued

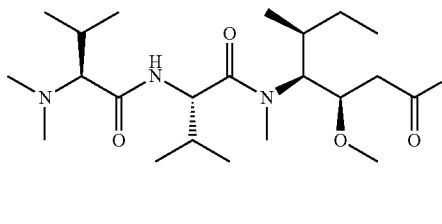
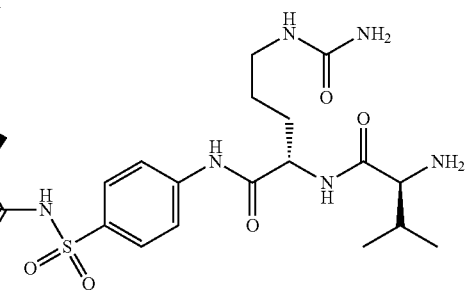

13

To a solution of Compound 12 (0.926 g, 0.834 mmol) was added a mixture of dichloromethane (10 mL) and trifluoroacetic acid (2.0 mL). The reaction was monitored by HPLC-MS for consumption of starting material (~45 minutes). The reaction was co-evaporated with acetonitrile (2×10 mL) and dichloromethane (2×10 mL) under reduced pressure to remove excess trifluoroacetic acid. The resulting residue was dissolved in a minimal amount of dichloromethane and methanol (3:1, v/v, ~2 mL), and added to a stirred solution of diethyl ether (200 mL) and hexanes (100 mL) dropwise via pipette, producing a suspension of light white solids. The solids were filtered and dried under vacuum to afford the title compound in the form of a white powder, as the trifluoroacetate salt (1.04 g, quantitative yield with some residual solvents). MS m/z obs.=505.8 ((M+2)/2).

L. (S)—N-(4-(N-((2R,3R)-3-((S)-1-((3R,4S,5R)-4-((S)-2-((S)-2-(dimethylamino)-3-methylbutanamido)-N,3-dimethylbutanamido)-3-methoxy-5-methylheptanoyl)pyrrolidin-2-yl)-3-methoxy-2-methylpropanoyl)sulfamoyl)phenyl)-2-((S)-1-(2,5-dioxo-2,5-dihydro-1H-pyrrol-1-yl)-14-isopropyl-12-oxo-3,6,9-trioxa-13-azapentadecanamido)-5-ureidopentanamide (Linker-Toxin 001)

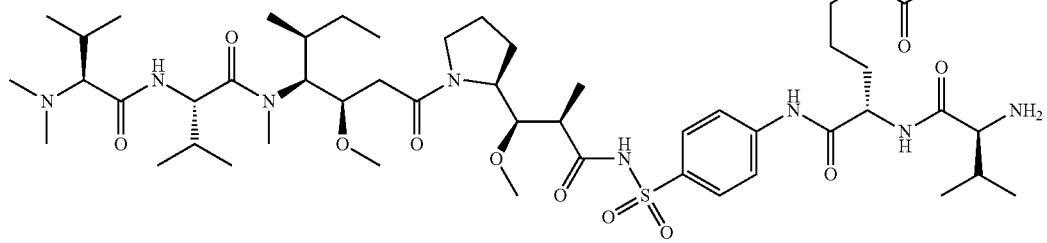

13

| Compound 15
| NaHCO₃
| H

To a stirred solution of Compound 13 (0.722 g, 0.584 mmol) in N,N-dimethylformamide (4 mL) was added Compound 15 (0.314 g, 1.2 equiv) and diisopropylethylamine (0.305 mL, 3.0 equiv). HPLC-MS analysis at 2 h indicated no remaining starting material. The reaction was acidified with TFA (300 μL) and then diluted with diH$_2$O+0.1% TFA (9 mL). The resultant solution was loaded onto a 120 g Biotage® SNAP Ultra C18 column (Biotage, Uppsala, Sweden) and purified under an ACN/H$_2$O+0.1% TFA gradient: 20-60% ACN over 10 column volumes, 60-100% ACN over 5 column volumes. Product eluted near 40% ACN. Pure fractions as identified by LCMS were pooled and lyophilized. A white powder solid was recovered from the lyophilizer. The lyophilization was repeated at higher concentration (approx. 50 mg/mL in 2:1 H$_2$O/ACN) into a vial to produce a denser, less flocculant lyophilized solid (754.2 mg, 91%). MS m/z obs.=647.4 ((M+2)/2), 1292.8 (M+1).

Example 6: Preparation of v10000 Conjugated to Linker-Toxin 001

A solution (138.9 mL) of the antibody v10000 (2.0 g) in 10 mM sodium acetate, 9% (w/v) sucrose, pH 4.5 was pH-adjusted by addition of 200 mM Na$_2$HPO$_4$, pH 8.9 (15.4 mL). After addition of a DTPA solution (44 mL in PBS, pH 7.4, final concentration 1.0 mM), reduction of the interchain disulfides was initiated by addition of an aqueous 10 mM TCEP solution (1.68 mL, 1.05 eq.). After 90 minutes at 37° C., the reaction was cooled on ice before addition of an excess of Linker-Toxin 001 (4.81 mL; 6 eq) from a 20 mM DMSO stock solution. The conjugation reaction was quenched after 90 minutes by addition of an excess of a 20 mM N-acetyl cysteine solution (4.81 mL; 6 eq.).

The quenched antibody drug conjugate (ADC) solution was purified with 9-15 diavolumes of 10 mM sodium acetate, 9% (w/v) sucrose, pH 4.5 on a Millipore Labscale™ Tangential Flow Filtration instrument using a Pellicon® XL Ultrafiltration Module (Ultracel® 30 kDa 0.005 m$^2$; Millipore Sigma). The eluted ADC was sterile filtered (0.22 um). ADCs produced on small scale were purified over 40 KDa MWCO Zeba™ columns (ThermoFisher Scientific, Waltham, MA) preconditioned with either PBS or 10 mM sodium acetate, 9% (w/v) sucrose, pH 4.5.

Following purification, the concentration of the ADC was determined by a BCA assay with reference to a standard curve generated from v10000. Alternatively, concentrations were estimated by measurement of absorption at 280 nm (ε=195065 M$^{-1}$ cm$^{-1}$).

Samples of the ADCs were assessed by non-reducing and reducing SDS-PAGE. No extraneous bands were observed.

Antibody and ADC were analyzed by hydrophobic interaction chromatography (HIC) to estimate the drug-to-antibody ratio (DAR). Chromatography was on a Proteomix® HIC Ethyl column (7.8×50 mm, 5 μm) (Sepax Technologies Inc., Newark, DE) employing a gradient of 80% MPA/20% MPB to 35% MPA/65% MPB over a period of 13.5 minutes at a flow rate of 1 mL/min (MPA=1.5 M (NH$_4$)$_2$SO$_4$, 25 mM Na$_x$PO$_4$, and MPB=75% 25 mM Na$_x$PO$_4$, 25% isopropanol).

The average drug to antibody ratio (DAR) of an ADC can vary depending on the number of disulphide bonds liberated during the reduction of the antibody. A single conjugation reaction that yields an ADC with a particular average DAR comprises a mixture of species. For v10000 conjugated to Linker-Toxin 001, a mixture of four species was generated: unconjugated antibody, ADC with a DAR of 2, ADC with a DAR of 4 and ADC with a DAR of 6.

The results of the HIC indicated that the ADC comprising v10000 conjugated to Linker-Toxin 001 had an average DAR of 2.07. The individual contributions of the DAR0, DAR2, DAR4 and DARE species to the average DAR of the purified ADC were assessed by the integration of the HPLC-HIC chromatogram. Each peak in the HIC chromatogram was isolated by preparative chromatography and the identity of the peak was verified by LC-MS. The % content of individual DAR species for each variant (as determined by HIC) is shown in Table 15.

TABLE 15

DAR Distribution for ADC Comprising v10000 and Linker-Toxin 001

| DAR | Area % |
| --- | --- |
| 0 | 23 |
| 2 | 56 |
| 4 | 17 |
| 6 | 4 |

The various embodiments described above can be combined to provide further embodiments. All U.S. patents, U.S. patent application publications, U.S. patent application, foreign patents, foreign patent application and non-patent publications referred to in this specification and/or listed in the Application Data Sheet are incorporated herein by reference, in their entirety. Aspects of the embodiments can be modified if necessary to employ concepts of the various patents, applications, and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

We claim:

1. A method of treating a patient with human epidermal growth factor receptor 2 (HER2)-positive, hormone receptor (HR)-positive breast cancer, the method comprising administering to the patient:
   I) a palbociclib 75 mg, 100 mg or 125 mg capsule administered orally (PO) once daily (QD) for the first 21 days of each 28-day cycle;
   II) 15 mg/kg to 20 mg/kg of a bispecific anti-HER2 antigen-binding construct every 2 weeks (Q2W) or 15 mg/kg to 50 mg/kg of a bispecific anti-HER2 antigen-binding construct every 3 weeks (Q3W); and
   III) fulvestrant administered at 250 mg-500 mg Q2W for the first 3 doses, then once every 4 weeks (Q4W),
   wherein the bispecific anti-HER2 antigen-binding construct comprises a heavy chain H1, a heavy chain H2, and a light chain L1,
   wherein:
      a) heavy chain H1 comprises the CDR sequences set forth in SEQ ID NO:39, SEQ ID NO:40, and SEQ ID NO:41;
      b) heavy chain H2 comprises the CDR sequences set forth in SEQ ID NO:67, SEQ ID NO:68, SEQ ID NO: 69, SEQ ID NO:70, SEQ ID NO:71, and SEQ ID NO:72; and
      c) light chain L1 comprises the CDR sequences set forth in SEQ ID NO:27, SEQ ID NO:28, and SEQ ID NO:29.

2. The method according to claim 1, wherein the breast cancer is resectable, partially resectable, or unresectable.

3. The method according to claim 1, wherein the breast cancer is locally advanced and/or metastatic.

4. The method according to claim 1, wherein the bispecific anti-HER2 antigen-binding construct comprises a heavy chain H1 comprising the amino acid sequence set forth in SEQ ID NO:36, a heavy chain H2 comprising the amino acid sequence set forth in SEQ ID NO:63, and a light chain L1 comprising the amino acid sequence set forth in SEQ ID NO:24.

5. The method according to claim 4, wherein the effective amount of the bispecific anti-HER2 antigen-binding construct is 20 mg/kg every two weeks.

6. The method according to claim 4, wherein the effective amount of the bispecific anti-HER2 antigen-binding construct is 30 mg/kg every three weeks.

7. The method according to claim 1, wherein the administrations of I, II and III result in a complete response (CR), partial response (PR) or stable disease (SD) in the patient.

8. The method according to claim 1, wherein the disease control rate in a group of patients administered I, II, and III is greater than 60%, 70%, or 80%.

9. The method according to claim 1, wherein the administrations of I, II and III are administered following at least one, two, or three first-line therapies.

10. The method according to claim 1, wherein the patient has prior progression or intolerance following prior trastuzumab, pertuzumab and T-DM1 treatment.

11. The method according to claim 1, wherein the method further comprises administration of one or more chemotherapeutic agents.

12. The method according to claim 11, wherein the one or more chemotherapeutic agents is gemcitabine and/or cisplatin.

13. The method according to claim 1, wherein the method further comprises administration of gonadotropin-releasing hormone analogue.

14. A method of treating a patient with human epidermal growth factor receptor 2 (HER2)-positive, hormone receptor (HR)-positive breast cancer, the method comprising administering to the patient:
   I) a palbociclib 125 mg capsule administered orally (PO) once daily (QD) for the first 21 days of each 28-day cycle;
   II) 20 mg/kg of a bispecific anti-HER2 antigen binding construct thereof every 2 weeks (Q2W); and
   III) fulvestrant administered at 500 mg Q2W for the first 3 doses, then once every 4 weeks (Q4W),
   wherein the bispecific anti-HER2 antigen-binding construct comprises a heavy chain H1, a heavy chain H2, and a light chain L1,
   wherein:
      a) heavy chain H1 comprises the CDR sequences set forth in SEQ ID NO:39, SEQ ID NO:40, and SEQ ID NO:41;
      b) heavy chain H2 comprises the CDR sequences set forth in SEQ ID NO:67, SEQ ID NO:68, SEQ ID NO:69, SEQ ID NO:70, SEQ ID NO:71, and SEQ ID NO:72; and
      c) light chain L1 comprises the CDR sequences set forth in SEQ ID NO:27, SEQ ID NO:28, and SEQ ID NO:29.

15. The method according to claim 14, wherein the bispecific anti-HER2 antigen-binding construct comprises a heavy chain H1 comprising the amino acid sequence set forth in SEQ ID NO:36, a heavy chain H2 comprising the amino acid sequence set forth in SEQ ID NO:63, and a light chain L1 comprising the amino acid sequence set forth in SEQ ID NO:24.

16. The method according to claim 15, wherein the administrations of I, II, and III result in a complete response (CR), partial response (PR) or stable disease (SD) in the patient.

17. The method of claim 1, wherein the bispecific anti-HER2 antigen-binding construct is an antibody drug conjugate (ADC).

18. The method of claim 14, wherein the bispecific anti-HER2 antigen-binding construct is an antibody drug conjugate (ADC).

* * * * *